United States Patent
Harpold et al.

(10) Patent No.: US 7,063,950 B1
(45) Date of Patent: Jun. 20, 2006

(54) NUCLEIC ACIDS ENCODING HUMAN CALCIUM CHANNEL AND METHODS OF USE THEREOF

(76) Inventors: Michael M. Harpold, 15630 Creek Hills, El Cajon, CA (US) 92021; Steven B. Ellis, 8939 Oviedo St., San Diego, CA (US) 92129; Mark E. Williams, 6919 Pear Tree Dr., Carlsbad, CA (US) 92009

(*) Notice: Subject to any disclaimer, the term of this patent is extended or adjusted under 35 U.S.C. 154(b) by 1420 days.

(21) Appl. No.: 08/404,950

(22) Filed: Mar. 13, 1995

Related U.S. Application Data

(63) Continuation-in-part of application No. 08/193,078, filed as application No. PCT/US92/06903 on Aug. 14, 1992, now Pat. No. 5,846,757, which is a continuation of application No. 08/105,536, filed on Aug. 11, 1993, now abandoned, which is a continuation-in-part of application No. 07/868,354, filed on Apr. 19, 1992, now abandoned, which is a continuation-in-part of application No. 07/745,206, filed on Aug. 15, 1991, now Pat. No. 5,429,921, which is a continuation-in-part of application No. 07/620,250, filed on Nov. 30, 1990, now abandoned, and a continuation-in-part of application No. 07/482,384, filed on Feb. 20, 1990, now Pat. No. 5,386,025, which is a continuation-in-part of application No. 07/176,899, filed on Apr. 4, 1988, now abandoned, application No. 08/404,950, which is a continuation-in-part of application No. 07/914,231, filed on Jul. 13, 1992, now Pat. No. 5,407,820, which is a continuation of application No. 07/603,751, filed on Nov. 8, 1990, now abandoned, application No. 08/404,950, and a continuation-in-part of application No. PCT/US89/01408, filed on Apr. 4, 1988.

(51) Int. Cl.
*C12N 5/10* (2006.01)
*C12N 15/12* (2006.01)
*C12N 15/63* (2006.01)
*G01N 33/53* (2006.01)

(52) U.S. Cl. .................... 435/7.21; 435/71.1; 435/71.2; 435/252.3; 435/254.11; 435/69.1; 435/325; 435/354; 435/358; 435/320.1; 435/471; 536/23.5

(58) Field of Classification Search ................ 536/23.5; 435/69.1, 320.1, 240.2, 254.11, 7.21, 29, 435/471, 325, 71.1, 71.2, 252.3, 356, 358
See application file for complete search history.

(56) References Cited

U.S. PATENT DOCUMENTS

| | | | |
|---|---|---|---|
| 4,788,135 A | 11/1988 | Davis et al. .................... 435/6 |
| 4,912,202 A | 3/1990 | Campbell et al. ........... 530/387 |
| 4,954,436 A | 9/1990 | Froehner et al. ................ 435/7 |
| 5,024,939 A | 6/1991 | Gorman ..................... 435/69.1 |
| 5,051,403 A | 9/1991 | Miljanich et al. ............. 514/12 |
| 5,189,020 A | 2/1993 | Miljanich et al. ............. 514/12 |
| 5,264,371 A | 11/1993 | Miljanich et al. ........... 436/503 |
| 5,424,218 A | 6/1995 | Miljanich et al. ........... 436/503 |

FOREIGN PATENT DOCUMENTS

| | | |
|---|---|---|
| CA | 2085502 | 2/1993 |
| EP | 0507170 | 3/1992 |
| EP | 0556651 | 4/1993 |
| WO | 8907608 | 8/1989 |
| WO | 8909834 | 10/1989 |
| WO | 9113077 | 9/1991 |
| WO | 9202639 | 2/1992 |
| WO | 9308469 | 4/1993 |
| WO | 93/14098 | * 7/1993 |
| WO | 9402511 | 2/1994 |
| WO | 9504144 | 2/1995 |

OTHER PUBLICATIONS

Adams, M. D., et al. (Jun. 30, 1993) GenBank Record No. T05783, "EST03672" [attached to Office action] —(Jun. 30, 1993) Gen Bank Record No. T06059, "EST03948" [attached to action].*

Powers, et al., "Assignment of the human gene for the $\alpha_1$ subunit of the cardiac DHP–sensitive $Ca^{2+}$ channel (CCHL1A1) to Chromosome 12p12–pter," *Genomics*, 10: 835–839 (1991).

Kim, et al., "IgG from patients with Lambert–Eaton syndrome blocks voltage–dependent calcium channels," *Science*, 239: 405–408 (1988).

Claudio, et al., "Genetic reconstitution of functional acetylcholine receptor channels in mouse fibroblasts," *Science*, 238: 1688–1694 (1987).

Tanabe, et al., "Primary structure of the receptor for calcium channel blockers from skeletal muscle," *Nature*, 328: 313–318 (1987).

Nakayama, et al., "Purification of a putative $Ca^{2+}$ channel protein from rabbit skeletal muscle," *J.Biol.Chem.*, 262: 6572–6576 (1987).

Vaghy, et al., "Identification of a novel 1,4–dihydropyridine–and phenylalkylamine–binding polypeptide in calcium channel preparations," *J.Biol.Chem.*, 262(29): 14337–14342 (1987).

Leung, et al., "Structural characterization of the 1,4–dihydropyridine receptor of the voltage–dependent $Ca^{2+}$ channel from rabbit skeletal muscle," *J.Biol.Chem.*, 262(17): 7943–7946 (1987).

Sharp, et al., "Identification and characterization of the dihydropyridine–binding subunit of the skeletal muscle dihydropyridine receptor," *J.Biol.Chem.*, 62(25): 12309–12315 (1987).

(Continued)

*Primary Examiner*—Prema Mertz

(57) ABSTRACT

Isolated DNA encoding each of human calcium channel $\alpha_1$-, $\alpha_2$-, β- and γ-subunits, including subunits that arise as splice variants of primary transcripts, is provided. Cells and vectors containing the DNA and methods for identifying compounds that modulate the activity of human calcium channels are also provided.

68 Claims, No Drawings

U.S. PATENT DOCUMENTS

Takahashi, et al., "Subunit structure of dihydropyridine–sensitive calcium channels from skeletal muscle," *Proc.Natl.Acad.Sci.* (*USA*), 84: 5478–5482 (1987).

Morton et al. "Monoclonal antibody identifies a 200–kDA subunit of the dihydropyri–dine–sensitive calcium channel," *J.Biol.Chem.*, 262(25): 11904–11907 (1987).

Barhanin, et al., "The calcium channel antagonists receptor from rabbit skeletal muscle: reconstitution after purification and subunit characterization," *Eur.J.Biochem.*, 164: 525–531 (1987).

Sieber, et al., "The 165–kDa peptide of the purified skeletal muscle dihydropyridine receptor contains the known regulatory sites of the calcium channel," *Eur.J.Biochem.*, 167: 117–122 (1987).

Lang, et al., "The effect of myasthenic syndrome antibody on presynaptic calcium channels in the mouse," *J.Physiol.*, 390: 257–270 (1987).

Curran and Morgan, "Barium modules c–fos expression and post–translational modification," *Proc.Natl.Acad.Sci.*, 83: 3521–8524 (1986).

Fisch, et al., "c–fos sequences necessary for basal expression and induction by epidermal growth factor, 12–0–tetradecanoyl phorbol–13–acetate, and the calcium inophore," *Mol.Cell.Biol.*, 7(10): 3490–3502 (1987).

Noda, et al., "Existence of distinct sodium channel messenger RNAs in rat brain," *Nature*, 320: 188–192 (1986).

Noda, et al., "Expression of functional sodium channels from cloned cDNA," *Nature*, 322: 826–828 (1986).

Mierendorf, et al., "Gene isolation by screening kgtll libraries with antibodies," *Methods in Enz.*, 152: 458–469 (1986).

Gustin, et al., "Ion channels in yeast," *Science*, 233: 1195–1197 (1986).

Striessnig, et al., "Photoaffinity labelling of the phenylalkylamine receptor of the skeletal muscle transverse–tubule calcium channel," *FEBS Letters*, 212(2):247–253 (1987).

Froehner, "New insights into the molecular structure of the dihydropyridine–sensitive calcium channel," *TINS*, 11(3): 90–92 (1988).

Catterall, et al., "Molecular properties of dihydropyridine–sensitive calcium channels in skeletal muscle," *J.Biol.Chem.*, 263(8): 3535–3538 (1988).

Curtis, et al., "Purification fo the calcium antagonist receptor of the voltage–sensitive calcium channel from skeletal muscle transverse tubules," *Biochemistry*, 23(10): 2113–2118 (1984).

Borsotto, et al., "The 1,4–dihydropyridine receptor associated with the skeletal muscle voltage–dependent $Ca^{2+}$ channel," *J.Biol.Chem.*, 260(26): 14255–14263 (1985).

Cooper, et al., "Purification and characterization of the dihydropyridine–sensitive voltage–dependent calcium channel from cardiac from cardiac tissue," *J.Biol.Chem.*, 262(2): 509–512 (1987).

Wood, "Gene cloning based on long oligonucleotide probes," *Methods in Enzymology*, 152: 443–447 (1987).

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry*, 25: 3492–3495 (1986).

Mishina, et al., "Location of functional regions of acetylcholine receptor α–subunit by site–directed mutagenesis," *Nature*, 313: 364–369 (1985).

Hamill, et al., "Improved patch–clamp techniques for high––resolution current recording from cells and cell–free membrane patches," *Pfluger Archiv.European Journal of Physiology*, 391: 85–100 (1981).

Hess, et al., "Different modes of Ca channel gating behavior favored by dihydropyridine Ca agonist and antagonists," *Nature*, 311: 538–544 (1984).

Leung, et al., "Biochemical and ultrastructural characterization of the 1,4–dihydropyridine receptor from rabbit skeletal muscle," *J. of Biol.Chem.*, 263(2): 994–1001 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol.Chem.*, 262(17): 8333–8339 (1987).

Miller, "Multiple calcium channels and neuronal function," *Science*, 235: 46–52 (1987).

Kozak, "An analysis of 5'–noncoding sequences from 699 vertebrate messenger RNAs," *Nucleic Acids Research*, 15(20): 8125–8148 (1987).

von Heijne, "Signal sequences: the limits of variation," *Jour. of Mol.Biol.*, 184: 99–105 (1985).

Hubbard, et al., "Synthesis and processing of asparagine–linked oligosaccharides[1,2]," *Ann.Rev.Biochem.*, 50: 555–583 (1981).

Feramisco, et al., "Optimal spatial requirements for the location of basic residues in peptide substrates for the cyclic AMP–dependent protein kinase," *Journal of Biological Chemistry*, 255(9): 4240–4245 (1980).

Takahashi, et al., "Identification of an α subunit of dihydropyridine–sensitive brain calcium channels," *Science*, 236: 88–91 (1987).

Hofmann, et al., "Regulation of the L–type calcium channel," *TINS*, 8: 393–398 (1987).

Curtis, et al., "Reconstitution of the voltage–sensitive calcium channel purified from skeletal muscle transverse tubules," *Biochemistry*, 25: 3077–3083 (1986).

Smith, et al., "Calcium channel activity in a purified dihydropyridine–receptor preparation of skeletal muscle," *Biochemistry*, 26: 7182–7188 (1987).

Meshi, et al., "Nucleotide sequence of the 30K protein cistron of cowpea strain of tobacco mosaic virus," *Nucleic Acids Research*, 10(19): 6111–6117 (1982).

Nikaido, et al., "Molecular cloning of cDNA encoding human interleukin–2 receptor," *Nature*, 311: 631–636 (1984).

Roberts, et al., "Paraneoplastic myasthenic syndrome IgG inhibits $^{45}Ca^{2+}$ flux in a human small cell carcinoma line," *Nature*, 317: 737–739 (1985).

Starr, et al., "Primary structure of a calcium channel that is highly expressed in rat cerebellum," *Proc.Natl.Acad.Sci. USA*, 88: 5621–5625 (1991).

Snutch, et al., "Distinct calcium channels are generated by alternative splicing and are differentially expressed in the mammalian CNS," *Neuron*, 7: 45–57 (1991).

Hui, et al., "Molecular cloning of multiple sybtypes of a novel rat brain isoform of the $a_1$ subunit of the voltage–dependent calcium channel," *Neuron*, 7: 35–44 (1991).

Bean, et al., "Classes of calcium channels in vertebrate cells," *Annu.Rev. Physiol.*, 51: 367–384 (1989).

Swandulla, et al., "Do calcium channel classifications account for neuronal calcium channel diversity?" *TINS*, 14(2): 46–51 (1991).

Ruth, et al., "Primary structure of the α subunit of the DHP–sensitive calcium channel from skeletal muscle," *Science*, 245: 1115–1118 (1989).

Mikami, et al., "Primary structure and functional expression of the cardiac dihydropyridine–sensitive calcium channel," *Nature*, 340: 230–233 (1989).

Biel, et al., "Primary structure and functional expression of a highly voltage activated calcium channel from rabbit lung," *FEBS Letters*, 269(2): 409–412 (1990).

Mori, et al., "Primary structure and functional expression from complementary DNA of a brain calcium channel," *Nature*, 350: 398–402 (1991).

Snutch, et al., "Rat brain expresses a heterogeneous family of calcium channels," *Proc.Natl.Acad.Sci. USA*, 87: 3391–3395 (1990).

Perez–Reyes, et al., "Molecular diversity of L–type calcium channels," *J. of Biol.Chem.*, 265(33): 20430–20436 (1990).

Perez–Reyes, et al., "Induction of calcium currents by the expression of the $\alpha_1$–subunit of the dihydropyridine receptor from skeletal muscle," *Nature*, 340: 233–236 (1989).

Koch, et al., "Characterization of cDNA clones encoding two putative isoforms of the $\alpha_1$–subunit of the dihydropyridine–sensitive voltage–dependent calcium channel isolated from rat brain and rat aorta," *FEBS Letters*, 250(2): 386–388 (1989).

Slish, et al., "Evidence for the existence of a cardiac specific isoform of the $\alpha_1$–subunit of the voltage dependent calcium channel," *FEBS Letters*, 250(2): 509–514 (1989).

Varadi, et al., "Development regulation of expression of the $\alpha_1$ and $\alpha_2$ subunits mRNAs of the voltage–dependent calcium channel in a differentiating myogenic cell line," *FEBS Letters*, 250(2)CE: 515–518 (1989).

Ruth, et al., "Primary structure of the α–subunit of the DHP–sensitive calcium channel from skeletal muscle," *Science*, 245: 1115–1118 (1989).

Jongh, et al., "Subunits of purified calcium channels: a 212–kDa form of $\alpha_1$ and partial amino acid sequences of a phosphorylation site of an independent β–subunit," *Proc.Natl.Acad.Sci. USA*, 86: 8585–8589 (1989).

Hamilton, et al., "Subunit composition of the purified dihydropyridine binding protein from skeletal muscle," *Biochemistry*, 28: 7820–7828 (1989).

Nunoki, et al., "Activation of purified calcium channels by stoichiometric protein phosphorylation," *Proc.Natl.Acad.Sci. USA*, 86: 6816–6820 (1989).

Ichida, et al., "Photoaffinity labeling with dihydropyridine derivatives of crude membranes from rat skeletal, cardiac, ileal, and uterine muscles and whole brain," *J.Biochem.*, 105: 767–774 (1989).

Sharp and Campbell, "Characterization of the 1,4–dihydropyridine receptor using subunit–specific polyclonal antibodies," *J.Biol.Chem.*, 264(5): 2816–2825 (1989).

Campbell, et al., "The biochemistry and molecular biology of the dihydropyridine–sensitive calcium channel," *TINS*, 11(10): 425–430 (1988).

Pelzer, et al., "Properties and regulation of calcium channels in muscle cells," *Rev.Physiol.Biochem.Pharmacol.*, 114: 107–207 (1990).

Kim, et al., "Studies on the structural requirements for the activity of the skeletal muscle dihydropyridine receptor/slow $Ca^{2+}$ channel," *J.Biol.Chem.*, 11858–11863 (1990).

Lotan, et al., "Specific block of calcium channel expression by a fragment of dihydropyridine receptor cDNA," *Science*, 243: 666–669 (1989).

Rampe, et al., "[$^3$H]Pn200–110 binding in a fibroblast cell line transformed with the $\alpha_1$ subunit of the skeletal muscle L–type $Ca^{2+}$ channel," *Biochem. and Biophys.Research Communications*, 169(3): 825–831 (1990).

Adams, et al., "Intramembrane charge movement restored in dysgenic skeletal muscle by injection of dihydropyridine receptor cDNAs," *Nature*, 346: 569–572 (1990).

Tanabe, et al., "Cardiac–type excitation–contraction coupling in dysgenic skeletal muscle injected with cardiac dihydropyridine receptor cDNA," *Nature*, 344: 451–453 (1990).

Tanabe, et al., "Regions of the skeletal muscle dihydropyridine receptor critical for excitation–contraction coupling," *Nature*, 346: 567–569 (1991).

Regulla, et al., "Identification of the site of interaction of the dihydropyridine channel blockers nitrendipine and azidopine with the calcium–channel $\alpha_1$ subunit," *EMBO Journal*, 10(1): 45–49 (1991).

Williams, et al., "Structure and functional expression of $\alpha_1$, $\alpha_2$ and β subunits of a novel human neuronal calcium channel subtype," *Neuron*, 8:71–84 (1992).

Olivera, et al., "Conotoxins," *J. of Biol.Chem.*, 266(33): 22067–22070 (1991).

Seino, et al., "Cloning of $\alpha_1$ subunit of a voltage–dependent calcium channel expressed in pancreatic β cells," *Proc.Natl.Acad.Sci. USA*, 89: 584–588 (1992).

Perez–Reyes et al., "Cloning and expression of a cardiac/brain β subunit of the L–type calcium channel," *J. of Biol.Chem.*, 267(3): 1792–1797 (1992).

Miller, R., "Voltage–sensitive $Ca^{2+}$ channels," *J. of Biol.Chem.*, 267(3): 1403–1406 (1992).

Artalejo, et al., "w–Conotoxin GVIA blocks a $Ca^{2+}$ current in bovine chromaffin cells that is not of the 'classic' N type," *Neuron*, 8: 85–95 (1992).

Kasai, H., "Tonic inhibition and rebound facilitation of a neuronal calcium channel by a GTP–binding protein," *Proc.Natl.Acad.Sci. USA*, 88: 8855–8859 (1991).

Sher, et al., "Voltage–operated calcium channels in small cell lung carcinoma cell lines: pharmacological, functional, and immunological properties," *Cancer Research*, 5: 3892–3896 (1990).

Sher, et al., "w–Conotoxin binding and effects on calcium channel function in human neuroblastoma and rat pheochromocytoma cell lines," *FEBS Letters*, 235: (1,2): 178–182 (1988).

Koch, et al., "cDNA cloning of a dihydropyridine–sensitive calcium channel from rat aorta," *J. of Biol.Chem.*, 265(29): 17786–17791 (1990).

Cohen, et al., "Distribution of $Ca^{2+}$ channels on frog motor nerve terminals revealed by fluorescent w–conotoxin," *J. of Neuroscience*, 11(4): 1032–1039 (1991).

Bosse, et al., "The cDNA and deduced amino acid sequence of the γ subunit of the L–type calcium channel from rabbit skeletal muscle," *FEBS*, 267(1): 153–156 (1990).

Burns, et al., "Calcium channel activity of purified human synexin and structure of the human synexin gene," *Proc.Natl.Acad.Sci.*, 86: 3798–3802 (1989).

Campbell, et al., "32,000–Dalton subunit of the 1,4–dihydropyridine receptor," *Ann.N.Y.Acad.Sci.*, 560: 251–257 (1989).

Dascal, N., "The use of *Xenopus oocytes* for the study of ion channels," *CRC Critical Rev.Biochem.*, 22(4): 317–387 (1987).

DeJongh, et al., "Subunits of purified calcium channels," *J.Biol.Chem.*, 265(25): 14738–14741 (1990) (best available copy submitted).

Jay, et al., "Primary Structure of the γ subunit of the DHP–sensitive calcium channel from skeletal muscle," *Science*, 248: 490–492 (1990).

Jay, et al., "Structural characterization of the dihydropyridine–sensitive calcium channel $\alpha_2$–subunit and the associated δ peptides," *J.Biol.Chem.*, 266(5): 3287–3293 (1991).

Leung, et al., "Monoclonal antibody characterization of the 1,4–dihydropyridine receptor of rabbit skeletal muscle," *Ann.N.Y.Acad.Sci.*, 522: 43–46 (1988).

Starr, et al., "Primary structure of a calcium channel that is highly expressed in the rat cerebellum," *Proc.Natl.Acad.Sci.*, 88: 5621–5625 (1991).

Vaghy, et al., "Mechanism of action of calcium channel modulator drugs," *Ann.N.Y.Acad.Sci.*, 522: 176–186 (1988).

Ahlijanian, et al., "Subunit structure and localization of dihydropyridine–sensitive calcium channels in mammalian brain, spinal cord, and retina," *Neuron*, 4: 819–832 (1990).

Blount, et al., "Assembly intermediates of the mouse muscle nicotinic Acetylcholine receptor in stably transfected fibroblasts," *J.Cell.Biol.*, 111: 2601 (1990).

Carbone, et al., "Ca currents in human neuroblastoma IMR32 cells: kinetics, permeability and pharmacology," *Pfluegers Arch.* 416: 170–179 (1990) (best available copy submitted).

Dascal et al., "Expression of modulation of voltage–gated calcium channels after RNA injection in *Xenopus oocytes*," *Science*, 231: 1147–1150 (1986).

Hess, et al., "Calcium channels in vertebrate cells," *Ann.Rev.Neurosci.*, 13: 337–356 (1990).

Stanley et al., "Characterization of a calcium current in a vertebrate cholinergic presynaptic nerve terminal," *J. Neurosci.*, 11: 985 (1991).

Wei, et al., "Heterologous regulation of the cardiac $Ca^{2+}$ channel $\alpha_1$ subunit by skeletal muscle β and γ subunits," *J.Biol.Chem.*, 266: 21943–21947 (1991).

Ahlijanian, et al., "Phosphorylation of an α1–like subunit of an w–conotoxin–sensitive brain calcium channel by cAMP–dependent protein kinase and protein kinase C," *J.Biol.Chem.*, 266: 20192 (1991).

Claudio, T., "Stable expression of transfected Torpedo acetylcholine receptor α subunits in mouse fibroblast L cells," *Proc.Natl.Acad.Sci.*, 84: 5967–5971 (1987).

Hullin, et al., "Calcium channel β subunit heterogeneity: functional expression of cloned cDNA from heart, aorta and brain," *EMBO J.*, 11: 885 (1992).

Kim, et al., "Rat brain expresses an alternatively spliced form of the dihydropyridine–sensitive L–type calcium channel α2 subunit," *Proc.Natl.Acad.Sci.*, 89:3251 (1992).

Pragnell, et al., "Cloning and tissue–specific expression of the brain calcium channel β–subunit," *FEBS Letters*, 291: 253 (1991).

Sakamoto, et al., "A monoclonal antibody to the β subunit of the skeletal muscle dihydropyridine receptor immunoprecipitates the brain w–conotoxin GVIA receptor," *J.Biol.Chem.*, 266: 18914 (1991).

Seager, et al., "Molecular properties of dehydropyrine–sensitive calcium channels," *Ann.N.Y.Acad.Sci.*, 552: 162–175 (1988).

Tsien, et al., "Molecular diversity of voltage–dependent $Ca^{2+}$ channels," *Trends in Pharmacol.Sci.*, 12: 349 (1991).

Takahashi and Catterall, "Dihydropyridine–sensitive calcium channels in cardiac and skeletal muscle membranes: studies with antibodies against the α–subunits," *Biochemistry*, 26(17): 1518–1526 (1987).

Cruz et al., "Characterization of ω–Conotoxin Target. Evidence for Tissue–Specific Heterogeneity ion Calcium Channel Types", *Biochem. J.* 26:820 (1987).

Breitbart et al., "Alternative Splicing: A Ubiquitous Mechanism for the Generation of Multiple Protein Isoforms From Single Genes", *Ann. Rev. Biochem.* 56:467–495.

William et al., "Structure and Functional Expression of an ω–Conotoxin–Sensitive Human N–Type Calcium Channel", *Science* 257:389–395 (1992).

Rosenfield et al., "Cloning and Characterization of a Lambert–Eaton Myasthenic Syndrome Antigen", *Annals of Neurology* 33:113–120 (1993).

Powers et al., "Skeletal Muscle and Brain Isoforms of a β–Subunit of Human Voltage–dependent Calcium Channels Are Encoded by a Single Gene", *J. Biol. Chem.* 267:22967–22972 (1992).

Wah et al., "Structure and Functional Expression of a Member of the Low–Voltage–Activated Calcium channel Family", *Science* 260:1133–1136.

Horne et al., "Molecular diversity of $Ca^{2+}$ channel, $\alpha_1$ subunits from the marine ray *Discopyge ommata*", *Proc. Natl.Acad.Sci.* 90:3787–3791 (1993).

Yu et al., "Molecular characterization and nephron distribution of a family of transcripts encoding the pore–forming subunit of $Ca^{2+}$ channels in the kidney", *Proc.Natl.Acad.Sci.* 89:10494–10498 (1992).

Dubel et al., "Molecular cloning of the α–1 subunit of an ω–conotoxin–sensitive calcium channel", *Proc.Natl.Acad.Sci.* 89:5058–5062 (1992).

Soldatov, "Molecular diversity of L–type $Ca^{2+}$ channel transcripts in human fibroblasts", *Proc.Natl.Acad.Sci.* 89:4628–4632 (1992).

Leveque et al., "The synaptic vesicle protein synaptotagmim associates with calcium channels and is a putative Lambert–Eaton myasthenic syndrome antigen", *Proc.Natl.Acad. Sci.* 89:3625–3629 (1992).

Niidome et al., "Molecular cloning and characterization of a novel calcium channel from rabbit brain", *FEBS LTTRS* 308:7–13 (1992).

Elinor et al., "Functional expression of a rapidly inactivating neuronal calcium channel", *Nature* 363:455–458 (1993).

Spedding et al., 'Calcium Antgonists': A Class of Drugs with a Bright Future. Part II. Determination of Basic Pharmacological Properties, *Life Sciences* 35:575–587 (1984).

Soong et al., "Structure and Functional Expression of a Member of the Low Voltage–Activated Calcium Channel Family", *Science* 260:1133–1136 (1993).

Brust et al., "Human Neuronal Voltage–Dependent Calcium Channels: Studies on Subunit Structure and Role in Channel Assembly", *Neuropharmacology* 32(11):1089–1102 (1993).

Williams, et al., "Structure and Functional Characterization of Neuronal $\alpha_{1E}$ Calcium Channel Subtypes," *J. Biol. Chem.* 269(35):22347–22357 (1994).

\* cited by examiner

NUCLEIC ACIDS ENCODING HUMAN CALCIUM CHANNEL AND METHODS OF USE THEREOF

This is a continuation of application Ser. No. 08/105,536, filed Aug. 11, 1993, now abandoned which is a continuation-in-part of International PCT application Serial No. PCT/US92/06903, filed Aug. 14, 1997, now U.S. patent application Ser. No. 08/193,078, filed Feb. 7, 1994, now U.S. Pat. No. 5,846,757, which is a continuation-in-part of U.S. application Ser. No. 07/868,354, filed Apr. 10, 1992, now abandoned which is a continuation-in-part of U.S. application Ser. No. 07/745,206, filed Aug. 15, 1991, now U.S. Pat. No. 5,629,921 which is a continuation-in-part of U.S. application Ser. No. 07/620,250, filed Nov. 30, 1990, now abandoned, which is a continuation-in-part of U.S. application Ser. No. 07/176,899, filed Apr. 4, 1988, now abandoned, and is also a continuation-in-part of U.S. Ser. No. 07/482,384, filed Feb. 20, 1990, now U.S. Pat. No. 5,386,025. This application is also a continuation-in-part of U.S. Ser. No. 07/914,231, filed Jul. 13, 1992 now U.S. Pat. No. 5,607,820, which in turn is a continuation of U.S. Ser. No. 07/603,751, filed Nov. 8, 1990, now abandoned. This application is also a continuation-in-part of International Application Serial No. PCT/US89/01408, filed Apr. 4, 1988. U.S. application Ser. No. 07/603,751 is International Application Serial No. PCT/89/01408.

The subject matter of each of International PCT Application Ser. No. PCT/92/06903, U.S. Ser. No. 07/914,231, U.S. application Ser. No. 07/868,354, U.S. application Ser. No. 07/745,206 U.S. application Ser. No. 07/620,250, U.S. application Ser. No. 07/603,751, U.S. application Ser. No. 07/482,384, U.S. application Ser. No. 07/176,899 and International Application Ser. No. PCT/89/01408 is incorporated herein in its entirety.

TECHNICAL FIELD

The present invention relates to molecular biology and pharmacology. More particularly, the invention relates to calcium channel compositions and methods of making and using the same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. "Opening" of a voltage-dependent channel to allow an influx of $Ca^{2+}$ ions into the cells requires a depolarization to a certain level of the potential difference between the inside of the cell bearing the channel and the extracellular medium bathing the cell. The rate of influx of $Ca^{2+}$ into the cell depends on this potential difference. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Multiple types of calcium channels have been identified in mammalian cells from various tissues, including skeletal muscle, cardiac muscle, lung, smooth muscle and brain, [see, e.g., Bean, B. P. (1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists.

Calcium channels are multisubunit proteins. For example, rabbit skeletal muscle calcium channel contains two large subunits, designated $\alpha_1$ and $\alpha_2$, which have molecular weights between about 130 and about 200 kilodaltons ("kD"), and one to three different smaller subunits of less than about 60 kD in molecular weight. At least one of the larger subunits and possibly some of the smaller subunits are glycosylated. Some of the subunits are capable of being phosphorylated. The $\alpha_1$ subunit has a molecular weight of about 150 to about 170 kD when analyzed by sodium dodecylsulfate (SDS)-polyacrylamide gel electrophoresis (PAGE) after isolation from mammalian muscle tissue and has specific binding sites for various 1,4-dihydropyridines (DHPs) and phenylalkylamines. Under non-reducing conditions (in the presence of N-ethylmaleimide), the $\alpha_2$ subunit migrates in SDS-PAGE as a band corresponding to a molecular weight of about 160–190 kD. Upon reduction, a large fragment and smaller fragments are released. The $\beta$ subunit of the rabbit skeletal muscle calcium channel is a phosphorylated protein that has a molecular weight of 52–65 kD as determined by SDS-PAGE analysis. This subunit is insensitive to reducing conditions. The $\gamma$ subunit of the calcium channel, which is not observed in all purified preparations, appears to be a glycoprotein with an apparent molecular weight of 30–33 kD, as determined by SDS-PAGE analysis.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, difficulties in obtaining tissues of interest, and the modifications of the native protein that can occur during the isolation procedure, it is extremely difficult to obtain large amounts of highly purified, completely intact calcium channel protein.

Characterization of a particular type of calcium channel by analysis of whole cells is severely restricted by the presence of mixed populations of different types of calcium channels in the majority of cells. Single-channel recording methods that are used to examine individual calcium channels do not reveal any information regarding the molecular structure or biochemical composition of the channel. Furthermore, in performing this type of analysis, the channel is isolated from other cellular constituents that might be important for natural functions and pharmacological interactions.

Characterization of the gene or genes encoding calcium channels provides another means of characterization of different types of calcium channels. The amino acid sequence determined from a complete nucleotide sequence of the coding region of a gene encoding a calcium channel protein represents the primary structure of the protein. Furthermore, secondary structure of the calcium channel protein and the relationship of the protein to the membrane may be predicted based on analysis of the primary structure. For instance, hydropathy plots of the $\alpha_1$ subunit protein of the rabbit skeletal muscle calcium channel indicate that it contains four internal repeats, each containing six putative transmembrane regions [Tanabe, T. et al. (1987) *Nature* 328:313].

The cDNA and corresponding amino acid sequences of the $\alpha_1$, $\alpha_2$, $\beta$ and $\gamma$ subunits of the rabbit skeletal muscle calcium channel [see, Tanabe et al. (1987) *Nature* 328:313–318; International Application No. WO 89/09834, which is U.S. application Ser. No. 07/603,751, which is a continuation-in-part of U.S. application Ser. No. 07/176, 899; Ruth et al. (1989) *Science* 245:1115–1118; and U.S. patent application Ser. No. 482,384, filed Feb. 20, 1990] have been determined. The cDNA and corresponding amino acid sequences of $\alpha_1$ subunits of rabbit cardiac muscle [Mikami, A. et al. (1989) *Nature* 340:230–233] and lung [Biel, M. (1990) *FEBS Letters* 269:409–412] calcium channels have been determined.

In addition, a cDNA clone encoding a rabbit brain calcium channel (designated the BI channel) has been isolated [Mori, Y. et al. (1991) *Nature* 350:398–402). Partial cDNA clones encoding portions of several different subtypes, referred to as rat brain class A, B, C and D, of the calcium channel $\alpha_1$ subunit have been isolated from rat brain cDNA libraries (Snutch, T. et al. (1990) *Proc. Natl. Acad. Sci. USA* 87:3391–3395]. More recently full-length rat brain class A [Starr, T. et al. (1991) *Proc. Natl. Acad. Sci. USA* 88:5621–5625] and class C [Snutch, T. et al. (1991) *Neuron* 7:45–57] cDNA clones have been isolated. Although the amino acid sequence encoded by the rat brain class C DNA is approximately 95% identical to that encoded by the rabbit cardiac muscle calcium channel $\alpha_1$ subunit-encoding DNA, the amino acid sequence encoded by the rat brain class A DNA shares only 33% sequence identity with the amino acid sequence encoded by the rabbit skeletal or cardiac muscle $\alpha_1$ subunit-encoding DNA. A cDNA clone encoding another rat brain calcium channel $\alpha_1$ subunit has also been obtained [Hui, A. et al. (1991) *Neuron* 7:35–44]. The amino acid sequence encoded by this clone is ~70% homologous to the proteins encoded by the rabbit skeletal and cardiac muscle calcium channel DNA. A cDNA clone closely related to the rat brain class C $\alpha_1$ subunit-encoding cDNA and sequences of partial cDNA clones closely related to other partial cDNA clones encoding apparently different calcium channel $\alpha_1$ subunits have also been isolated [see Snutch, T. et al. (1991) *Neuron* 7:45–57; Perez-Reyes, E. et al. (1990) *J. Biol. Chem.* 265:20430; and Hui, A. et al. (1991) *Neuron* 7:35–44). DNA clones encoding other calcium channels have also been identified and isolated.

Expression of cDNA encoding calcium channel subunits has been achieved with several of the different rabbit or rat $\alpha_1$ subunit cDNA clones discussed above. Voltage-dependent calcium currents have been detected in murine L cells transfected with DNA encoding the rabbit skeletal muscle calcium channel $\alpha_1$ subunit [Perez-Reyes et al. (1989) *Nature* 340:233–236 (1989)]. These currents were enhanced in the presence of the calcium channel agonist Bay K 8644. Bay K 8644-sensitive $Ba^+$ currents have been detected in oocytes injected with in vitro transcripts of the rabbit cardiac muscle calcium channel $\alpha_1$ subunit cDNA [Mikami, A. et al. (1989) *Nature* 340:230–233]. These currents were substantially reduced in the presence of the calcium channel antagonist nifedipine. Barium currents of an oocyte co-injected with RNA encoding the rabbit cardiac muscle calcium channel $\alpha_1$ subunit and the RNA encoding the rabbit skeletal muscle calcium channel $\alpha_2$ subunit were more than 2-fold larger than those of oocytes injected with transcripts of the rabbit cardiac calcium channel $\alpha_1$ subunit-encoding cDNA. Similar results were obtained when oocytes were co-injected with RNA encoding the rabbit lung calcium channel $\alpha_1$ subunit and the rabbit skeletal muscle calcium channel $\alpha_2$ subunit. The barium current was greater than that detected in oocytes injected only with RNA encoding the rabbit lung calcium channel $\alpha_1$ subunit [Biel, M. et al. (1990) *FEBS Letters* 269:409–412]. Inward barium currents have been detected in oocytes injected with in vitro RNA transcripts encoding the rabbit brain BI channel [Mori et al. (1991) *Nature* 350:398–402]. These currents were increased by two orders of magnitude when in vitro transcripts of the rabbit skeletal muscle calcium channel $\alpha_2$, $\beta$, or $\alpha_2$, $\beta$ and $\gamma$ subunits were co-injected with transcripts of the BI-encoding cDNA. Barium currents in oocytes co-injected with transcripts encoding the BI channel and the rabbit skeletal muscle calcium channel $\alpha_2$ and $\beta$ were unaffected by the calcium channel antagonists nifedipine or $\omega$-CgTx and inhibited by Bay K 8644 and crude venom from *Agelenopsis aperta*.

The results of studies of recombinant expression of rabbit calcium channel $\alpha_1$ subunit-encoding cDNA clones and transcripts of the cDNA clones indicate that the $\alpha_1$ subunit forms the pore through which calcium enters cells. The relevance of the barium currents generated in these recombinant cells to the actual current generated by calcium channels containing as one component the respective $\alpha_1$ subunits in vivo is unclear. In order to completely and accurately characterize and evaluate different calcium channel types, however, it is essential to examine the functional properties of recombinant channels containing all of the subunits as found in vivo.

Although there has been limited success in expressing DNA encoding rabbit and rat calcium channel subunits, far less has been achieved with respect to human calcium channels. Little is known about human calcium channel structure and function and gene expression. An understanding of the structure and function of human calcium channels would permit identification of substances that, in some manner, modulate the activity of calcium channels and that have potential for use in treating such disorders.

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as CNS and cardiovascular diseases. Calcium channels, thus, are also implicated in numerous disorders. A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

An understanding of the pharmacology of compounds that interact with calcium channels in other organ systems, such as the CNS, may aid in the rational design of compounds that specifically interact with subtypes of human calcium channels to have desired therapeutic effects, such as in the treatment of neurodegenerative and cardiovascular disorders. Such understanding and the ability to rationally design therapeutically effective compounds, however, have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

Therefore, it is an object herein, to provide DNA encoding specific calcium channel subunits and to provide eukaryotic cells bearing recombinant tissue-specific or subtype-specific calcium channels. It is also an object to provide assays for identification of potentially therapeutic compounds that act as calcium channel antagonists and agonists.

SUMMARY OF THE INVENTION

Isolated and purified DNA fragments that encode human calcium channel subunits are provided. DNA encoding $\alpha_1$ subunits of a human calcium channel, and RNA, encoding such subunits, made upon transcription of such DNA are provided. In particular, DNA fragments encoding $\alpha_1$ subunits of voltage-dependent human calcium channels (VDCCs) type A, type B (also referred to as VDCC IV), type C (also referred to as VDCC II) type D (also referred to as VDCC III) and type E are provided.

DNA encoding $\alpha_{1A}$, $\alpha_{1B}$, $\alpha_{1C}$, $\alpha_{1D}$ and $\alpha_{1E}$ subunits is provided. DNA encoding an $\alpha_{1D}$ subunit that includes the amino acids substantially as set forth as residues 10–2161 of SEQ ID No. 1 is provided. DNA encoding an $\alpha_{1D}$ subunit that includes substantially the amino acids set forth as amino acids 1–34 in SEQ ID No. 2 in place of amino acids 373–406 of SEQ ID No. 1 is also provided. DNA encoding an $\alpha_{1C}$ subunit that includes the amino acids substantially as set forth in SEQ ID No. 3 or SEQ ID No. 6 and DNA encoding an $\alpha_{1B}$ subunit that includes an amino acid sequence substantially as set forth in SEQ ID No. 7 or in SEQ ID No. 8 is also provided.

DNA encoding $\alpha_{1A}$ subunits is also provided. Such DNA includes DNA encoding an $\alpha_{1A}$ subunit that has substantially the same sequence of amino acids as that set forth in SEQ ID No. 22 or No. 23 or other splice variants of $\alpha_{1A}$ that include all or part of the sequence set forth in SEQ ID No. 22 or 23. The sequence set forth in SEQ ID NO. 22 is a splice variant designated $\alpha_{1A-1}$; and the sequence set forth in SEQ ID NO. 23 is a splice variant designated $\alpha_{1A-2}$. $\alpha_{1A}$ subunits also include subunits that can be isolated using all or a portion of the DNA having SEQ ID NO. 21, 22 or 23 or DNA obtained from the phage lysate of an *E. coli* host containing DNA encoding an $\alpha_{1A}$ subunit that has been deposited in the American Type Culture Collection, 12301 Parklawn Drive, Rockville, Md. 20852 U.S.A. under Accession No. 75293 in accord with the Budapest Treaty. The DNA in such phage includes a DNA fragment having the sequence set forth in SEQ ID No. 21. This fragment selectively hybridizes under conditions of high stringency to DNA encoding $\alpha_{1A}$ but not to DNA encoding $\alpha_{1B}$ and, thus, can be used to isolate DNA that encodes $\alpha_{1A}$ subunits.

DNA encoding $\alpha_{1E}$ subunits of a human calcium channel is also provided. This DNA includes DNA that encodes an $\alpha_{1E}$ splice variant designated $\alpha_{1E-1}$ encoded by the DNA set forth in SEQ ID No. 24, and a variant designated $\alpha_{1E-3}$ encoded by SEQ. ID No. 24 with the fragment set forth in SEQ ID No. 25 inserted between nucleotides 2405 and 2406. The resulting sequence of $\alpha_{1E-3}$ is set forth in SEQ ID No. 27. This DNA also includes other splice variants thereof that include sequences of amino acids encoded by all or a portion of the sequences of nucleotides set forth in SEQ ID Nos. 24 and 25 and DNA that hybridizes under conditions of high stringency to the DNA of SEQ ID. No. 24 or 25 and that encodes an $\alpha_{1E}$ splice variant.

DNA encoding $\alpha_2$ subunits of a human calcium channel, and RNA encoding such subunits, made upon transcription of such a DNA are provided. DNA encoding splice variants of the $\alpha_2$ subunit, including tissue specific splice variants, are also provided. In particular, DNA encoding the $\alpha_{2a}$–$\alpha_{2e}$ subunit subtypes is provided. In particularly preferred embodiments, the DNA encoding the $\alpha_2$ subunit is produced by alternative processing of a primary transcript that includes DNA encoding the amino acids set forth in SEQ ID 11 and the DNA of SEQ ID No. 13 inserted between nucleotides 1624 and 1625 of SEQ ID No. 11.

The resulting sequences of each of the $\alpha_2$-subunits are set forth in Sequence ID NO. 11 ($\alpha_{2b}$), SEQ ID NO. 28 ($\alpha_{2a}$), SEQ ID NO. 29 ($\alpha_{2c}$), SEQ ID NO. 30 ($\alpha_{2d}$), an d SEQ ID NO. 31 ($\alpha_{2e}$).

Isolated and purified DNA fragments encoding human calcium channel β subunits, including DNA encoding $\beta_1$ and $\beta_2$ subunit splice variants and the $\beta_3$ subunit is provided. RNA encoding β subunits, made upon transcription of the DNA is also provided. In particular, DNA encoding the $\beta_1$, $\beta_2$ and $\beta_3$ subunits, including the $\beta_1$ subunit splice variants $\beta_{1-1}$–$\beta_{1-5}$, described below, the $\beta_2$ subunit splice variants $\beta_{2A}$–$\beta_{2E}$, that include all or a portion of SEQ ID No. 26, and the $\beta_3$ subunit, that includes sequence set forth in SEQ ID Nos 19 and 20, is provided. *Escherichia coli* (*E. coli*) host cells harboring plasmids containing DNA encoding $\beta_3$ have been deposited in accord with the Budapest Treaty under Accession No. 69048 at the American Type Culture Collection. A partial sequence of the deposited clone is set forth in SEQ ID No. 19 (sequence from the 5' end) and SEQ ID No. 20 (sequence from the 3' end).

DNA encoding $\beta_1$ subunits that are produced by alternative processing of a primary transcript encoding a β subunit, including a transcript that includes DNA encoding the amino acids set forth in SEQ ID No. 9 or including a primary transcript that encodes $\beta_3$ as deposited under ATCC Accession No. 69048, but lacking and including alternative exons are provided or may be constructed from the DNA provided herein. For example, DNA encoding a $\beta_1$ subunit that is produced by alternative processing of a primary transcript that includes DNA encoding the amino acids set forth in SEQ ID No. 9, but including the DNA set forth in SEQ ID No. 12 inserted in place of nucleotides 615–781 of SEQ ID No. 9 is also provided. DNA encoding $\beta_1$ subunits that are encoded by transcripts that have the sequence set forth in SEQ ID No. 9 including the DNA set forth in SEQ ID No. 12 inserted in place of nucleotides 615–781 of SEQ ID No. 9, but that lack one or more of the following sequences of nucleotides: nucleotides 14–34 of SEQ ID No. 12, nucleotides 13–34 of SEQ ID No. 12, nucleotides 35–55 of SEQ ID No 12, nucleotides 56–190 of SEQ ID No. 12 and nucleotides 191–271 of SEQ ID No. 12 are also provided.

DNA encoding γ subunits of human calcium channels is also provided. RNA, encoding γ subunits, made upon transcription of the DNA are also provided. In particular, DNA containing the sequence of nucleotides set forth in SEQ ID No. 14 is provided.

Full-length DNA clones and corresponding RNA transcripts, encoding the $\alpha_1$, including splice variants of $\alpha_{1D}$, $\alpha_{1B}$, and $\alpha_{1E}$, $\alpha_2$ and β subunits, including $\beta_{1-1}$–$\beta_{1-5}$ and $\beta_{2D}$ of human calcium channels are provided. Also provided are DNA clones encoding substantial portions of the $\alpha_{1A}$, $\alpha_{1C}$, $\beta_3$ and γ subunits of voltage-dependent human calcium channels for the preparation of full-length DNA clones encoding the full-length $\alpha_{1A}$, $\alpha_{1C}$, $\beta_3$ and γ subunits.

Eukaryotic cells containing heterologous DNA encoding one or more calcium channel subunits, particularly human calcium channel subunits, or containing RNA transcripts of DNA clones encoding one or more of the subunits are provided. In preferred embodiments, the cells contain DNA or RNA encoding a human $\alpha_1$ subunit, preferably at least an $\alpha_{1D}$, $\alpha_{1B}$ or $\alpha_{1E}$ subunit. In more preferred embodiments, the cells contain DNA or RNA encoding additional heterologous subunits, including at least one $\beta$, $\alpha_2$ or $\gamma$ subunits. In such embodiments, eukaryotic cells stably or transiently transfected with any combination of one, two, three or four of the subunit-encoding DNA clones, such as DNA encoding any of $\alpha_1$, $\alpha_1+\beta$, $\alpha_1+\beta+\alpha_2$, are provided.

In preferred embodiments, the cells express such heterologous calcium channel subunits and include one or more of the subunits in membrane spanning heterologous calcium channels. In more preferred embodiments, the eukaryotic cells express functional, heterologous calcium channels that are capable of gating the passage of calcium channel selective ions and/or binding compounds that, at physiological concentrations, modulate the activity of the heterologous calcium channel. In certain embodiments, the heterologous calcium channels include at least one heterologous calcium channel subunit. In most preferred embodiments, the calcium channels that are expressed on the surface of the eukaryotic cells are composed substantially or entirely of subunits encoded by the heterologous DNA or RNA. In preferred embodiments, the heterologous calcium channels of such cells are distinguishable from any endogenous calcium channels of the host cell. Such cells provide a means to obtain homogeneous populations of calcium channels.

In certain embodiments the recombinant eukaryotic cells that contain the heterologous DNA encoding the calcium channel subunits are produced by transfection with DNA encoding one or more of the subunits or are injected with RNA transcripts of DNA encoding one or more of the calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous calcium channels may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

The recombinant eukaryotic cells that express membrane spanning heterologous calcium channels may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions. Because the cells constitute homogeneous populations of calcium channels, they provide a means to identify agonists or antagonists of calcium channel activity that are specific for each such population.

The assays that use the eukaryotic cells for identifying compounds that modulate calcium channel activity are also provided. In practicing these assays the eukaryotic cell that expresses a heterologous calcium channel, containing at least on subunit encoded by the DNA provided herein, is in a solution containing a test compound and a calcium channel selective ion, the cell membrane is depolarized, and current flowing into said cell is detected. The current that is detected is different from that produced by depolarizing the same or a substantially identical cell in the presence of the same calcium channel selective ion but in the absence of said compound. In preferred embodiments, prior to the depolarization step, the cell is maintained at a holding potential which substantially inactivates calcium channels which are endogenous to said cell. Also in preferred embodiments, the cells are mammalian cells, most preferably HEK cells, or amphibian oöcytes.

Nucleic acid probes containing at least about 14 contiguous nucleotides of $\alpha_{1D}$, $\alpha_{1C}$, $\alpha_{1B}$, $\alpha_{1A}$ and $\alpha_{1E}$, $\alpha_2$, $\beta$, including $\beta_1$ and $\beta_2$ splice variants and $\beta_3$, and $\gamma$ subunit-encoding DNA are provided. Methods using the probes for the isolation and cloning of calcium channel subunit-encoding DNA, including splice variants within tissues and inter-tissue variants are also provided.

Purified human calcium channel subunits and purified human calcium channels are provided. The subunits and channels can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. *E. coli* fusion proteins including a fragment of a human calcium channel subunit may also be used as immunogen. Such fusion proteins may contain a bacterial protein or portion thereof, such as the *E. coli* TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample. Such antibodies may also be used to selectively isolate cells that express calcium channels that contain the subunit for which the antibodies are specific.

A diagnostic method for determining the presence of Lambert Eaton Syndrome (LES) in a human based on immunological reactivity of LES immunoglobulin G (IgG) with a human calcium channel subunit or a eukaryotic cell which expresses a recombinant human calcium channel or a subunit thereof is also provided. In particular, an immunoassay method for diagnosing Lambert-Eaton Syndrome in a person by combining serum or an IgG fraction from the person (test serum) with calcium channel proteins, including the α and 62 subunits, and ascertaining whether antibodies in the test serum react with one or more of the subunits, or a recombinant cell which expresses one or more of the subunits to a greater extent than antibodies in control serum, obtained from a person or group of persons known to be free of the Syndrome, is provided. Any immunoassay procedure known in the art for detecting antibodies against a given antigen in serum can be employed in the method.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference herein.

Reference to each of the calcium channel subunits includes the subunits that are specifically disclosed herein and human calcium channel subunits encoded by DNA that can be isolated by using the DNA disclosed as probes and screening an appropriate human cDNA or genomic library under at least low stringency. Such DNA also includes DNA that encodes proteins that have about 40% homology to any of the subunits proteins described herein or DNA that hybridizes under conditions of at least low stringency to the DNA provided herein and the protein encoded by such DNA exhibits additional identifying characteristics, such as function or molecular weight.

It is understood that subunits that are encoded by transcripts that represent splice variants of the disclosed subunits or other such subunits may exhibit less than 40% overall homology to any single subunit, but will include regions of such homology to one or more such subunits. It is also understood that 40% homology refers to proteins that share approximately 40% of their amino acids in common or that share somewhat less, but include conservative amino acid substitutions, whereby the activity of the protein is not substantially altered.

As used herein, the $\alpha_1$ subunits types, encoded by different genes, are designated as type $\alpha_{1A}$, $\alpha_{1B}$, $\alpha_{1C}$, $\alpha_{1D}$ and $\alpha_{1E}$. These types may also be also referred to as VDCC IV for $\alpha_{1B}$, VDCC II for $\alpha_{1C}$ and VDCC III for $\alpha_{1D}$. Subunit subtypes, which are splice variants, are referred to, for example as $\alpha_{1B-1}$, $\alpha_{1B-2}$, $\alpha_{1C-1}$ etc.

Thus, as used herein, DNA encoding the $\alpha_1$ subunit refers to DNA that hybridizes to the DNA provided herein under conditions of at least low stringency or encodes a subunit that has roughly about 40% homology to protein encoded by DNA disclosed herein that encodes an $\alpha_1$ subunit of a human calcium. An $\alpha_1$ subunit may be identified by its ability to form a calcium channel. Typically, $\alpha_1$ subunits have molecular weights greater than at least about 120 kD. The activity of a calcium channel may be assessed in vitro by methods known to those of skill in the art, including the electrophysiological and other methods described herein. Typically, $\alpha_1$ subunits include regions to which one or more modulators of calcium channel activity, such as a 1,4 DHP or ω-CgTX, interact directly or indirectly. Types of $\alpha_1$ subunits may be distinguished by any method known to those of skill in the art, including on the basis of binding specificity. For example, it has been found herein that $\alpha_{1B}$ subunits participate in the formation channels that have previously been referred to as N-type channels, $\alpha_{1D}$ subunits participate in the formation of channels that had previously been referred to as L-type channels, and $\alpha_{1A}$ subunits appear to participate in the formation of channels that exhibit characteristics typical of channels that had previously been designated P-type channels. Thus, for example, the activity of channels that contain the $\alpha_{1B}$ subunit are insensitive to 1,4 DHPs; whereas the activity of channels that contain the $\alpha_{1D}$ subunit are modulated or altered by a 1,4 DHP. It is presently preferable to refer to calcium channels based on pharmacological characteristics and current kinetics and to avoid historical designations. Types and subtypes of $\alpha_1$ subunits may be characterized on the basis of the effects of such modulators on the subunit or a channel containing the subunit as well as differences in currents and current kinetics produced by calcium channels containing the subunit.

As used herein, an $\alpha_2$ subunit is encoded by DNA that hybridizes to the DNA provided herein under conditions of low stringency or encodes a protein that has about 40% homology with that disclosed herein. Such DNA encodes a protein that typically has a molecular weight greater than about 120 kD, but does not form a calcium channel in the absence of an $\alpha_1$ subunit, and may alter the activity of a calcium channel that contains an $\alpha_1$ subunit. Subtypes of the $\alpha_2$ subunit that arise as splice variants are designated by lower case letter, such as $\alpha_{2a}$, . . . $\alpha_{2e}$. In addition, the $\alpha_2$ subunit and the large fragment produced under reducing conditions appear to be glycosylated with at least N-linked sugars and do not specifically bind to the 1,4-DHPs and phenylalkylamines that specifically bind to the $\alpha_1$ subunit. The smaller fragment, the C-terminal fragment, is referred to as the δ subunit and includes amino acids from about 946 (SEQ ID No. 11) through about the C-terminus. This fragment may dissociate from the remaining portion of $\alpha_2$ when the $\alpha_2$ subunit is exposed to reducing conditions.

As used herein, a β subunit is encoded by DNA that hybridizes to the DNA provided herein under conditions of low stringency or encodes a protein that has about 40% homology with that disclosed herein and is a protein that typically has a molecular weight lower than the a subunits and on the order of about 50–80 kD, does not form a detectable calcium channel in the absence of an $\alpha_1$ subunit, but may alter the activity of a calcium channel that contains an $\alpha_1$ subunit or that contains an $\alpha_1$ and $\alpha_2$ subunit.

Types of the β subunit that are encoded by different genes are designated with subscripts, such as $\beta_1$, $\beta_2$ and $\beta_3$. Subtypes of β subunits that arise as splice variants of a particular type are designated with a numerical subscript referring to the subtype and to the variant. Such subtypes include, but are not limited to the $\beta_1$ splice variants, including $\beta_{1-1}$–$\beta_{1-5}$ and $\beta_2$ variants, including $\beta_{2A}$–$\beta_{2E}$.

As used herein, a γ subunit is a subunit encoded by DNA disclosed herein as encoding the γ subunit and may be isolated and identified using the DNA disclosed herein as a probe by hybridization or other such method known to those of skill in the art, whereby full-length clones encoding a γ subunit may be isolated or constructed. A γ subunit will be encoded by DNA that hybridizes to the DNA provided herein under conditions of low stringency or exhibits sufficient sequence homology to encode a protein that has about 40% homology with the γ subunit described herein.

Thus, one of skill in the art, in light of the disclosure herein, can identify DNA encoding $\alpha_1$, $\alpha_2$, β, δ and calcium channel subunits, including types encoded by different genes and subtypes that represent splice variants. For example, DNA probes based on the DNA disclosed herein may be used to screen an appropriate library, including a genomic or cDNA library, and obtain DNA in one or more clones that includes an open reading fragment that encodes an entire protein. Subsequent to screening an appropriate library with the DNA disclosed herein, the isolated DNA can be examined for the presence of an open reading frame from which the sequence of the encoded protein may be deduced. Determination of the molecular weight and comparison with the sequences herein should reveal the identity of the subunit as an $\alpha_1$, $\alpha_2$ etc. subunit. Functional assays may, if necessary, be used to determine whether the subunit is an $\alpha_1$, $\alpha_2$ subunit or β subunit.

For example, DNA encoding an $\alpha_{1A}$ subunit may be isolated by screening an appropriate library with DNA, encoding all or a portion of the human $\alpha_{1A}$ subunit. Such DNA includes the DNA in the phage deposited under ATCC Accession No. 75293 that encodes an $\alpha_1$ subunit. DNA encoding an $\alpha_{1A}$ subunit may obtained from an appropriate library by screening with an oligonucleotide having all or a portion of the sequence set forth in SEQ ID No, 21, 22 and/or 23 or with the DNA in the deposited phage. Alternatively, such DNA may have a sequence that encodes an $\alpha_{1A}$ subunit that is encoded by SEQ ID NO. 22 or 23.

Similarly, DNA encoding $\beta_3$ may be isolated by screening a human cDNA library with DNA probes prepared from the plasmid β1.42 deposited under ATCC Accession No. 69048 or obtained from an appropriate library using probes having sequences prepared according to the sequences set forth in SEQ ID Nos. 19, 20 and/or 30. Any method known to those of skill in the art for isolation and identification of DNA and preparation of full-length genomic or cDNA clones, including methods exemplified herein, may be used.

The subunit encoded by isolated DNA may be identified by comparison with the DNA and amino acid sequences of the subunits provided herein. Splice variants share extensive regions of homology, but include non-homologous regions, subunits encoded by different genes share a uniform distribution of non-homologous sequences.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have regions of identical amino acids and regions of different amino acid sequences are referred to herein as "splice variants".

As used herein, a "calcium channel selective ion" is an ion that is capable of flowing through, or being blocked from flowing through, a calcium channel which spans a cellular membrane under conditions which would substantially similarly permit or block the flow of $Ca^{2+}$. $Ba^+$ is an example of an ion which is a calcium channel selective ion.

As used herein, a compound that modulates calcium channel activity is one that affects the ability of the calcium channel to pass calcium channel selective ions or affects other detectable calcium channel features, such as current kinetics. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, selectively hybridize means that a DNA fragment hybridizes to second fragment with sufficient specificity to permit the second fragment to be identified or isolated from among a plurality of fragments. In general, selective hybridization occurs at conditions of high stringency.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding the calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art (see, e.g., Maniatis et al. (1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cells that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel selective ions, including, but not limited to, $Ca^{2+}$ or $Ba^+$, in response to a stimulus and/or bind ligands with affinity for the channel. Preferably such calcium channel activity is distinguishable, such as electrophysiological, pharmacological and other means known to those of skill in the art, from any endogenous calcium channel activity that in the host cell.

As used herein, a peptide having an amino acid sequence substantially as set forth in a particular SEQ ID No. includes peptides that have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel selective ion is a concentration of the calcium channel selective ion necessary and sufficient to provide an inward current when the channels open.

As used herein, activity of a calcium channel refers to the movement of a calcium selective ion through a calcium channel. Such activity may be measured by any method known to those of skill in the art, including, but not limited to, measurement of the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally requires comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of test cell to the test compound compared to the response (or lack of response) of the receptor-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

Identification and Isolation of DNA Encoding Human Calcium Channel Subunits

Methods for identifying and isolating DNA encoding $\alpha_1$, $\alpha_2$, $\beta$ and $\gamma$ subunits of human calcium channels are provided.

Identification and isolation of such DNA may be accomplished by hybridizing, under appropriate conditions, at least low stringency whereby DNA that encodes the desired subunit is isolated, restriction enzyme-digested human DNA with a labeled probe having at least 14 nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. Full-length clones may be identified by the presence of a complete open reading frame and the identity of the encoded protein verified by sequence comparison with the subunits provided herein and by functional assays to assess calcium channel forming ability or other function. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences the DNA. Such sequence differences may indicate that the transcripts from which the cDNA was produced result from alternative splicing of a primary transcript, if the non-homologous and homologous regions are clustered, or from a different gene if the non-homologous regions are distributed throughout the cloned DNA.

Any suitable method for isolating genes using the DNA provided herein may be used. For example, oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled, including, but not limited to, radioactively or enzymatically labeled, RNA or single-stranded DNA of at least 14 substantially contiguous bases, preferably at least 30 contiguous bases of a nucleic acid which encodes at least a portion of a human calcium channel subunit, the sequence of which nucleic acid corresponds to a segment of a nucleic acid sequence disclosed herein by reference to a SEQ ID No. are provided. Such nucleic acid segments may be used as probes in the methods provided herein for cloning DNA encoding calcium channel subunits. See, generally, Sambrook et al. (1989) *Molecular Cloning: A Laboratory Manual*, 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization can yield DNA containing multiple exons, separated by introns, that correspond to different splice variants of transcripts encoding human calcium channel subunits.

DNA encoding types and subtypes of each of the $\alpha_1$, $\alpha_2$, $\beta$ and $\gamma$ subunit of voltage-dependent human calcium channels has been cloned herein by screening human cDNA libraries prepared from isolated poly A+ mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

With respect to each of the respective subunits of a human calcium channel ($\alpha_1$, $\alpha_2$, $\beta$ or $\gamma$), once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5' noncoding region and other transcriptional and translational control regions of such a clone may be replaced with an efficient ribosome binding site and other regulatory regions as known in the art. Other modifications of the 5' end, known to those of skill in the art, that may be required to optimize translation and/or transcription efficiency may also be effected, if deemed necessary.

Examples II–VI, below, describe in detail the cloning of each of the various subunits of a human calcium channel as well as subtypes and splice variants, including tissue-specific variants thereof. In the instances in which partial sequences of a subunit are disclosed, it is well within the skill of the art, in view of the teaching herein, to obtain the corresponding full-length nucleotide sequence encoding the subunit, subtype or splice variant thereof.

Identification and Isolation of DNA Encoding $\alpha_1$ Subunits

A number of voltage-dependent calcium channel $\alpha_1$ subunit genes, which are expressed in the human CNS and in other tissues, have been identified and have been designated as $\alpha_{1A}$, $\alpha_{1B}$ (or VDCC IV), $\alpha_{1C}$ (or VDCC II), $\alpha_{1D}$ (or VDCC III) and $\alpha_{1E}$. DNA, isolated from a human neuronal cDNA library, that encodes each of the subunit types has been isolated. DNA encoding subtypes of each of the types, which arise as splice variants are also provided. Subtypes are herein designated, for example, as $\alpha_{1B-1}$, $\alpha_{1B-2}$.

The $\alpha_1$ subunits types A B, C, D and E of voltage-dependent calcium channels, and subtypes thereof, differ with respect to sensitivity to known classes of calcium channel agonists and antagonists, such as DHPs, phenylalkylamines, omega conotoxin ($\omega$-CgTx), the funnel web spider toxin $\omega$-Aga-IV, and pyrazonoylguanidines. They also appear to differ in the holding potential and ion the kinetics of currents produced upon depolarization of cell membranes containing calcium channels that include different types of $\alpha_1$ subunits.

DNA that encodes an $\alpha_1$-subunit that binds to at least one compound selected from among dihydropyridines, phenylalkylamines, $\omega$-CgTx, components of funnel web spider toxin, and pyrazonoylguanidines is provided. For example, the $\alpha_{1B}$ subunit provided herein appears to specifically interact with $\omega$-CgTx in N-type channels, and the $\alpha_{1D}$ subunit provided herein specifically interacts with DHPs in L-type channels.

Identification and Isolation of DNA Encoding the $\alpha_{1D}$ Human Calcium Channel Subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone $\alpha$1.36. This clone was used as a probe to screen additional IMR32 cell cDNA libraries to obtain overlapping clones, which were then employed for screening until a sufficient series of clones to span the length of the nucleotide sequence encoding the human $\alpha_{1D}$ subunit were obtained. Full-length clones encoding $\alpha_{1D}$ were constructed by ligating portions of partial $\alpha_{1D}$ clones as described in Example II. SEQ ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in SEQ ID No. 1).

SEQ ID No. 2 provides the sequence of an alternative exon encoding the IS6 transmembrane domain [see Tanabe, T., et al. (1987) *Nature* 328:313–318 for a description of transmembrane domain terminology] of the $\alpha_{1D}$ subunit.

SEQ ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The $\alpha_{1D}$ subunit of the calcium channel contains four putative internal repeated sequence regions. Four internally repeated regions represent 24 putative transmembrane segments, and the amino- and carboxyl-termini extend intracellularly.

The $\alpha_{1D}$ subunit has been shown to mediate DHP-sensitive, high-voltage-activated, long-lasting calcium channel activity. This calcium channel activity was detected when oöcytes were co-injected with RNA transcripts encoding an $\alpha_{1D}$ and $\beta_1$ or $\alpha_{1D}$, $\alpha_2$ and $\beta_1$ subunits. This activity was distinguished from $Ba^{2+}$ currents detected when oöcytes were injected with RNA transcripts encoding the $\beta_1 \pm \alpha_2$ subunits. These currents pharmacologically and biophysically resembled $Ca^{2+}$ currents reported for uninjected oöcytes.

Identification and Isolation DNA Encoding the $\alpha_{1A}$ Human Calcium Channel Subunit Biological material containing DNA encoding the $\alpha_{1A}$ subunit had been deposited in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

An $\alpha_{1A}$ subunit is encoded by an approximately 3 kb insert in $\lambda$gt10 phage designated $\alpha$1.254 in *E. coli* host strain NM514. A phage lysate of this material has been deposited as at the American Type Culture Collection under ATCC Accession No. 75293, as described above. DNA encoding $\alpha_{1A}$ may also be identified by screening with a probe prepared from DNA that has SEQ ID No. 21:

5° CTCAGTACCATCTCTGATACCAGCCCCA 3'.

$\alpha_{1A}$ splice variants have been obtained. The sequences of two $\alpha_{1A}$ splice variants, $\alpha_{1a-1}$ and $\alpha_{1a-2}$ are set forth in SEQ. ID Nos. 22 and 23. Other splice variants may be obtained by screening a human library as described above or using all or a portion of the sequences set forth in SEQ ID Nos. 22 and 23.

Identification and Isolation of DNA Encoding the $\alpha_{1B}$ Human Calcium Channel Subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. PCR amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. SEQ ID Nos. 7 and 8 show the nucleotide sequences of DNA clones encoding the $\alpha_{1B}$ subunit as well as the deduced amino acid sequences. The $\alpha_{1B}$ subunit encoded by SEQ ID No. 7 is referred to as the $\alpha_{1B-1}$ subunit to distinguish it from another $\alpha_{1B}$ subunit, $\alpha_{1b-2}$, encoded by the nucleotide sequence shown as SEQ ID No. 8, which is derived from alternative splicing of the $\alpha_{1B}$ subunit transcript.

PCR amplification of IMR32 cell mRNA using oligonucleotide primers designed according to nucleotide sequences within the $\alpha_{1B-1}$-encoding DNA has identified variants of the $\alpha_{1B}$ transcript that appear to be splice variants because they contain divergent coding sequences.

Identification and Isolation of DNA Encoding the $\alpha_{1C}$ Human Calcium Channel Subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. SEQ ID No. 3 sets forth DNA encoding an $\alpha_{1C}$ subunit. The DNA sequences set forth in SEQ ID No. 4 and No. 5 encode two possible amino terminal ends of the tic protein. SEQ ID No. 6 encodes an alternative exon for the IV S3 transmembrane domain.

The isolation and identification of DNA clones encoding portions of the $\alpha_{1C}$ subunit is described in detail in Example II.

Identification and Isolation of DNA Encoding the $\alpha_{1E}$ Human Calcium Channel Subunit DNA encoding $\alpha_{1E}$ human calcium channel subunits have been isolated from an oligo dT-primed human hippocampus library. The resulting clones, which are splice variants, were designated $\alpha_{1E-1}$ and $\alpha_{1E-3}$. The subunit designated $\alpha_{1E-1}$ has the amino acid sequence set forth in SEQ ID No. 24, and a subunit designated $\alpha_{1E-3}$ has the amino acid sequence set forth by SEQ. ID No. 24 with the fragment encoded by the DNA set forth in SEQ ID No. 25 inserted between nucleotides 2405 and 2406. The resulting sequence of $\alpha_{1E-3}$ is set forth in SEQ ID No. 27.

The $\alpha_{1E}$ subunits propvided herein appear to participate in the formation of calcium channels that have properties of high-voltage activated calcium channels and low-voltage activated channels. These channels are rapidly inactivating compared to other high voltage-activated calcium channels. In addition these channels exhibit pharmacological profiles that are similar to voltage-activated channels, but are also sensitive to DHPs and ω-Aga-IVA, which block certain high voltage activated channels. Additional details regarding the electrophysiology and pharmacology of channels containing $\alpha_{1E}$ subunits is provided in Example VII. F.

Identification and Isolation of DNA Encoding the Other $\alpha_1$ Human Calcium Channel Subunit Types and Subtypes DNA encoding other $\alpha_1$ subunits has also been isolated. Additional such subunits may also be isolated and identified using the DNA provided herein as described for the $\alpha_{1B}$, $\alpha_{1C}$ and $\alpha_{1D}$ subunits or using other methods known to those of skill in the art. In particular, the DNA provided herein may be used to screen appropriate libraries to isolate related DNA. Full-length clones can be constructed using methods, such as those described herein, and the resulting subunits characterized by comparison of their sequences and electrophysiological and pharmacological properties with the subunits exemplified herein.

Identification and Isolation DNA Encoding β Human Calcium Channel Subunits

DNA Encoding $\beta_1$

To isolate DNA encoding the $\beta_1$ subunit, a human hippocampus cDNA library was screened by hybridization to a DNA fragment encoding a rabbit skeletal muscle calcium channel β subunit. A hybridizing clone was selected and was in turn used to isolate overlapping clones until the overlapping clones encompassing DNA encoding the entire the human calcium channel β subunit were isolated and sequenced.

Five alternatively spliced forms of the human calcium channel $\beta_1$ subunit have been identified and DNA encoding a number of forms have been isolated. These forms are designated $\beta_{1-1}$, expressed in skeletal muscle, $\beta_{1-2}$, expressed in the CNS, $\beta_{1-3}$, also expressed in the in the CNS, $\beta_{1-4}$, expressed in aorta tissue and HEK 293 cells, and $\beta_{1-5}$, expressed in HEK 293 cells. A full-length DNA clone encoding the $\beta_{1-2}$ subunit has been constructed. The subunits $\beta_{1-1}$, $\beta_{1-2}$, $\beta_{1-4}$ and $\beta_{1-5}$ have been identified by PCR analysis as alternatively spliced forms of the β subunit.

The alternatively spliced variants were identified by comparison of amino acid sequences encoded by the human neuronal and rabbit skeletal muscle calcium channel β subunit-encoding DNA. This comparison revealed a 45-amino acid deletion in the human β subunit compared to the rabbit β subunit. Using DNA from the region as a probe for DNA cloning, as well as PCR analysis and DNA sequencing of this area of sequence divergence, alternatively spliced forms of the human calcium channel β subunit transcript were identified. For example, the sequence of DNA encoding one splice variant $\beta_{1-2}$ is set forth in SEQ ID No. 9. SEQ ID No. 10 sets forth the sequence of the $\beta_{1-3}$ subunit (nt 1–1851, including 3' untranslated sequence nt 1795–1851), which is another splice variant of the β subunit primary transcript. $\beta_{1-2}$ and $\beta_{1-3}$ are human neuronal β subunits. DNA distinctive for a portion of a β subunit ($\beta_{1-4}$) of a human aortic calcium channel and also human embryonic kidney (HEK) cells is set forth in SEQ ID No. 12 (nt 1–13 and 191–271). The sequence of DNA encoding a portion of a human calcium channel β subunit expressed in skeletal muscle ($\beta_{1-1}$) is shown in SEQ ID No. 12 (nt 1–13 and 35–271). The sequences of the $\beta_1$ splice variants designated $\oplus_{1-1}$, $\beta_{1-2}$, $\beta_{1-3}$, $\beta_{1-4}$ and $\beta_{1-5}$ are set forth in Sequence ID Nos. 32, 9, 10, 33 and 34, respectively.

DNA Encoding $\beta_2$

DNA encoding the $\beta_2$ splice variants has been obtained. These splice variants include $\beta_{2A}$–$\beta_{2F}$. Splice variants $\beta_{2C}$–$\beta_{2F}$ include all of sequence set forth in SEQ ID No. 26, except for the portion at the 5' end (up to nucleotide 182), which differs among splice variants. The sequence set forth in SEQ ID No. 26 encodes at least about 90% of $\beta_{2D}$. Additional splice variants may be isolated using the methods described herein and oligonucleotides including all or portions of the DNA set forth in SEQ ID. No. 26 or as described in the Examples.

DNA Encoding $\beta_3$

DNA encoding the $\beta_3$ subunit and any splice variants thereof may be isolated by screening a library, as described above for the $\beta_1$ subunit, using DNA probes prepared according to SEQ ID Nos. 19, 20 or using all or a portion of the deposited $\beta_3$ clone plasmid $\beta$1.42 (ATCC Accession No. 69048).

The *E. coli* host containing plasmid $\beta$1.42 that includes DNA encoding a $\beta_3$ subunit has been deposited as ATCC Accession No. 69048 in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The $\beta_3$ encoding plasmid is designated $\beta$1.42. The plasmid contains a 2.5 kb EcoRI fragment encoding $\beta_3$ inserted into vector pGem˙7zF(+) and has been deposited in *E. coli* host strain DN5α. A partial DNA sequence of the 5' and 3' ends of $\beta_3$ are set forth in SEQ ID Nos. 19 and 20, respectively.

Identification and Isolation DNA Encoding the $\alpha_2$ Human Calcium Channel Subunit DNA encoding a human neuronal calcium channel $\alpha_2$ subunit was isolated in a manner substantially similar to that used for isolating DNA encoding an $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520, which is a continuation-in-part of U.S. Ser. No. 176,899, filed Apr. 4, 1988, which applications have been incorporated herein by reference. Example IV describes the isolation of DNA clones encoding $\alpha_2$ subunits of a human calcium channel from a human DNA library using genomic DNA and cDNA clones, identified by hybridization to the genomic DNA, as probes.

SEQ ID No. 11 shows the sequence of DNA encoding an $\alpha_2$ subunit. As described in Example V, PCR analysis of RNA from human skeletal muscle, brain tissue and aorta using oligonucleotide primers specific for a region of the human neuronal $\alpha_2$ subunit cDNA that diverges from the rabbit skeletal muscle calcium channel $\alpha_2$ subunit cDNA identified splice variants of the human calcium channel $\alpha_2$ subunit transcript.

Identification and Isolation of DNA Encoding γ Human Calcium Channel Subunits

DNA encoding a human neuronal calcium channel γ subunit has been isolated as described in detail in Example VI. SEQ ID No. 14 shows the nucleotide sequence at the 3'-end of this DNA which includes a reading frame encoding a sequence of 43 amino acid residues.

Preparation of Recombinant Eukaryotic Cells Containing DNA Encoding Heterologous Calcium Channel Subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning: A Laboratory Manual, Second Edition*, Cold Spring Harbor Laboratory Press].

Cloned full-length DNA encoding any of the subunits of a human calcium channel may be introduced into a plasmid vector for expression in a eukaryotic cell. Such DNA may be genomic DNA or cDNA. Host cells may be transfected with one or a combination of said plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* [see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV or pCDNA1, and MMTV promoter-based vectors. DNA encoding the human calcium channel subunits has been inserted in the vector pCDNA1 at a position immediately following the CMV promoter.

Stably or transiently transfected mammalian cells may be prepared by methods known in the art by transfecting cells with an expression vector having a selectable marker gene such as the gene for thymidine kinase, dihydrofolate reductase, neomycin resistance or the like, and, for transient transfection, growing the transfected cells under conditions selective for cells expressing the marker gene. Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to cells of mammalian origin, such as COS cells, mouse L cells, CHO cells, human embryonic kidney cells, African green monkey cells and other such cells known to those of skill in the art, amphibian cells, such as *Xenopus laevis* oöcytes, or those of yeast such as *Saccharomyces cerevisiae* or *Pichia pastoris*. Preferred cells for expressing injected RNA transcripts include *Xenopus laevis* oöcytes. Cells that are preferred for transfection of DNA are those that can be readily and efficiently transfected. Such cells are known to those of skill in the art or may be empirically identified. Preferred cells include DG44 cells and HEK 293 cells, particularly HEK 293 cells that have been adapted for growth in suspension and that can be frozen in liquid nitrogen and then thawed and regrown. Such HEK 293 cells are described, for example in U.S. Pat. No. 5,024,939 to Gorman [see, also Stillman et al. (1985) *Mol. Cell.Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or calcium channels containing the subunits.

Substantially pure subunits of a human calcium channel $\alpha_1$ subunits of a human calcium channel, $\alpha_2$ subunits of a human calcium channel, $\beta$ subunits of a human calcium channel and $\gamma$ subunits of a human calcium channel are provided. Substantially pure isolated calcium channels that contain at least one of the human calcium channel subunits are also provided. Substantially pure calcium channels that contain a mixture of one or more subunits encoded by the host cell and one or more subunits encoded by heterologous DNA or RNA that has been introduced into the cell are also provided. Substantially pure subtype- or tissue-type specific calcium channels are also provided.

In other embodiments, eukaryotic cells that contain heterologous DNA encoding at least one of an $\alpha_1$ subunit of a human calcium channel, an $\alpha_2$ subunit of a human calcium channel, a $\alpha$subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

Expression of Heterologous Calcium Channels: Electrophysiology and Pharmacology

Electrophysiological methods for measuring calcium channel activity are kwown to those of skill in the art and are exemplified herein. Any such methods may be used in order to detect the formation of functional calcium channels and to characterize the kinetics and other characteristics of the resulting currents. Pharmacological studies may be combined with the electrophysiological measurements in order to further characterize the calcium channels.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, pharmacological and electrophysiological means, including the use of differential holding potential, to increase the S/N ratio of the measured heterologous calcium channel activity.

Thus, various combinations of subunits encoded by the DNA provided herein are introduced into eukaryotic cells. The resulting cells can be examined to ascertain whether functional channels are expressed and to determine the properties of the channels. In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude not exhibited in the untransfected cell.

The eukaryotic cells can be transfected with various combinations of the subunit subtypes provided herein. The resulting cells will provide a uniform population of calcium channels for study of calcium channel activity and for use in the drug screening assays provided herein. Experiments that have been performed have demonstrate the inadequacy of prior classification schemes.

Preferred among transfected cells is a recombinant eukaryotic cell with a functional heterologous calcium channel. The recombinant cell can be produced by introduction of and expression of heteroloqous DNA or RNA transcripts encoding an $\alpha_1$ subunit of a human calcium channel, more preferably also expressing, a heterologous DNA encoding a $\beta$ subunit of a human calcium channel and/or heterologous DNA encoding an $\alpha_2$ subunit of a human calcium channel. Especially preferred is the expression in such a recombinant cell of each of the $\alpha_1$, $\beta$ and $\alpha_2$ subunits encoded by such heterologous DNA or RNA transcripts, and optionally expression of heterologous DNA or an RNA transcript encoding a $\gamma$ subunit of a human calcium channel. The functional calcium channels may preferably include at least an $\alpha_1$ subunit and a P subunit of a human calcium channel. Eukaryotic cells expressing these two subunits and also cells expressing additional subunits, have been prepared by transfection of DNA and by injection of RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a $\beta$ subunit have been shown to exhibit increased calcium selective ion flow across the cellular membrane in response to depolarization, indicating that the $\alpha_2$ subunit may potentiate calcium channel function.

Eukaryotic cells which express heterologous calcium channels containing at least a human $\alpha_1$ subunit, a human $\beta$ subunit and a human $\alpha_2$ subunit are preferred. Eukaryotic cells transformed with a composition containing cDNA or an RNA transcript that encodes an $\alpha_1$ subunit alone or in combination with a $\beta$ and/or an $\alpha_2$ subunit may be used to produce cells that express functional calcium channels. Since recombinant cells expressing human calcium channels containing all of the of the human subunits encoded by the heterologous cDNA or RNA are especially preferred, it is desirable to inject or transfect such host cells with a sufficient concentration of the subunit-encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

In particular, mammalian cells have been transiently and stably transfected with DNA encoding one or more human calcium channel subunits. Such cells express heterologous calcium channels that exhibit pharmacological and electrophysiological properties characteristic that can be ascribed to human calcium channels. Such cells, however, represent homogeneous populations and the pharmacological and electrophysiological data provides insights into human calcium channel activity heretofore unattainable. For example, HEK cells that have been transiently transfected with DNA encoding the α1E-1, $α_{2b}$, and $β_{1-3}$ subunits. The resulting cells transiently express these subunits, which form a calcium channels that appear to exhibit properties of L-, N-, T- and P-type channels.

HEK cells that have been transfiently transfected with DNA encoding $α_{1B-1}$ $α_{2b}$, and $β_{1-2}$ express heterologous calcium channels that exhibt sensitivity to ω-conotoxin and currents typical of N-type channels. It has been found that alteration of the molar raios of $α_{1B-1}$, $α_{2b}$ and $β_{1-2}$ introduced into the cells into to achieve equivalent mRNA levles significantly incresed the number of receptors per cell, the current density, and affected the $K_d$ for ω-conotoxin.

The electrophyiology of these channels produced from $α_{1B-1}$ $α_{2b}$, and $β_{1-2}$ was compared with channels produced by transiently transfecting HEK cells with DNA encoding $α_{1B-1}$ $α_{2b}$, and $β_{1-3}$. The channels exhibited similar voltage dependence of activation, substantially identical voltage dependence, similar kinetics of activation and tail currents that could be fit by a single exponential. The voltage dependence of the kinetics of inactivation was significantly different at all voltages examined.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $α_1$ subunit of a human calcium channel. More preferably, the composition that is introduced contains an RNA transcript which encodes an $α_1$ subunit of a human calcium channel and also contains (1) an RNA transcript which encodes a β subunit of a human calcium channel and/or (2) an RNA transcript which encodes an $α_2$ subunit of a human calcium channel. Especially preferred is the introduction of RNA encoding an $α_1$, a β and an $α_2$ human calcium channel subunit, and, optionally, a γ subunit of a human calcium channel.

Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oöcytes are particularly preferred for expression of in vitro transcripts of the human calcium channel subunit cDNA clones provided herein. Amphibian oöcytes that express functional heterologous calcium channels have been produced by this method.

Assays
Assays for Identifying Compounds that Modulate Calcium Channel Activity

Among the uses for eukaryotic cells which recombinantly express one or more subunits are assays for determining whether a test compound has calcium channel agonist or antagonist activity. These eukaryotic cells may also be used to select from among known calcium channel agonists and antagonists those exhibiting a particular calcium channe subtype specificity and to thereby select compounds that have potential as disease- or tissue-specific therapeutic agents.

In vitro methods for identifying compounds, such as calcium channel agonist and antagonists, that modulate the activity of calcium channels using eukaryotic cells that express heterologous human calcium channels are provided.

In particular, the assays use eukaryotic cells that express heterologous human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit subtype- or tissue-specific calcium channel antagonist and agonist activities.

These assays should accurately predict the relative therapeutic efficacy of a compound for the treatment of certain disorders in humans. In addition, since subtype- and tissue-specific calcium channel subunits are provided, cells with tissue-specific or subtype-specific recombinant calcium channels may be prepared and used in assays for identification of human calcium channel tissue- or subtype-specific drugs.

Desirably, the host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays. Also, the host cells preferably should not produce endogenous calcium channels which detectably interact with compounds having, at physiological concentrations (generally nanomolar or picomolar concentrations), affinity for calcium channels that contain one or all of the human calcium channel subunits provided herein.

With respect to ligand binding assays for identifying a compound which has affinity for calcium channels, cells are employed which express, preferably, at least a heterologous $α_1$ subunit. Transfected eukaryotic cells which express at least an $α_1$ subunit may be used to determine the ability of a test compound to specifically alter the activity of a calcium channel. Such ligand binding assays may be performed on intact transfected cells or membranes prepared therefrom.

The capacity of a test compound to bind to or otherwise interact with membranes that contain heterologous calcium channels or subunits thereof may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

The assays involve contacting the cell membrane of a recombinant eukaryotic cell which expresses at least one subunit of a human calcium channel, preferably at least an $α_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell that has a calcium channel containing an $α_1$ subunit of a human calcium channel in combination with a β-subunit of a human calcium channel and/or an $α_2$ subunit of a human calcium channel. Recombinant cells expressing heterologous calcium channels containing each of the $α_1$, β and $α_2$ human subunits, and, optionally, a γ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel selective ion and comparing the measured calcium channel activity to the calcium channel activity of the same cell or a substantially identical control cell in a solution not containing the test compound. The cell is maintained in a solution having a concentration of calcium channel selective ions sufficient to provide an inward current when the channels open. Especially preferred for use, is a recombinant cell expressing calcium channels that include each of the $α_1$, β and $α_2$ human subunits, and, optionally, a γ subunit of a human calcium channel. Methods for practicing such assays are known to those of skill in the art. For example, for similar methods applied with *Xenopus laevis* oöcytes and acetylcholine receptors, see, Mishina et al. [(1985) *Nature* 313:364] and, with such oöcytes and sodium channels [see, Noda et al. (1986) *Nature* 322:826–828]. For similar studies which have been carried out with the acetylcholine receptor, see, e.g., Claudio et al. [(1987) *Science* 238:1688–1694].

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium selective ions through heterologous calcium channels of a recombinant cell containing DNA encoding one or more of the subunits provided herein has been measured using electrophysiological recordings using a two electrode and the whole-cell patch clamp techniques. In order to improve the sensitivity of the assays, known methods can be used to eliminate or reduce non-calcium currents and calcium currents resulting from endogenous calcium channels, when measuring calcium currents through recombinant channels. For example, the DHP Bay K 8644 specifically enhances L-type calcium channel function by increasing the duration of the open state of the channels [see, e.g., Hess, J. B., et al. (1984) *Nature* 311:538–544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

In practicing these assays, stably or transiently transfected cells or injected cells that express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium through a human calcium channel can be accomplished by (a) maintaining a eukaryotic cell which is transfected or injected to express a heterologous functional calcium channel capable of regulating the flow of calcium channel selective ions into the cell in a medium containing calcium channel selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

The assays thus use cells, provided herein, that express heterologous functional calcium channels and measure functionally, such as electrophysiologically, the ability of a test compound to potentiate, antagonize or otherwise modulate the magnitude and duration of the flow of calcium channel selective ions, such as $Ca^{++}$ or $Ba^{++}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner.

Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel selective ion, such as $Ca^{2+}$ and $Ba^+$. The details of such transcriptional based assays are described in commonly owned PCT International Patent Application No. PCT/US91/5625, filed Aug. 7, 1991, which claims priority to copending commonly owned U.S. application Ser. No. 07/563,751, filed Aug. 7, 1990, the contents of which applications are herein incorporated by reference thereto.

Assays for Diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, *Science* 239:405–408 (1988)]. A diagnostic assay for Lambert Eaton Syndrome (LES) is provided herein. The diagnostic assay for LES relies on the immunological reactivity of LES IgG with the human calcium channels or particular subunits alone or in combination or expressed on the surface of recombinant cells. For example, such an assay may be based on immunoprecipitation of LES IgG by the human calcium channel subunits and cells that express such subunits provided herein.

EXAMPLES

The following examples are included for illustrative purposes only and are not intended to limit the scope of the invention.

Example I
Preparation of Libraries Used for Isolation of DNA Encoding Human Neuronal Voltage-dependent Calcium Channel Subunits

A. RNA Isolation
1. IMR32 Cells

IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [(1988) *Nucleic Acids Research* 16:1487–1497]. Poly($A^+$) RNA was selected according to standard procedures [see, e.g., Sambrook et al. (1989) *Molecular Cloning, A Laboratory Manual*, Cold Spring Harbor Laboratory Press; pg. 7.26–7.29].

2. Human Thalamus Tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5 M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7 M CsCl, 0.1 M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25 M NaCl and two volumes of 95% ethanol.

The precipitate was collected by centrifugation and resuspended in 4 ml PK buffer (0.05 M TRIS, pH 8.4, 0.14 M NaCl, 0.01 M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly $A^+$ RNA (30 μg) was isolated from the total RNA according to standard methods as stated in Example I.A.1.

B. Library Construction

Double-stranded cDNA was synthesized according to standard methods [see, e.g., Sambrook et al. (1989) IN: *Molecular Cloning, A Laboratory Manual*, Cold Spring Harbor Laboratory Press, Chapter 8]. Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA library #1

Single-stranded cDNA was synthesized using IMR32 poly($A^+$) RNA (Example I.A.1.) as a template and was primed using oligo $(dT)_{12-18}$ (Collaborative Research Inc., Bedford, Mass.). The single-stranded cDNA was converted to double-stranded cDNA and the yield was approximately 2 μg. EcoI adapters:

5'-AATTCGGTACGTACACTCGAGC-3'=22-mer (SEQ ID No.15)

3'-GCCATGCATGTGAGCTCG-5'=18-mer (SEQ ID No.16)

also containing SnaBI and XhoI restriction sites were then added to the double-stranded cDNA according to the following procedure.

a. Phosphorylation of 18-mer

The 18-mer was phosphorylated using standard methods [see, e.g., Sambrook et al. (1989) IN: *Molecular Cloning, A Laboratory Manual*, Cold Spring Harbor Laboratory Press, Chapter 8] by combining in a 10 μl total volume the 18-mer (225 pmoles) with [$^{32}$P]γ-ATP (7000 Ci/mmole; 1.0 μl) and kinase (2 U) and incubating at 37° C. for 15 minutes. After incubation, 1 μl 10 mM ATP and an additional 2 U of kinase were added and incubated at 37° C. for 15 minutes.

Kinase was then inactivated by boiling for 10 minutes.

b. Hybridization of 22-mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slow cool to room temperature.

The adapters were thus present at a concentration of 15 pmoles/μl, and were ready for cDNA-adapter ligation.

c. Ligation of Adapters to cDNA

After the EcoRI, SnaBI, XhoI adapters were ligated to the double-stranded cDNA using a standard protocol [see, e.g., Sambrook et al. (1989) IN: *Molecular Cloning, A Laboratory Manual*, Cold Spring Harbor Laboratory Press, Chapter 8], the ligase was inactivated by heating the mixture to 72° C. for 15 minutes. The following reagents were added to the cDNA ligation reaction and heated at 37° C. for 30 minutes: cDNA ligation reaction (20 μl), water (24 μl), 10×kinase buffer (3 μl), 10 mM ATP (1 μl) and kinase (2 μl of 2 U/μl). The reaction was stopped by the addition of 2 μl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St. Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λgt11 in a 5 μl reaction volume at a 2- to 4-fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 CDNA Library #2

This library was prepared as described (Example I.B.1.) with the exception that 3 to 9 kb cDNA fragments were ligated into the λgt11 phage vector rather than the 1 to 3 kb fragments.

3. IMR32 cDNA Library #3

IMR32 cell poly(A$^+$) RNA (Example I.A.1.) was used as a template to synthesize single-stranded cDNA. The primers for the first strand cDNA synthesis were random primers (hexadeoxy-nucleotides [pd(N)$_6$] Cat #5020-1, Clontech, Palo Alto, Calif.). The double-stranded cDNA was synthesized, EcoRI, SnaBI, XhoI adapters were added to the cDNA, the unligated adapters were removed, and the double-stranded cDNA with the ligated adapters was fractionated on an agarose gel, as described in Example I.B.1. The cDNA fraction greater than 1.8 kb was eluted from the agarose, ligated into λgt11, packaged, and plated into a bacterial lawn of Y1088 (as described in Example I.B.1.).

4. IMR32 cDNA Library #4

IMR32 cell poly(A$^+$) RNA (Example I.A.1.) was used as a template to synthesize single-stranded cDNA. The primers for the first strand cDNA synthesis were oligonucleotides: 89-365a specific for the $\alpha_{1D}$ (VDCC III) type $\alpha_1$-subunit (see Example II.A.) coding sequence (the complementary sequence of nt 2927 to 2956, SEQ ID No. 1), 89-495 specific for the $\alpha_{1C}$ (VDCC II) type $\alpha_1$-subunit (see Example II.B.) coding sequence (the complementary sequence of nt 852 to 873, SEQ ID No. 3), and 90-12 specific for the $\alpha_{1C}$-subunit coding sequence (the complementary sequence of nt 2496 to 2520, SEQ ID No. 3). The cDNA library was then constructed as described (Example I.B.3), except that the cDNA size-fraction greater than 1.5 kb was eluted from the agarose rather than the greater than 1.8 kb fraction.

5. IMR32 cDNA Library #5

The cDNA library was constructed as described (Example I.B.3.) with the exception that the size-fraction greater than 1.2 kb was eluted from the agarose rather than the greater than 1.8 kb fraction.

6. Human Thalamus cDNA Library #6

Human thalamus poly (A$^+$) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

5' CCATGGTACCTTCGTTGACG 3'=20-mer (SEQ ID NO. 17)

3' GGTACCATGGAAGCAACTGCTTAA 5'=24-mer (SEQ ID NO. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 µl) were collected and 1 µl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [hybridization: 50% deionized formamide, 200 µg/ml sonicated herring sperm DNA (Cat #223646, Boehringer Mannheim Biochemicals, Indianapolis, Ind.), 5×SSPE, 5×Denhardt's, 42° C.; wash :0.2×SSPE, 0.1% SDS, 65° C.].

The recipes for SSPE and Denhardt's and the preparation of deionized formamide are described, for example, in Sambrook et al. (1989) *Molecular Cloning, A Laboratory Manual,* Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

Example II

Isolation of DNA Encoding the Human Neuronal Calcium Channel $\alpha_1$ Subunit

A. Isolation of DNA Encoding the $\alpha_{1D}$ Subunit

1. Reference List of Partial $\alpha_{1D}$ cDNA Clones

Numerous $\alpha_{1D}$-specific cDNA clones were isolated in order to characterize the complete $\alpha_{1D}$ coding sequence plus portions of the 5' and 3' untranslated sequences. SEQ ID No. 1 shows the complete $\alpha_{1D}$ DNA coding sequence, plus 510 nucleotides of $\alpha_{1D}$ 5' untranslated sequence ending in the guanidine nucleotide adjacent to the adenine nucleotide of the proposed initiation of translation as well as 642 nucleotides of 3' untranslated sequence. Also shown in SEQ ID No. 1 is the deduced amino acid sequence. A list of partial cDNA clones used to characterize the $\alpha_{1D}$ sequence and the nucleotide position of each clone relative to the full-length $\alpha_{1D}$ cDNA sequence, which is set forth in SEQ ID No. 1, is shown below. The isolation and characterization of these clones are described below (Example II.A.2.).

| IMR32 | 1.144 | nt 1 to 510 of 5' untranslated sequence, nt 511 to 2431, | SEQ ID No. 1 SEQ ID No. 1 |
|---|---|---|---|
| IMR32* | 1.136 | nt 1627 to 2988, nt 1 to 104 of SEQ ID No. 2 additional exon, | SEQ ID No. 1 |
| IMR32@ | 1.80 | nt 2083 to 6468, | SEQ ID No. 1 |
| IMR32# | 1.36 | nt 2857 to 4281, | SEQ ID No. 1 |
| IMR32 | 1.163 | nt 5200 to 7635, | SEQ ID No. 1 |

*5' of nt 1627, IMR32 1.136 encodes an intron and an additional exon described in Example II.A.2.d.
@IMR32 1.80 contains two deletions, nt 2984 to 3131 and nt 5303 to 5349 (SEQ ID No. 1). The 148 nt deletion (nt 2984 to 3131) was corrected by performing a polymerase chain reaction described in Example II.A.3.b.
IMR32 1.36 contains a 132 nt deletion (nt 3081 to 3212).

2. Isolation and Characterization of Individual Clones Listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel $\alpha_1$ cDNA [for the sequence of the rabbit skeletal muscle calcium channel $\alpha_1$ subunit cDNA, see, Tanabe et al. (1987). *Nature* 328:313–318]:

| Fragment | Nucleotides |
|---|---|
| KpnI-EcoRI | −78 to 1006 |
| EcoRI-XhoI | 1006 to 2653 |
| ApaI-ApaI | 3093 to 4182 |
| BglII-SacI | 4487 to 5310 |

The hybridization was performed using low stringency hybridization conditions (Example I.C.) and the filters were washed under low stringency (Example I.C.). Only one $\alpha_{1D}$-specific recombinant (IMR32 1.36) of the 2×10$^6$ screened was identified. IMR32 1.36 was plaque purified by standard methods (J. Sambrook et al. (1989) *Molecular Cloning, A Laboratory Manual*, Cold Spring Harbor Laboratory Press, Chapter 8) subcloned into pGEM3 (Promega, Madison, Wis.) and characterized by DNA sequencing.

b. IMR32 1.80

Approximately 1×10$^6$ recombinants of the IMR32 cDNA library #2 (Example I.B.2.) were screened in duplicate at a density of approximately 100,000 plaques per 150 mm plate using the IMR32 1.36 cDNA fragment (Example II.A.1) as a probe. Standard hybridization conditions were used, and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

c. IMR32 1.144

Approximately 1×10$^6$ recombinants of the IMR32 cDNA library #3 (Example I.B.3) were screened with the EcoRI-PvuII fragment (nt 2083 to 2518, SEQ ID No. 1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 511 to 531, SEQ ID No. 1). PCR analysis, and DNA sequencing of cloned PCR products encoding these seven ATG codons confirmed that this sequence is present in the $\alpha_{1D}$ transcript expressed in dbcAMP-induced IMR32 cells.

d. IMR32 1.136

Approximately 1×10$^6$ recombinants of the IMR32 cDNA library #4 (Example I.B.4) were screened with the EcoRI-PvuII fragment (nt 2083 to 2518, SEQ ID No. 1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, pSP72 (Promega, Madison, Wis.), and characterized by DNA sequencing. This characterization revealed that IMR32 1.136 encodes an incompletely spliced $\alpha_{1D}$ transcript. The clone contains nucleotides 1627 to 2988 of SEQ ID No. 1 preceded by an approximate 640 bp intron. This intron is then preceded by a 104 nt exon (SEQ ID No. 2) which is an alternative exon encoding the IS6 transmembrane domain [see, e.g., Tanabe et al. (1987) *Nature* 328:313–318 for a description of the IS1 to IVS6 transmembrane terminology] of the $\alpha_{1D}$ subunit and can replace nt 1627 to 1730, SEQ ID No. 1, to produce a completely spliced $\alpha_{1D}$ transcript.

e. IMR32 1.163

Approximately 1×10$^6$ recombinants of the IMR32 cDNA library #3 (Example I.B.3.) were screened with the NcoI-XhoI fragment of IMR32 1.80 (Example II.A.1.) containing nt 5811 to 6468 (SEQ ID No. 1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, pSP72 (Promega, Madison, Wis.), and characterized by DNA sequencing. This characterization revealed that IMR32 1.163 contains the $\alpha_{1D}$ termination codon, nt 6994 to 6996 (SEQ ID No. 1).

3. Construction of a Full-length $\alpha_{1D}$ cDNA [pVDCCIII(A)]

$\alpha_{1D}$ cDNA clones IMR32 1.144, IMR32 1.136, IMR32 1.80, and IMR32 1.163 (Example II.A.2.) overlap and include the entire $\alpha_{1D}$ coding sequence, nt 511 to 6993 (SEQ ID No. 1), with the exception of a 148 bp deletion, nt 2984 to 3131 (SEQ ID No. 1). Portions of these partial cDNA clones were ligated to generate a full-length $\alpha_{1D}$ cDNA in a eukaryotic expression vector. The resulting vector was called pVDCCIII(A). The construction of pVDCCIII(A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII(A). The vector pcDNA1 is a eukaryotic expression vector containing a cytomegalovirus (CMV) promoter which is a constitutive promoter recognized by mammalian host cell RNA polymerase II.

Each of the DNA fragments used in preparing the full-length construct was purified by electrophoresis through an agarose gel onto DE81 filter paper (Whatman, Clifton, N.J.) and elution from the filter paper using 1.0 M NaCl, 10 mM TRIS, pH 8.0, 1 mM EDTA. The ligations typically were performed in a 10 μl reaction volume with an equal molar ratio of insert fragment and a two-fold molar excess of the total insert relative to the vector. The amount of DNA used was normally about 50 ng to 100 ng.

a. pVDCCIII/5'

To construct pVDCCIII/5', IMR32 1.144 (Example II.A.2.c.) was digested with XhoI and EcoRI and the fragment containing the vector (pGEM7Z), $\alpha_{1D}$ nt 1 to 510 (SEQ ID No. 1), and $\alpha_{1D}$ nt 511 to 1732 (SEQ ID No. 1) was isolated by gel electrophoresis. The EcoRI-ApaI fragment of IMR32 1.136 (Example II.A.2.d.) nucleotides 1733 to 2671 (SEQ ID No. 1) was isolated, and the ApaI-HindIII fragment of IMR32 1.80 (Example II.A.2.b.), nucleotides 2672 to 4492 (SEQ ID No. 1) was isolated. The three DNA clones were ligated to form pVDCCIII/5' containing nt 1 to 510 (5' untranslated sequence; SEQ ID No. 1) and nt 511 to 4492 (SEQ ID No. 1).

b. pVDCCIII/5'.3

Comparison of the IMR32 1.36 and IMR32 1.80 DNA sequences revealed that these two cDNA clones differ through the $\alpha_{1D}$ coding sequence, nucleotides 2984 to 3212. PCR analysis of IMR32 1.80 and dbcAMP-induced (1.0 mM, 10 days) IMR32 cytoplasmic RNA (isolated according to Ausubel, F. M. et al. (Eds) (1988) *Current Protocols in Molecular Biology*, John Wiley and Sons, New York)

revealed that IMR32 1.80 had a 148 nt deletion, nt 2984 to 3131 (SEQ ID No. 1), and that IMR32 1.36 had a 132 nt deletion, nt 3081 to 3212. To perform the PCR analysis, amplification was primed with $\alpha_{1D}$-specific oligonucleotides 112 (nt 2548 to 2572, SEQ ID No. 1) and 311 (the complementary sequence of nt 3928 to 3957, SEQ ID No. 1). These products were then reamplified using $\alpha_{1D}$-specific oligonucleotides 310 (nt 2583 to 2608 SEQ ID No. 1) and 312 (the complementary sequence of nt 3883 to 3909). This reamplified product, which contains AccI and BGlII restriction sites, was digested with AccI and BGlII and the AccI-BGlII fragment, nt 2765 to 3890 (SEQ ID No. 1) was cloned into AccI-BGlII digested pVDCCIII/5' to replace the AccI-BGlII pVDCCIII/5' fragment that had the deletion. This new construct was named pVDCCIII/5'.3. DNA sequence determination of pVDCCIII/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (Example I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of $\alpha_{1D}$ sequences in DH5α cells transformed with this plasmid due to fusion with the lacZ gene. This plasmid was then digested with HindIII and BGlII and the HindIII-BGlII fragment (the HindIII site comes from the vector and the BGlII site is at nt 6220, SEQ ID No. 1) was eliminated, thus deleting nt 5200 to 6220 (SEQ ID No. 1) of the IMR32 1.163 clone and removing this sequence from the remainder of the plasmid which contained the 3' BGlII-XhoI fragment, nt 6221 to 7635 (SEQ ID No. 1). pVDCCIII/3'.1 was then made by splicing together the HindIII-PvuII fragment from IMR32 1.80 (nucleotides 4493–5296, SEQ ID No. 1), the PvuII-BGlII fragment of IMR32 1.163 (nucleotides 5294 to 6220, SEQ ID No. 1) and the HindIII-BGlII-digested pBluescript plasmid containing the 3' BGlII/XhoI IMR32 1.163 fragment (nt 6221 to 7635, SEQ ID No. 1).

d. pVDCCIII(A): The Full-length $\alpha_{1D}$ Construct

To construct pVDCCIII(A), the DraI-HindIII fragment (5' untranslated sequence nt 330 to 510, SEQ ID No. 1 and coding sequence nt 511 to 4492, SEQ ID No. 1) of pVDCCIII/5'.3 (Example II.A.3.b.) was isolated; the HindIII-XhoI fragment of pVDCCIII/3'.1 (containing nt 4493 to 7635, SEQ ID No. 1, plus the XhoI site of the adapter) (Example II.A.3.c.) was isolated; and the plasmid vector, pcDNA1, was digested with EcoRV and XhoI and isolated on an agarose gel. The three DNA fragments were ligated and MC1061-P3 (Invitrogen, San Diego, Calif.) was transformed. Isolated clones were analyzed by restriction mapping and DNA sequencing and PVDCCIII (A) was identified which had the fragments correctly ligated together: DraI-HindIII, HindIII-XhoI, XhoI-EcoRV with the blunt-end DraI and EcoRV site ligating together to form the circular plasmid.

The amino-terminus of the $\alpha_{1D}$ subunit is encoded by the seven consecutive 5' methionine codons (nt 511 to 531, SEQ ID No. 1). This 5' portion plus nt 532 to 537, encoding two lysine residues, were deleted from pVDCCIII(A) and replaced with an efficient ribosomal binding site (5'-ACCACC-3') to form pVDCCIII.RBS(A). Expression experiments in which transcripts of this construct were injected into *Xenopus laevis* oöcytes did not result in an enhancement in the recombinant voltage-dependent calcium channel expression level relative to the level of expression in oöcytes injected with transcripts of pVDCCIII(A).

B. Isolation of DNA Encoding the $\alpha_{1C}$ Subunit

1. Reference List of Partial $\alpha_{1C}$ cDNA Clones

Numerous $\alpha_{1C}$-specific cDNA clones were isolated in order to characterize the $\alpha_{1C}$ coding sequence, the $\alpha_{1C}$ initiation of translation, and an alternatively spliced region of $\alpha_{1C}$. SEQ ID No. 3 sets forth the characterized $\alpha_{1C}$ coding sequence (nt 1 to 5904) and deduced amino acid sequence. SEQ ID No. 4 and No. 5 encode two possible amino terminal ends of the $\alpha_{1C}$ protein. SEQ ID No. 6 encodes an alternative exon for the IV S3 transmembrane domain. Shown below is a list of clones used to characterize the $\alpha_{1C}$ sequence and the nucleotide position of each clone relative to the characterized $\alpha_{1C}$ sequence (SEQ ID No. 3). The isolation and characterization of these cDNA clones are described below (Example II.B.2).

| | | |
|---|---|---|
| IMR32 | 1.66 | nt 1 to 916, SEQ ID No. 3 |
| | | nt 1 to 132, SEQ ID No. 4 |
| IMR32 | 1.157 | nt 1 to 873, SEQ ID No. 3 |
| | | nt 1 to 89, SEQ ID No. 5 |
| IMR32 | 1.67 | nt 50 to 1717, SEQ ID No. 3 |
| *IMR32 | 1.86 | nt 1366 to 2583, SEQ ID No. 3 |
| @1.16G | | nt 758 to 867, SEQ ID No. 3 |
| IMR32 | 1.37 | nt 2804 to 5904, SEQ ID No. 3 |
| CNS | 1.30 | nt 2199 to 3903, SEQ ID No. 3 |
| | | nt 1 to 84 of alternative exon, SEQ ID No. 6 |
| IMR32 | 1.38 | nt 2448 to 4702, SEQ ID No. 3 |
| | | nt 1 to 84 of alternative exon, SEQ ID No. 6 |

*IMR32 1.86 has a 73 nt deletion compared to the rabbit cardiac muscle calcium channel $\alpha_1$ subunit cDNA sequence.
@1.16G is an $\alpha_{1C}$ genomic clone.

2. Isolation and Characterization of Clones Described in Example II.B.1.

a. CNS 1.30

Approximately $1 \times 10^6$ recombinants of the human thalamus cDNA library No. 6 (Example I.B.6.) were screened with fragments of the rabbit skeletal muscle calcium channel $\alpha_1$ cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes $\alpha_{1C}$-specific sequence nt 2199 to 3903 (SEQ ID No. 3) followed by nt 1 to 84 of one of two identified alternative $\alpha_{1C}$ exons (SEQ ID No. 6). 3' of SEQ ID No. 6, CNS 1.30 contains an intron and, thus, CNS 1.30 encodes a partially spliced $\alpha_{1C}$ transcript.

b. 1.16G

Approximately $1 \times 10^6$ recombinants of a λEMBL3-based human genomic DNA library (Cat # HL1006d Clontech Corp., Palo Alto, Calif.) were screened using a rabbit skeletal muscle cDNA fragment (nt −78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes $\alpha_{1C}$-specific sequence as described in Example II.B.1.

c. IMR32 1.66 and IMR32 1.67

Approximately 1×10⁶ recombinants of IMR32 cDNA library #5 (Example I.B.5.) were screened with a 151 bp KpnI-SacI fragment of 1.16G (Example II.B.2.b.) encoding $\alpha_{1C}$ sequence (nt 758 to 867, SEQ ID No. 3). The hybridization was performed using standard hybridization conditions (Example I.C.). The filters were then washed in 0.5× SSPE at 65° C. Of the positive plaques, IMR32 1.66 and IMR32 1.67 were identified. The hybridizing plaques were purified, restriction mapped, subcloned, and characterized by DNA sequencing. Two of these cDNA clones, IMR32 1.66 and 1.67, encode $\alpha_{1C}$ subunits as described (Example II.B.1.). In addition, IMR32 1.66 encodes a partially spliced $\alpha_{1C}$ transcript marked by a GT splice donor dinucleotide beginning at the nucleotide 3' of nt 916 (SEQ ID No. 3). The intron sequence within 1.66 is 101 nt long. IMR32 1.66 encodes the $\alpha_{1C}$ initiation of translation, nt 1 to 3 (SEQ ID No. 3) and 132 nt of 5' untranslated sequence (SEQ ID No. 4) precede the start codon in IMR32 1.66.

d. IMR32 1.37 and IMR32 1.38

Approximately 2×10⁶ recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of the clones, IMR32 1.37 and IMR32 1.38 encode $\alpha_{1C}$-specific sequences as described in Example II.B.1.

DNA sequence comparison of IMR32 1.37 and IMR32 1.38 revealed that the $\alpha_{1C}$ transcript includes two exons that encode the IVS3 transmembrane domain. IMR32 1.37 has a single exon, nt 3904 to 3987 (SEQ ID No. 3) and IMR32 1.38 appears to be anomalously spliced to contain both exons juxtaposed, nt 3904 to 3987 (SEQ ID No. 3) followed by nt 1 to 84 (SEQ ID No. 6). The alternative splice of the $\alpha_{1C}$ transcript to contain either of the two exons encoding the IVS3 region was confirmed by comparing the CNS 1.30 sequence to the IMR32 1.37 sequence. CNS 1.30 contains nt 1 to 84 (SEQ ID No. 6) preceded by the identical sequence contained in IMR32 1.37 for nt 2199 to 3903 (SEQ ID No. 3). As described in Example II.B.2.a., an intron follows nt 1 to 84 (SEQ ID No. 6). Two alternative exons have been spliced adjacent to nt 3903 (SEQ ID No. 3) represented by CNS 1.30 and IMR32 1.37.

e. IMR32 1.86

IMR32 cDNA library #1 (Example I.B.1.) was screened in duplicate using oligonucleotide probes 90-9 (nt 1462 to 1491, SEQ ID No. 3) and 90-12 (nt 2496 to 2520, SEQ ID No. 3). These oligonucleotide probes were chosen in order to isolate a clone that encodes the $\alpha_{1C}$ subunit between the 3' end of IMR32 1.67 (nt 1717, SEQ ID No. 3) and the 5' end of CNS 1.30 (nt 2199, SEQ ID No. 3). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes $\alpha_{1C}$ sequences as described in Example II.B.1. Characterization by DNA sequencing revealed that IMR32 1.86 contains a 73 nt deletion compared to the DNA encoding rabbit cardiac muscle calcium channel $\alpha_1$ subunit [Mikami et al. (1989) *Nature* 340:230], nt 2191 to 2263. These missing nucleotides correspond to nt 2176–2248 of SEQ ID No. 3.

Because the 5'-end of CNS 1.30 overlaps the 3'-end of IMR32 1.86, some of these missing nucleotides, i.e., nt 2205–2248 of SEQ ID No. 3, are accounted for by CNS 1.30. The remaining missing nucleotides of the 73 nucleotide deletion in IMR32 1.86 (i.e., nt 2176–2204 SEQ ID No. 3) were determined by PCR analysis of dbcAMP-induced IMR32 cell RNA. The 73 nt deletion is a frame-shift mutation and, thus, needs to be corrected. The exact human sequence through this region, (which has been determined by the DNA sequence of CNS 1.30 and PCR analysis of IMR32 cell RNA) can be inserted into IMR32 1.86 by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding $\alpha_{1C}$ nt 50 to 774 (SEQ ID No. 3). The hybridization was performed using standard hybridization conditions (Example I. C.). The filters were washed under high stringency (Example I.C.). One of the positive plaques identified was IMR32 1.157. This plaque was purified, the insert was restriction mapped and subcloned to a standard plasmid vector pGEM7Z (Promega, Madison, Wis.). The DNA was characterized by sequencing. IMR32 1.157 appears to encodes an alternative 5' portion of the $\alpha_1$ sequence beginning with nt 1 to 89 (SEQ ID No. 5) and followed by nt 1 to 873 (SEQ ID No. 3). Analysis of the 1.66 and 1.157 5' sequence is described below (Example II.B.3.).

3. Characterization of the $\alpha_{1C}$ Initiation of Translation Site

Portions of the sequences of IMR32 1.157 (nt 57 to 89, SEQ ID No. 5; nt 1 to 67, SEQ ID No. 3), IMR32 1.66 (nt 100 to 132, SEQ ID No. 4; nt 1 to 67, SEQ ID No. 3), were compared to the rabbit lung CaCB-receptor cDNA sequence, nt −33 to 67 [Biel et al. (1990) *FEBS Lett.* 269:409]. The human sequences are possible alternative 5' ends of the $\alpha_{1C}$ transcript encoding the region of initiation of translation. IMR32 1.66 closely matches the CaCB receptor cDNA sequence and diverges from the CaCB receptor cDNA sequence in the 5' direction beginning at nt 122 (SEQ ID No. 4). The start codon identified in the CaCB receptor cDNA sequence is the same start codon used to describe the $\alpha_{1C}$ coding sequence, nt 1 to 3 (SEQ ID No. 3). The functional significance of the IMR32 1.157 sequence, nt 1 to 89 (SEQ ID No. 5), is not clear. Chimeras containing sequence between 1.157 and the $\alpha_{1C}$ coding sequence can be constructed and functional differences can be tested.

C. Isolation of Partial cDNA Clones Encoding the $\alpha_{1B}$ Subunit and Construction of a Full-length Clone A human basal ganglia cDNA library was screened with the rabbit skeletal muscle $\alpha_1$ subunit cDNA fragments (see Example II.A.2.a for description of fragments) under low stringency conditions. One of the hybridizing clones was used to screen an IMR32 cell cDNA library to obtain additional partial $\alpha_{1B}$ cDNA clones, which were in turn used to further screen an IMR32 cell cDNA library for additional partial cDNA clones. One of the partial IMR32 $\alpha_{1B}$ clones was used to screen a human hippocampus library to obtain a partial $\alpha_{1B}$ clone encoding the 3' end of the $\alpha_{1B}$ coding sequence. The sequence of some of the regions of the partial cDNA clones was compared to the sequence of products of PCR analysis of IMR32 cell RNA to determine the accuracy of the cDNA sequences.

PCR analysis of IMR32 cell RNA and genomic DNA using oligonucleotide primers corresponding to sequences located 5' and 3' of the STOP codon of the DNA encoding the $\alpha_{1B}$ subunit revealed an alternatively spliced $\alpha_{1B}$-encoding mRNA in IMR32 cells. This second mRNA product is the result of differential splicing of the $\alpha_{1B}$ subunit transcript to include another exon that is not present in the mRNA corresponding to the other 3' $\alpha_{1B}$ cDNA sequence that was initially isolated. To distinguish these splice variants of the $\alpha_{1B}$ subunit, the subunit encoded by a DNA sequence corresponding to the form containing the additional exon is referred to as $\alpha_{1B-1}$ (SEQ ID No. 7), whereas the subunit encoded by a DNA sequence corresponding to the form lacking the additional exon is referred to as $\alpha_{1B-2}$ (SEQ ID No. 8). The sequence of $\alpha_{1B-1}$ diverges from that of $\alpha_{1B-2}$ beginning at nt 6633 (SEQ ID No. 7). Following the sequence of the additional exon in $\alpha_{1B-1}$ (nt 6633–6819; SEQ ID No. 7), the $\alpha_{1B-1}$ and $\alpha_{1B-2}$ sequences are identical (i.e., nt 6820–7362 in SEQ ID No. 7 and nt 6633–7175 in SEQ ID No. 8). SEQ ID No. 7 and No. 8 set forth 143 nt of 5' untranslated sequence (nt 1–143) as well as 202 nt of 3' untranslated sequence (nt 7161–7362, SEQ ID No. 7) of the DNA encoding $\alpha_{1B-1}$ and 321 nt of 3' untranslated sequence (nt 6855–7175, SEQ ID No. 8) of the DNA encoding $\alpha_{1B-2}$.

PCR analysis of the IS6 region of the $\alpha_{1B}$ transcript revealed what appear to be additional splice variants based on multiple fragment sizes seen on an ethidium bromide-stained agarose gel containing the products of the PCR reaction.

A full-length $\alpha_{1B-1}$ cDNA clone designated pcDNA-$\alpha_{1B-1}$ was prepared in an eight-step process as follows.

Step 1

The SacI restriction site of pGEM3 (Promega, Madison, Wis.) was destroyed by digestion at the SacI site, producing blunt ends by treatment with T4 DNA polymerase, and religation. The new vector was designated pGEMΔSac.

Step 2

Fragment 1 (HindIII/KpnI; nt 2337 to 4303 of SEQ ID No. 7) was ligated into HindIII/KpnI digested pGEM3ΔSac to produce pα1.177HK.

Step 3

Fragment 1 has a 2 nucleotide deletion (nt 3852 and 3853 of SEQ ID No. 7). The deletion was repaired by inserting a PCR fragment (fragment 2) of IMR32 RNA into pα1.177HK. Thus, fragment 2 (NarI/KpnI; nt 3828 to 4303 of SEQ ID No. 7) was inserted into NarI/KpnI digested pα1.177HK replacing the NarI/KpnI portion of fragment 1 and producing pα1.177HK/PCR.

Step 4

Fragment 3 (KpnI/KpnI; nt 4303 to 5663 of SEQ ID No. 7) was ligated into KpnI digested pα1.177HK/PCR to produce pα1B5'K.

Step 5

Fragment 4 (EcoRI/HindIII; EcoRI adaptor plus nt 1 to 2337 of SEQ ID No. 7) and fragment 5 (HindIII/XhoI fragment of pα1B5'K; nt 2337 to 5446 of SEQ ID No. 7) were ligated together into EcoRI/XhoI digested pcDNA1 (Invitrogen, San Diego, Calif.) to produce pα1B5'.

Step 6

Fragment 6 (EcoRI/EcoRI; EcoRI adapters on both ends plus nt 5749 to 7362 of SEQ ID No. 7) was ligated into EcoRI digested pBluescript II KS (Stratagene, La Jolla, Calif.) with the 5' end of the fragment proximal to the KpnI site in the polylinker to produce pα1.230.

Step 7

Fragment 7 (KpnI/XhoI; nt 4303 to 5446 of SEQ ID No. 7), and fragment 8 (XhoI/CspI; nt 5446 to 6259 of SEQ ID No. 7) were ligated into KpnI/CspI digested pα1.230 (removes nt 5749 to 6259 of SEQ ID No. 7 that was encoded in pα1.230 and maintains nt 6259 to 7362 of SEQ ID No. 7) to produce pα1B3'.

Step 8

Fragment 9 (SphI/XhoI; nt 4993 to 5446 of SEQ ID No. 7) and fragment 10 (XhoI/XbaI of pα1B3'; nt 5446 to 7319 of SEQ ID No. 7) were ligated into SphI/XbaI digested pα1B5' (removes nt 4993 to 5446 of SEQ ID No. 7 that were encoded in pα1B5' and maintains nt 1 to 4850 of SEQ ID No. 7) to produce pcDNAα$_{1B-1}$.

The resulting construct, pcDNAα$_{1B-1}$, contains, in pCDNA1, a full-length coding region encoding $\alpha_{1B-1}$ (nt 144–7362, SEQ ID No. 7), plus 5' untranslated sequence (nt 1–143, SEQ ID No. 7) and 3' untranslated sequence (nt 7161–7319, SEQ ID No. 7) under the transcriptional control of the CMV promoter.

D. Isolation of DNA Encoding Human Calcium Channel $\alpha_{1A}$ Subunits

1. Isolation of Partial Clones

DNA clones encoding portions of human calcium channel $\alpha_{1A}$ subunits were obtained by hybridization screening of human cerebellum cDNA libraries and nucleic acid amplification of human cerebellum RNA. Clones corresponding to the 3' end of the $\alpha_{1A}$ coding sequence were isolated by screening $1 \times 10^6$ recombinants of a randomly primed cerebellum cDNA library (size-selected for inserts greater than 2.8 kb in length) under low stringency conditions (6×SSPE, 5×Denhart's solution, 0.2% SDS, 200 μg/ml sonicated herring sperm DNA, 42° C.) with oligonucleotide 704 containing nt 6190–6217 of the rat $\alpha_{1A}$ coding sequence [Starr et al. (1992) *Proc. Natl. Acad. Sci. U.S.A.* 88:5621–5625]. Washes were performed under low stringency conditions. Several clones that hybridized to the probe (clones 60 1.251–α1.259 and α1.244) were purified and characterized by restriction enzyme mapping and DNA sequence analysis. At least two of the clones, α1.244 and α1.254, contained a translation termination codon. Although clones α1.244 and α1.254 are different lengths, they both contain a sequence of nucleotides that corresponds to the extreme 3' end of the $\alpha_{1A}$ transcript, i.e., the two clones overlap. These two clones are identical in the region of overlap, except, clone α1.244 contains a 5 and 12 nucleotides that are not present in α1.254.

To obtain additional $\alpha_{1A}$-encoding clones, $1 \times 10^6$ recombinants of a randomly primed cerebellum cDNA library (size-selected for inserts ranging from 1.0 to 2.8 kb in length) was screened for hybridization to three oligonucleotides: oligonucleotide 701 (containing nucleotides 2288–2315 of the rat $\alpha_{1A}$ coding sequence), oligonucleotide 702 (containing nucleotides 3559–3585 of the rat $\alpha_{1A}$ coding sequence) and oligonucleotide 703 (containing nucleotides 4798–4827 of the rat $\alpha_{1A}$ coding sequence). Hybridization and washes were performed using the same conditions as used for the first screening with oligonucleotide 704, except that washes were conducted at 45° C. Twenty clones (clones α1.269–α1.288) hybridized to the probe. Several clones were plaque-purified and characterized by restriction enzyme mapping and DNA sequence analysis. One clone, α1.279, contained about 170 nucleotides that is not present in other clones corresponding to the same region of the coding sequence. This region may be present in other splice variant. None of the clones contained a translation intiation codon.

To obtain clones corresponding to the 5' end of the human $\alpha_{1A}$ coding sequence, another cerebellum cDNA library was prepared using oligonucleotide 720 (containing nucleotides 2485–2510 of SEQ ID No. 22 to specifically prime first-strand cDNA synthesis. The library ($8 \times 10^5$ recombinants) was screened for hybridization to three oligonucleotides: oligonucleotide 701, oligonucleotide 726 (containing nucleotides 2333–2360 of the rat $\alpha_{1A}$ coding sequence) and oligonucleotide 700 (containing nucleotides 767–796 of the rat $\alpha_{1A}$ coding sequence) under low stringency hybridization and washing conditions. Approximately 50 plaques hybridized to the probe. Hybridizing clones α1.381–α1.390 were plaque-purified and characterized by restriction enzyme maping and DNA sequence analysis. At least one of the clones, α1.381, contained a translation initiation codon.

Alignment of the sequences of the purified clones revealed that the sequences overlapped to comprise the entire $\alpha_{1A}$ coding sequence. However, not all the overlapping sequences of partial clones contained convenient enzyme restriction sites for use in ligating partial clones to construct a full-length $\alpha_{1A}$ coding sequence. To obtain DNA fragments containing convenient restriction enzyme sites that could be used in constructing a full-length $\alpha_{1A}$ DNA, cDNA was synthesized from RNA isolated from human cerebellum tissue and subjected to nucleic acid amplification. The oligonucleotides used as primers corresponded to human $\alpha_{1A}$ coding sequence located 5' and 3' of selected restriction enzyme sites. Thus, in the first amplification reaction, oligonucleotides 753 (containing nucleotides 2368–2391 of SEQ ID No. 22) and 728 (containing nucleotides 3179–3202 of SEQ ID No. 22) were used as the primer pair. To provide a sufficient amount of the desired DNA fragment, the product of this amplification was reamplified using oligonucleotides 753 and 754 (containing nucleotides 3112–3135 of SEQ ID No. 22 as the primer pair. The resulting product was 768 bp in length. In the second amplification reaction, oligonucleotides 719 (containing nucleotides 4950–4975 of SEQ ID No. 22 and 752 (containing nucleotides 5647–5670 of SEQ ID No. 22) were used as the primer pair. To provide a sufficient amount of the desired second DNA fragment, the product of this amplification was reamplified using oligonucleotides 756 (containing nucleotides 5112–5135 of SEQ ID No. 22) and 752 as the primer pair. The resulting product was 559 bp in length.

2. Construction of Full-Length $\alpha_{1A}$ Coding Sequences

Portions of clone α1.381, the 768-bp nucleic acid amplification product, clone α1.278, the 559-bp nucleic acid amplification product, and clone α1.244 were ligated at convenient restriction sites to generate a full-length $\alpha_{1A}$ coding sequence referred to as $\alpha_{1A-1}$.

Comparison of the results of sequence analysis of clones α1.244 and α1.254 indicated that the primary transcript of the $\alpha_{1A}$ subunit gene is alternatively spliced to yield at least two variant mRNAs encoding different forms of the $\alpha_{1A}$ subunit. One form, $\alpha_{1A-1}$, is encoded by the sequence shown in SEQ ID No. 22. The sequence encoding a second form, $\alpha_{1A-2}$, differs from the $\alpha_{1A-1}$-encoding sequence at the 3' end in that it lacks a 5-nt sequence found in clone α1.244 (nucleotides 7035–7039 of SEQ ID No. 22). This deletion shifts the reading frame and introduces a translation termination codon resulting in an $\alpha_{1A-2}$ coding sequence that encodes a shorter $\alpha_{1A}$ subunit than that encoded by the $\alpha_{1A-1}$ splice variant. Consequently, a portion of the 3' end of the $\alpha_{1A-1}$ coding sequence is actually 3' untranslated sequence in the $\alpha_{1A-2}$ DNA. The complete sequence of $\alpha_{1A-12}$, which can be constructed by ligating portions of clone α1.381, the 768-bp nucleic acid amplification product, clone α1.278, the 559-bp nucleic acid amplification product and clone α1.254, is set forth in SEQ ID No. 23.

E. Isolation of DNA Encoding the $\alpha_{1E}$ Subunit

DNA encoding $\alpha_{1E}$ subunits of the human calcium channel were isolated from human hippocampus libraries. The selected clones sequenced. DNA sequence analysis of DNA clones encoding the $\alpha_{1E}$ subunit indicated that at least two alternatively spliced forms of the same $\alpha_{1E}$ subunit primary transcript are expressed. One form has the sequence set forth in SEQ ID No. 24 and was designated $\alpha_{1E-1}$ and the other was designated $\alpha_{1E-3}$, which has the sequence obtained by inserting SEQ ID No. 25 between nucleotides 2405 and 2406 of SEQ ID No. 24. The resulting sequence of $\alpha_{1E-3}$ is set forth in SEQ ID No. 27.

The subunit designated $\alpha_{1E-1}$ has a calculated molecular weight of 254,836 and the subunit designated $\alpha_{1E-3}$ has a calculated molecular weight of 257,348. $\alpha_{1E-3}$ has a 19 amino acid insertion (encoded by SEQ ID No. 25) relative to $\alpha_{1E-1}$ in the region that appears to be the cytoplasmic loop between transmembrane domains IIS6 and IIIS1.

Example III

Isolation of cDNA Clones Encoding the Human Neuronal Calcium Channel $\beta_1$ Subunit A. Isolation of Partial cDNA Clones Encoding the β Subunit and Construction of a Full-length Clone Encoding the $\beta_1$ Subunit A human hippocampus cDNA library was screened with the rabbit skeletal muscle calcium channel $\beta_1$ subunit cDNA fragment (nt 441 to 1379) [for isolation and sequence of the rabbit skeletal muscle calcium channel $\beta_1$ subunit cDNA, see U.S. patent application Ser. No. 482,384 or Ruth et al. (1989) *Science* 245:1115] using standard hybridization conditions (Example I.C.). A portion of one of the hybridizing clones was used to rescreen the hippocampus library to obtain additional cDNA clones. The cDNA inserts of hybridizing clones were characterized by restriction mapping and DNA sequencing and compared to the rabbit skeletal muscle calcium channel $\beta_1$ subunit cDNA sequence.

Portions of the partial $\beta_1$ subunit cDNA clones were ligated to generate a full-length clone encoding the entire $\beta_1$ subunit. SEQ ID No. 9 shows the $\beta_1$ subunit coding sequence (nt 1–1434) as well as a portion of the 3' untranslated sequence (nt 1435–1546). The deduced amino acid sequence is also provided in SEQ ID No. 9. In order to perform expression experiments, full-length $\beta_1$ subunit cDNA clones were constructed as follows.

Step 1

DNA fragment 1 (~800 bp of 5' untranslated sequence plus nt 1–277 of SEQ ID No. 9) was ligated to DNA fragment 2 (nt 277–1546 of SEQ ID No. 9 plus 448 bp of intron sequence) and cloned into pGEM7Z. The resulting plasmid, pβ1-1.18, contained a full-length $\beta_1$ subunit clone that included a 448-bp intron.

Step 2

To replace the 5' untranslated sequence of pβ1-1.18 with a ribosome binding site, a double-stranded adapter was synthesized that contains an EcoRI site, sequence encoding a ribosome binding site (5'-ACCACC-3') and nt 1–25 of SEQ ID No. 9. The adapter was ligated to SmaI-digested pβ1-1.18, and the products of the ligation reaction were digested with EcoRI.

Step 3

The EcoRI fragment from step 2 containing the EcoRI adapter, efficient ribosome binding site and nt 1–1546 of SEQ ID No. 9 plus intron sequence was cloned into a plasmid vector and designated pβ1-1.18RBS. The EcoRI fragment of pβ1-1.18RBS was subcloned into EcoRI-digested pcDNA1 with the initiation codon proximal to CMV promoter to form pHBCaCHβ$_{1a}$RBS(A).

Step 4

To generate a full-length clone encoding the $\beta_1$ subunit lacking intron sequence, DNA fragment 3 (nt 69–1146 of SEQ ID No. 9 plus 448 bp of intron sequence followed by nt 1147–1546 of SEQ ID No. 9), was subjected to site-directed mutagenesis to delete the intron sequence, thereby yielding pβ1(−). The EcoRI-XhoI fragment of pβ1-1.18RBS (containing of the ribosome binding site and nt 1–277 of SEQ ID No. 9) was ligated to the XhoI-EcoRI fragment of pβ1(−) (containing of nt 277–1546 of SEQ ID No. 9) and cloned into pcDNA1 with the initiation of translation proximal to the CMV promoter. The resulting expression plasmid was designated pHBCaCHβ$_{1b}$RBS(A).

B. Splice Variant β$_{1-3}$

DNA sequence analysis of the DNA clones encoding the β$_1$ subunit indicated that in the CNS at least two alternatively spliced forms of the same human β$_1$ subunit primary transcript are expressed. One form is represented by the sequence shown in SEQ ID No. 9 and is referred to as β$_{1-2}$. The sequences of β$_{1-2}$ and the alternative form, β$_{1-3}$, diverge at nt 1334 (SEQ ID No. 9). The complete β$_{1-3}$ sequence (nt 1–1851), including 3' untranslated sequence (nt 1795–1851), is set forth in SEQ ID No. 10.

Example IV
Isolation of cDNA Clones Encoding the Human Neuronal Calcium Channel α$_2$-subunit A. Isolation of cDNA Clones The complete human neuronal α$_2$ coding sequence (nt 35–3307) plus a portion of the 5' untranslated sequence (nt 1 to 34) as well as a portion of the 3' untranslated sequence (nt 3308–3600) is set forth in SEQ ID No. 11.

To isolate DNA encoding the human neuronal α$_2$ subunit, human α$_2$ genomic clones first were isolated by probing human genomic Southern blots using a rabbit skeletal muscle calcium channel α$_2$ subunit cDNA fragment [nt 43 to 272, Ellis et al. (1988) *Science* 240:1661]. Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a λgt11 library containing human genomic EcoRI fragments ranging from 2.2 kb to 4.3 kb. The library was screened as described above using the rabbit α$_2$ probe, hybridizing clones were isolated and characterized by DNA sequencing. HGCaCHα2.20 contained the 3.5 kb fragment and HGCaCHα2.9 contained the 3.0 kb fragment.

Restriction mapping and DNA sequencing revealed that HGCaCHα2.20 contains an 82 bp exon (nt 130 to 211 of the human α$_2$ coding sequence, SEQ ID No. 11) on a 650 bp PstI-XbaI restriction fragment and that HGCaCHα2.9 contains 105 bp of an exon (nt 212 to 316 of the coding sequence, SEQ ID No. 11) on a 750 bp XbaI-BGlII restriction fragment. These restriction fragments were used to screen the human basal ganglia cDNA library (Example II.C.2.a.). HBCaCHα2.1 was isolated (nt 29 to 1163, SEQ ID No. 11) and used to screen a human brain stem cDNA library (ATCC Accession No. 37432) obtained from the American Type Culture Collection, 12301 Parklawn Drive, Rockville, Md. 20852. Two clones were isolated, HBCaCHα2.5 (nt 1 to 1162, SEQ ID No. 11) and HBCaCHα2.8 (nt 714 to 1562, SEQ ID No. 11, followed by 1600 nt of intervening sequence). A 2400 bp fragment of HBCaCHα2.8 (beginning at nt 759 of SEQ ID No. 11 and ending at a SmaI site in the intron) was used to rescreen the brain stem library and to isolate HBCaCHα2.11 (nt 879 to 3600, SEQ ID No. 11). Clones HBCaCHα2.5 and HBCaCHα2.11 overlap to encode an entire human brain α$_2$ protein.

B. Construction of pHBCaCHα$_2$A

To construct pHBCaCHα$_2$A containing DNA encoding a full-length human calcium channel α$_2$ subunit, an (EcoRI)-PvuII fragment of HBCaCHα2.5 (nt 1 to 1061, SEQ ID No. 11, EcoRI adapter, PvuII partial digest) and a PvuII-PstI fragment of HBCaCHα2.11 (nt 1061 to 2424 SEQ ID No. 11; PvuII partial digest) were ligated into EcoRI-PstI-digested pIBI24 (Stratagene, La Jolla, Calif.). Subsequently, an (EcoRI)-PstI fragment (nt 1 to 2424 SEQ ID No. 11) was isolated and ligated to a PstI-(EcoRI) fragment (nt 2424 to 3600 SEQ ID No. 11) of HBCaCHα2.11 in EcoRI-digested pIBI24 to produce DNA, HBCaCHα2, encoding a full-length human brain α$_2$ subunit. The 3600 bp EcoRI insert of HBCaCHα2 (nt 1 to 3600, SEQ ID No. 11) was subcloned into pcDNA1 (pHBCaCHα2A) with the methionine initiating codon proximal to the CMV promoter. The 3600 bp EcoRI insert of HBCaCHα2 was also subcloned into pSV2dHFR [Subramani et al. (1981). *Mol. Cell. Biol.* 1:854–864] which contains the SV40 early promoter, mouse dihydrofolate reductase (dhfr) gene, SV40 polyadenylation and splice sites and sequences required for maintenance of the vector in bacteria.

Example V
Differential Processing of the Human β$_1$ Transcript and the Human α$_2$ Transcript A. Differential Processing of the β$_1$ Transcript PCR analysis of the human β$_1$ transcript present in skeletal muscle, aorta, hippocampus and basal ganglia, and HEK 293 cells revealed differential processing of the region corresponding to nt 615–781 of SEQ ID No. 9 in each of the tissues. Four different sequences that result in five different processed transcripts through this region were identified. The β$_1$ transcripts from the different tissues contained different combinations of the four sequences, except for one of the β$_1$ transcripts expressed in HEK 293 cells (β$_{1-5}$) which lacked all four sequences.

None of the β$_1$ transcripts contained each of the four sequences; however, for ease of reference, all four sequences are set forth end-to-end as a single long sequence in SEQ ID No. 12. The four sequences that are differentially processed are sequence 1 (nt 14–34 in SEQ ID No. 12), sequence 2 (nt 35–55 in SEQ ID No. 12), sequence 3 (nt 56–190 in SEQ ID No. 12) and sequence 4 (nt 191–271 in SEQ ID No. 12). The forms of the β$_1$ transcript that have been identified include: (1) a form that lacks sequence 1 called β$_{1-1}$ (expressed in skeletal muscle), (2) a form that lacks sequences 2 and 3 called β$_{1-2}$ (expressed in CNS), (3) a form that lacks sequences 1, 2 and 3 called β$_{1-4}$ (expressed in aorta and HEK cells) and (4) a form that lacks sequences 1–4 called β$_{1-5}$ (expressed in HEK cells). Additionally, the β$_{1-4}$ and β$_{1-5}$ forms contain the guanine nucleotide (nt 13 in SEQ ID No. 12) which is absent in the β$_{1-1}$ and β$_{1-2}$ forms. The sequences of these splice variants designated β$_{1-1}$, β$_{1-2}$, β$_{1-3}$, β$_{1-4}$ and β$_{1-5}$ are set forth in Sequence ID Nos. 32, 9, 10, 33 and 34, respectively.

B. Differential Processing of Transcripts Encoding the α$_2$ Subunit

The complete human neuronal α$_2$ coding sequence (nt 35–3307) plus a portion of the 5' untranslated sequence (nt 1 to 34) as well as a portion of the 3' untranslated sequence (nt 3308–3600) is set forth as SEQ ID No. 11.

PCR analysis of the human α$_2$ transcript present in skeletal muscle, aorta, and CNS revealed differential processing of the region corresponding to nt 1595–1942 of SEQ ID No. 11 in each of the tissues.

The analysis indicated that the primary transcript of the genomic DNA that includes the nucleotides corresponding to nt 1595–1942 also includes an additional sequence (SEQ ID No. 13: 5'CCTATTGGTGTAGGTATACCAACAAT-TAATTTAAGAAAAAGGAGACCCAATATCCAG 3') inserted between nt 1624 and 1625 of SEQ ID No. 11. Five alternatively spliced variant transcripts that differ in the presence or absence of one to three different portions of the region of the primary transcript that includes the region of nt 1595–1942 of SEQ ID No. 11 plus SEQ ID No. 13 inserted between nt 1624 and 1625 have been identified. The five $\alpha_2$-encoding transcripts from the different tissues include different combinations of the three sequences, except for one of the $\alpha_2$ transcripts expressed in aorta which lacks all three sequences. None of the $\alpha_2$ transcripts contained each of the three sequences. The sequences of the three regions that are differentially processed are sequence 1 (SEQ ID No. 13), sequence 2 (5' AACCCCAAATCTCAG 3', which is nt 1625–1639 of SEQ ID No. 11), and sequence 3 (5' CAAAAAAGGGCAAAATGAAGG 3', which is nt 1908–1928 of SEQ ID No. 11). The five $\alpha_2$ forms identified are (1) a form that lacks sequence 3 called $\alpha_{2a}$ (expressed in skeletal muscle), (2) a form that lacks sequence 1 called $\alpha_{2b}$ (expressed in CNS), (3) a form that lacks sequences 1 and 2 called $\alpha_{2c}$ expressed in aorta), (4) a form that lacks sequences 1, 2 and 3 called $\alpha_{2d}$ (expressed in aorta) and (5) a form that lacks sequences 1 and 3 called $\alpha_{2e}$ (expressed in aorta). The sequences of each of these subunits are set forth in sequence ID NOs. 11 ($\alpha_{2b}$), SEQ ID NO. 28 ($\alpha_{2a}$) SEQ ID NO. 29 ($\alpha_{2c}$), SEQ ID NO. 30 ($\alpha_{2d}$), and SEQ ID NO. 31 ($\alpha_{2e}$).

Example VI
Isolation of DNA Encoding a Calcium Channel γ Subunit from a Human Brain cDNA Library
A. Isolation of DNA Encoding the γ Subunit Approximately 1×10⁶ recombinants from a λgt11-based human hippocampus cDNA library (Clontech catalog #HL1088b, Palo Alto, Calif.) were screened by hybridization to a 484 bp sequence of the rabbit skeletal muscle calcium channel γ subunit cDNA (nucleotides 621–626 of the coding sequence plus 438 nucleotides of 3'-untranslated sequence) contained in vector γJ10 [Jay, S. et al. (1990). *Science* 248:490–492]. Hybridization was performed using moderate stringency conditions (20% deionized formamide, 5×Denhardt's, 6×SSPE, 0.2% SDS, 20 µg/ml herring sperm DNA, 42° C.) and the filters were washed under low stringency (see Example I.C.). A plaque that hybridized to this probe was purified and insert DNA was subcloned into pGEM7Z. This cDNA insert was designated γ1.4.
B. Characterization of γ1.4

γ1.4 was confirmed by DNA hybridization and characterized by DNA sequencing. The 1500 bp SstI fragment of γ1.4 hybridized to the rabbit skeletal muscle calcium channel γ subunit cDNA γJ10 on a Southern blot. SEQ analysis of this fragment revealed that it contains of approximately 500 nt of human DNA sequence and ~1000 nt of λgt11 sequence (included due to apparent destruction of one of the EcoRI cloning sites in λgt11). The human DNA sequence contains of 129 nt of coding sequence followed immediately by a translational STOP codon and 3' untranslated sequence (SEQ ID No. 14).

To isolate the remaining 5' sequence of the human γ subunit cDNA, human CNS cDNA libraries and/or preparations of mRNA from human CNS tissues can first be assayed by PCR methods using oligonucleotide primers based on the γ cDNA-specific sequence of γ14. Additional human neuronal γ subunit-encoding DNA can isolated from cDNA libraries that, based on the results of the PCR assay, contain γ-specific amplifiable cDNA. Alternatively, cDNA libraries can be constructed from mRNA preparations that, based on the results of PCR assays, contain γ-specific amplifiable transcripts. Such libraries are constructed by standard methods using oligo dT to prime first-strand cDNA synthesis from poly A⁺ RNA (see Example I.B.). Alternatively, first-strand cDNA can be specified by priming first-strand cDNA synthesis with a δ cDNA-specific oligonucleotide based on the human DNA sequence in γ1.4. A cDNA library can then be constructed based on this first-strand synthesis and screened with the γ-specific portion of γ1.4.

Example VII
Isolation of cDNA Clones Encoding the Human Neuronal Ca Channel $\beta_2$ Subunit
Isolation of DNA Encoding Human Calcium Channel $\beta_2$ Subunits Sequencing of clones isolated as described in Example III revealed a clone encoding a substantial portion of a human neuronal calcium channel $\beta_2$ subunit (designated $\beta_{2D}$ see, nucleotides 1–1866 SEQ ID No. 26). An oligonucleotide based on the 5' end of this clone was used to prime a human hippocampus cDNA library. The library was screened with this $\beta_2$ clone under conditions of low to medium stringency (final wash 0.5×SSPE, 50° C.). Several hybridizing clones were isolated and sequenced. Among these clones were those that appear to encode $\beta_{2C},\beta_{2E}$ and $\beta_{2F}$.

A randomly primed hoppocampus library was then screened using a combination of the clone encoding $\beta_{2D}$ and a portion of the $\beta_3$ clone deposited under ATCC Accession No. 69048. Multiple hybridizing clones were isolated. Among were clones designated β101, β102 and β104. β101 appears to encodes the 5' end of a splice variant of $\beta_2$, designated $_{2E}$. β102 and β104 encode portions of the 3' end of $\beta_2$.

It appears that the $\beta_2$ splice variants include nucleotide 182–2264 of SEQ ID No. 26 and differ only between the start codon and nucleotides that correspond to 182 of SEQ. ID No. 26.

EXAMPLE VIII
Isolation of cDNA Clones Encoding the Human Neuronal Ca Channel $\beta_3$ Subunit Sequencing of clones isolated as described in Example III also revealed a clone encoding a human neuronal calcium channel $\beta_3$ subunit. This clone includes nucleotides having the sequence set forth in SEQ ID Nos. 19 and 20 and also includes DNA that has been deposited as plasmid β1.42 (ATCC Accession No. 69048).

EXAMPLE IX
Recombinant Expression of Human Neuronal Calcium Channel Subunit-ncoding cDNA and RNA Transcripts in Mammalian Cells
A. Recombinant Expression of the Human Neuronal Calcium Channel $\alpha_2$ Subunit cDNA in DG44 Cells
1. Stable Transfection of DG44 Cells DG44 cells [dhfr⁻ Chinese hamster ovary cells; see, e.g., Urlaub, G. et al. (1986) *Som. Cell Molec. Genet.* 12:555–566] obtained from Lawrence Chasin at Columbia University were stably transfected by CaPO₄ precipitation methods [Wigler et al. (1979) *Proc. Natl. Acad. Sci. USA* 76:1373–1376) with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ Subunit cDNA Expression in Transfected DG44 Cells

Total RNA was extracted according to the method of Birnboim [(1988) *Nuc. Acids Res.* 16:1487–1497] from four of the DG44 cell lines that had been stably transfected with pSV2dhfr containing the human neuronal calcium channel $\alpha_2$ subunit cDNA. RNA (~15 µg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5×Denhardt's, 42° C.; wash: 0.2×SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter (Gorman, C. and Howard, B. (1983) *Nucleic Acids Res.* 11:1631]. This cell line, 44$\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 µl of a solution containing 50 mM HEPES, 1 mM EDTA, 1 mM PMSF. An equal volume of 2×loading dye [Laemmli, U. K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at –70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110 kD immunoreactive protein that may be either a product of proteolytic degradation of the full-length $\alpha_2$ subunit or a product of translation of one Qf the shorter (<5000 nt) mRNAs produced in this cell line that hybridized to the $\alpha_2$ subunit cDNA probe.

B. Expression of DNA Encoding Human Neuronal Calcium Channel $\alpha_1$, $\alpha_2$ and $\beta_1$ Subunits in HEK Cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels were.

1. Transfection of HEK 293 Cells

Separate expression vectors containing DNA encoding human neuronal calcium channel $\alpha_{1D}$, $\alpha_2$ and $\beta_1$ subunits, plasmids pVDCCIII(A), pHBCaCH$\alpha_2$A, and pHBCaCH$\beta_{1a}$RBS(A), respectively, were constructed as described in Examples II.A.3, IV.B. and III.B.3., respectively. These three vectors were used to transiently co-transfect HEK 293 cells. For stable transfection of HEK 293 cells, vector pHBCaCH$\beta_{1b}$RBS(A) (Example III.B.3.) was used in place of pHBCaCH$\beta_{1a}$RBS(A) to introduce the DNA encoding the $\beta_1$ subunit into the cells along with pVDCCIII(A) and pHBCaCH$\alpha_2$A.

a. Transient Transfection

Expression vectors pVDCCIII(A), pHBCaCH$\alpha_2$A and pHBCaCH$\beta_{1a}$RBS(A) were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta_1$ subunit cDNA expression plasmid and plasmid pCMVβgal (Clontech Laboratories, Palo Alto, Calif.). Plasmid pCMVβgal contains the lacZ gene (encoding *E. coli* β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII(A) and pCMVβgal. In both transfections, 2–4×10$^6$ HEK 293 cells in a 10-cm tissue culture plate were transiently co-transfected with 5 µg of each of the plasmids included in the experiment according to standard CaPO$_4$ precipitation transfection procedures (Wigler et al. (1979) *Proc. Natl. Acad. Sci. USA* 76:1373–1376). The transfectants were analyzed for β-galactosidase expression by direct staining of the product of a reaction involving β-galactosidase and the X-gal substrate [Jones, J. R. (1986) *EMBO* 5:3133–3142] and by measurement of β-galactosidase activity [Miller, J. H. (1972) Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable Transfection

HEK 293 cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 µg pVDCCIII(A), 5 µg pHBCaCH$\alpha_2$A, 5 µg pHBCaCH$\beta_{1bRBS}$(A), 5 µg pCMVβgal and 1 µpSV2neo (as a selectable marker). After 10–20 days of growth in media containing 500 µg G418, colonies had formed and were isolated using cloning cylinders.

2. Analysis of HEK 293 Cells Transiently Transfected with DNA Encoding Human Neuronal Calcium Channel Subunits a. Analysis of β-galactosidase Expression Transient transfectants were assayed for β-galactosidase expression by β-galactosidase activity assays (Miller, J. H., (1972) Experiments in Molecular Genetics, pp. 352–355, Cold Spring Harbor Press) of cell lysates (prepared as described in Example VII.A.2) and staining of fixed cells (Jones, J. R. (1986) *EMBO* 5:3133–3142). The results of these assays indicated that approximately 30% of the HEK 293 cells had been transfected.

b. Northern Analysis

PolyA+ RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta_1$ subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit-encoding cDNA, human neuronal calcium channel $\alpha_2$ subunit-encoding cDNA or human neuronal calcium channel $\beta_1$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta_1$ subunits and the lacZ gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacZ gene was detected in cells transfected with the $\alpha_1$, $\alpha_2$ and $\beta_1$ subunit-encoding cDNA and the lacZ gene and in cells transfected with the $\alpha_1$ subunit cDNA and the lacZ gene by hybridization to the lacZ gene sequence.

RNA from cells transfected with the $\alpha_1$, $\alpha_2$ and $\beta_1$ subunit-encoding cDNA and the lacz gene was also hybridized with the $\alpha_2$ and $\beta_1$ subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta_1$ subunit-encoding cDNA and the lacZ gene hybridized to the $\beta_1$ subunit cDNA probe. Multiple β-subunit transcripts of varying sizes were produced since the β subunit cDNA expression vector contains two potential polyA+ addition sites.

c. Electrophysiological Analysis

Individual transiently transfected HEK 293 cells were assayed for the presence of voltage-dependent barium currents using the whole-cell variant of the patch clamp technique [Hamill et al. (1981). *Pflugers Arch.* 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath solution before they were applied.

Twenty-one negative control HEK 293 cells (transiently transfected with the lacZ gene expression vector pCMVβgal only) were analyzed by the whole-cell variant of the patch clamp method for recording currents. Only one cell displayed a discernable inward barium current; this current was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\alpha_2$ and $\beta_1$ subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 μM Bay K 8644 was recorded. The inward barium current was significantly enhanced in magnitude by the addition of Bay K 8644. The largest inward barium current (~160 pA) was recorded when the membrane was depolarized to 0 mV in the presence of 1 μM Bay K 8644. A comparison of the I-V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta_1$ subunit-encoding cDNA and the lacZ gene, indicating that the recombinant calcium channels responsible for the voltage-activated barium currents recorded in this transfected appear to be DHP-sensitive.

The second of the two transfected cells that displayed inward barium currents expressed a ~50 pA current when the membrane was depolarized from −90 mV. This current was nearly completely blocked by 200 μM cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 µM Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 Cells Stably Transfected with DNA Encoding Human Neuronal Calcium Channel Subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) *Rev. Physiol. Biochem. Pharmacol.* 114:107–207], cAMP (Na salt, 250 µM) was added to the pipet solution and forskolin (10 µM) was added to the bath solution in some of the recordings. Qualitatively similar results were obtained whether these compounds were present or not.

Barium currents were recorded from stably transfected cells in the absence and presence of Bay K 8644 (1 µM). When the cell was depolarized to −10 mV from a holding potential of −90 mV in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-based Vectors and pcDNA1-based Vectors for Expression of DNA Encoding Human Neuronal Calcium Channel Subunits 1. Preparation of Constructs To determine if the levels of recombinant expression of human calcium channel subunit-encoding DNA in host cells could be enhanced by using pCMV-based instead of pcDNA1-based expression vectors, additional expression vectors were constructed. The full-length $\alpha_{1D}$ cDNA from pVDCCIII(A) (see Example II.A.3.d), the full-length $\alpha_2$ cDNA, contained on a 3600 bp EcoRI fragment from HBCaCH$\alpha_2$ (see Example IV.B) and a full-length $\beta_1$ subunit cDNA from pHBCaCH$\beta_{1b}$RBS(A) (see Example III.B.3) were separately subcloned into plasmid pCMVβgal. Plasmid pCMVβgal was digested with NotI to remove the lacZ gene. The remaining vector portion of the plasmid, referred to as pCMV, was blunt-ended at the NotI sites. The full-length $\alpha_2$-encoding DNA and $\beta_1$-encoding DNA, contained on separate EcoRI fragments, were isolated, blunt-ended and separately ligated to the blunt-ended vector fragment of PCMV locating the cDNAs between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from PCMV. A polylinker was added at the NotI site. The polylinker had the following sequence of restriction enzyme recognition sites:

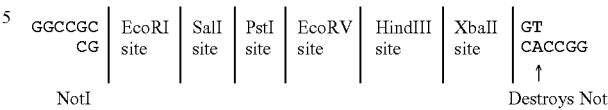

The $\alpha_{1D}$-encoding DNA, isolated as a BamHI/XhoI fragment from pVDCCIII(A), was then ligated to XbaII/SalI-digested pCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 Cells

HEK 293 cells were transiently co-transfected with the $\alpha_{1D}$, $\alpha_2$ and $\beta_1$ subunit-encoding DNA in PCMV or with the $\alpha_{1D}$, $\alpha_2$ and $\beta$ subunit-encoding DNA in pcDNA1 (vectors pVDCCIII(A), pHBCaCH$\alpha_2$A and pHBCaCH$\beta_{1b}$RBS(A), respectively), as described in Example VII.B.1.a. Plasmid pCMVβgal was included in each transfection to as a measure of transfection efficiency. The results of β-galactosidase assays of the transfectants (see Example VII.B.2.), indicated that HEK 293 cells were transfected equally efficiently with pCMV- and pcDNA1-based plasmids.

3. Northern Analysis

Total and polyA$^+$ RNA were isolated from the transiently transfected cells as described in Examples VII.A.2 and VII.B.2.b. Northern blots of the RNA were hybridized with the following radiolabeled probes: $\alpha_{1D}$ cDNA, human neuronal calcium channel 2 subunit cDNA and DNA encoding the human neuronal calcium channel $\beta_1$ subunit. Messenger RNA of sizes expected for $\alpha_{1D}$, $\alpha_2$ and $\beta_1$ subunit transcripts were detected in all transfectants. A greater amount of the $\alpha_{1D}$ transcript was present in cells that were co-transfected with pCMV-based plasmids then in cells that were co-transfected with pcDNA1-based plasmids. Equivalent amounts of $\alpha_2$ and $\beta_1$ subunit transcripts were detected in all transfectants.

D. Expression in *Xenopus laevis* Oöcytes of RNA Encoding Human Neuronal Calcium Channel Subunits Various combinations of the transcripts of DNA encoding the human neuronal $\alpha_{1D}$, $\alpha_2$ and $\beta_1$ subunits prepared in vitro were injected into *Xenopus laevis* oöcytes. Those injected with combinations that included $\alpha_{1D}$ exhibited voltage-activated barium currents.

1. Preparation of Transcripts

Transcripts encoding the human neuronal calcium channel $\alpha_{1D}$, $\alpha_2$ and $\beta_1$ subunits were synthesized according to the instructions of the mCAP mRNA CAPPING KIT (Strategene, La Jolla, Calif. catalog #200350). Plasmids pVDCC III.RBS(A), containing of pcDNA1 and the $\alpha_{1D}$ cDNA that begins with a ribosome binding site and the eighth ATG codon of the coding sequence (see Example III.A.3.d), plasmid pHBCaCH$\alpha_1$A containing of pcDNA1 and an $\alpha_2$ subunit cDNA (see Example IV), and plasmid pHBCaCH$\beta_{1b}$RBS(A) containing pcDNA1 and the $\beta_1$ DNA lacking intron sequence and containing a ribosome binding site (see Example III), were linearized by restriction digestion. The $\alpha_{1D}$ cDNA- and $\alpha_2$ subunit-encoding plasmids were digested with XhoI, and the $\beta_1$ subunit-encoding plasmid was digested with EcoRV. The DNA insert was transcribed with T7 RNA polymerase.

2. Injection of Oöcytes

*Xenopus laevis* oöcytes were isolated and defolliculated by collagenase treatment and maintained in 100 mM NaCl, 2 mM KCl, 1.8 mM $CaCl_2$, 1 mM $MgCl_2$, 5 mM HEPES, pH 7.6, 20 µg/ml ampicillin and 25 µg/ml streptomycin at 19–25° C. for 2 to 5 days after injection and prior to recording. For each transcript that was injected into the oöcyte, 6 ng of the specific mRNA was injected per cell in a total volume of 50 nl.

3. Intracellular Voltage Recordings

Injected oöcytes were examined for voltage-dependent barium currents using two-electrode voltage clamp methods [Dascal, N. (1987) *CRC Crit. Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM $BaCl_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological Analysis of Oöcytes Injected with Transcripts Encoding the Human Neuronal Calcium Channel $\alpha_1$, $\alpha_2$ and $\beta_1$-subunits Uninjected oöcytes were examined by two-electrode voltage clamp methods and a very small (25 nA) endogenous inward $Ba^{2+}$ current was detected in only one of seven analyzed cells.

Oöcytes coinjected with $\alpha_{1D}$, $\alpha_2$ and $\beta_1$ subunit transcripts expressed sustained inward barium currents upon depolarization of the membrane from a holding potential of −90 mV or −50 mV (154±129 nA, n=21). These currents typically showed little inactivation when test pulses ranging from 140 to 700 msec. were administered. Depolarization to a series of voltages revealed currents that first appeared at approximately −30 mV and peaked at approximately 0 mV.

Application of the DHP Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10× concentrate directly into the 60 µl bath while the perfusion pump was turned off. The DMSO concentration of the final diluted drug solutions in contact with the cell never exceeded 0.1%. Control experiments showed that 0.1% DMSO had no effect on membrane currents.

Application of the DHP antagonist nifedipine (stock solution prepared in DMSO and applied to the cell as described for application of Bay K 8644) blocked a substantial fraction (91±6%, n=7) of the inward barium current in oöcytes coinjected with transcripts of the $\alpha_{1D}$, $\alpha_2$ and $\beta_1$ subunits. A residual inactivating component of the inward barium current typically remained after nifedipine application. The inward barium current was blocked completely by 50 µM $Cd^{2+}$, but only approximately 15% by 100 µM $Ni^{2+}$.

The effect of ωCgTX on the inward barium currents in oöcytes co-injected with transcripts of the $\alpha_{1D}$, $\alpha_2$, and $\beta_1$ subunits was investigated. ωcgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 µM) of ωCgTX. The test currents and the accompanying tail currents were blocked progressively within two to three minutes after application of ωCgTX, but both recovered partially as the ωCgTX was flushed from the bath.

b. Analysis of Oöcytes Injected with Only a Transcripts Encoding the Human Neuronal Calcium Channel $\alpha_{1D}$ or Transcripts Encoding an $\alpha_{1D}$ and Other Subunits The contribution of the $\alpha_2$ and $\beta_1$ subunits to the inward barium current in oöcytes injected with transcripts encoding the $\alpha_{1D}$, $\alpha_2$ and $\beta_1$ subunits was assessed by expression of the $\alpha_{1D}$ subunit alone or in combination with either the $\beta_1$ subunit or the $\alpha_2$ subunit. In oöcytes injected with only the transcript of a $\alpha_{1D}$ cDNA, no $Ba^{2+}$ currents were detected (n=3). In oöcytes injected with transcripts of $\alpha_{1D}$ and $\beta_1$ cDNAs, small (108±39 nA) $Ba^{2+}$ currents were detected upon depolarization of the membrane from a holding potential of −90 mV that resembled the currents observed in cells injected with transcripts of $\alpha_{1D}$, $\alpha_2$ and $\beta_1$ cDNAs, although the magnitude of the current was less. In two of the four oöcytes injected with transcripts of the $\alpha_{1D}$-encoding and $\beta_{1D}$-encoding DNA, the $Ba^{2+}$ currents exhibited a sensitivity to Bay K 8644 that was similar to the Bay K 8644 sensitivity of $Ba^{2+}$ currents expressed in oöcytes injected with transcripts encoding the $\alpha_{1D}$ $\alpha_1$-, $\alpha_2$- and $\beta_1$ subunits.

Three of five oöcytes injected with transcripts encoding the $\alpha_{1D}$ and $\alpha_2$ subunits exhibited very small $Ba^{2+}$ currents (15–30 nA) upon depolarization of the membrane from a holding potential of −90 mV. These barium currents showed little or no response to Bay K 8644.

c. Analysis of Oöcytes Injected with Transcripts Encoding the Human Neuronal Calcium Channel $\alpha_2$ and/or $\beta_1$ Subunit To evaluate the contribution of the $\alpha_{1D}$ $\alpha_1$-subunit to the inward barium currents detected in oöcytes co-injected with transcripts encoding the $\alpha_{1D}$, $\alpha_2$ and $\beta_1$ subunits, oöcytes injected with transcripts encoding the human neuronal calcium channel $\alpha_2$ and/or $\beta_1$ subunits were assayed for barium currents. Oöcytes injected with transcripts encoding the $\alpha_2$ subunit displayed no detectable inward barium currents (n=5). Oöcytes injected with transcripts encoding a $\beta_1$ subunit displayed measurable (54±23 nA, n=5) inward barium currents upon depolarization and oöcytes injected with transcripts encoding the $\alpha_2$ and $\beta_1$ subunits displayed inward barium currents that were approximately 50% larger (80±61 nA, n=18) than those detected in oöcytes injected with transcripts of the $\beta_1$-encoding DNA only.

The inward barium currents in oöcytes injected with transcripts encoding the $\beta_1$ subunit or $\alpha_2$ and $\beta_1$ subunits typically were first observed when the membrane was depolarized to −30 mV from a holding potential of −90 mV and peaked when the membrane was depolarized to 10 to 20 mV. Macroscopically, the currents in oöcytes injected with transcripts encoding the $\alpha_2$ and $\beta_1$ subunits or with transcripts encoding the $\beta_1$ subunit were indistinguishable. In contrast to the currents in oöcytes co-injected with transcripts of $\alpha_{1D}$, $\alpha_2$ and $\beta_1$ subunit cDNAs, these currents showed a significant inactivation during the test pulse and a strong sensitivity to the holding potential. The inward barium currents in oöcytes co-injected with transcripts encoding the $\alpha_2$ and $\beta_1$ subunits usually inactivated to 10–60% of the peak magnitude during a 140-msec pulse and were significantly more sensitive to holding potential than those in oöcytes co-injected with transcripts encoding the $\alpha_{1D}$, $\alpha_2$ and $\beta_1$ subunits. Changing the holding potential of the membranes of oöcytes co-injected with transcripts encoding the $\alpha_2$ and $\beta_1$ subunits from −90 to −50 mV resulted in an approximately 81% (n=11) reduction in the magnitude of the inward barium current of these cells. In contrast, the inward barium current measured in oöcytes co-injected with transcripts encoding the $\alpha_{1D}$, $\alpha_2$ and $\beta_1$ subunits were reduced approximately 24% (n=11) when the holding potential was changed from −90 to −50 mV.

The inward barium currents detected in oöcytes injected with transcripts encoding the $\alpha_2$ and $\beta_1$ subunits were pharmacologically distinct from those observed in oöcytes co-injected with transcripts encoding the $\alpha_{1D}$, $\alpha_2$ and $\beta_1$ subunits. Oöcytes injected with transcripts encoding the $\alpha_2$ and $\beta_1$ subunits displayed inward barium currents that were insensitive to Bay K 8644 (n=11). Nifedipine sensitivity was difficult to measure because of the holding potential sensitivity of nifedipine and the current observed in oöcytes injected with transcripts encoding the $\alpha_2$ and $\beta_1$ subunits. Nevertheless, two oöcytes that were co-injected with transcripts encoding the $\alpha_2$ and $\beta_1$ subunits displayed measurable (25 to 45 nA) inward barium currents when depolarized from a holding potential of −50 mV. These currents were insensitive to nifedipine (5 to 10 μM). The inward barium currents in oöcytes injected with transcripts encoding the $\alpha_2$ and $\beta_1$ subunits showed the same sensitivity to heavy metals as the currents detected in oöcytes injected with transcripts encoding the $\alpha_{1D}$, $\alpha_2$ and $\beta_1$ subunits.

The inward barium current detected in oöcytes injected with transcripts encoding the human neuronal $\alpha_2$ and $\beta_1$ subunits has pharmacological and biophysical properties that resemble calcium currents in uninjected Xenopus oöcytes. Because the amino acids of this human neuronal calcium channel $\beta_1$ subunit lack hydrophobic segments capable of forming transmembrane domains, it is unlikely that recombinant $\beta_1$ subunits alone can form an ion channel. It is more probable that a homologous endogenous $\alpha_1$ subunit exists in oöcytes and that the activity mediated by such an $\alpha_1$ subunit is enhanced by expression of a human neuronal $\beta_1$ subunit.

E. Expression of DNA Encoding Human Neuronal Calcium Channel $\alpha_{1B}$, $\alpha_{2B}$ and $\beta_{1-2}$ Subunits in HEK Cells 1. Transfection of HEK Cells The transient expression of the human neuronal $\alpha_{1B-1}$, $\alpha_{2b}$ and $\beta_{1-2}$ subunits was studied in HEK293 cells. The HEK293 cells were grown as a monolayer culture in Dulbecco's modified Eagle's medium (Gibco) containing 5% defined-supplemented bovine calf serum (Hyclone) plus penicillin G (100 U/ml) and steptomycin sulfate (100 μg/ml). HEK293 cell transfections were mediated by calcium phosphate as described above. Transfected cells were examined for inward $Ba^{2+}$ currents ($I_{Ba}$) mediated by voltage-dependent $Ca^{2+}$ channels.

Cells were transfected ($2×10^6$ per polylysine-coated plate. Standard transfections (10-cm dish) contained 8 μg of pcDNA$\alpha_{1B-1}$, 5 μg of pHBCaCH$\alpha_2$A, 2 μg pHBCaCH$\beta_{1b}$RBS(A) (see, Examples II.A.3, IV.B. and III) and 2 μg of CMV$\beta$ (Clontech) β-glactosidase expression plasmid, and pUC18 to maintain a constant mass of 20 μg/ml. Cells were analyzed 48 to 72 hours after transfection. Transfection efficiencies (±10%), which were determined by in situ histochemical staining for β-galactosidase activity (Sanes et al. (1986) EMBO J., 5:3133), generally were greater than 50%.

2. Electrophysiological Analysis of Transfectant Currents

1. Materials and Methods

Properties of recombinantly expressed $Ca^{2+}$ channels were studied by whole cell patch-clamp techniques. Recordings were performed on transfected HEK293 cells 2 to 3 days after transfection. Cells were plated at 100,000 to 300,000 cells per polylysine-coated, 35-mm tissue culture dishes (Falcon, Oxnard, Calif.) 24 hours before recordings. Cells were perfused with 15 mM $BaCl_2$, 125 mM choline chloride, 1 mM $MgCl_2$, and 10 mM Hepes (pH=7.3) adjusted with tetraethylammonium hydroxide (bath solution). Pipettes were filled with 135 mM CsCl, 10 mM EGTA, 10 mM Hepes, 4 mM Mg-adenosine triphosphate (pH=7.5) adjusted with tetraethylammonium hydroxide. Sylgard (Dow-Corning, Midland, Mich,)-coated, fire-polished, and filled pipettes had resistances of 1 to 2 megohm before gigohm seals were established to cells.

Bay K 8644 and nifedipine (Research Biochemicals, Natick, Mass.) were prepared from stock solutions (in dimethyl sulfoxide) and diluted into the bath solution. The dimethyl sulfoxide concentration in the final drug solutions in contact with the cells never exceeded 0.1%. Control experiments showed that 0.1% dimethyl sulfoxide had no efect on membrane currents. ωCgTX (Bachem, Inc., Torrance Calif.) was prepared in the 15 mM $BaCl_2$ bath solution plus 0.1% cytochrome C (Sigma, St. Louis Mo.) to serve as a carrier protein. Control experiments showed that cytochrome C had no effect on currents. These drugs were dissolved in bath solution, and continuously applied by means of puffer pipettes as required for a given experiment. Recordings were performed at room temperature (22° to 25° C.). Series resistance compensation (70 to 85%) was employed to minimize voltage error that resulted from pipette access resistance, typically 2 to 3.5 megohm. Current signals were filtered (−3 dB, 4-pole Bessel) at a frequency of 1/4 to 1/5 the sampling rate, which ranged from 0.5 to 3 kHz. Voltage commands were generated and data were acquired with CLAMPEX (pClamp, Axon Instruments, Foster City, Calif.). All reported data are corrected for linear leak and capacitive components. Exponential fitting of currents was performed with CLAMPFIT (Axon Instruments, Foster City, Calif.).

2. Results

Transfectants were examined for inward $Ba^{2+}$ currents ($I_{Ba}$). Cells cotransfected with DNA encoding $\alpha_{1B-1}$, $\alpha_{2B}$, and $\beta_{1-2}$ subunits expressed high-voltage-activated $Ca^{2+}$ channels. $I_{Ba}$ first appeared when the membrane was depolarized from a holding potential of −90 mV to −20 mV and peaked in magnitude at 10 mV. Thirty-nine of 95 cells (12 independent transfections) had $I_{Ba}$ that ranged from 30 to 2700 pA, with a mean of 433 pA. The mean current density was 26 pA/pF, and the highest density was 150 pA/pF. The $I_{Ba}$ typically increased by 2- to 20-fold during the first 5 minutes of recording. Repeated depolarizations during long records often revealed rundown of $I_{Ba}$ usually not exceeding 20% within 10 min. $I_{Ba}$ typically activated within 10 ms and inactivated with both a fast time constant ranging from 46 to 105 ms and a slow time constant ranging from 291 to 453 ms (n=3). Inactivation showed a complex voltage dependence, such that $I_{Ba}$ elicited at ≧20 mV inactivated more slowly than $I_{Ba}$ elicited at lower test voltages, possibly a result of an increase in the magnitude of slow compared to fast inactivation components at higher test voltages.

Recombinant $\alpha_{1B-1}\alpha_{2b}\beta_{1-2}$ channels were sensitive to holding potential. Steady-state inactivation of $I_{Ba}$, measured after a 30- to 60-s conditioning at various holding potentials, was approximately 50% at holding potential between −60 and −70 mV and approximately 90% at −40 mV. Recovery of $I_{Ba}$ from inactivation was usually incomplete, measuring 55 to 75% of the original magnitude within 1 min. after the holding potential was returned to more negative potentials, possibly indicating some rundown or a slow recovery rate.

Recombinant $\alpha_{1B-1}\alpha_{2b}\beta_{1-2}$ channels were also blocked irreversibly by ω-CgTx concentrations ranging from 0.5 to 10 µM during the time scale of the experiments. Application of 5 µM toxin (n=7) blocked the activity completely within 2 min., and no recovery of $I_{Ba}$ was observed after washing ω-CgTx from the bath for up to 15 min. $d^{2+}$ blockage (50 µM) was rapid, complete, and reversible; the DHPs Bay K 8644 (1 µM; n=4) or nifedipine (5 µM; n=3) had no discernable effect.

Cells cotransfected with DNA encoding $\alpha_{1B-1}$, $\alpha_{2b}$, $\beta_{1-2}$ subunits predominantly displayed a single class of saturable, high-affinity ω-CgTx binding sites. The determined dissociation constant ($K_d$) value was 54.6±14.5 pM (n=4). Cells transfected with the vector containing only β-galactosidase-encoding DNA or $\alpha_{2b}\beta$-encoding DNA showed no specific binding. The binding capacity ($B_{max}$) of the $\alpha_{1B-1}\alpha_{2b}\beta$-transfected cells was 28,710±11,950 sites per cell (n=4).

These results demonstrate that $\alpha_{1B-1}\alpha_{2b}\beta_{1-2}$-transfected cells express high-voltage-activated, inactivating $Ca^{2+}$ channel activity that is irreversibly blocked by ω-CgTx, insensitive to DHPs, and sensitive to holding potential. The activation and inactivation kinetics and voltage sensitivity of the channel formed in these cells are generally consistent with previous characterizations of neuronal N-type $Ca^{2+}$ channels.

F. Expression of DNA Encoding Human Neuronal Calcium Channel $\alpha_{1B-1}$, $\alpha_{1B-2}$, $\alpha_{2B}$, $\beta_{1-2}$ and $\beta_{1-3}$ Subunits in HEK Cells Significant $Ba^{2+}$ currents were not detected in untransfected HEK293 cells. Furthermore, untransfected HEK293 cells do not express detectable ω-CgTx GVIA binding sites.

In order to approximate the expression of a homogeneous population of trimeric $\alpha_{1B}$, $\alpha_{2b}$ and $\beta_1$ protein complexes in transfected HEK293 cells, the $\alpha_{1B}$, $\alpha_{2b}$, $\beta_1$ expression levels were altered. The efficiency of expression and assembly of channel complexes at the cell surface were optimized by adjusting the molar ratio of $\alpha_{1B}$, $\alpha_{2b}$ and $\beta_1$ expression plasmids used in the transfections. The transfectants were analyzed for mRNA levels, ω-CgTx GVIA binding and $Ca^{2+}$ channel current density in order to determine near optimal channel expression in the absence of immunological reagents for evaluating protein expression.

1. Transfections

HEK293 cells were maintained in DMEM (Gibco #320-1965AJ), 5.5% Defined/Supplemented bovine calf serum (Hyclone #A-2151-L), 100 U/ml penicillin G and 100 µg/ml streptomycin. $Ca^{2+}$-phosphate based transient transfections were performed and analyzed as described above. Cells were co-transfected with either 8 µg pcDNA1$\alpha_{1B-1}$ (described in Example II.C), 5 µg pHBCaCH$\alpha_2$A (see, Example IV.B.), 2 µg pHBCaCH$\beta_{1b}$RBS(A) ($\beta_{1-2}$ expression plasmid; see Examples III.A. and IX.E.), and 2 µg pCMVβ-gal [Clontech, Palo Alto, Calif.] (2:1.8:1 molar ratio of $Ca^{2+}$ channel subunit expression plasmids) or with 3 µg pcDNA1$\alpha_{1B-1}$ or pcDNA1$\alpha_{1B-2}$, 11.25 µg pHBCaCH$\alpha_2$A, 0.75 or 1.0 µg pHBCaCH$\beta_{1b}$RBS(A) or pcDNA1$\beta_{1-3}$ and 2 µg pCMVβ-gal (2:10.9:1 molar ratio of $Ca^{2+}$ channel subunit expression plasmids). Plasmid pCMVβ-gal, a β-galactosidase expression plasmid, was included in the transfections as a marker to permit transfection efficiency estimates by histochemical staining. When less than three subunits were expressed, pCMVPL2, a pCMV promoter-containing vector that lacks a cDNA insert, was substituted to maintain equal moles of pCMV-based DNA in the transfection. pUC18 DNA was used to maintain the total mass of DNA in the transfection at 20 µg/plate.

RNA from the transfected cells was analyzed by Northern blot analysis for calcium channel subunit mRNA expression using random primed $^{32}$P-labeled subunit specific probes. HEK293 cells co-transfected with $\alpha_{1B-1}$, $\alpha_{2b}$ and $\beta_{1-2}$ expression plasmids (8, 5 and 2 µg, respectively; molar ratio=2:1.8:1) did not express equivalent levels of each $Ca^{2+}$ channel subunit mRNA. Relatively high levels of $\alpha_{1B-1}$ and $\beta_{1-2}$ mRNAs were expressed, but significantly lower levels of $\alpha_{2b}$ mRNA were expressed. Based on autoradiograph exposures required to produce equivalent signals for all three mRNAs, $\alpha_{2b}$ transcript levels were estimated to be 5 to 10 times lower than $\alpha_{1B-1}$ and $\beta_{1-2}$ transcript levels. Untransfected HEK293 cells did not express detectable levels of $\alpha_{1B-1}$, $\alpha_{2b}$, or $\beta_{1-2}$ mRNAs.

To achieve equivalent $Ca^{2+}$ channel subunit mRNA expression levels, a series of transfections was performed with various amounts of $\alpha_{1B-1}$, $\alpha_{2b}$ and $\beta_{1-2}$ expression plasmids. Because the $\alpha_{1B-1}$ and $\beta_{1-2}$ mRNAs were expressed at very high levels compared to $\alpha_{2b}$ mRNA, the mass of $\alpha_{1B-1}$ and $\beta_{1-2}$ plasmids was lowered and the mass of $\alpha_{2b}$ plasmid was increased in the transfection experiments. Co-transfection with 3, 11.25 and 0.75 µg of $\alpha_{1B-1}$, $\alpha_{2b}$ and $\beta_{1-2}$ expression plasmids, respectively (molar ratio= 2:10.9:1), approached equivalent expression levels of each $Ca^{2+}$ channel subunit mRNA. The relative molar quantity of $\alpha_{2b}$ expression plasmid to $\alpha_{1B-1}$ and $\beta_{1-2}$ expression plasmids was increased 6-fold. The mass of $\alpha_{1B-1}$ and $\beta_{1-2}$ plasmids in the transfection was decreased 2.67-fold and the mass of $\alpha_{2b}$ plasmid was increased 2.25-fold. The 6-fold molar increase of $\alpha_{2b}$ relative to $\alpha_{1B-1}$ and $\beta_{1-2}$ required to achieve near equal abundance mRNA levels is consistent with the previous 5- to 10-fold lower estimate of relative $\alpha_{2b}$ mRNA abundance. ω-CgTx GVIA binding to cells transfected with various amounts of expression plasmids indicated that the 3, 11.25 and 0.75 µg of $\alpha_{1B-1}$, $\alpha_{2b}$ and $\beta_{1-2}$ plasmids, respectively, improved the level of cell surface expression of channel complexes. Further increases in the mass of $\alpha_{2b}$ and $\beta_{1-2}$ expression plasmids while $\alpha_{1B-1}$ was held constant, and alterations in the mass of the $\alpha_{1B-1}$ expression plasmid while $\alpha_{2b}$ and $\beta_{1-2}$ were held constant, indicated that the cell surface expression of ω-CgTx GVIA binding sites per cell was nearly optimal. All subsequent transfections were performed with 3, 11.25 and 0.75 µg or 1.0 µg of $\alpha_{1B-1}$ or $\alpha_{1B-2}$, $\alpha_{2b}$ and $\beta_{1-2}$ or $\beta_{1-3}$ expression plasmids, respectively.

2. $^{125}$I-ω-CgTx GVIA Binding to Transfected Cells

Statistical analysis of the $K_d$ and $B_{max}$ values was performed using one-way analysis of variance (ANOVA) followed by the Tukey-Kramer test for multiple pairwise comparisons ($p \leq 0.05$).

Combinations of human voltage-dependent $Ca^{2+}$ channel subunits, $\alpha_{1B-1}$, $\alpha_{1B-2}$, $\alpha_{2b}$, $\beta_{1-2}$ and $\beta_{1-3}$, were analyzed for saturation binding of $^{125}$I-ω-CgTx GVIA. About 200,000 cells were used per assay, except for the $\alpha_{1B-1}$, $\alpha_{1B-2}$, $\alpha_{1B-1}\alpha_{2b}$ and $\alpha_{1B-2}\alpha_{2b}$ combinations which were assayed with 1×10$^6$ cells per tube. The transfected cells displayed a single-class of saturable, high-affinity binding sites. The values for the dissociation constants ($K_d$) and binding capacities ($B_{max}$) were determined for the different combinations. The results are summarized as follows:

| Subunit Combination | $K_d$ (pM) | $B_{max}$ (sites/cell) |
|---|---|---|
| $\alpha_{1B-1}\alpha_{2b}\beta_{1-2}$ | 54.9 ± 11.1 (n = 4) | 45,324 ± 15,606 |
| $\alpha_{1B-1}\alpha_{2b}\beta_{1-3}$ | 53.2 ± 3.6 (n = 3) | 91,004 ± 37,654 |
| $\alpha_{1B-1}\beta_{1-2}$ | 17.9 ± 1.9 (n = 3) | 5,756 ± 2,163 |
| $\alpha_{1B-1}\beta_{1-3}$ | 17.9 ± 1.6 (n = 3) | 8,729 ± 2,980 |
| $\alpha_{1B-1}\alpha_{2B}$ | 84.6 ± 15.3 (n = 3) | 2,256 ± 356 |
| $\alpha_{1B-1}$ | 31.7 ± 4.2 (n = 3) | 757 ± 128 |
| $\alpha_{1B-2}\alpha_{2b}\beta_{1-2}$ | 53.0 ± 4.8 (n = 3) | 19,371 ± 3,798 |
| $\alpha_{1B-2}\alpha_{2b}\beta_{1-3}$ | 44.3 ± 8.1 (n = 3) | 37,652 ± 8,129 |
| $\alpha_{1B-2}\beta_{1-2}$ | 16.4 ± 1.2 (n = 3) | 2,126 ± 412 |
| $\alpha_{1B-2}\beta_{1-3}$ | 22.2 ± 5.8 (n = 3) | 2,944 ± 1,168 |
| $\alpha_{1B-2}\alpha_{2b}$ | N.D.* (n = 3) | N.D. |
| $\alpha_{1B-2}$ | N.D. | N.D. |

*N.D. = not detectable

Cells transfected with subunit combinations lacking either the $\alpha_{1B-1}$ or the $\alpha_{1B-2}$ subunit did not exhibit any detectable $^{125}$I-ωCgTx GVIA binding (≤600 sites/cell). In addition $^{125}$I-ω-CgTx GVIA binding to HEK293 cells transfected with $\alpha_{1B-2}$ alone or $\alpha_{1B-2}\alpha_{2b}$ was too low for reliable Scatchard analysis of the data.

Comparison of the $K_d$ and $B_{max}$ values revealed several relationships between specific combinations of subunits and the binding affinities and capacities of the transfected cells. In cells transfected with all three subunits, ($\alpha_{1B-1}\alpha_{2b}\beta_{1-2}$-, $\alpha_{1B-1}\alpha_{2b}\beta_{1-3}$-, $\alpha_{1B-2}\alpha_{2b}\beta_{1-2}$-, or $\alpha_{1B-2}\alpha_{2b}\beta_{1-3}$-transfectants) the $K_d$ values were indistinguishable (p>0.05), ranging from 44.3±8.1 pM to 54.9±11.1 pM. In cells transfected with two-subunit combinations lacking the $\alpha_{2b}$ subunit ($\alpha_{1B-1}\beta_{1-2}$, $\alpha_{1B-1}\beta_{1-3}$, $\alpha_{1B-2}\beta_{1-2}$ or $\alpha_{1B-2}\beta_{1-3}$) the $K_d$ values were significantly lower than the three-subunit combinations (p<0.01), ranging from 16.4±1.2 to 22.2±5.8 pM. Cells transfected with only the $\alpha_{1B-1}$ subunit had a $K_d$ value of 31.7±4.2 pM, a value that was not different from the two-subunit combinations lacking $\alpha_{2b}$ (p<0.05). As with the comparison between the four $\alpha_{1B}\alpha_{2b}\beta_1$ versus $\alpha_{1B}\beta_1$ combinations, when the $\alpha_{1B-1}$ was co-expressed with $\alpha_{2b}$, the $K_d$ increased significantly (p<0.05) from 31.7±4.2 to 84.6±5.3 pM. These data demonstrate that co-expression of the $\alpha_{2b}$ subunit with $\alpha_{1B-1}$, $\alpha_{1B-1}\beta_{1-2}$, $\alpha_{1B-1}\beta_{1-3}$, $\alpha_{1B-2}\beta_{1-2}$ or $\alpha_{1B-2}\beta_{1-3}$ subunit combinations results in lower binding affinity of the cell surface receptors for $^{125}$I-ω-CgTx GVIA. The $B_{max}$ values of cells transfected with various subunit combinations also differed considerably. Cells transfected with the $\alpha_{1B-1}$ subunit alone expressed a low but detectable number of binding sites (approximately 750 binding sites/cell). When the $\alpha_{1B-1}$ subunit was co-expressed with the $\alpha_{2b}$ subunit, the binding capacity increased approximately threefold while co-expression of a $\beta_{1-2}$ or $\beta_{1-3}$ subunit with $\alpha_{1B-1}$ resulted in 8- to 10-fold higher expression of surface binding. However, cells transfected with all three subunits expressed the highest number of cell surface receptors. The binding capacities of cells transfected with $\alpha_{1B-1}\alpha_{2b}\beta_{1-3}$ or $\alpha_{1B-2}\alpha_{2b}\beta_{1-3}$ combinations were approximately two-fold higher than the corresponding combinations containing the $\beta_{1-2}$ subunit. Likewise, cells transfected with $\alpha_{1B-1}\alpha_{2b}\beta_{1-2}$ or $\alpha_{1B-1}\alpha_{2b}\beta_{1-3}$ combinations expressed approximately 2.5-fold more binding sites per cell than the corresponding combinations containing $\alpha_{1B-2}$. In all cases, co-expression of the $\alpha_{2b}$ subunit with $\alpha_{1B}$ and $\beta_1$ increased the surface receptor density compared to cells transfected with only the corresponding $\alpha_{1B}$ and $\beta_1$ combinations; approximately 8-fold for $\alpha_{1B-1}\alpha_{2b}\beta_{1-2}$, 10-fold for $\alpha_{1B-1}\alpha_{2b}\beta_{1-3}$, 9-fold for $\alpha_{1B-2}\alpha_{2b}\beta_{1-2}$, and 13-fold for $\alpha_{1B-2}\alpha_{2b}\beta_{1-3}$. Thus, in summary, the comparison of the $B_{max}$ values suggests that the toxin-binding subunit, $\alpha_{1B-1}$ or $\alpha_{1B-2}$, is more efficiently expressed and assembled on the cell surface when co-expressed with either the $\alpha_{2b}$ or the $\beta_{1-2}$ or $\beta_{1-3}$ subunit, and most efficiently expressed when both $\alpha_{2b}$ and $\beta_1$ subunits are present.

3. Electrophysiology

Functional expression of $\alpha_{1B-1}\alpha_{2b}\beta_{1-2}$ and $\alpha_{1B-1}\beta_{1-2}$ subunit combinations was evaluated using the whole-cell recording technique. Transfected cells that had no contacts with surrounding cells and simple morphology were used approximately 48 hours after transfection for recording. The pipette solution was (in mM) 135 CsCl, 10 EGTA, 1 $MgCl_2$, 10 HEPES, and 4 mM Mg-ATP (pH 7.3, adjusted with TEA-OH). The external solution was (in MM) 15 $BaCl_2$, 125 Choline Cl, 1 $MgCl_2$, and 10 HEPES (pH 7.3, adjusted with TEA-OH). ω-CgTx GVIA (Bachem) was prepared in the external solution with 0.1% cytochrome C (Sigma) to serve as a carrier. Control experiments showed that cytochrome C had no effect on the $Ba^{2+}$ current.

The macroscopic electrophysiological properties of $Ba^{2+}$ currents in cells transfected with various amounts of the $\alpha_{2b}$ expression plasmid with the relative amounts of $\alpha_{1B-1}$ and $\beta_{1-2}$ plasmids held constant were examined. The amplitudes and densities of the $Ba^{2+}$ currents (15 mM $BaCl_2$) recorded from whole cells of these transfectants differed dramatically. The average currents from 7 to 11 cells of three types of transfections (no $\alpha_{2b}$; 2:1.8:1 [$\alpha_{1B-1}$:$\alpha_{2b}$:$\beta_{1-2}$] molar ratio; and 2:10.9:1 [$\alpha_{1B-1}$:$\alpha_{2b}$:$\beta_{1-2}$] molar ratio) were determined. The smallest currents (range: 10 to 205 pA) were recorded when $\alpha_{2b}$ was not included in the transfection, and the largest currents (range: 50 to 8300 pA) were recorded with the 2:10.9:1 ratio of $\alpha_{1B-1}\alpha_{2b}\beta_{1-2}$ plasmids, the ratio that resulted in near equivalent mRNA levels for each subunit transcript. When the amount of $\alpha_{2b}$ plasmid was adjusted to yield approximately an equal abundance of subunit mRNAs, the average peak $Ba^{2+}$ current increased from 433 pA to 1,824 pA (4.2-fold) with a corresponding increase in average current density from 26 pA/pF to 127 pA/pF (4.9-fold). This increase is in the presence of a 2.7-fold decrease in the mass of $\alpha_{1B-1}$ and $\beta_{1-2}$ expression plasmids in the transfections. In all transfections, the magnitudes of the $Ba^{2+}$ currents did not follow a normal distribution.

To compare the subunit combinations and determine the effects of $\alpha_{2b}$, the current-voltage properties of cells transfected with $\alpha_{1B-1}\beta_{1-2}$ or with $\alpha_{1B-1}\alpha_{2b}\beta_{1-2}$ in either the 2:1.8:1 ($\alpha_{1B-1}$:$\alpha_{2b}$:$\beta_{1-2}$) molar ratio or the 2:10.9:1 ($\alpha_{1B-1}$:$\alpha_{2b}$:$\beta_{1-2}$) molar ratio transfectants were examined. The extreme examples of no $\alpha_{2b}$ and 11.25 μg $\alpha_{2b}$ (2:10.9:1 molar ratio) showed no significant differences in the current voltage plot at test potentials between 0 mV and +40 mV (p<0.05). The slight differences observed at either side of the peak region of the current voltage plot were likely due to normalization. The very small currents observed in the $\alpha_{1B-1}\beta_{1-2}$ transfected cells have a substantially higher component of residual leak relative to the barium current that is activated by the test pulse. When the current voltage plots are normalized, this leak is a much greater component than in the $\alpha_{1B-1}\alpha_{2b}\beta_{1-2}$ transfected cells and as a result, the current-voltage plot appears broader. This is the most likely explanation of the apparent differences in the current voltage plots, especially given the fact that the current-voltage plot for the $\alpha_{1B-1}\beta_{1-2}$ transfected cells diverge on both sides of the peak. Typically, when the voltage-dependence activation is shifted, the entire current-voltage plot is shifted, which was not observed. To qualitatively compare the kinetics of each, the average responses of test pulses from −90 mV to 10 mV were normalized and plotted. No significant differences in activation or inactivation kinetics of whole-cell $Ba^{2+}$ currents were observed with any combination.

G. Expression of DNA Encoding Human Neuronal Calcium Channel $\alpha_{1E\text{-}3}\alpha_{2B}\beta_{1\text{-}3}$ and $\alpha_{1E\text{-}1}\alpha_{2B}\beta_{1\text{-}3}$ Subunits in HEK Cells Functional expression of the $\alpha_{1E\text{-}1}\alpha_{2B}\beta_{1\text{-}3}$ and $\alpha_{1E\text{-}3}\alpha_{2B}\beta_{1\text{-}3}$, as well as $\alpha_{1E\text{-}1}$ was evaluated using the whole cell recording technique.

1. Methods

Recordings were performed on transiently transfected HEK 293 cells two days following the transfection, from cells that had no contacts with surrounding cells and which had simple morphology.

The internal solution used to fill pipettes for recording the barium current from the transfected recombinant calcium channels was (in mM) 135 CsCl, 10 EGTA, 1 $MgCl_2$, 10 HEPES, and 4 mM Mg-ATP (pH 7.3, adjusted with TEA-OH). The external solution for recording the barium current was (in mM) 15 $BaCl_2$, 125 Choline Cl, 1 $MgCl_2$, and 10 HEPES (pH 7.3, adjusted with TEA-OH). In experiments in which $Ca^{2+}$ was replaced for $Ba^{2+}$, a Laminar flow chamber was used in order to completely exchange the extracellular solution and prevent any mixing of $Ba^{2+}$ and $Ca^{2+}$. ω-CgTx GVIA was prepared in the external solution with 0.1% cytochrome C to serve as a carrier, the toxin was applied by pressurized puffer pipette. Series resistance was compensated 70–85% and currents were analyzed only if the voltage error from series resistance was less than 5 mV. Leak resistance and capacitance was corrected by subtracting the scaled current observed with the P/-4 or -6 protocol as implemented by pClamp (Axon Instruments).

2. Results a. Electrophysiology

Cells transfected with $\alpha_{1E\text{-}1}\alpha_{2b}\beta_{1\text{-}3}$ or $\alpha_{1E\text{-}3}\alpha_{2b}\beta_{1\text{-}3}$ showed strong barium currents with whole cell patch clamp recordings. Cells expressing $\alpha_{1E\text{-}3}\alpha_{2b}\beta_{1\text{-}3}$ had larger peak currents than those expressing $\alpha_{1E\text{-}1}\alpha_{2b}\beta_{1\text{-}3}$. In addition, the kinetics of activation and inactivation are clearly substantially faster in the cells expressing $\alpha_{1E}$ calcium channels. HEK 293 cells expressing $\alpha_{1E\text{-}1}$ or $\alpha_{1E\text{-}3}$ alone have a significant degree of functional calcium channels, with properties similar to those expressing $\alpha_{1E}\alpha_{2b}\beta_{1\text{-}3}$ but with substantially smaller peak barium currents. Thus, with $\alpha_{1E}$, the $\alpha_2$ and $\beta_1$ subunits are not required for functional expression of $\alpha_{1E}$ mediated calcium channels, but do substantially increase the number of functional calcium channels.

Examination of the current voltage properties of $\alpha_{1E}\alpha_{2b}\beta_{1\text{-}3}$ expressing cells indicates that $\alpha_{1E\text{-}3}\alpha_{2b}\beta_{1\text{-}3}$ is a high-voltage activated calcium channel and the peak current is reached at a potential only slightly less positive than other neuronal calcium channels also expressing $\alpha_{2b}$ and $\beta_1$, and $\alpha_{1B}$ and $\alpha_{1D}$. Current voltage properties of $\alpha_{1E\text{-}1}\alpha_{2b}\beta_{1\text{-}3}$ are statistically different from those of $\alpha_{1B\text{-}1}\alpha_{2b}\beta_{1\text{-}3}$. Current voltage curves for $\alpha_{1E\text{-}1}\alpha_{2b}\beta_{1\text{-}3}$ and $\alpha_{1E\text{-}3}\alpha_{2b}\beta_{1\text{-}3}$ both peak at approximately +5 mV, as does the current voltage curve for $\alpha_{1E\text{-}3}$ alone.

The kinetics and voltage dependence of inactivation using both prepulse (200 ms) and steady-state inactivation was examined. $\alpha_{1E}$ mediated calcium channels are rapidly inactivated relative to previously cloned calcium channels and other high voltage-activated calcium channels. $\alpha_{1E\text{-}3}\alpha_{2b}\beta_{1\text{-}3}$ mediated calcium channels are inactivated rapidly and are thus sensitive to relatively brief (200 ms) prepulses as well as long prepulses (>20 s steady state inactivation), but recover rapidly from steady state inactivation. The kinetics of the rapid inactivation has two components, one with a time constant of approximately 25 ms and the other approximately 400 ms.

To determine whether $\alpha_{1E}$ mediated calcium channels have properties of low voltage activated calcium channels, the details of tail currents activated by a test pulse ranging −60 to +80 mV were measured at −60 mV. Tail currents recorded at −60 mV could be well fit by a single exponential of 150 to 300 μs; at least an order of magnitude faster than those typically observed with low voltage-activated calcium channels.

HEK 293 cells expressing $\alpha_{1E\text{-}3}\alpha_{2b}\beta_{1\text{-}3}$ flux more current with $Ba^{2+}$ as the charge carrier and currents carried by $Ba^{2+}$ and $Ca^{2+}$ have different current-voltage properties. Furthermore, the time course of inactivation is slower and the amount of prepulse inactivation less with $Ca^{2+}$ as the charge carrier.

b. Pharmacology

The current of cells transfected with $\alpha_{1E\text{-}1}\alpha_{2b}\beta_{1\text{-}3}$ and $\alpha_{1E\text{-}3}\alpha_{2b}\beta_{1\text{-}3}$ showed sensitivity to both organic and inorganic calcium channel blockers. Maximal blocking was observed with the non-specific calcium channel blocker, inorganic $Cd^{2+}$, which reversibly blocked 95±2% (n=30) of the barium current. A reversible block was observed with 50 μM $Ni^{2+}$ of 65±10% ($\alpha_{1E\text{-}1}\alpha_{2b}\beta_{1\text{-}3}$, n=3) to 74±7% ($\alpha_{1E\text{-}3}\alpha_{2b}\beta_{1\text{-}3}$, n=3). In addition, blocking was observed with 300 μM amiloride (66±18%, n=4) and ethosuximide (67±10%, n=3). A high sensitivity was observed with ω-Aga-IVa (73±2% block at 10 nM in $\alpha_{1E\text{-}3}\alpha_{2b}\beta_{1\text{-}3}$, n=3) and block by Bay K 8644 (69±3% in $\alpha_{1E\text{-}3}\alpha_{2b}\beta_{1\text{-}3}$ at 5 μM, n=3). Bay K 8644 had no effect on the time course of the tail current and a slowing of the inactivation during the test pulse. Little reversal of the block by either Bay K 8644 or ω-Aga-IVa was observed even following the application of brief strongly depolarizing pulses. Further, Bay K 8644 applied to HEK 293 cells transfected with $\alpha_{1E}$ alone resulted in 56±6% (n=3) block. Funnel web spider toxin (nFTX, 1:500) resulted in 78±0% in $\alpha_{1E\text{-}3}\alpha_{2b}\beta_{1\text{-}3}$. Little sensitivity was observed to synthetic FTX or the conus snail toxin ω-CgTx GVIA.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

What is claimed is:

1. An isolated nucleic acid molecule selected from the group consisting of:
   (a) a nucleic acid molecule that encodes an $\alpha 1_E$-subunit of a human calcium channel and comprises the coding portion of the sequence of nucleotides set forth in SEQ ID NO: 24;
   (b) a nucleic acid molecule that encodes an $\alpha 1_E$ subunit of a human calcium channel and comprises the coding portion of the sequence of nucleotides set forth in SEQ ID NO: 27;
   (c) a nucleic acid molecule that encodes an $\alpha_{1E}$ subunit of a human calcium channel and comprises the sequence of nucleotides set forth in SEQ ID NO: 25, wherein the encoded $\alpha 1_E$ subunit has a molecular weight greater than about 120 kilodaltons (kD) and is a full-length $\alpha 1_E$ subunit of a human calcium channel that can form an ion channel;
   (d) a nucleic acid molecule comprising a sequence of nucleotides with codons that are degenerate to the codons in the coding portion of the sequence of nucleotides set forth in (a) or (b) above;
   (e) a nucleic acid molecule comprising a sequence of nucleotides that encodes an $\alpha 1_E$ subunit of a human calcium channel that comprises a sequence of amino acid sequence encoded by the nucleic acid molecule of any one of (a), (b), (c) or (d) above; and
   (f) a nucleic acid molecule that encodes an $\alpha 1_E$ subunit of a human calcium channel polypeptide, wherein the nucleic acid molecule hybridizes under stringent wash condition, 0.1.times.SSC, 0.1% SDS at 65° C., to the complement of the nucleotide sequence of (a), (b), (c), (d) or (e) above.

2. The isolated nucleic acid molecule of claim 1, wherein the subunit is an $\alpha_{1E}$ subunit or $\alpha_{1E-3}$-subunit.

3. The isolated nucleic acid molecule of claim 2, wherein the subunit is an $\alpha_{1E-1}$-subunit.

4. The isolated nucleic acid molecule of claim 1, wherein the $\alpha_1$ subunit is an $\alpha_{1E-3}$ subunit.

5. A eukaryotic cell transfected with a heterologous nucleic acid molecule comprising a sequence of nucleotides that encodes an $\alpha_{1E}$-subunit of a human calcium channel, wherein the $\alpha_{1E}$-subunit has an amino sequence of a subunit encoded by the isolated nucleic acid molecule of claim 1.

6. The eukaryotic cell of claim 5, wherein the heterologous nucleic acid molecule is a DNA molecule, wherein the DNA molecule encodes an $\alpha_{1E-1}$-subunit of a human calcium channel.

7. The eukaryotic cell of claim 5, wherein the heterologous nucleic acid molecule is a DNA molecule, wherein the DNA molecule encodes an $\alpha_{1E-3}$-subunit of a human calcium channel.

8. The eukaryotic cell of claim 5, wherein said cell expresses a functional heterologous calcium channel comprising at least one subunit encoded by the heterologous nucleic acid molecule.

9. The eukaryotic cell of claim 6 wherein said cell that expresses a functional heterologous calcium channel comprising at least one subunit encoded by the heterologous nucleic acid molecule.

10. The eukaryotic cell of claim 7 wherein said cell that expresses a functional heterologous calcium channel comprising at least one subunit encoded by the heterologous nucleic acid molecule.

11. A method for identifying a compound that modulates the activity of a calcium channel, comprising:
   suspending the eukaryotic cell of claim 8 in a solution containing the compound and a calcium channel selective ion;
   depolarizing the cell membranes of the cell;
   detecting the current flowing into the cell; and
   comparing the current with the current flowing into a control cell, wherein:
      the control cell is treated substantially the same as the cell exposed to the test compound except that the control culture is (I) not exposed to the test compound or the control cell is identical to the cell of claim 8 except that the control cell does not express functional calcium channels.

12. The cell of claim 11 selected from the group consisting of an HEK 293 cell, a Chinese hamster ovary cell, an African green monkey cell, and a mouse L cell.

13. A method for identifying a compound that modulates the activity of a calcium channel, comprising:
   suspending the cell of claim 9 a solution containing the compound and a calcium channel selective ion;
   depolarizing the cell membrane of the cell;
   detecting the current flowing into the cell; and
   comparing the current with the current flowing into a control cell, wherein the current that is detected differs from that detected in the control cell and wherein:
      the control cell is treated substantially the same as the cell exposed to the test compound except that the control culture is not exposed to the test compound or the control cell is identical to the cell of claim 9 except that the control cell does not express functional calcium channels.

14. A method for identifying a compound that modulates the activity of a calcium channel, comprising:
   suspending the cell of claim 10 in a solution containing the compound and a calcium channel selective ion;
   depolarizing the cell membrane of the cell;
   detecting the current flowing into the cell; and comparing the current with the current flowing into a control cell, wherein the current that is detected differs from that detected in the control cell and wherein:
the control cell is treated substantially the same as the cell exposed to the test compound except that the control culture is not exposed to the test compound or the control cell is identical to the cell of claim 10 except that the control cell does not express functional calcium channels.

15. A recombinant eukaryotic cell that expresses a functional, heterologous calcium channel, which is produced by a process comprising
(a) introducing into suitable host cells an RNA transcript encoding an $\alpha_{1E}$-subunit of a human calcium channel;
(b) culturing and harvesting the host cells of step (a) under conditions favoring expression of the $\alpha_{1E}$-subunit of a human calcium channels in said cell; and
(c) isolating said cell, wherein:
the $\alpha_1$-subunit has an amino sequence of a subunit encoded by the nucleic acid molecule of claim 1;
the heterologous calcium channels are the only heterologous ion channels expressed by the cell; and
the cell is an amphibian oocyte.

16. The eukaryotic cell of claim 15, wherein:
the process further comprises introducing a second RNA that is translatable in the cell into an $\alpha_2$-subunit of a calcium channel.

17. The eukaryotic cell of claim 15, wherein:
the calcium channels also comprise a $\beta_1$-subunit of a calcium channel.

18. The eukaryotic cell of claim 17, wherein:
the calcium channels also comprise a $\alpha_2$-subunit of a calcium channel.

19. The eukaryotic cell of claim 5, further comprising a heterologous nucleic acid molecule comprising a sequence of nucleotides that encodes an $\alpha_2$-subunit of a calcium channel.

20. The eukaryotic cell of claim 5, wherein the $\alpha 1E$-subunit is an $\alpha_{1E-1}$-subunit of a human calcium channel.

21. The eukaryotic cell of claim 19 which is selected from the group consisting of an HEK 293 cell, a Chinese hamster ovary cell, an African green monkey cell and a mouse L cell.

22. The eukaryotic cell of claim 15, wherein:
the process further comprises introducing a second RNA that is translatable in the cell into a $\beta_1$-subunit of a calcium channel.

23. The eukaryotic cell of claim 22, wherein:
the process further comprises introducing a third mRNA that is translatable in the cell into an $\alpha_2$-subunit of a human calcium channel.

24. A method for identifying a compound that modulates the activity of a calcium channel, comprising:
suspending the cell of claim 15 in a solution containing the compound and a calcium channel selective ion;
depolarizing the cell membrane of the cell; and
detecting the current flowing into the cell.

25. An expression vector comprising the nucleic acid molecule of claim 1, operably linked to a regulatory nucleotide sequence that controls expression of the nucleic acid molecule in a host cell.

26. The expression vector of claim 25, wherein said vector is a plasmid.

27. An expression vector comprising the nucleic acid molecule of claim 2, operably linked to a regulatory nucleotide sequence that controls expression of the nucleic acid molecule in a host cell.

28. The expression vector of claim 27, wherein said vector is a plasmid.

29. An isolated nucleic acid molecule, comprising a sequence of amino acids encoded by the sequence of nucleotides set forth in SEQ ID NO. 24.

30. A eukaryotic cell transfected with a heterologous nucleic acid molecule comprising a sequence of nucleotides that encodes an $\alpha_{1E}$-subunit of a human calcium channel, wherein the $\alpha_{1E}$-subunit is encoded by the isolated nucleic acid molecule of claim 29.

31. The eukaryotic cell of claim 30 wherein said cell expresses a functional heterologous calcium channel comprising at least one subunit encoded by the heterologous nucleic acid molecule.

32. A method for identifying a compound that modulates the activity of a calcium channel, comprising:
suspending the cell of claim 31 in a solution containing the compound and a calcium channel selective ion;
depolarizing the cell membrane of the cell;
detecting the current flowing into the cell; and
comparing the current with the current flowing into a control cell, wherein the current that is detected differs from that detected in the control cell and wherein:
the control cell is treated substantially the same as the cell exposed to the test compound except that the control culture is not exposed to the test compound or the control cell is identical to the cell of claim 31 except that the control cell does not express functional calcium channels.

33. A recombinant eukaryotic cell that expresses a functional, heterologous calcium channel, which is produced by a process comprising
(a) introducing into suitable host cells an RNA transcript encoding an $\alpha_{1E}$-subunit of a human calcium channel;
(b) culturing and harvesting the host cells of step (a) under conditions favoring expression of the $\alpha_{1E}$-subunit of a human calcium channels in said cell; and
(c) isolating said cell, wherein:
the $\alpha_1$-subunit has an amino sequence of a subunit encoded by the nucleic acid molecule of claim 29;
the heterologous calcium channels are the only heterologous ion channels expressed by the cell; and
the cell is an amphibian oocyte.

34. A method for identifying a compound that modulates the activity of a calcium channel, comprising:
suspending the cell of claim 33 in a solution containing the compound and a calcium channel selective ion;
depolarizing the cell membrane of the cell; and
detecting the current flowing into the cell; and
comparing the current with the current flowing into a control cell, wherein the current that is detected differs from that detected in the control cell and wherein:
control cell is treated substantially the same as the cell exposed to the test compound except that the control culture is not exposed to the test compound or the control cell is identical to the cell of claim 33 except that the control cell does not express functional calcium channels.

35. An expression vector comprising the nucleic acid molecule of claim 29, operably linked to a regulatory nucleotide sequence that controls expression of the nucleic acid molecule in a host cell.

36. The expression vector of claim 35, wherein said vector is a plasmid.

37. An isolated nucleic acid molecule, comprising a sequence of amino acids encoded by the sequence of nucleotides set forth in SEQ ID NO. 27.

38. A eukaryotic cell transfected with a heterologous nucleic acid molecule comprising a sequence of nucleotides that encodes an $\alpha_{1E}$-subunit of a human calcium channel, wherein the $\alpha_{1E}$-subunit is encoded by the molecule of claim 37.

39. The eukaryotic cell of claim 38 wherein said cell expresses a functional heterologous calcium channel comprising at least one subunit encoded by the heterologous nucleic acid molecule.

40. A method for identifying a compound that modulates the activity of a calcium channel, comprising:
suspending the cell of claim 39 in a solution containing the compound and a calcium channel selective ion;
depolarizing the cell membrane of the cell;
detecting the current flowing into the cell; and
comparing the current with the current flowing into a control cell, wherein the current that is detected differs from that detected in the control cell and wherein:
the control cell is treated substantially the same as the cell exposed to the test compound except that the control culture is not exposed to the test compound or the control cell is identical to the cell of claim 39 except that the control cell does not express functional calcium channels.

41. A recombinant eukaryotic cell that expresses a functional, heterologous calcium channel, which is produced by a process comprising
(a) introducing into suitable host cells an RNA transcript encoding an $\alpha_{1E}$-subunit of a human calcium channel;
(b) culturing and harvesting the host cells of step (a) under conditions favoring expression of the $\alpha_{1E}$-subunit of a human calcium channels in said cell; and
(c) isolating said cell, wherein:
the $\alpha_1$-subunit has an amino sequence of a subunit encoded by the nucleic acid molecule of claim 37;
the heterologous calcium channels are the only heterologous ion channels expressed by the cell; and
the cell is an amphibian oöcyte.

42. A method for identifying a compound that modulates the activity of a calcium channel, comprising:
suspending a cell of claim 41 in a solution containing the compound and a calcium channel selective ion;
depolarizing the cell membrane of the cell;
detecting the current flowing into the cell; and
comparing the current with the current flowing into a control cell, wherein:
control cell is treated substantially the same as the cell exposed to the test compound except that the control culture is not exposed to the test compound or the control cell is_identical to the cell of claim 41 except that the control cell does not express functional calcium channels.

43. An expression vector comprising the nucleic acid molecule of claim 37, operably linked to a regulatory nucleotide sequence that controls expression of the nucleic acid molecule in a host cell.

44. The expression vector of claim 43, wherein said vector is a plasmid.

45. An isolated nucleic acid molecule, comprising the sequence of nucleotides set forth in nucleotides 169–6921 of SEQ ID No. 24.

46. A eukaryotic cell transfected with a heterologous nucleic acid molecule comprising a sequence of nucleotides that encodes an $\alpha_{1E}$-subunit of a human calcium channel, wherein the $\alpha_{1E}$-subunit is encoded by the molecule of claim 45.

47. The eukaryotic cell of claim 46 wherein said cell expresses a functional heterologous calcium channel comprising at least one subunit encoded by the heterologous nucleic acid molecule.

48. A method for identifying a compound that modulates the activity of a calcium channel, comprising:
suspending the cell of claim 47 in a solution containing the compound and a calcium channel selective ion;
depolarizing the cell membrane of the cell;
detecting the current flowing into the cell; and
comparing the current thus detected to a current flowing into a control cell, wherein the current that is detected differs from that detected in the control cell and wherein:
control cell is treated substantially the same as the cell exposed to the test compound except that the control culture is not exposed to the test compound or the control cell is identical to the cell of claim 47 except that the control cell does not express functional calcium channels.

49. An expression vector comprising the nucleic acid molecule of claim 45, operably linked to a regulatory nucleotide sequence that controls expression of the nucleic acid molecule in a host cell.

50. The expression vector of claim 49, wherein said vector is a plasmid.

51. An isolated nucleic acid molecule that encodes an $\alpha_{1E}$ subunit of a human calcium channel and comprises a sequence of amino acids encoded by the sequence of nucleotides set forth in nucleotides 166–6978 of SEQ ID NO. 27.

52. A eukaryotic cell transfected with a heterologous nucleic acid molecule comprising a sequence of nucleotides that encodes an $\alpha_{1E}$-subunit of a human calcium channel, wherein the $\alpha_{1E}$-subunit is encoded by the molecule of claim 51.

53. The eukaryotic cell of claim 52 wherein said cell expresses a functional heterologous calcium channel comprising at least one subunit encoded by the heterologous nucleic acid molecule.

54. A method for identifying a compound that modulates the activity of a calcium channel, comprising:
suspending the cell of claim 53 in a solution containing the compound and a calcium channel selective ion;
depolarizing the cell membrane of the cell;
detecting the current flowing into the cell; and
comparing the current with the current flowing into a control cell, wherein the current that is detected differs from that detected in the control cell, and wherein:
the control cell is treated substantially the same as the cell exposed to the test compound except that the control culture is not exposed to the test compound or the control cell is identical to the cell of claim 53 except that the control cell does not express functional calcium channels.

55. An expression vector comprising the nucleic acid molecule of claim 51, operably linked to a regulatory nucleotide sequence that controls expression of the nucleic acid molecule in a host cell.

56. The expression vector of claim 55, wherein said vector is a plasmid.

57. An isolated nucleic acid molecule, comprising the sequence of nucleotides set forth in nucleotides 166–6978 of SEQ ID NO. 27.

58. A eukaryotic cell transfected with a heterologous nucleic acid molecule comprising a sequence of nucleotides that encodes an $\alpha_{1E}$-subunit of a human calcium channel, wherein the $\alpha_{1E}$-subunit is encoded by the molecule of claim 57.

59. The eukaryotic cell of claim 58 wherein said cell expresses a functional heterologous calcium channel comprising at least one subunit encoded by the heterologous DNA.

60. A method for identifying a compound that modulates the activity of a calcium channel, comprising:
  suspending the cell of claim 59 in a solution containing the compound and a calcium channel selective ion;
  depolarizing the cell membrane of the cell; and
  detecting the current flowing into the cell; and
  comparing the current with the current flowing into a control cell, wherein the current that is detected differs from that detected in the control cell and wherein:
    control cell is treated substantially the same as the cell exposed to the test compound except that the control culture is not exposed to the test compound or the control cell is identical to the cell of claim 59 except that the control cell does not express functional calcium channels.

61. An expression vector comprising the nucleic acid molecule of claim 57, operably linked to a regulatory nucleotide sequence that controls expression of the nucleic acid molecule in a host cell.

62. The expression vector of claim 61, wherein said vector is a plasmid.

63. An isolated nucleic acid molecule that encodes an $\alpha_{1E}$-subunit of a human calcium channel comprising a sequence of amino acids encoded by the sequence of nucleotides set forth in nucleotides 166–6978 of SEQ ID NO. 27.

64. A eukaryotic cell transferred with a heterologous nucleic acid molecule comprising a sequence of nucleotides that encodes an $\alpha_{1E}$-subunit is encoded by the molecule of claim 63.

65. An expression vector comprising the nucleic acid molecule of claim 63, operably linked to a regulatory nucleotide sequence that controls expression of the nucleic acid molecule in a host cell.

66. The expression vector of claim 65, wherein said vector is a plasmid.

67. An isolated RNA molecule selected from the group consisting of:
  (a) a nucleic acid molecule that encodes an $\alpha_{1E}$-subunit of a human calcium channel and comprises the coding portion of the sequence of nucleotides set forth in SEQ ID NO: 24;
  (b) a nucleic acid molecule that encodes an $\alpha_{1E}$ subunit of a human calcium channel and comprises the coding portion of the sequence of nucleotides set forth in SEQ ID NO: 27;
  (c) a nucleic acid molecule that encodes an $\alpha_{1E}$ subunit of a human calcium channel and comprises the sequence of nucleotides set forth in SEQ ID NO: 25, wherein the encoded $\alpha_{1E}$ subunit has a molecular weight greater than about 120 kilodaltons (kD) and is a full-length $\alpha_{1E}$ subunit of a human calcium channel that can form an ion channel;
  (d) a nucleic acid molecule comprising a sequence of nucleotides with codons that are degenerate to the codons in the coding portion of the sequence of nucleotides set forth in (a) or (b) above;
  (e) a nucleic acid molecule comprising a sequence of nucleotides that encodes an $\alpha_{1E}$ subunit of a human calcium channel that comprises a sequence of amino acid sequence encoded by the nucleic acid molecule of any one of (a), (b), (c) or (d) above; and
  (f) a nucleic acid molecule that encodes an $\alpha_{1E}$ subunit of a human calcium channel polypeptide, wherein the nucleic acid molecule hybridizes under stringent wash condition, 0.1.times.SSC, 0.1% SDS at 65° C., to the complement of the nucleotide sequence of (a), (b), (c), (d) or (e) above.

68. An isolated nucleic acid molecule that encodes an $\alpha_{1E}$-subunit of a human calcium channel, wherein the $\alpha_{1E}$-subunit can form a functional calcium channel.

* * * * *

SEQUENCE LISTING (1) GENERAL INFORMATION:

(iii) NUMBER OF SEQUENCES: 34

-continued (2) INFORMATION FOR SEQ ID NO:1:

(i) SEQUENCE CHARACTERISTICS:
        (A) LENGTH: 7635 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 511..6996

(ix) FEATURE:
        (A) NAME/KEY: 5'UTR
        (B) LOCATION: 1..510

(ix) FEATURE:
        (A) NAME/KEY: 3'UTR
        (B) LOCATION: 6994..7635

(xi) SEQUENCE DESCRIPTION: SEQ ID NO:1:

```
GGGCGAGCGC CTCCGTCCCC GGATGTGAGC TCCGGCTGCC CGCGGTCCCG AGCCAGCGGC        60

GCGCGGGCGG CGGCGGCGGG CACCGGGCAC CGCGGCGGGC GGGCAGACGG GCGGGCATGG       120

GGGGAGCGCC GAGCGGCCCC GGCGGCCGGG CCGGCATCAC CGCGGCGTCT CTCCGCTAGA       180

GGAGGGGACA AGCCAGTTCT CCTTTGCAGC AAAAAATTAC ATGTATATAT TATTAAGATA       240

ATATATACAT TGGATTTTAT TTTTTTAAAA AGTTTATTTT GCTCCATTTT TGAAAAAGAG       300

AGAGCTTGGG TGGCGAGCGG TTTTTTTTTA AAATCAATTA TCCTTATTTT CTGTTATTTG       360

TCCCCGTCCC TCCCCACCCC CCTGCTGAAG CGAGAATAAG GGCAGGGACC GCGGCTCCTA       420

CCTCTTGGTG ATCCCCTTCC CCATTCCGCC CCCGCCCCAA CGCCCAGCAC AGTGCCCTGC       480

ACACAGTAGT CGCTCAATAA ATGTTCGTGG ATG ATG ATG ATG ATG ATG ATG AAA        534
                                Met Met Met Met Met Met Met Lys
                                 1               5

AAA ATG CAG CAT CAA CGG CAG CAG CAA GCG GAC CAC GCG AAC GAG GCA         582
Lys Met Gln His Gln Arg Gln Gln Gln Ala Asp His Ala Asn Glu Ala
         10                  15                  20

AAC TAT GCA AGA GGC ACC AGA CTT CCT CTT TCT GGT GAA GGA CCA ACT         630
Asn Tyr Ala Arg Gly Thr Arg Leu Pro Leu Ser Gly Glu Gly Pro Thr
 25                  30                  35                  40

TCT CAG CCG AAT AGC TCC AAG CAA ACT GTC CTG TCT TGG CAA GCT GCA         678
Ser Gln Pro Asn Ser Ser Lys Gln Thr Val Leu Ser Trp Gln Ala Ala
                 45                  50                  55

ATC GAT GCT GCT AGA CAG GCC AAG GCT GCC CAA ACT ATG AGC ACC TCT         726
Ile Asp Ala Ala Arg Gln Ala Lys Ala Ala Gln Thr Met Ser Thr Ser
             60                  65                  70

GCA CCC CCA CCT GTA GGA TCT CTC TCC CAA AGA AAA CGT CAG CAA TAC         774
Ala Pro Pro Pro Val Gly Ser Leu Ser Gln Arg Lys Arg Gln Gln Tyr
         75                  80                  85

GCC AAG AGC AAA AAA CAG GGT AAC TCG TCC AAC AGC CGA CCT GCC CGC         822
Ala Lys Ser Lys Lys Gln Gly Asn Ser Ser Asn Ser Arg Pro Ala Arg
 90                  95                 100

GCC CTT TTC TGT TTA TCA CTC AAT AAC CCC ATC CGA AGA GCC TGC ATT         870
Ala Leu Phe Cys Leu Ser Leu Asn Asn Pro Ile Arg Arg Ala Cys Ile
105                 110                 115                 120

AGT ATA GTG GAA TGG AAA CCA TTT GAC ATA TTT ATA TTA TTG GCT ATT         918
Ser Ile Val Glu Trp Lys Pro Phe Asp Ile Phe Ile Leu Leu Ala Ile
                125                 130                 135

TTT GCC AAT TGT GTG GCC TTA GCT ATT TAC ATC CCA TTC CCT GAA GAT         966
Phe Ala Asn Cys Val Ala Leu Ala Ile Tyr Ile Pro Phe Pro Glu Asp
```

```
                     140                  145                  150
GAT TCT AAT TCA ACA AAT CAT AAC TTG GAA AAA GTA GAA TAT GCC TTC     1014
Asp Ser Asn Ser Thr Asn His Asn Leu Glu Lys Val Glu Tyr Ala Phe
            155                  160                  165

CTG ATT ATT TTT ACA GTC GAG ACA TTT TTG AAG ATT ATA GCG TAT GGA     1062
Leu Ile Ile Phe Thr Val Glu Thr Phe Leu Lys Ile Ile Ala Tyr Gly
        170                  175                  180

TTA TTG CTA CAT CCT AAT GCT TAT GTT AGG AAT GGA TGG AAT TTA CTG     1110
Leu Leu Leu His Pro Asn Ala Tyr Val Arg Asn Gly Trp Asn Leu Leu
185                  190                  195                  200

GAT TTT GTT ATA GTA ATA GTA GGA TTG TTT AGT GTA ATT TTG GAA CAA     1158
Asp Phe Val Ile Val Ile Val Gly Leu Phe Ser Val Ile Leu Glu Gln
            205                  210                  215

TTA ACC AAA GAA ACA GAA GGC GGG AAC CAC TCA AGC GGC AAA TCT GGA     1206
Leu Thr Lys Glu Thr Glu Gly Gly Asn His Ser Ser Gly Lys Ser Gly
        220                  225                  230

GGC TTT GAT GTC AAA GCC CTC CGT GCC TTT CGA GTG TTG CGA CCA CTT     1254
Gly Phe Asp Val Lys Ala Leu Arg Ala Phe Arg Val Leu Arg Pro Leu
    235                  240                  245

CGA CTA GTG TCA GGA GTG CCC AGT TTA CAA GTT GTC CTG AAC TCC ATT     1302
Arg Leu Val Ser Gly Val Pro Ser Leu Gln Val Val Leu Asn Ser Ile
250                  255                  260

ATA AAA GCC ATG GTT CCC CTC CTT CAC ATA GCC CTT TTG GTA TTA TTT     1350
Ile Lys Ala Met Val Pro Leu Leu His Ile Ala Leu Leu Val Leu Phe
265                  270                  275                  280

GTA ATC ATA ATC TAT GCT ATT ATA GGA TTG GAA CTT TTT ATT GGA AAA     1398
Val Ile Ile Ile Tyr Ala Ile Ile Gly Leu Glu Leu Phe Ile Gly Lys
                285                  290                  295

ATG CAC AAA ACA TGT TTT TTT GCT GAC TCA GAT ATC GTA GCT GAA GAG     1446
Met His Lys Thr Cys Phe Phe Ala Asp Ser Asp Ile Val Ala Glu Glu
            300                  305                  310

GAC CCA GCT CCA TGT GCG TTC TCA GGG AAT GGA CGC CAG TGT ACT GCC     1494
Asp Pro Ala Pro Cys Ala Phe Ser Gly Asn Gly Arg Gln Cys Thr Ala
        315                  320                  325

AAT GGC ACG GAA TGT AGG AGT GGC TGG GTT GGC CCG AAC GGA GGC ATC     1542
Asn Gly Thr Glu Cys Arg Ser Gly Trp Val Gly Pro Asn Gly Gly Ile
330                  335                  340

ACC AAC TTT GAT AAC TTT GCC TTT GCC ATG CTT ACT GTG TTT CAG TGC     1590
Thr Asn Phe Asp Asn Phe Ala Phe Ala Met Leu Thr Val Phe Gln Cys
345                  350                  355                  360

ATC ACC ATG GAG GGC TGG ACA GAC GTG CTC TAC TGG ATG AAT GAT GCT     1638
Ile Thr Met Glu Gly Trp Thr Asp Val Leu Tyr Trp Met Asn Asp Ala
                365                  370                  375

ATG GGA TTT GAA TTG CCC TGG GTG TAT TTT GTC AGT CTC GTC ATC TTT     1686
Met Gly Phe Glu Leu Pro Trp Val Tyr Phe Val Ser Leu Val Ile Phe
            380                  385                  390

GGG TCA TTT TTC GTA CTA AAT CTT GTA CTT GGT GTA TTG AGC GGA GAA     1734
Gly Ser Phe Phe Val Leu Asn Leu Val Leu Gly Val Leu Ser Gly Glu
        395                  400                  405

TTC TCA AAG GAA AGA GAG AAG GCA AAA GCA CGG GGA GAT TTC CAG AAG     1782
Phe Ser Lys Glu Arg Glu Lys Ala Lys Ala Arg Gly Asp Phe Gln Lys
    410                  415                  420

CTC CGG GAG AAG CAG CAG CTG GAG GAG GAT CTA AAG GGC TAC TTG GAT     1830
Leu Arg Glu Lys Gln Gln Leu Glu Glu Asp Leu Lys Gly Tyr Leu Asp
425                  430                  435                  440

TGG ATC ACC CAA GCT GAG GAC ATC GAT CCG GAG AAT GAG GAA GAA GGA     1878
Trp Ile Thr Gln Ala Glu Asp Ile Asp Pro Glu Asn Glu Glu Glu Gly
                445                  450                  455

GGA GAG GAA GGC AAA CGA AAT ACT AGC ATG CCC ACC AGC GAG ACT GAG     1926
```

```
                Gly Glu Glu Gly Lys Arg Asn Thr Ser Met Pro Thr Ser Glu Thr Glu
                                460                 465                 470

TCT GTG AAC ACA GAG AAC GTC AGC GGT GAA GGC GAG AAC CGA GGC TGC                1974
Ser Val Asn Thr Glu Asn Val Ser Gly Glu Gly Glu Asn Arg Gly Cys
            475                 480                 485

TGT GGA AGT CTC TGT CAA GCC ATC TCA AAA TCC AAA CTC AGC CGA CGC                2022
Cys Gly Ser Leu Cys Gln Ala Ile Ser Lys Ser Lys Leu Ser Arg Arg
        490                 495                 500

TGG CGT CGC TGG AAC CGA TTC AAT CGC AGA AGA TGT AGG GCC GCC GTG                2070
Trp Arg Arg Trp Asn Arg Phe Asn Arg Arg Arg Cys Arg Ala Ala Val
505                 510                 515                 520

AAG TCT GTC ACG TTT TAC TGG CTG GTT ATC GTC CTG GTG TTT CTG AAC                2118
Lys Ser Val Thr Phe Tyr Trp Leu Val Ile Val Leu Val Phe Leu Asn
                525                 530                 535

ACC TTA ACC ATT TCC TCT GAG CAC TAC AAT CAG CCA GAT TGG TTG ACA                2166
Thr Leu Thr Ile Ser Ser Glu His Tyr Asn Gln Pro Asp Trp Leu Thr
            540                 545                 550

CAG ATT CAA GAT ATT GCC AAC AAA GTC CTC TTG GCT CTG TTC ACC TGC                2214
Gln Ile Gln Asp Ile Ala Asn Lys Val Leu Leu Ala Leu Phe Thr Cys
        555                 560                 565

GAG ATG CTG GTA AAA ATG TAC AGC TTG GGC CTC CAA GCA TAT TTC GTC                2262
Glu Met Leu Val Lys Met Tyr Ser Leu Gly Leu Gln Ala Tyr Phe Val
570                 575                 580

TCT CTT TTC AAC CGG TTT GAT TGC TTC GTG GTG TGT GGT GGA ATC ACT                2310
Ser Leu Phe Asn Arg Phe Asp Cys Phe Val Val Cys Gly Gly Ile Thr
585                 590                 595                 600

GAG ACG ATC TTG GTG GAA CTG GAA ATC ATG TCT CCC CTG GGG ATC TCT                2358
Glu Thr Ile Leu Val Glu Leu Glu Ile Met Ser Pro Leu Gly Ile Ser
                605                 610                 615

GTG TTT CGG TGT GTG CGC CTC TTA AGA ATC TTC AAA GTG ACC AGG CAC                2406
Val Phe Arg Cys Val Arg Leu Leu Arg Ile Phe Lys Val Thr Arg His
            620                 625                 630

TGG ACT TCC CTG AGC AAC TTA GTG GCA TCC TTA TTA AAC TCC ATG AAG                2454
Trp Thr Ser Leu Ser Asn Leu Val Ala Ser Leu Leu Asn Ser Met Lys
        635                 640                 645

TCC ATC GCT TCG CTG TTG CTT CTG CTT TTT CTC TTC ATT ATC ATC TTT                2502
Ser Ile Ala Ser Leu Leu Leu Leu Phe Leu Phe Ile Ile Ile Phe
650                 655                 660

TCC TTG CTT GGG ATG CAG CTG TTT GGC GGC AAG TTT AAT TTT GAT GAA                2550
Ser Leu Leu Gly Met Gln Leu Phe Gly Gly Lys Phe Asn Phe Asp Glu
665                 670                 675                 680

ACG CAA ACC AAG CGG AGC ACC TTT GAC AAT TTC CCT CAA GCA CTT CTC                2598
Thr Gln Thr Lys Arg Ser Thr Phe Asp Asn Phe Pro Gln Ala Leu Leu
                685                 690                 695

ACA GTG TTC CAG ATC CTG ACA GGC GAA GAC TGG AAT GCT GTG ATG TAC                2646
Thr Val Phe Gln Ile Leu Thr Gly Glu Asp Trp Asn Ala Val Met Tyr
            700                 705                 710

GAT GGC ATC ATG GCT TAC GGG GGC CCA TCC TCT TCA GGA ATG ATC GTC                2694
Asp Gly Ile Met Ala Tyr Gly Gly Pro Ser Ser Ser Gly Met Ile Val
        715                 720                 725

TGC ATC TAC TTC ATC ATC CTC TTC ATT TGT GGT AAC TAT ATT CTA CTG                2742
Cys Ile Tyr Phe Ile Ile Leu Phe Ile Cys Gly Asn Tyr Ile Leu Leu
730                 735                 740

AAT GTC TTC TTG GCC ATC GCT GTA GAC AAT TTG GCT GAT GCT GAA AGT                2790
Asn Val Phe Leu Ala Ile Ala Val Asp Asn Leu Ala Asp Ala Glu Ser
745                 750                 755                 760

CTG AAC ACT GCT CAG AAA GAA GAA GCG GAA GAA AAG GAG AGG AAA AAG                2838
Leu Asn Thr Ala Gln Lys Glu Glu Ala Glu Glu Lys Glu Arg Lys Lys
                765                 770                 775
```

```
ATT GCC AGA AAA GAG AGC CTA GAA AAT AAA AAG AAC AAC AAA CCA GAA      2886
Ile Ala Arg Lys Glu Ser Leu Glu Asn Lys Lys Asn Asn Lys Pro Glu
            780                 785                 790

GTC AAC CAG ATA GCC AAC AGT GAC AAC AAG GTT ACA ATT GAC GAC TAT      2934
Val Asn Gln Ile Ala Asn Ser Asp Asn Lys Val Thr Ile Asp Asp Tyr
        795                 800                 805

AGA GAA GAG GAT GAA GAC AAG GAC CCC TAT CCG CCT TGC GAT GTG CCA      2982
Arg Glu Glu Asp Glu Asp Lys Asp Pro Tyr Pro Pro Cys Asp Val Pro
810                 815                 820

GTA GGG GAA GAG GAA GAG GAA GAG GAG GAT GAA CCT GAG GTT CCT          3030
Val Gly Glu Glu Glu Glu Glu Glu Glu Asp Glu Pro Glu Val Pro
825                 830                 835                 840

GCC GGA CCC CGT CCT CGA AGG ATC TCG GAG TTG AAC ATG AAG GAA AAA      3078
Ala Gly Pro Arg Pro Arg Arg Ile Ser Glu Leu Asn Met Lys Glu Lys
                845                 850                 855

ATT GCC CCC ATC CCT GAA GGG AGC GCT TTC TTC ATT CTT AGC AAG ACC      3126
Ile Ala Pro Ile Pro Glu Gly Ser Ala Phe Phe Ile Leu Ser Lys Thr
            860                 865                 870

AAC CCG ATC CGC GTA GGC TGC CAC AAG CTC ATC AAC CAC CAC ATC TTC      3174
Asn Pro Ile Arg Val Gly Cys His Lys Leu Ile Asn His His Ile Phe
        875                 880                 885

ACC AAC CTC ATC CTT GTC TTC ATC ATG CTG AGC AGT GCT GCC CTG GCC      3222
Thr Asn Leu Ile Leu Val Phe Ile Met Leu Ser Ser Ala Ala Leu Ala
    890                 895                 900

GCA GAG GAC CCC ATC CGC AGC CAC TCC TTC CGG AAC ACG ATA CTG GGT      3270
Ala Glu Asp Pro Ile Arg Ser His Ser Phe Arg Asn Thr Ile Leu Gly
905                 910                 915                 920

TAC TTT GAC TAT GCC TTC ACA GCC ATC TTT ACT GTT GAG ATC CTG TTG      3318
Tyr Phe Asp Tyr Ala Phe Thr Ala Ile Phe Thr Val Glu Ile Leu Leu
                925                 930                 935

AAG ATG ACA ACT TTT GGA GCT TTC CTC CAC AAA GGG GCC TTC TGC AGG      3366
Lys Met Thr Thr Phe Gly Ala Phe Leu His Lys Gly Ala Phe Cys Arg
            940                 945                 950

AAC TAC TTC AAT TTG CTG GAT ATG CTG GTG GTT GGG GTG TCT CTG GTG      3414
Asn Tyr Phe Asn Leu Leu Asp Met Leu Val Val Gly Val Ser Leu Val
        955                 960                 965

TCA TTT GGG ATT CAA TCC AGT GCC ATC TCC GTT GTG AAG ATT CTG AGG      3462
Ser Phe Gly Ile Gln Ser Ser Ala Ile Ser Val Val Lys Ile Leu Arg
    970                 975                 980

GTC TTA AGG GTC CTG CGT CCC CTC AGG GCC ATC AAC AGA GCA AAA GGA      3510
Val Leu Arg Val Leu Arg Pro Leu Arg Ala Ile Asn Arg Ala Lys Gly
985                 990                 995                 1000

CTT AAG CAC GTG GTC CAG TGC GTC TTC GTG GCC ATC CGG ACC ATC GGC      3558
Leu Lys His Val Val Gln Cys Val Phe Val Ala Ile Arg Thr Ile Gly
                1005                1010                1015

AAC ATC ATG ATC GTC ACC ACC CTC CTG CAG TTC ATG TTT GCC TGT ATC      3606
Asn Ile Met Ile Val Thr Thr Leu Leu Gln Phe Met Phe Ala Cys Ile
            1020                1025                1030

GGG GTC CAG TTG TTC AAG GGG AAG TTC TAT CGC TGT ACG GAT GAA GCC      3654
Gly Val Gln Leu Phe Lys Gly Lys Phe Tyr Arg Cys Thr Asp Glu Ala
        1035                1040                1045

AAA AGT AAC CCT GAA GAA TGC AGG GGA CTT TTC ATC CTC TAC AAG GAT      3702
Lys Ser Asn Pro Glu Glu Cys Arg Gly Leu Phe Ile Leu Tyr Lys Asp
    1050                1055                1060

GGG GAT GTT GAC AGT CCT GTG GTC CGT GAA CGG ATC TGG CAA AAC AGT      3750
Gly Asp Val Asp Ser Pro Val Val Arg Glu Arg Ile Trp Gln Asn Ser
1065                1070                1075                1080

GAT TTC AAC TTC GAC AAC GTC CTC TCT GCT ATG ATG GCG CTC TTC ACA      3798
Asp Phe Asn Phe Asp Asn Val Leu Ser Ala Met Met Ala Leu Phe Thr
                1085                1090                1095
```

```
GTC TCC ACG TTT GAG GGC TGG CCT GCG TTG CTG TAT AAA GCC ATC GAC      3846
Val Ser Thr Phe Glu Gly Trp Pro Ala Leu Leu Tyr Lys Ala Ile Asp
         1100                1105                1110

TCG AAT GGA GAG AAC ATC GGC CCA ATC TAC AAC CAC CGC GTG GAG ATC      3894
Ser Asn Gly Glu Asn Ile Gly Pro Ile Tyr Asn His Arg Val Glu Ile
         1115                1120                1125

TCC ATC TTC TTC ATC ATC TAC ATC ATT GTA GCT TTC TTC ATG ATG          3942
Ser Ile Phe Phe Ile Ile Tyr Ile Ile Val Ala Phe Phe Met Met
     1130                1135                1140

AAC ATC TTT GTG GGC TTT GTC ATC GTT ACA TTT CAG GAA CAA GGA GAA      3990
Asn Ile Phe Val Gly Phe Val Ile Val Thr Phe Gln Glu Gln Gly Glu
1145                1150                1155                1160

AAA GAG TAT AAG AAC TGT GAG CTG GAC AAA AAT CAG CGT CAG TGT GTT      4038
Lys Glu Tyr Lys Asn Cys Glu Leu Asp Lys Asn Gln Arg Gln Cys Val
             1165                1170                1175

GAA TAC GCC TTG AAA GCA CGT CCC TTG CGG AGA TAC ATC CCC AAA AAC      4086
Glu Tyr Ala Leu Lys Ala Arg Pro Leu Arg Arg Tyr Ile Pro Lys Asn
         1180                1185                1190

CCC TAC CAG TAC AAG TTC TGG TAC GTG GTG AAC TCT TCG CCT TTC GAA      4134
Pro Tyr Gln Tyr Lys Phe Trp Tyr Val Val Asn Ser Ser Pro Phe Glu
         1195                1200                1205

TAC ATG ATG TTT GTC CTC ATC ATG CTC AAC ACA CTC TGC TTG GCC ATG      4182
Tyr Met Met Phe Val Leu Ile Met Leu Asn Thr Leu Cys Leu Ala Met
         1210                1215                1220

CAG CAC TAC GAG CAG TCC AAG ATG TTC AAT GAT GCC ATG GAC ATT CTG      4230
Gln His Tyr Glu Gln Ser Lys Met Phe Asn Asp Ala Met Asp Ile Leu
1225                1230                1235                1240

AAC ATG GTC TTC ACC GGG GTG TTC ACC GTC GAG ATG GTT TTG AAA GTC      4278
Asn Met Val Phe Thr Gly Val Phe Thr Val Glu Met Val Leu Lys Val
             1245                1250                1255

ATC GCA TTT AAG CCT AAG GGG TAT TTT AGT GAC GCC TGG AAC ACG TTT      4326
Ile Ala Phe Lys Pro Lys Gly Tyr Phe Ser Asp Ala Trp Asn Thr Phe
         1260                1265                1270

GAC TCC CTC ATC GTA ATC GGC AGC ATT ATA GAC GTG GCC CTC AGC GAA      4374
Asp Ser Leu Ile Val Ile Gly Ser Ile Ile Asp Val Ala Leu Ser Glu
         1275                1280                1285

GCA GAC CCA ACT GAA AGT GAA AAT GTC CCT GTC CCA ACT GCT ACA CCT      4422
Ala Asp Pro Thr Glu Ser Glu Asn Val Pro Val Pro Thr Ala Thr Pro
         1290                1295                1300

GGG AAC TCT GAA GAG AGC AAT AGA ATC TCC ATC ACC TTT TTC CGT CTT      4470
Gly Asn Ser Glu Glu Ser Asn Arg Ile Ser Ile Thr Phe Phe Arg Leu
1305                1310                1315                1320

TTC CGA GTG ATG CGA TTG GTG AAG CTT CTC AGC AGG GGG GAA GGC ATC      4518
Phe Arg Val Met Arg Leu Val Lys Leu Leu Ser Arg Gly Glu Gly Ile
             1325                1330                1335

CGG ACA TTG CTG TGG ACT TTT ATT AAG TTC TTT CAG GCG CTC CCG TAT      4566
Arg Thr Leu Leu Trp Thr Phe Ile Lys Phe Phe Gln Ala Leu Pro Tyr
         1340                1345                1350

GTG GCC CTC CTC ATA GCC ATG CTG TTC TTC ATC TAT GCG GTC ATT GGC      4614
Val Ala Leu Leu Ile Ala Met Leu Phe Phe Ile Tyr Ala Val Ile Gly
         1355                1360                1365

ATG CAG ATG TTT GGG AAA GTT GCC ATG AGA GAT AAC AAC CAG ATC AAT      4662
Met Gln Met Phe Gly Lys Val Ala Met Arg Asp Asn Asn Gln Ile Asn
         1370                1375                1380

AGG AAC AAT AAC TTC CAG ACG TTT CCC CAG GCG GTG CTG CTG CTC TTC      4710
Arg Asn Asn Asn Phe Gln Thr Phe Pro Gln Ala Val Leu Leu Leu Phe
1385                1390                1395                1400

AGG TGT GCA ACA GGT GAG GCC TGG CAG GAG ATC ATG CTG GCC TGT CTC      4758
Arg Cys Ala Thr Gly Glu Ala Trp Gln Glu Ile Met Leu Ala Cys Leu
```

-continued

| | | |
|---|---|---|
| CCA GGG AAG CTC TGT GAC CCT GAG TCA GAT TAC AAC CCC GGG GAG GAG<br>Pro Gly Lys Leu Cys Asp Pro Glu Ser Asp Tyr Asn Pro Gly Glu Glu<br>              1420                             1425                            1430 | 4806 |

```
                    1405                1410                1415

CCA GGG AAG CTC TGT GAC CCT GAG TCA GAT TAC AAC CCC GGG GAG GAG      4806
Pro Gly Lys Leu Cys Asp Pro Glu Ser Asp Tyr Asn Pro Gly Glu Glu
             1420                1425                1430

CAT ACA TGT GGG AGC AAC TTT GCC ATT GTC TAT TTC ATC AGT TTT TAC      4854
His Thr Cys Gly Ser Asn Phe Ala Ile Val Tyr Phe Ile Ser Phe Tyr
         1435                1440                1445

ATG CTC TGT GCA TTT CTG ATC ATC AAT CTG TTT GTG GCT GTC ATC ATG      4902
Met Leu Cys Ala Phe Leu Ile Ile Asn Leu Phe Val Ala Val Ile Met
1450                1455                1460

GAT AAT TTC GAC TAT CTG ACC CGG GAC TGG TCT ATT TTG GGG CCT CAC      4950
Asp Asn Phe Asp Tyr Leu Thr Arg Asp Trp Ser Ile Leu Gly Pro His
1465                1470                1475                1480

CAT TTA GAT GAA TTC AAA AGA ATA TGG TCA GAA TAT GAC CCT GAG GCA      4998
His Leu Asp Glu Phe Lys Arg Ile Trp Ser Glu Tyr Asp Pro Glu Ala
             1485                1490                1495

AAG GGA AGG ATA AAA CAC CTT GAT GTG GTC ACT CTG CTT CGA CGC ATC      5046
Lys Gly Arg Ile Lys His Leu Asp Val Val Thr Leu Leu Arg Arg Ile
             1500                1505                1510

CAG CCT CCC CTG GGG TTT GGG AAG TTA TGT CCA CAC AGG GTA GCG TGC      5094
Gln Pro Pro Leu Gly Phe Gly Lys Leu Cys Pro His Arg Val Ala Cys
         1515                1520                1525

AAG AGA TTA GTT GCC ATG AAC ATG CCT CTC AAC AGT GAC GGG ACA GTC      5142
Lys Arg Leu Val Ala Met Asn Met Pro Leu Asn Ser Asp Gly Thr Val
         1530                1535                1540

ATG TTT AAT GCA ACC CTG TTT GCT TTG GTT CGA ACG GCT CTT AAG ATC      5190
Met Phe Asn Ala Thr Leu Phe Ala Leu Val Arg Thr Ala Leu Lys Ile
1545                1550                1555                1560

AAG ACC GAA GGG AAC CTG GAG CAA GCT AAT GAA GAA CTT CGG GCT GTG      5238
Lys Thr Glu Gly Asn Leu Glu Gln Ala Asn Glu Glu Leu Arg Ala Val
             1565                1570                1575

ATA AAG AAA ATT TGG AAG AAA ACC AGC ATG AAA TTA CTT GAC CAA GTT      5286
Ile Lys Lys Ile Trp Lys Lys Thr Ser Met Lys Leu Leu Asp Gln Val
             1580                1585                1590

GTC CCT CCA GCT GGT GAT GAT GAG GTA ACC GTG GGG AAG TTC TAT GCC      5334
Val Pro Pro Ala Gly Asp Asp Glu Val Thr Val Gly Lys Phe Tyr Ala
         1595                1600                1605

ACT TTC CTG ATA CAG GAC TAC TTT AGG AAA TTC AAG AAA CGG AAA GAA      5382
Thr Phe Leu Ile Gln Asp Tyr Phe Arg Lys Phe Lys Lys Arg Lys Glu
         1610                1615                1620

CAA GGA CTG GTG GGA AAG TAC CCT GCG AAG AAC ACC ACA ATT GCC CTA      5430
Gln Gly Leu Val Gly Lys Tyr Pro Ala Lys Asn Thr Thr Ile Ala Leu
1625                1630                1635                1640

CAG GCG GGA TTA AGG ACA CTG CAT GAC ATT GGG CCA GAA ATC CGG CGT      5478
Gln Ala Gly Leu Arg Thr Leu His Asp Ile Gly Pro Glu Ile Arg Arg
             1645                1650                1655

GCT ATA TCG TGT GAT TTG CAA GAT GAC GAG CCT GAG GAA ACA AAA CGA      5526
Ala Ile Ser Cys Asp Leu Gln Asp Asp Glu Pro Glu Glu Thr Lys Arg
             1660                1665                1670

GAA GAA GAA GAT GAT GTG TTC AAA AGA AAT GGT GCC CTG CTT GGA AAC      5574
Glu Glu Glu Asp Asp Val Phe Lys Arg Asn Gly Ala Leu Leu Gly Asn
             1675                1680                1685

CAT GTC AAT CAT GTT AAT AGT GAT AGG AGA GAT TCC CTT CAG CAG ACC      5622
His Val Asn His Val Asn Ser Asp Arg Arg Asp Ser Leu Gln Gln Thr
             1690                1695                1700

AAT ACC ACC CAC CGT CCC CTG CAT GTC CAA AGG CCT TCA ATT CCA CCT      5670
Asn Thr Thr His Arg Pro Leu His Val Gln Arg Pro Ser Ile Pro Pro
1705                1710                1715                1720

GCA AGT GAT ACT GAG AAA CCG CTG TTT CCT CCA GCA GGA AAT TCG GTG      5718
```

```
                                       -continued

Ala Ser Asp Thr Glu Lys Pro Leu Phe Pro Pro Ala Gly Asn Ser Val
            1725                1730                1735

TGT CAT AAC CAT CAT AAC CAT AAT TCC ATA GGA AAG CAA GTT CCC ACC      5766
Cys His Asn His His Asn His Asn Ser Ile Gly Lys Gln Val Pro Thr
                1740                1745                1750

TCA ACA AAT GCC AAT CTC AAT AAT GCC AAT ATG TCC AAA GCT GCC CAT      5814
Ser Thr Asn Ala Asn Leu Asn Asn Ala Asn Met Ser Lys Ala Ala His
            1755                1760                1765

GGA AAG CGG CCC AGC ATT GGG AAC CTT GAG CAT GTG TCT GAA AAT GGG      5862
Gly Lys Arg Pro Ser Ile Gly Asn Leu Glu His Val Ser Glu Asn Gly
        1770                1775                1780

CAT CAT TCT TCC CAC AAG CAT GAC CGG GAG CCT CAG AGA AGG TCC AGT      5910
His His Ser Ser His Lys His Asp Arg Glu Pro Gln Arg Arg Ser Ser
1785                1790                1795                1800

GTG AAA AGA ACC CGC TAT TAT GAA ACT TAC ATT AGG TCC GAC TCA GGA      5958
Val Lys Arg Thr Arg Tyr Tyr Glu Thr Tyr Ile Arg Ser Asp Ser Gly
            1805                1810                1815

GAT GAA CAG CTC CCA ACT ATT TGC CGG GAA GAC CCA GAG ATA CAT GGC      6006
Asp Glu Gln Leu Pro Thr Ile Cys Arg Glu Asp Pro Glu Ile His Gly
                1820                1825                1830

TAT TTC AGG GAC CCC CAC TGC TTG GGG GAG CAG GAG TAT TTC AGT AGT      6054
Tyr Phe Arg Asp Pro His Cys Leu Gly Glu Gln Glu Tyr Phe Ser Ser
            1835                1840                1845

GAG GAA TGC TAC GAG GAT GAC AGC TCG CCC ACC TGG AGC AGG CAA AAC      6102
Glu Glu Cys Tyr Glu Asp Asp Ser Ser Pro Thr Trp Ser Arg Gln Asn
        1850                1855                1860

TAT GGC TAC TAC AGC AGA TAC CCA GGC AGA AAC ATC GAC TCT GAG AGG      6150
Tyr Gly Tyr Tyr Ser Arg Tyr Pro Gly Arg Asn Ile Asp Ser Glu Arg
1865                1870                1875                1880

CCC CGA GGC TAC CAT CAT CCC CAA GGA TTC TTG GAG GAC GAT GAC TCG      6198
Pro Arg Gly Tyr His His Pro Gln Gly Phe Leu Glu Asp Asp Asp Ser
            1885                1890                1895

CCC GTT TGC TAT GAT TCA CGG AGA TCT CCA AGG AGA CGC CTA CTA CCT      6246
Pro Val Cys Tyr Asp Ser Arg Arg Ser Pro Arg Arg Arg Leu Leu Pro
                1900                1905                1910

CCC ACC CCA GCA TCC CAC CGG AGA TCC TCC TTC AAC TTT GAG TGC CTG      6294
Pro Thr Pro Ala Ser His Arg Arg Ser Ser Phe Asn Phe Glu Cys Leu
            1915                1920                1925

CGC CGG CAG AGC AGC CAG GAA GAG GTC CCG TCG TCT CCC ATC TTC CCC      6342
Arg Arg Gln Ser Ser Gln Glu Glu Val Pro Ser Ser Pro Ile Phe Pro
        1930                1935                1940

CAT CGC ACG GCC CTG CCT CTG CAT CTA ATG CAG CAA CAG ATC ATG GCA      6390
His Arg Thr Ala Leu Pro Leu His Leu Met Gln Gln Gln Ile Met Ala
1945                1950                1955                1960

GTT GCC GGC CTA GAT TCA AGT AAA GCC CAG AAG TAC TCA CCG AGT CAC      6438
Val Ala Gly Leu Asp Ser Ser Lys Ala Gln Lys Tyr Ser Pro Ser His
            1965                1970                1975

TCG ACC CGG TCG TGG GCC ACC CCT CCA GCA ACC CCT CCC TAC CGG GAC      6486
Ser Thr Arg Ser Trp Ala Thr Pro Pro Ala Thr Pro Pro Tyr Arg Asp
                1980                1985                1990

TGG ACA CCG TGC TAC ACC CCC CTG ATC CAA GTG GAG CAG TCA GAG GCC      6534
Trp Thr Pro Cys Tyr Thr Pro Leu Ile Gln Val Glu Gln Ser Glu Ala
            1995                2000                2005

CTG GAC CAG GTG AAC GGC AGC CTG CCG TCC CTG CAC CGC AGC TCC TGG      6582
Leu Asp Gln Val Asn Gly Ser Leu Pro Ser Leu His Arg Ser Ser Trp
        2010                2015                2020

TAC ACA GAC GAG CCC GAC ATC TCC TAC CGG ACT TTC ACA CCA GCC AGC      6630
Tyr Thr Asp Glu Pro Asp Ile Ser Tyr Arg Thr Phe Thr Pro Ala Ser
2025                2030                2035                2040
```

```
CTG ACT GTC CCC AGC AGC TTC CGG AAC AAA AAC AGC GAC AAG CAG AGG        6678
Leu Thr Val Pro Ser Ser Phe Arg Asn Lys Asn Ser Asp Lys Gln Arg
            2045                2050                2055

AGT GCG GAC AGC TTG GTG GAG GCA GTC CTG ATA TCC GAA GGC TTG GGA        6726
Ser Ala Asp Ser Leu Val Glu Ala Val Leu Ile Ser Glu Gly Leu Gly
            2060                2065                2070

CGC TAT GCA AGG GAC CCA AAA TTT GTG TCA GCA ACA AAA CAC GAA ATC        6774
Arg Tyr Ala Arg Asp Pro Lys Phe Val Ser Ala Thr Lys His Glu Ile
            2075                2080                2085

GCT GAT GCC TGT GAC CTC ACC ATC GAC GAG ATG GAG AGT GCA GCC AGC        6822
Ala Asp Ala Cys Asp Leu Thr Ile Asp Glu Met Glu Ser Ala Ala Ser
            2090                2095                2100

ACC CTG CTT AAT GGG AAC GTG CGT CCC CGA GCC AAC GGG GAT GTG GGC        6870
Thr Leu Leu Asn Gly Asn Val Arg Pro Arg Ala Asn Gly Asp Val Gly
2105                2110                2115                2120

CCC CTC TCA CAC CGG CAG GAC TAT GAG CTA CAG GAC TTT GGT CCT GGC        6918
Pro Leu Ser His Arg Gln Asp Tyr Glu Leu Gln Asp Phe Gly Pro Gly
            2125                2130                2135

TAC AGC GAC GAA GAG CCA GAC CCT GGG AGG GAT GAG GAG GAC CTG GCG        6966
Tyr Ser Asp Glu Glu Pro Asp Pro Gly Arg Asp Glu Glu Asp Leu Ala
            2140                2145                2150

GAT GAA ATG ATA TGC ATC ACC ACC TTG TAGCCCCCAG CGAGGGGCAG             7013
Asp Glu Met Ile Cys Ile Thr Thr Leu
            2155                2160

ACTGGCTCTG GCCTCAGGTG GGGCGCAGGA GAGCCAGGGG AAAAGTGCCT CATAGTTAGG     7073

AAAGTTTAGG CACTAGTTGG GAGTAATATT CAATTAATTA GACTTTTGTA TAAGAGATGT     7133

CATGCCTCAA GAAAGCCATA AACCTGGTAG GAACAGGTCC CAAGCGGTTG AGCCTGGCAG     7193

AGTACCATGC GCTCGGCCCC AGCTGCAGGA ACAGCAGGC CCCGCCCTCT CACAGAGGAT      7253

GGGTGAGGAG GCCAGACCTG CCCTGCCCCA TTGTCCAGAT GGGCACTGCT GTGGAGTCTG     7313

CTTCTCCCAT GTACCAGGGC ACCAGGCCCA CCCAACTGAA GGCATGGCGG CGGGGTGCAG     7373

GGGAAAGTTA AAGGTGATGA CGATCATCAC ACCTGTGTCG TTACCTCAGC CATCGGTCTA    7433

GCATATCAGT CACTGGGCCC AACATATCCA TTTTTAAACC CTTTCCCCCA AATACACTGC     7493

GTCCTGGTTC CTGTTTAGCT GTTCTGAAAT ACGGTGTGTA AGTAAGTCAG AACCCAGCTA    7553

CCAGTGATTA TTGCGAGGGC AATGGGACCT CATAAATAAG GTTTTCTGTG ATGTGACGCC    7613

AGTTTACATA AGAGAATATC AC                                              7635
```

(2) INFORMATION FOR SEQ ID NO:2:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..102

(ix) FEATURE:
        (A) NAME/KEY: misc_feature
        (B) LOCATION: 1..104
        (D) OTHER INFORMATION: /note= "A 104-nucleotide
           alternative exon of alpha-1D."

(xi) SEQUENCE DESCRIPTION: SEQ ID NO:2:

```
GTA AAT GAT GCG ATA GGA TGG GAA TGG CCA TGG GTG TAT TTT GTT AGT         48
Val Asn Asp Ala Ile Gly Trp Glu Trp Pro Trp Val Tyr Phe Val Ser
```

```
               1               5              10              15
CTG ATC ATC CTT GGC TCA TTT TTC GTC CTT AAC CTG GTT CTT GGT GTC           96
Leu Ile Ile Leu Gly Ser Phe Phe Val Leu Asn Leu Val Leu Gly Val
                20              25              30

CTT AGT GG                                                              104
Leu Ser (2) INFORMATION FOR SEQ ID NO:3:

(i) SEQUENCE CHARACTERISTICS:
        (A) LENGTH: 5904 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..5904

(xi) SEQUENCE DESCRIPTION: SEQ ID NO:3:

ATG GTC AAT GAG AAT ACG AGG ATG TAC ATT CCA GAG GAA AAC CAC CAA          48
Met Val Asn Glu Asn Thr Arg Met Tyr Ile Pro Glu Glu Asn His Gln
 1               5              10              15

GGT TCC AAC TAT GGG AGC CCA CGC CCC GCC CAT GCC AAC ATG AAT GCC          96
Gly Ser Asn Tyr Gly Ser Pro Arg Pro Ala His Ala Asn Met Asn Ala
                20              25              30

AAT GCG GCA GCG GGG CTG GCC CCT GAG CAC ATC CCC ACC CCG GGG GCT         144
Asn Ala Ala Ala Gly Leu Ala Pro Glu His Ile Pro Thr Pro Gly Ala
            35              40              45

GCC CTG TCG TGG CAG GCG GCC ATC GAC GCA GCC CGG CAG GCT AAG CTG         192
Ala Leu Ser Trp Gln Ala Ala Ile Asp Ala Ala Arg Gln Ala Lys Leu
        50              55              60

ATG GGC AGC GCT GGC AAT GCG ACC ATC TCC ACA GTC AGC TCC ACG CAG         240
Met Gly Ser Ala Gly Asn Ala Thr Ile Ser Thr Val Ser Ser Thr Gln
65              70              75              80

CGG AAG CGC CAG CAA TAT GGG AAA CCC AAG AAG CAG GGC AGC ACC ACG         288
Arg Lys Arg Gln Gln Tyr Gly Lys Pro Lys Lys Gln Gly Ser Thr Thr
                85              90              95

GCC ACA CGC CCG CCC CGA GCC CTG CTC TGC CTG ACC CTG AAG AAC CCC         336
Ala Thr Arg Pro Pro Arg Ala Leu Leu Cys Leu Thr Leu Lys Asn Pro
            100             105             110

ATC CGG AGG GCC TGC ATC AGC ATT GTC GAA TGG AAA CCA TTT GAA ATA         384
Ile Arg Arg Ala Cys Ile Ser Ile Val Glu Trp Lys Pro Phe Glu Ile
        115             120             125

ATT ATT TTA CTG ACT ATT TTT GCC AAT TGT GTG GCC TTA GCG ATC TAT         432
Ile Ile Leu Leu Thr Ile Phe Ala Asn Cys Val Ala Leu Ala Ile Tyr
130             135             140

ATT CCC TTT CCA GAA GAT GAT TCC AAC GCC ACC AAT TCC AAC CTG GAA         480
Ile Pro Phe Pro Glu Asp Asp Ser Asn Ala Thr Asn Ser Asn Leu Glu
145             150             155             160

CGA GTG GAA TAT CTC TTT CTC ATA ATT TTT ACG GTG GAA GCG TTT TTA         528
Arg Val Glu Tyr Leu Phe Leu Ile Ile Phe Thr Val Glu Ala Phe Leu
                165             170             175

AAA GTA ATC GCC TAT GGA CTC CTC TTT CAC CCC AAT GCC TAC CTC CGC         576
Lys Val Ile Ala Tyr Gly Leu Leu Phe His Pro Asn Ala Tyr Leu Arg
            180             185             190

AAC GGC TGG AAC CTA CTA GAT TTT ATA ATT GTG GTT GTG GGG CTT TTT         624
Asn Gly Trp Asn Leu Leu Asp Phe Ile Ile Val Val Val Gly Leu Phe
        195             200             205

AGT GCA ATT TTA GAA CAA GCA ACC AAA GCA GAT GGG GCA AAC GCT CTC         672
```

```
Ser Ala Ile Leu Glu Gln Ala Thr Lys Ala Asp Gly Ala Asn Ala Leu
    210             215             220

GGA GGG AAA GGG GCC GGA TTT GAT GTG AAG GCG CTG AGG GCC TTC CGC        720
Gly Gly Lys Gly Ala Gly Phe Asp Val Lys Ala Leu Arg Ala Phe Arg
225             230             235             240

GTG CTG CGC CCC CTG CGG CTG GTG TCC GGA GTC CCA AGT CTC CAG GTG        768
Val Leu Arg Pro Leu Arg Leu Val Ser Gly Val Pro Ser Leu Gln Val
                245             250             255

GTC CTG AAT TCC ATC ATC AAG GCC ATG GTC CCC CTG CTG CAC ATC GCC        816
Val Leu Asn Ser Ile Ile Lys Ala Met Val Pro Leu Leu His Ile Ala
            260             265             270

CTG CTT GTG CTG TTT GTC ATC ATC ATC TAC GCC ATC ATC GGC TTG GAG        864
Leu Leu Val Leu Phe Val Ile Ile Ile Tyr Ala Ile Ile Gly Leu Glu
        275             280             285

CTC TTC ATG GGG AAG ATG CAC AAG ACC TGC TAC AAC CAG GAG GGC ATA        912
Leu Phe Met Gly Lys Met His Lys Thr Cys Tyr Asn Gln Glu Gly Ile
    290             295             300

GCA GAT GTT CCA GCA GAA GAT GAC CCT TCC CCT TGT GCG CTG GAA ACG        960
Ala Asp Val Pro Ala Glu Asp Asp Pro Ser Pro Cys Ala Leu Glu Thr
305             310             315             320

GGC CAC GGG CGG CAG TGC CAG AAC GGC ACG GTG TGC AAG CCC GGC TGG       1008
Gly His Gly Arg Gln Cys Gln Asn Gly Thr Val Cys Lys Pro Gly Trp
                325             330             335

GAT GGT CCC AAG CAC GGC ATC ACC AAC TTT GAC AAC TTT GCC TTC GCC       1056
Asp Gly Pro Lys His Gly Ile Thr Asn Phe Asp Asn Phe Ala Phe Ala
            340             345             350

ATG CTC ACG GTG TTC CAG TGC ATC ACC ATG GAG GGC TGG ACG GAC GTG       1104
Met Leu Thr Val Phe Gln Cys Ile Thr Met Glu Gly Trp Thr Asp Val
        355             360             365

CTG TAC TGG GTC AAT GAT GCC GTA GGA AGG GAC TGG CCC TGG ATC TAT       1152
Leu Tyr Trp Val Asn Asp Ala Val Gly Arg Asp Trp Pro Trp Ile Tyr
    370             375             380

TTT GTT ACA CTA ATC ATC ATA GGG TCA TTT TTT GTA CTT AAC TTG GTT       1200
Phe Val Thr Leu Ile Ile Ile Gly Ser Phe Phe Val Leu Asn Leu Val
385             390             395             400

CTC GGT GTG CTT AGC GGA GAG TTT TCC AAA GAG AGG GAG AAG GCC AAG       1248
Leu Gly Val Leu Ser Gly Glu Phe Ser Lys Glu Arg Glu Lys Ala Lys
                405             410             415

GCC CGG GGA GAT TTC CAG AAG CTG CGG GAG AAG CAG CAG CTA GAA GAG       1296
Ala Arg Gly Asp Phe Gln Lys Leu Arg Glu Lys Gln Gln Leu Glu Glu
            420             425             430

GAT CTC AAA GGC TAC CTG GAT TGG ATC ACT CAG GCC GAA GAC ATC GNT       1344
Asp Leu Lys Gly Tyr Leu Asp Trp Ile Thr Gln Ala Glu Asp Ile Xaa
        435             440             445

CCT GAG AAT GAG GAC GAA GGC ATG GAT GAG GAG AAG CCC CGA AAC AGA       1392
Pro Glu Asn Glu Asp Glu Gly Met Asp Glu Glu Lys Pro Arg Asn Arg
    450             455             460

GGC ACT CCG GCG GGC ATG CTT GAT CAG AAG AAA GGG AAG TTT GCT TGG       1440
Gly Thr Pro Ala Gly Met Leu Asp Gln Lys Lys Gly Lys Phe Ala Trp
465             470             475             480

TTT AGT CAC TCC ACA GAA ACC CAT GTG AGC ATG CCC ACC AGT GAG ACC       1488
Phe Ser His Ser Thr Glu Thr His Val Ser Met Pro Thr Ser Glu Thr
                485             490             495

GAG TCC GTC AAC ACC GAA AAC GTG GCT GGA GGT GAC ATC GAG GGA GAA       1536
Glu Ser Val Asn Thr Glu Asn Val Ala Gly Gly Asp Ile Glu Gly Glu
            500             505             510

AAC TGC GGG GCC AGG CTG GCC CAC CGG ATC TCC AAG TCA AAG TTC AGC       1584
Asn Cys Gly Ala Arg Leu Ala His Arg Ile Ser Lys Ser Lys Phe Ser
        515             520             525
```

-continued

| | |
|---|---|
| CGC TAC TGG CGC CGG TGG AAT CGG TTC TGC AGA AGG AAG TGC CGC GCC<br>Arg Tyr Trp Arg Arg Trp Asn Arg Phe Cys Arg Arg Lys Cys Arg Ala<br>530                                        535                          540 | 1632 |
| GCA GTC AAG TCT AAT GTC TTC TAC TGG CTG GTG ATT TTC CTG GTG TTC<br>Ala Val Lys Ser Asn Val Phe Tyr Trp Leu Val Ile Phe Leu Val Phe<br>545                        550                        555                    560 | 1680 |
| CTC AAC ACG CTC ACC ATT GCC TCT GAG CAC TAC AAC CAG CCC AAC TGG<br>Leu Asn Thr Leu Thr Ile Ala Ser Glu His Tyr Asn Gln Pro Asn Trp<br>                      565                        570                        575 | 1728 |
| CTC ACA GAA GTC CAA GAC ACG GCA AAC AAG GCC CTG CTG GCC CTG TTC<br>Leu Thr Glu Val Gln Asp Thr Ala Asn Lys Ala Leu Leu Ala Leu Phe<br>            580                                585                        590 | 1776 |
| ACG GCA GAG ATG CTC CTG AAG ATG TAC AGC CTG GGC CTG CAG GCC TAC<br>Thr Ala Glu Met Leu Leu Lys Met Tyr Ser Leu Gly Leu Gln Ala Tyr<br>                      595                        600                        605 | 1824 |
| TTC GTG TCC CTC TTC AAC CGC TTT GAC TGC TTC GTC GTG TGT GGC GGC<br>Phe Val Ser Leu Phe Asn Arg Phe Asp Cys Phe Val Val Cys Gly Gly<br>610                                        615 | 1872 |
| ATC CTG GAG ACC ATC CTG GTG GAG ACC AAG ATC ATG TCC CCA CTG GGC<br>Ile Leu Glu Thr Ile Leu Val Glu Thr Lys Ile Met Ser Pro Leu Gly<br>625                                      630                        635                    640 | 1920 |
| ATC TCC GTG CTC AGA TGC GTC CGG CTG CTG AGG ATT TTC AAG ATC ACG<br>Ile Ser Val Leu Arg Cys Val Arg Leu Leu Arg Ile Phe Lys Ile Thr<br>                      645                        650                        655 | 1968 |
| AGG TAC TGG AAC TCC TTG AGC AAC CTG GTG GCA TCC TTG CTG AAC TCT<br>Arg Tyr Trp Asn Ser Leu Ser Asn Leu Val Ala Ser Leu Leu Asn Ser<br>            660                                665                        670 | 2016 |
| GTG CGC TCC ATC GCC TCC CTG CTC CTT CTC CTC TTC CTC TTC ATC ATC<br>Val Arg Ser Ile Ala Ser Leu Leu Leu Leu Leu Phe Leu Phe Ile Ile<br>                      675                        680                        685 | 2064 |
| ATC TTC TCC CTC CTG GGG ATG CAG CTC TTT GGA GGA AAG TTC AAC TTT<br>Ile Phe Ser Leu Leu Gly Met Gln Leu Phe Gly Gly Lys Phe Asn Phe<br>690                                      695                        700 | 2112 |
| GAT GAG ATG CAG ACC CGG AGG AGC ACA TTC GAT AAC TTC CCC CAG TCC<br>Asp Glu Met Gln Thr Arg Arg Ser Thr Phe Asp Asn Phe Pro Gln Ser<br>705                                      710                        715                    720 | 2160 |
| CTC CTC ACT GTG TTT CAG ATC CTG ACC GGG GAG GAC TGG AAT TCG GTG<br>Leu Leu Thr Val Phe Gln Ile Leu Thr Gly Glu Asp Trp Asn Ser Val<br>                      725                        730                        735 | 2208 |
| ATG TAT GAT GGG ATC ATG GCT TAT GGG GGC CCC TCT TTT CCA GGG ATG<br>Met Tyr Asp Gly Ile Met Ala Tyr Gly Gly Pro Ser Phe Pro Gly Met<br>            740                                745                        750 | 2256 |
| TTA GTC TGT ATT TAC TTC ATC ATC CTC TTC ATC TCT GGA AAC TAT ATC<br>Leu Val Cys Ile Tyr Phe Ile Ile Leu Phe Ile Ser Gly Asn Tyr Ile<br>                      755                        760                        765 | 2304 |
| CTA CTG AAT GTG TTC TTG GCC ATT GCT GTG GAC AAC CTG GCT GAT GCT<br>Leu Leu Asn Val Phe Leu Ala Ile Ala Val Asp Asn Leu Ala Asp Ala<br>            770                                775                        780 | 2352 |
| GAG AGC CTC ACA TCT GCC CTA AAG GAG GAG GAA GAG GAG AAG GAG AGA<br>Glu Ser Leu Thr Ser Ala Leu Lys Glu Glu Glu Glu Glu Lys Glu Arg<br>785                                      790                        795                    800 | 2400 |
| AAG AAG CTG GCC AGG ACT GCC AGC CCA GAG AAG AAA CAA GAG TTG GTG<br>Lys Lys Leu Ala Arg Thr Ala Ser Pro Glu Lys Lys Gln Glu Leu Val<br>                      805                        810                        815 | 2448 |
| GAG AAG CCG GCA GTG GGG GAA TCC AAG GAG GAG AAG ATT GAG CTG AAA<br>Glu Lys Pro Ala Val Gly Glu Ser Lys Glu Glu Lys Ile Glu Leu Lys<br>            820                        825                        830 | 2496 |
| TCC ATC ACG GCT GAC GGA GAG TCT CCA CCC GCC ACC AAG ATC AAC ATG<br>Ser Ile Thr Ala Asp Gly Glu Ser Pro Pro Ala Thr Lys Ile Asn Met<br>                      835                        840                        845 | 2544 |

-continued

| | |
|---|---|
| GAT GAC CTC CAG CCC AAT GAA AAT GAG GAT AAG AGC CCC TAC CCC AAC<br>Asp Asp Leu Gln Pro Asn Glu Asn Glu Asp Lys Ser Pro Tyr Pro Asn<br>850                855                860 | 2592 |
| CCA GAA ACT ACA GGA GAA GAG GAT GAG GAG GAG CCA GAG ATG CCT GTC<br>Pro Glu Thr Thr Gly Glu Glu Asp Glu Glu Glu Pro Glu Met Pro Val<br>865                870                875                880 | 2640 |
| GGC CCT CGC CCA CGA CCA CTC TCT GAG CTT CAC CTT AAG GAA AAG GCA<br>Gly Pro Arg Pro Arg Pro Leu Ser Glu Leu His Leu Lys Glu Lys Ala<br>                885                890                895 | 2688 |
| GTG CCC ATG CCA GAA GCC AGC GCG TTT TTC ATC TTC AGC TCT AAC AAC<br>Val Pro Met Pro Glu Ala Ser Ala Phe Phe Ile Phe Ser Ser Asn Asn<br>900                905                910 | 2736 |
| AGG TTT CGC CTC CAG TGC CAC CGC ATT GTC AAT GAC ACG ATC TTC ACC<br>Arg Phe Arg Leu Gln Cys His Arg Ile Val Asn Asp Thr Ile Phe Thr<br>        915                920                925 | 2784 |
| AAC CTG ATC CTC TTC TTC ATT CTG CTC AGC AGC ATT TCC CTG GCT GCT<br>Asn Leu Ile Leu Phe Phe Ile Leu Leu Ser Ser Ile Ser Leu Ala Ala<br>        930                935                940 | 2832 |
| GAG GAC CCG GTC CAG CAC ACC TCC TTC AGG AAC CAT ATT CTG TTT TAT<br>Glu Asp Pro Val Gln His Thr Ser Phe Arg Asn His Ile Leu Phe Tyr<br>945                950                955                960 | 2880 |
| TTT GAT ATT GTT TTT ACC ACC ATT TTC ACC ATT GAA ATT GCT CTG AAG<br>Phe Asp Ile Val Phe Thr Thr Ile Phe Thr Ile Glu Ile Ala Leu Lys<br>                965                970                975 | 2928 |
| ATG ACT GCT TAT GGG GCT TTC TTG CAC AAG GGT TCT TTC TGC CGG AAC<br>Met Thr Ala Tyr Gly Ala Phe Leu His Lys Gly Ser Phe Cys Arg Asn<br>        980                985                990 | 2976 |
| TAC TTC AAC ATC CTG GAC CTG CTG GTG GTC AGC GTG TCC CTC ATC TCC<br>Tyr Phe Asn Ile Leu Asp Leu Leu Val Val Ser Val Ser Leu Ile Ser<br>        995                1000                1005 | 3024 |
| TTT GGC ATC CAG TCC AGT GCA ATC AAT GTC GTG AAG ATC TTG CGA GTC<br>Phe Gly Ile Gln Ser Ser Ala Ile Asn Val Val Lys Ile Leu Arg Val<br>1010                1015                1020 | 3072 |
| CTG CGA GTA CTC AGG CCC CTG AGG GCC ATC AAC AGG GCC AAG GGG CTA<br>Leu Arg Val Leu Arg Pro Leu Arg Ala Ile Asn Arg Ala Lys Gly Leu<br>1025                1030                1035                1040 | 3120 |
| AAG CAT GTG GTT CAG TGT GTG TTT GTC GCC ATC CGG ACC ATC GGG AAC<br>Lys His Val Val Gln Cys Val Phe Val Ala Ile Arg Thr Ile Gly Asn<br>                1045                1050                1055 | 3168 |
| ATC GTG ATT GTC ACC ACC CTG CTG CAG TTC ATG TTT GCC TGC ATC GGG<br>Ile Val Ile Val Thr Thr Leu Leu Gln Phe Met Phe Ala Cys Ile Gly<br>        1060                1065                1070 | 3216 |
| GTC CAG CTC TTC AAG GGA AAG CTG TAC ACC TGT TCA GAC AGT TCC AAG<br>Val Gln Leu Phe Lys Gly Lys Leu Tyr Thr Cys Ser Asp Ser Ser Lys<br>        1075                1080                1085 | 3264 |
| CAG ACA GAG GCG GAA TGC AAG GGC AAC TAC ATC ACG TAC AAA GAC GGG<br>Gln Thr Glu Ala Glu Cys Lys Gly Asn Tyr Ile Thr Tyr Lys Asp Gly<br>1090                1095                1100 | 3312 |
| GAG GTT GAC CAC CCC ATC ATC CAA CCC CGC AGC TGG GAG AAC AGC AAG<br>Glu Val Asp His Pro Ile Ile Gln Pro Arg Ser Trp Glu Asn Ser Lys<br>1105                1110                1115                1120 | 3360 |
| TTT GAC TTT GAC AAT GTT CTG GCA GCC ATG ATG GCC CTC TTC ACC GTC<br>Phe Asp Phe Asp Asn Val Leu Ala Ala Met Met Ala Leu Phe Thr Val<br>                1125                1130                1135 | 3408 |
| TCC ACC TTC GAA GGG TGG CCA GAG CTG CTG TAC CGC TCC ATC GAC TCC<br>Ser Thr Phe Glu Gly Trp Pro Glu Leu Leu Tyr Arg Ser Ile Asp Ser<br>        1140                1145                1150 | 3456 |
| CAC ACG GAA GAC AAG GGC CCC ATC TAC AAC TAC CGT GTG GAG ATC TCC<br>His Thr Glu Asp Lys Gly Pro Ile Tyr Asn Tyr Arg Val Glu Ile Ser | 3504 |

```
                1155                1160                1165
ATC TTC TTC ATC ATC TAC ATC ATC ATC GCC TTC TTC ATG ATG AAC       3552
Ile Phe Phe Ile Ile Tyr Ile Ile Ile Ala Phe Phe Met Met Asn
    1170                1175                1180

ATC TTC GTG GGC TTC GTC ATC GTC ACC TTT CAG GAG CAG GGG GAG CAG   3600
Ile Phe Val Gly Phe Val Ile Val Thr Phe Gln Glu Gln Gly Glu Gln
1185                1190                1195                1200

GAG TAC AAG AAC TGT GAG CTG GAC AAG AAC CAG CGA CAG TGC GTG GAA   3648
Glu Tyr Lys Asn Cys Glu Leu Asp Lys Asn Gln Arg Gln Cys Val Glu
            1205                1210                1215

TAC GCC CTC AAG GCC CGG CCC CTG CGG AGG TAC ATC CCC AAG AAC CAG   3696
Tyr Ala Leu Lys Ala Arg Pro Leu Arg Arg Tyr Ile Pro Lys Asn Gln
            1220                1225                1230

CAC CAG TAC AAA GTG TGG TAC GTG GTC AAC TCC ACC TAC TTC GAG TAC   3744
His Gln Tyr Lys Val Trp Tyr Val Val Asn Ser Thr Tyr Phe Glu Tyr
            1235                1240                1245

CTG ATG TTC GTC CTC ATC CTG CTC AAC ACC ATC TGC CTG GCC ATG CAG   3792
Leu Met Phe Val Leu Ile Leu Leu Asn Thr Ile Cys Leu Ala Met Gln
    1250                1255                1260

CAC TAC GGC CAG AGC TGC CTG TTC AAA ATC GCC ATG AAC ATC CTC AAC   3840
His Tyr Gly Gln Ser Cys Leu Phe Lys Ile Ala Met Asn Ile Leu Asn
1265                1270                1275                1280

ATG CTC TTC ACT GGC CTC TTC ACC GTG GAG ATG ATC CTG AAG CTC ATT   3888
Met Leu Phe Thr Gly Leu Phe Thr Val Glu Met Ile Leu Lys Leu Ile
            1285                1290                1295

GCC TTC AAA CCC AAG GGT TAC TTT AGT GAT CCC TGG AAT GTT TTT GAC   3936
Ala Phe Lys Pro Lys Gly Tyr Phe Ser Asp Pro Trp Asn Val Phe Asp
            1300                1305                1310

TTC CTC ATC GTA ATT GGC AGC ATA ATT GAC GTC ATT CTC AGT GAG ACT   3984
Phe Leu Ile Val Ile Gly Ser Ile Ile Asp Val Ile Leu Ser Glu Thr
            1315                1320                1325

AAT CCA GCT GAA CAT ACC CAA TGC TCT CCC TCT ATG AAC GCA GAG GAA   4032
Asn Pro Ala Glu His Thr Gln Cys Ser Pro Ser Met Asn Ala Glu Glu
            1330                1335                1340

AAC TCC CGC ATC TCC ATC ACC TTC TTC CGC CTG TTC CGG GTC ATG CGT   4080
Asn Ser Arg Ile Ser Ile Thr Phe Phe Arg Leu Phe Arg Val Met Arg
1345                1350                1355                1360

CTG GTG AAG CTG CTG AGC CGT GGG GAG GGC ATC CGG ACG CTG CTG TGG   4128
Leu Val Lys Leu Leu Ser Arg Gly Glu Gly Ile Arg Thr Leu Leu Trp
                1365                1370                1375

ACC TTC ATC AAG TCC TTC CAG GCC CTG CCC TAT GTG GCC CTC CTG ATC   4176
Thr Phe Ile Lys Ser Phe Gln Ala Leu Pro Tyr Val Ala Leu Leu Ile
            1380                1385                1390

GTG ATG CTG TTC TTC ATC TAC GCG GTG ATC GGG ATG CAG GTG TTT GGG   4224
Val Met Leu Phe Phe Ile Tyr Ala Val Ile Gly Met Gln Val Phe Gly
            1395                1400                1405

AAA ATT GCC CTG AAT GAT ACC ACA GAG ATC AAC CGG AAC AAC AAC TTT   4272
Lys Ile Ala Leu Asn Asp Thr Thr Glu Ile Asn Arg Asn Asn Asn Phe
    1410                1415                1420

CAG ACC TTC CCC CAG GCC GTG CTG CTC CTC TTC AGG TGT GCC ACC GGG   4320
Gln Thr Phe Pro Gln Ala Val Leu Leu Leu Phe Arg Cys Ala Thr Gly
1425                1430                1435                1440

GAG GCC TGG CAG GAC ATC ATG CTG GCC TGC ATG CCA GGC AAG AAG TGT   4368
Glu Ala Trp Gln Asp Ile Met Leu Ala Cys Met Pro Gly Lys Lys Cys
            1445                1450                1455

GCC CCA GAG TCC GAG CCC AGC AAC AGC ACG GAG GGT GAA ACA CCC TGT   4416
Ala Pro Glu Ser Glu Pro Ser Asn Ser Thr Glu Gly Glu Thr Pro Cys
            1460                1465                1470

GGT AGC AGC TTT GCT GTC TTC TAC TTC ATC AGC TTC TAC ATG CGC TGT   4464
Gly Ser Ser Phe Ala Val Phe Tyr Phe Ile Ser Phe Tyr Met Arg Cys
```

```
Gly Ser Ser Phe Ala Val Phe Tyr Phe Ile Ser Phe Tyr Met Arg Cys
        1475                1480                1485

GCC TTC CTG ATC ATC AAC CTC TTT GTA GCT GTC ATC ATG GAC AAC TTT       4512
Ala Phe Leu Ile Ile Asn Leu Phe Val Ala Val Ile Met Asp Asn Phe
        1490                1495                1500

GAC TAC CTG ACA AGG GAC TGG TCC ATC CTT GGT CCC CAC CAC CTG GAT       4560
Asp Tyr Leu Thr Arg Asp Trp Ser Ile Leu Gly Pro His His Leu Asp
1505                1510                1515                1520

GAG TTT AAA AGA ATC TGG GCA GAG TAT GAC CCT GAA GCC AAG GGT CGT       4608
Glu Phe Lys Arg Ile Trp Ala Glu Tyr Asp Pro Glu Ala Lys Gly Arg
                1525                1530                1535

ATC AAA CAC CTG GAT GTG GTG ACC CTC CTC CGG CGG ATT CAG CCG CCA       4656
Ile Lys His Leu Asp Val Val Thr Leu Leu Arg Arg Ile Gln Pro Pro
        1540                1545                1550

CTA GGT TTT GGG AAG CTG TGC CCT CAC CGC GTG GCT TGC AAA CGC CTG       4704
Leu Gly Phe Gly Lys Leu Cys Pro His Arg Val Ala Cys Lys Arg Leu
        1555                1560                1565

GTC TCC ATG AAC ATG CCT CTG AAC AGC GAC GGG ACA GTC ATG TTC AAT       4752
Val Ser Met Asn Met Pro Leu Asn Ser Asp Gly Thr Val Met Phe Asn
        1570                1575                1580

GCC ACC CTG TTT GCC CTG GTC AGG ACG GCC CTG AGG ATC AAA ACA GAA       4800
Ala Thr Leu Phe Ala Leu Val Arg Thr Ala Leu Arg Ile Lys Thr Glu
1585                1590                1595                1600

GGG AAC CTA GAA CAA GCC AAT GAG GAG CTG CGG GCG ATC ATC AAG AAG       4848
Gly Asn Leu Glu Gln Ala Asn Glu Glu Leu Arg Ala Ile Ile Lys Lys
                1605                1610                1615

ATC TGG AAG CGG ACC AGC ATG AAG CTG CTG GAC CAG GTG GTG CCC CCT       4896
Ile Trp Lys Arg Thr Ser Met Lys Leu Leu Asp Gln Val Val Pro Pro
        1620                1625                1630

GCA GGT GAT GAT GAG GTC ACC GTT GGC AAG TTC TAC GCC ACG TTC CTG       4944
Ala Gly Asp Asp Glu Val Thr Val Gly Lys Phe Tyr Ala Thr Phe Leu
        1635                1640                1645

ATC CAG GAG TAC TTC CGG AAG TTC AAG AAG CGC AAA GAG CAG GGC CTT       4992
Ile Gln Glu Tyr Phe Arg Lys Phe Lys Lys Arg Lys Glu Gln Gly Leu
        1650                1655                1660

GTG GGC AAG CCC TCC CAG AGG AAC GCG CTG TCT CTG CAG GCT GGC TTG       5040
Val Gly Lys Pro Ser Gln Arg Asn Ala Leu Ser Leu Gln Ala Gly Leu
1665                1670                1675                1680

CGC ACA CTG CAT GAC ATC GGG CCT GAG ATC CGA CGG GCC ATC TCT GGA       5088
Arg Thr Leu His Asp Ile Gly Pro Glu Ile Arg Arg Ala Ile Ser Gly
                1685                1690                1695

GAT CTC ACC GCT GAG GAG GAG CTG GAC AAG GCC ATG AAG GAG GCT GTG       5136
Asp Leu Thr Ala Glu Glu Glu Leu Asp Lys Ala Met Lys Glu Ala Val
                1700                1705                1710

TCC GCT GCT TCT GAA GAT GAC ATC TTC AGG AGG GCC GGT GGC CTG TTC       5184
Ser Ala Ala Ser Glu Asp Asp Ile Phe Arg Arg Ala Gly Gly Leu Phe
        1715                1720                1725

GGC AAC CAC GTC AGC TAC TAC CAA AGC GAC GGC CGG AGC GCC TTC CCC       5232
Gly Asn His Val Ser Tyr Tyr Gln Ser Asp Gly Arg Ser Ala Phe Pro
        1730                1735                1740

CAG ACC TTC ACC ACT CAG CGC CCG CTG CAC ATC AAC AAG GCG GGC AGC       5280
Gln Thr Phe Thr Thr Gln Arg Pro Leu His Ile Asn Lys Ala Gly Ser
1745                1750                1755                1760

AGC CAG GGC GAC ACT GAG TCG CCA TCC CAC GAG AAG CTG GTG GAC TCC       5328
Ser Gln Gly Asp Thr Glu Ser Pro Ser His Glu Lys Leu Val Asp Ser
                1765                1770                1775

ACC TTC ACC CCG AGC AGC TAC TCG TCC ACC GGC TCC AAC GCC AAC ATC       5376
Thr Phe Thr Pro Ser Ser Tyr Ser Ser Thr Gly Ser Asn Ala Asn Ile
        1780                1785                1790
```

-continued

```
AAC AAC GCC AAC AAC ACC GCC CTG GGT CGC CTC CCT CGC CCC GCC GGC      5424
Asn Asn Ala Asn Asn Thr Ala Leu Gly Arg Leu Pro Arg Pro Ala Gly
        1795                1800                1805

TAC CCC AGC ACA GTC AGC ACT GTG GAG GGC CAC GGG CCC CCC TTG TCC      5472
Tyr Pro Ser Thr Val Ser Thr Val Glu Gly His Gly Pro Pro Leu Ser
    1810                1815                1820

CCT GCC ATC CGG GTG CAG GAG GTG GCG TGG AAG CTC AGC TCC AAC AGG      5520
Pro Ala Ile Arg Val Gln Glu Val Ala Trp Lys Leu Ser Ser Asn Arg
1825                1830                1835                1840

TGC CAC TCC CGG GAG AGC CAG GCA GCC ATG GCG CGT CAG GAG GAG ACG      5568
Cys His Ser Arg Glu Ser Gln Ala Ala Met Ala Arg Gln Glu Glu Thr
                1845                1850                1855

TCT CAG GAT GAG ACC TAT GAA GTG AAG ATG AAC CAT GAC ACG GAG GCC      5616
Ser Gln Asp Glu Thr Tyr Glu Val Lys Met Asn His Asp Thr Glu Ala
            1860                1865                1870

TGC AGT GAG CCC AGC CTG CTC TCC ACA GAG ATG CTC TCC TAC CAG GAT      5664
Cys Ser Glu Pro Ser Leu Leu Ser Thr Glu Met Leu Ser Tyr Gln Asp
        1875                1880                1885

GAC GAA AAT CGG CAA CTG ACG CTC CCA GAG GAG GAC AAG AGG GAC ATC      5712
Asp Glu Asn Arg Gln Leu Thr Leu Pro Glu Glu Asp Lys Arg Asp Ile
    1890                1895                1900

CGG CAA TCT CCG AAG AGG GGT TTC CTC CGC TCT TCC TCA CTA GGT CGA      5760
Arg Gln Ser Pro Lys Arg Gly Phe Leu Arg Ser Ser Ser Leu Gly Arg
1905                1910                1915                1920

AGG GCC TCC TTC CAC CTG GAA TGT CTG AAG CGA CAG AAG GAC CGA GGG      5808
Arg Ala Ser Phe His Leu Glu Cys Leu Lys Arg Gln Lys Asp Arg Gly
                1925                1930                1935

GGA GAC ATC TCT CAG AAG ACA GTC CTG CCC TTG CAT CTG GTT CAT CAT      5856
Gly Asp Ile Ser Gln Lys Thr Val Leu Pro Leu His Leu Val His His
            1940                1945                1950

CAG GCA TTG GCA GTG GCA GGC CTG AGC CCC CTC CTC CAG AGA AGC CAT      5904
Gln Ala Leu Ala Val Ala Gly Leu Ser Pro Leu Leu Gln Arg Ser His
        1955                1960                1965
```

(2) INFORMATION FOR SEQ ID NO:4:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
AGACCACGGC TTCCTCGAAT CTTGCGCGAA GCCGCCGGCC TCGGAGGAGG GATTAATCCA      60

GACCCGCCGG GGGGTGTTTT CACATTTCTT CCTCTTCGTG GCTGCTCCTC CTATTAAAAC     120

CATTTTTGGT CC                                                         132
```

(2) INFORMATION FOR SEQ ID NO:5:

(i) SEQUENCE CHARACTERISTICS:
        (A) LENGTH: 89 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
CGCTGAGGGC CTTCCGCGTG CTGCGCCCCC TGCGGCTGGT GTCCGGAGTC CCAAGTCTCC      60

AGGTGGTCCT GAATTCCATC ATCAAGGCC                                       89
```

(2) INFORMATION FOR SEQ ID NO:6:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..84
        (D) OTHER INFORMATION: /note= "An alternative exon of
            alpha-1C."

(xi) SEQUENCE DESCRIPTION: SEQ ID NO:6:

```
CAC TAT TTC TGT GAT GCA TGG AAT ACA TTT GAC GCC TTG ATT GTT GTG        48
His Tyr Phe Cys Asp Ala Trp Asn Thr Phe Asp Ala Leu Ile Val Val
 1               5                  10                  15

GGT AGC ATT GTT GAT ATA GCA ATC ACC GAG GTA AAC                        84
Gly Ser Ile Val Asp Ile Ala Ile Thr Glu Val Asn
             20                  25
```

(2) INFORMATION FOR SEQ ID NO:7:

(i) SEQUENCE CHARACTERISTICS:
        (A) LENGTH: 7362 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 144..7163

(ix) FEATURE:
        (A) NAME/KEY: 5'UTR
        (B) LOCATION: 1..143

(ix) FEATURE:
        (A) NAME/KEY: 3'UTR
        (B) LOCATION: 7161..7362

(xi) SEQUENCE DESCRIPTION: SEQ ID NO:7:

```
GCGGCGGCGG CTGCGGCGGT GGGGCCGGGC GAGGTCCGTG CGGTCCCGGC GGCTCCGTGG        60

CTGCTCCGCT CTGAGCGCCT GCGCGCCCCG CGCCCTCCCT GCCGGGGCCG CTGGGCCGGG       120

GATGCACGCG GGGCCCGGGA GCC ATG GTC CGC TTC GGG GAC GAG CTG GGC          170
                          Met Val Arg Phe Gly Asp Glu Leu Gly
                           1               5

GGC CGC TAT GGA GGC CCC GGC GGC GGA GAG CGG GCC CGG GGC GGC GGG        218
Gly Arg Tyr Gly Gly Pro Gly Gly Gly Glu Arg Ala Arg Gly Gly Gly
 10                  15                  20                  25

GCC GGC GGG GCG GGG GGC CCG GGT CCC GGG GGG CTG CAG CCC GGC CAG        266
Ala Gly Gly Ala Gly Gly Pro Gly Pro Gly Gly Leu Gln Pro Gly Gln
                 30                  35                  40

CGG GTC CTC TAC AAG CAA TCG ATC GCG CAG CGC GCG CGG ACC ATG GCG        314
Arg Val Leu Tyr Lys Gln Ser Ile Ala Gln Arg Ala Arg Thr Met Ala
             45                  50                  55

CTG TAC AAC CCC ATC CCG GTC AAG CAG AAC TGC TTC ACC GTC AAC CGC        362
Leu Tyr Asn Pro Ile Pro Val Lys Gln Asn Cys Phe Thr Val Asn Arg
         60                  65                  70

TCG CTC TTC GTC TTC AGC GAG GAC AAC GTC GTC CGC AAA TAC GCG AAG        410
Ser Leu Phe Val Phe Ser Glu Asp Asn Val Val Arg Lys Tyr Ala Lys
```

```
                    75                      80                      85
CGC ATC ACC GAG TGG CCT CCA TTC GAG AAT ATG ATC CTG GCC ACC ATC          458
Arg Ile Thr Glu Trp Pro Pro Phe Glu Asn Met Ile Leu Ala Thr Ile
 90                  95                     100                 105

ATC GCC AAC TGC ATC GTG CTG GCC CTG GAG CAG CAC CTC CCT GAT GGG          506
Ile Ala Asn Cys Ile Val Leu Ala Leu Glu Gln His Leu Pro Asp Gly
                110                     115                     120

GAC AAA ACG CCC ATG TCC GAG CGG CTG GAC GAC ACG GAG CCC TAT TTC          554
Asp Lys Thr Pro Met Ser Glu Arg Leu Asp Asp Thr Glu Pro Tyr Phe
            125                     130                     135

ATC GGG ATC TTT TGC TTC GAG GCA GGG ATC AAA ATC ATC GCT CTG GGC          602
Ile Gly Ile Phe Cys Phe Glu Ala Gly Ile Lys Ile Ile Ala Leu Gly
        140                     145                     150

TTT GTC TTC CAC AAG GGC TCT TAC CTG CGG AAC GGC TGG AAC GTC ATG          650
Phe Val Phe His Lys Gly Ser Tyr Leu Arg Asn Gly Trp Asn Val Met
    155                     160                     165

GAC TTC GTG GTC GTC CTC ACA GGG ATC CTT GCC ACG GCT GGA ACT GAC          698
Asp Phe Val Val Val Leu Thr Gly Ile Leu Ala Thr Ala Gly Thr Asp
170                     175                     180                 185

TTC GAC CTG CGA ACA CTG AGG GCT GTG CGT GTG CTG AGG CCC CTG AAG          746
Phe Asp Leu Arg Thr Leu Arg Ala Val Arg Val Leu Arg Pro Leu Lys
                190                     195                     200

CTG GTG TCT GGG ATT CCA AGT TTG CAG GTG GTG CTC AAG TCC ATC ATG          794
Leu Val Ser Gly Ile Pro Ser Leu Gln Val Val Leu Lys Ser Ile Met
            205                     210                     215

AAG GCC ATG GTT CCA CTC CTG CAG ATT GGG CTG CTT CTC TTC TTT GCC          842
Lys Ala Met Val Pro Leu Leu Gln Ile Gly Leu Leu Leu Phe Phe Ala
        220                     225                     230

ATC CTC ATG TTT GCC ATC ATT GGC CTG GAG TTC TAC ATG GGC AAG TTC          890
Ile Leu Met Phe Ala Ile Ile Gly Leu Glu Phe Tyr Met Gly Lys Phe
    235                     240                     245

CAC AAG GCC TGT TTC CCC AAC AGC ACA GAT GCG GAG CCC GTG GGT GAC          938
His Lys Ala Cys Phe Pro Asn Ser Thr Asp Ala Glu Pro Val Gly Asp
250                     255                     260                 265

TTC CCC TGT GGC AAG GAG GCC CCA GCC CGG CTG TGC GAG GGC GAC ACT          986
Phe Pro Cys Gly Lys Glu Ala Pro Ala Arg Leu Cys Glu Gly Asp Thr
                270                     275                     280

GAG TGC CGG GAG TAC TGG CCA GGA CCC AAC TTT GGC ATC ACC AAC TTT         1034
Glu Cys Arg Glu Tyr Trp Pro Gly Pro Asn Phe Gly Ile Thr Asn Phe
            285                     290                     295

GAC AAT ATC CTG TTT GCC ATC TTG ACG GTG TTC CAG TGC ATC ACC ATG         1082
Asp Asn Ile Leu Phe Ala Ile Leu Thr Val Phe Gln Cys Ile Thr Met
        300                     305                     310

GAG GGC TGG ACT GAC ATC CTC TAT AAT ACA AAC GAT GCG GCC GGC AAC         1130
Glu Gly Trp Thr Asp Ile Leu Tyr Asn Thr Asn Asp Ala Ala Gly Asn
    315                     320                     325

ACC TGG AAC TGG CTC TAC TTC ATC CCT CTC ATC ATC ATC GGC TCC TTC         1178
Thr Trp Asn Trp Leu Tyr Phe Ile Pro Leu Ile Ile Ile Gly Ser Phe
330                     335                     340                 345

TTC ATG CTC AAC CTG GTG CTG GGC GTG CTC TCG GGG GAG TTT GCC AAG         1226
Phe Met Leu Asn Leu Val Leu Gly Val Leu Ser Gly Glu Phe Ala Lys
                350                     355                     360

GAG CGA GAG AGG GTG GAG AAC CGC CGC GCC TTC CTG AAG CTG CGC CGG         1274
Glu Arg Glu Arg Val Glu Asn Arg Arg Ala Phe Leu Lys Leu Arg Arg
            365                     370                     375

CAG CAG CAG ATC GAG CGA GAG CTC AAC GGG TAC CTG GAG TGG ATC TTC         1322
Gln Gln Gln Ile Glu Arg Glu Leu Asn Gly Tyr Leu Glu Trp Ile Phe
        380                     385                     390

AAG GCG GAG GAA GTC ATG CTG GCC GAG GAG GAC AGG AAT GCA GAG GAG         1370
```

```
                                     -continued

Lys Ala Glu Glu Val Met Leu Ala Glu Glu Asp Arg Asn Ala Glu Glu
395                 400                 405

AAG TCC CCT TTG GAC GTG CTG AAG AGA GCG GCC ACC AAG AAG AGC AGA        1418
Lys Ser Pro Leu Asp Val Leu Lys Arg Ala Ala Thr Lys Lys Ser Arg
410                 415                 420                 425

AAT GAC CTG ATC CAC GCA GAG GAG GGA GAG GAC CGG TTT GCA GAT CTC        1466
Asn Asp Leu Ile His Ala Glu Glu Gly Glu Asp Arg Phe Ala Asp Leu
                430                 435                 440

TGT GCT GTT GGA TCC CCC TTC GCC CGC GCC AGC CTC AAG AGC GGG AAG        1514
Cys Ala Val Gly Ser Pro Phe Ala Arg Ala Ser Leu Lys Ser Gly Lys
                445                 450                 455

ACA GAG AGC TCG TCA TAC TTC CGG AGG AAG GAG AAG ATG TTC CGG TTT        1562
Thr Glu Ser Ser Ser Tyr Phe Arg Arg Lys Glu Lys Met Phe Arg Phe
            460                 465                 470

TTT ATC CGG CGC ATG GTG AAG GCT CAG AGC TTC TAC TGG GTG GTG CTG        1610
Phe Ile Arg Arg Met Val Lys Ala Gln Ser Phe Tyr Trp Val Val Leu
        475                 480                 485

TGC GTG GTG GCC CTG AAC ACA CTG TGT GTG GCC ATG GTG CAT TAC AAC        1658
Cys Val Val Ala Leu Asn Thr Leu Cys Val Ala Met Val His Tyr Asn
490                 495                 500                 505

CAG CCG CGG CGG CTT ACC ACG ACC CTG TAT TTT GCA GAG TTT GTT TTC        1706
Gln Pro Arg Arg Leu Thr Thr Thr Leu Tyr Phe Ala Glu Phe Val Phe
                510                 515                 520

CTG GGT CTC TTC CTC ACA GAG ATG TCC CTG AAG ATG TAT GGC CTG GGG        1754
Leu Gly Leu Phe Leu Thr Glu Met Ser Leu Lys Met Tyr Gly Leu Gly
                525                 530                 535

CCC AGA AGC TAC TTC CGG TCC TCC TTC AAC TGC TTC GAC TTT GGG GTC        1802
Pro Arg Ser Tyr Phe Arg Ser Ser Phe Asn Cys Phe Asp Phe Gly Val
            540                 545                 550

ATC GTG GGG AGC GTC TTT GAA GTG GTC TGG GCG GCC ATC AAG CCG GGA        1850
Ile Val Gly Ser Val Phe Glu Val Val Trp Ala Ala Ile Lys Pro Gly
        555                 560                 565

AGC TCC TTT GGG ATC AGT GTG CTG CGG GCC CTC CGC CTG CTG AGG ATC        1898
Ser Ser Phe Gly Ile Ser Val Leu Arg Ala Leu Arg Leu Leu Arg Ile
570                 575                 580                 585

TTC AAA GTC ACG AAG TAC TGG AGC TCC CTG CGG AAC CTG GTG GTG TCC        1946
Phe Lys Val Thr Lys Tyr Trp Ser Ser Leu Arg Asn Leu Val Val Ser
                590                 595                 600

CTG CTG AAC TCC ATG AAG TCC ATC ATC AGC CTG CTC TTC TTG CTC TTC        1994
Leu Leu Asn Ser Met Lys Ser Ile Ile Ser Leu Leu Phe Leu Leu Phe
                605                 610                 615

CTG TTC ATT GTG GTC TTC GCC CTG CTG GGG ATG CAG CTG TTT GGG GGA        2042
Leu Phe Ile Val Val Phe Ala Leu Leu Gly Met Gln Leu Phe Gly Gly
            620                 625                 630

CAG TTC AAC TTC CAG GAT GAG ACT CCC ACA ACC AAC TTC GAC ACC TTC        2090
Gln Phe Asn Phe Gln Asp Glu Thr Pro Thr Thr Asn Phe Asp Thr Phe
        635                 640                 645

CCT GCC GCC ATC CTC ACT GTC TTC CAG ATC CTG ACG GGA GAG GAC TGG        2138
Pro Ala Ala Ile Leu Thr Val Phe Gln Ile Leu Thr Gly Glu Asp Trp
650                 655                 660                 665

AAT GCA GTG ATG TAT CAC GGG ATC GAA TCG CAA GGC GGC GTC AGC AAA        2186
Asn Ala Val Met Tyr His Gly Ile Glu Ser Gln Gly Gly Val Ser Lys
                670                 675                 680

GGC ATG TTC TCG TCC TTT TAC TTC ATT GTC CTG ACA CTG TTC GGA AAC        2234
Gly Met Phe Ser Ser Phe Tyr Phe Ile Val Leu Thr Leu Phe Gly Asn
                685                 690                 695

TAC ACT CTG CTG AAT GTC TTT CTG GCC ATC GCT GTG GAC AAC CTG GCC        2282
Tyr Thr Leu Leu Asn Val Phe Leu Ala Ile Ala Val Asp Asn Leu Ala
            700                 705                 710
```

```
AAC GCC CAA GAG CTG ACC AAG GAT GAA GAG GAG ATG GAA GAA GCA GCC     2330
Asn Ala Gln Glu Leu Thr Lys Asp Glu Glu Glu Met Glu Glu Ala Ala
715                 720                 725

AAT CAG AAG CTT GCT CTG CAA AAG GCC AAA GAA GTG GCT GAA GTC AGC     2378
Asn Gln Lys Leu Ala Leu Gln Lys Ala Lys Glu Val Ala Glu Val Ser
730                 735                 740                 745

CCC ATG TCT GCC GCG AAC ATC TCC ATC GCC GCC AGG CAG CAG AAC TCG     2426
Pro Met Ser Ala Ala Asn Ile Ser Ile Ala Ala Arg Gln Gln Asn Ser
            750                 755                 760

GCC AAG GCG CGC TCG GTG TGG GAG CAG CGG GCC AGC CAG CTA CGG CTG     2474
Ala Lys Ala Arg Ser Val Trp Glu Gln Arg Ala Ser Gln Leu Arg Leu
            765                 770                 775

CAG AAC CTG CGG GCC AGC TGC GAG GCG CTG TAC AGC GAG ATG GAC CCC     2522
Gln Asn Leu Arg Ala Ser Cys Glu Ala Leu Tyr Ser Glu Met Asp Pro
            780                 785                 790

GAG GAG CGG CTG CGC TTC GCC ACT ACG CGC CAC CTG CGG CCC GAC ATG     2570
Glu Glu Arg Leu Arg Phe Ala Thr Thr Arg His Leu Arg Pro Asp Met
795                 800                 805

AAG ACG CAC CTG GAC CGG CCG CTG GTG GTG GAG CTG GGC CGC GAC GGC     2618
Lys Thr His Leu Asp Arg Pro Leu Val Val Glu Leu Gly Arg Asp Gly
810                 815                 820                 825

GCG CGG GGG CCC GTG GGA GGC AAA GCC CGA CCT GAG GCT GCG GAG GCC     2666
Ala Arg Gly Pro Val Gly Gly Lys Ala Arg Pro Glu Ala Ala Glu Ala
            830                 835                 840

CCC GAG GGC GTC GAC CCT CCG CGC AGG CAC CAC CGG CAC CGC GAC AAG     2714
Pro Glu Gly Val Asp Pro Pro Arg Arg His His Arg His Arg Asp Lys
            845                 850                 855

GAC AAG ACC CCC GCG GCG GGG GAC CAG GAC CGA GCA GAG GCC CCG AAG     2762
Asp Lys Thr Pro Ala Ala Gly Asp Gln Asp Arg Ala Glu Ala Pro Lys
            860                 865                 870

GCG GAG AGC GGG GAG CCC GGT GCC CGG GAG GAG CGG CCG CGG CCG CAC     2810
Ala Glu Ser Gly Glu Pro Gly Ala Arg Glu Glu Arg Pro Arg Pro His
875                 880                 885

CGC AGC CAC AGC AAG GAG GCC GCG GGG CCC CCG GAG GCG CGG AGC GAG     2858
Arg Ser His Ser Lys Glu Ala Ala Gly Pro Pro Glu Ala Arg Ser Glu
890                 895                 900                 905

CGC GGC CGA GGC CCA GGC CCC GAG GGC GGC CGG CGG CAC CAC CGG CGC     2906
Arg Gly Arg Gly Pro Gly Pro Glu Gly Gly Arg Arg His His Arg Arg
            910                 915                 920

GGC TCC CCG GAG GAG GCG GCC GAG CGG GAG CCC CGA CGC CAC CGC GCG     2954
Gly Ser Pro Glu Glu Ala Ala Glu Arg Glu Pro Arg Arg His Arg Ala
            925                 930                 935

CAC CGG CAC CAG GAT CCG AGC AAG GAG TGC GCC GGC GCC AAG GGC GAG     3002
His Arg His Gln Asp Pro Ser Lys Glu Cys Ala Gly Ala Lys Gly Glu
            940                 945                 950

CGG CGC GCG CGG CAC CGC GGC GGC CCC CGA GCG GGG CCC CGG GAG GCG     3050
Arg Arg Ala Arg His Arg Gly Gly Pro Arg Ala Gly Pro Arg Glu Ala
955                 960                 965

GAG AGC GGG GAG GAG CCG GCG CGG CGG CAC CGG GCC CGG CAC AAG GCG     3098
Glu Ser Gly Glu Glu Pro Ala Arg Arg His Arg Ala Arg His Lys Ala
970                 975                 980                 985

CAG CCT GCT CAC GAG GCT GTG GAG AAG GAG ACC ACG GAG AAG GAG GCC     3146
Gln Pro Ala His Glu Ala Val Glu Lys Glu Thr Thr Glu Lys Glu Ala
            990                 995                 1000

ACG GAG AAG GAG GCT GAG ATA GTG GAA GCC GAC AAG GAA AAG GAG CTC     3194
Thr Glu Lys Glu Ala Glu Ile Val Glu Ala Asp Lys Glu Lys Glu Leu
            1005                1010                1015

CGG AAC CAC CAG CCC CGG GAG CCA CAC TGT GAC CTG GAG ACC AGT GGG     3242
Arg Asn His Gln Pro Arg Glu Pro His Cys Asp Leu Glu Thr Ser Gly
            1020                1025                1030
```

```
ACT GTG ACT GTG GGT CCC ATG CAC ACA CTG CCC AGC ACC TGT CTC CAG      3290
Thr Val Thr Val Gly Pro Met His Thr Leu Pro Ser Thr Cys Leu Gln
    1035                1040                1045

AAG GTG GAG GAA CAG CCA GAG GAT GCA GAC AAT CAG CGG AAC GTC ACT      3338
Lys Val Glu Glu Gln Pro Glu Asp Ala Asp Asn Gln Arg Asn Val Thr
1050                1055                1060                1065

CGC ATG GGC AGT CAG CCC CCA GAC CCG AAC ACT ATT GTA CAT ATC CCA      3386
Arg Met Gly Ser Gln Pro Pro Asp Pro Asn Thr Ile Val His Ile Pro
                1070                1075                1080

GTG ATG CTG ACG GGC CCT CTT GGG GAA GCC ACG GTC GTT CCC AGT GGT      3434
Val Met Leu Thr Gly Pro Leu Gly Glu Ala Thr Val Val Pro Ser Gly
            1085                1090                1095

AAC GTG GAC CTG GAA AGC CAA GCA GAG GGG AAG AAG GAG GTG GAA GCG      3482
Asn Val Asp Leu Glu Ser Gln Ala Glu Gly Lys Lys Glu Val Glu Ala
        1100                1105                1110

GAT GAC GTG ATG AGG AGC GGC CCC CGG CCT ATC GTC CCA TAC AGC TCC      3530
Asp Asp Val Met Arg Ser Gly Pro Arg Pro Ile Val Pro Tyr Ser Ser
    1115                1120                1125

ATG TTC TGT TTA AGC CCC ACC AAC CTG CTC CGC CGC TTC TGC CAC TAC      3578
Met Phe Cys Leu Ser Pro Thr Asn Leu Leu Arg Arg Phe Cys His Tyr
1130                1135                1140                1145

ATC GTG ACC ATG AGG TAC TTC GAG GTG GTC ATT CTC GTG GTC ATC GCC      3626
Ile Val Thr Met Arg Tyr Phe Glu Val Val Ile Leu Val Val Ile Ala
                1150                1155                1160

TTG AGC AGC ATC GCC CTG GCT GCT GAG GAC CCA GTG CGC ACA GAC TCG      3674
Leu Ser Ser Ile Ala Leu Ala Ala Glu Asp Pro Val Arg Thr Asp Ser
            1165                1170                1175

CCC AGG AAC AAC GCT CTG AAA TAC CTG GAT TAC ATT TTC ACT GGT GTC      3722
Pro Arg Asn Asn Ala Leu Lys Tyr Leu Asp Tyr Ile Phe Thr Gly Val
        1180                1185                1190

TTT ACC TTT GAG ATG GTG ATA AAG ATG ATC GAC TTG GGA CTG CTG CTT      3770
Phe Thr Phe Glu Met Val Ile Lys Met Ile Asp Leu Gly Leu Leu Leu
    1195                1200                1205

CAC CCT GGA GCC TAT TTC CGG GAC TTG TGG AAC ATT CTG GAC TTC ATT      3818
His Pro Gly Ala Tyr Phe Arg Asp Leu Trp Asn Ile Leu Asp Phe Ile
1210                1215                1220                1225

GTG GTC AGT GGC GCC CTG GTG GCG TTT GCT TTC TCA GGA TCC AAA GGG      3866
Val Val Ser Gly Ala Leu Val Ala Phe Ala Phe Ser Gly Ser Lys Gly
                1230                1235                1240

AAA GAC ATC AAT ACC ATC AAG TCT CTG AGA GTC CTT CGT GTC CTG CGG      3914
Lys Asp Ile Asn Thr Ile Lys Ser Leu Arg Val Leu Arg Val Leu Arg
            1245                1250                1255

CCC CTC AAG ACC ATC AAA CGG CTG CCC AAG CTC AAG GCT GTG TTT GAC      3962
Pro Leu Lys Thr Ile Lys Arg Leu Pro Lys Leu Lys Ala Val Phe Asp
        1260                1265                1270

TGT GTG GTG AAC TCC CTG AAG AAT GTC CTC AAC ATC TTG ATT GTC TAC      4010
Cys Val Val Asn Ser Leu Lys Asn Val Leu Asn Ile Leu Ile Val Tyr
    1275                1280                1285

ATG CTC TTC ATG TTC ATA TTT GCC GTC ATT GCG GTG CAG CTC TTC AAA      4058
Met Leu Phe Met Phe Ile Phe Ala Val Ile Ala Val Gln Leu Phe Lys
1290                1295                1300                1305

GGG AAG TTT TTC TAC TGC ACA GAT GAA TCC AAG GAG CTG GAG AGG GAC      4106
Gly Lys Phe Phe Tyr Cys Thr Asp Glu Ser Lys Glu Leu Glu Arg Asp
                1310                1315                1320

TGC AGG GGT CAG TAT TTG GAT TAT GAG AAG GAG GAA GTG GAA GCT CAG      4154
Cys Arg Gly Gln Tyr Leu Asp Tyr Glu Lys Glu Glu Val Glu Ala Gln
            1325                1330                1335

CCC AGG CAG TGG AAG AAA TAC GAC TTT CAC TAC GAC AAT GTG CTC TGG      4202
Pro Arg Gln Trp Lys Lys Tyr Asp Phe His Tyr Asp Asn Val Leu Trp
```

-continued

```
          1340                1345                1350
GCT CTG CTG ACG CTG TTC ACA GTG TCC ACG GGA GAA GGC TGG CCC ATG        4250
Ala Leu Leu Thr Leu Phe Thr Val Ser Thr Gly Glu Gly Trp Pro Met
          1355                1360                1365

GTG CTG AAA CAC TCC GTG GAT GCC ACC TAT GAG GAG CAG GGT CCA AGC        4298
Val Leu Lys His Ser Val Asp Ala Thr Tyr Glu Glu Gln Gly Pro Ser
1370                1375                1380                1385

CCT GGG TAC CGC ATG GAG CTG TCC ATC TTC TAC GTG GTC TAC TTT GTG        4346
Pro Gly Tyr Arg Met Glu Leu Ser Ile Phe Tyr Val Val Tyr Phe Val
              1390                1395                1400

GTC TTT CCC TTC TTC TTC GTC AAC ATC TTT GTG GCT TTG ATC ATC ATC        4394
Val Phe Pro Phe Phe Phe Val Asn Ile Phe Val Ala Leu Ile Ile Ile
          1405                1410                1415

ACC TTC CAG GAG CAG GGG GAC AAG GTG ATG TCT GAA TGC AGC CTG GAG        4442
Thr Phe Gln Glu Gln Gly Asp Lys Val Met Ser Glu Cys Ser Leu Glu
          1420                1425                1430

AAG AAC GAG AGG GCT TGC ATT GAC TTC GCC ATC AGC GCC AAA CCC CTG        4490
Lys Asn Glu Arg Ala Cys Ile Asp Phe Ala Ile Ser Ala Lys Pro Leu
          1435                1440                1445

ACA CGG TAC ATG CCC CAA AAC CGG CAG TCG TTC CAG TAT AAG ACG TGG        4538
Thr Arg Tyr Met Pro Gln Asn Arg Gln Ser Phe Gln Tyr Lys Thr Trp
1450                1455                1460                1465

ACA TTT GTG GTC TCC CCG CCC TTT GAA TAC TTC ATC ATG GCC ATG ATA        4586
Thr Phe Val Val Ser Pro Pro Phe Glu Tyr Phe Ile Met Ala Met Ile
              1470                1475                1480

GCC CTC AAC ACT GTG GTG CTG ATG ATG AAG TTC TAT GAT GCA CCC TAT        4634
Ala Leu Asn Thr Val Val Leu Met Met Lys Phe Tyr Asp Ala Pro Tyr
          1485                1490                1495

GAG TAC GAG CTG ATG CTG AAA TGC CTG AAC ATC GTG TTC ACA TCC ATG        4682
Glu Tyr Glu Leu Met Leu Lys Cys Leu Asn Ile Val Phe Thr Ser Met
          1500                1505                1510

TTC TCC ATG GAA TGC GTG CTG AAG ATC ATC GCC TTT GGG GTG CTG AAC        4730
Phe Ser Met Glu Cys Val Leu Lys Ile Ile Ala Phe Gly Val Leu Asn
          1515                1520                1525

TAT TTC AGA GAT GCC TGG AAT GTC TTT GAC TTT GTC ACT GTG TTG GGA        4778
Tyr Phe Arg Asp Ala Trp Asn Val Phe Asp Phe Val Thr Val Leu Gly
1530                1535                1540                1545

AGT ATT ACT GAT ATT TTA GTA ACA GAG ATT GCG GAA ACG AAC AAT TTC        4826
Ser Ile Thr Asp Ile Leu Val Thr Glu Ile Ala Glu Thr Asn Asn Phe
              1550                1555                1560

ATC AAC CTC AGC TTC CTC CGC CTC TTT CGA GCT GCG CGG CTG ATC AAG        4874
Ile Asn Leu Ser Phe Leu Arg Leu Phe Arg Ala Ala Arg Leu Ile Lys
          1565                1570                1575

CTG CTC CGC CAG GGC TAC ACC ATC CGC ATC CTG CTG TGG ACC TTT GTC        4922
Leu Leu Arg Gln Gly Tyr Thr Ile Arg Ile Leu Leu Trp Thr Phe Val
          1580                1585                1590

CAG TCC TTC AAG GCC CTG CCC TAC GTG TGT CTG CTC ATT GCC ATG CTG        4970
Gln Ser Phe Lys Ala Leu Pro Tyr Val Cys Leu Leu Ile Ala Met Leu
          1595                1600                1605

TTC TTC ATC TAC GCC ATC ATC GGC ATG CAG GTG TTT GGG AAT ATT GCC        5018
Phe Phe Ile Tyr Ala Ile Ile Gly Met Gln Val Phe Gly Asn Ile Ala
1610                1615                1620                1625

CTG GAT GAT GAC ACC AGC ATC AAC CGC CAC AAC AAC TTC CGG ACG TTT        5066
Leu Asp Asp Asp Thr Ser Ile Asn Arg His Asn Asn Phe Arg Thr Phe
              1630                1635                1640

TTG CAA GCC CTG ATG CTG CTG TTC AGG AGC GCC ACG GGG GAG GCC TGG        5114
Leu Gln Ala Leu Met Leu Leu Phe Arg Ser Ala Thr Gly Glu Ala Trp
          1645                1650                1655

CAC GAG ATC ATG CTG TCC TGC CTG AGC AAC CAG GCC TGT GAT GAG CAG        5162
```

```
                His Glu Ile Met Leu Ser Cys Leu Ser Asn Gln Ala Cys Asp Glu Gln
                                1660                1665                1670

GCC AAT GCC ACC GAG TGT GGA AGT GAC TTT GCC TAC TTC TAC TTC GTC              5210
Ala Asn Ala Thr Glu Cys Gly Ser Asp Phe Ala Tyr Phe Tyr Phe Val
            1675                1680                1685

TCC TTC ATC TTC CTG TGC TCC TTT CTG ATG TTG AAC CTC TTT GTG GCT              5258
Ser Phe Ile Phe Leu Cys Ser Phe Leu Met Leu Asn Leu Phe Val Ala
1690                1695                1700                1705

GTG ATC ATG GAC AAT TTT GAG TAC CTC ACG CGG GAC TCT TCC ATC CTA              5306
Val Ile Met Asp Asn Phe Glu Tyr Leu Thr Arg Asp Ser Ser Ile Leu
                1710                1715                1720

GGT CCT CAC CAC TTG GAT GAG TTC ATC CGG GTC TGG GCT GAA TAC GAC              5354
Gly Pro His His Leu Asp Glu Phe Ile Arg Val Trp Ala Glu Tyr Asp
            1725                1730                1735

CCG GCT GCG TGT GGG CGC ATC AGT TAC AAT GAC ATG TTT GAG ATG CTG              5402
Pro Ala Ala Cys Gly Arg Ile Ser Tyr Asn Asp Met Phe Glu Met Leu
            1740                1745                1750

AAA CAC ATG TCC CCG CCT CTG GGG CTG GGG AAG AAA TGC CCT GCT CGA              5450
Lys His Met Ser Pro Pro Leu Gly Leu Gly Lys Lys Cys Pro Ala Arg
            1755                1760                1765

GTT GCT TAC AAG CGC CTG GTT CGC ATG AAC ATG CCC ATC TCC AAC GAG              5498
Val Ala Tyr Lys Arg Leu Val Arg Met Asn Met Pro Ile Ser Asn Glu
1770                1775                1780                1785

GAC ATG ACT GTT CAC TTC ACG TCC ACG CTG ATG GCC CTC ATC CGG ACG              5546
Asp Met Thr Val His Phe Thr Ser Thr Leu Met Ala Leu Ile Arg Thr
                1790                1795                1800

GCA CTG GAG ATC AAG CTG GCC CCA GCT GGG ACA AAG CAG CAT CAG TGT              5594
Ala Leu Glu Ile Lys Leu Ala Pro Ala Gly Thr Lys Gln His Gln Cys
            1805                1810                1815

GAC GCG GAG TTG AGG AAG GAG ATT TCC GTT GTG TGG GCC AAT CTG CCC              5642
Asp Ala Glu Leu Arg Lys Glu Ile Ser Val Val Trp Ala Asn Leu Pro
            1820                1825                1830

CAG AAG ACT TTG GAC TTG CTG GTA CCA CCC CAT AAG CCT GAT GAG ATG              5690
Gln Lys Thr Leu Asp Leu Leu Val Pro Pro His Lys Pro Asp Glu Met
            1835                1840                1845

ACA GTG GGG AAG GTT TAT GCA GCT CTG ATG ATA TTT GAC TTC TAC AAG              5738
Thr Val Gly Lys Val Tyr Ala Ala Leu Met Ile Phe Asp Phe Tyr Lys
1850                1855                1860                1865

CAG AAC AAA ACC ACC AGA GAC CAG ATG CAG CAG GCT CCT GGA GGC CTC              5786
Gln Asn Lys Thr Thr Arg Asp Gln Met Gln Gln Ala Pro Gly Gly Leu
                1870                1875                1880

TCC CAG ATG GGT CCT GTG TCC CTG TTC CAC CCT CTG AAG GCC ACC CTG              5834
Ser Gln Met Gly Pro Val Ser Leu Phe His Pro Leu Lys Ala Thr Leu
            1885                1890                1895

GAG CAG ACA CAG CCG GCT GTG CTC CGA GGA GCC CGG GTT TTC CTT CGA              5882
Glu Gln Thr Gln Pro Ala Val Leu Arg Gly Ala Arg Val Phe Leu Arg
            1900                1905                1910

CAG AAG AGT TCC ACC TCC CTC AGC AAT GGC GGG GCC ATA CAA AAC CAA              5930
Gln Lys Ser Ser Thr Ser Leu Ser Asn Gly Gly Ala Ile Gln Asn Gln
            1915                1920                1925

GAG AGT GGC ATC AAA GAG TCT GTC TCC TGG GGC ACT CAA AGG ACC CAG              5978
Glu Ser Gly Ile Lys Glu Ser Val Ser Trp Gly Thr Gln Arg Thr Gln
1930                1935                1940                1945

GAT GCA CCC CAT GAG GCC AGG CCA CCC CTG GAG CGT GGC CAC TCC ACA              6026
Asp Ala Pro His Glu Ala Arg Pro Pro Leu Glu Arg Gly His Ser Thr
                1950                1955                1960

GAG ATC CCT GTG GGG CGG TCA GGA GCA CTG GCT GTG GAC GTT CAG ATG              6074
Glu Ile Pro Val Gly Arg Ser Gly Ala Leu Ala Val Asp Val Gln Met
                1965                1970                1975
```

```
CAG AGC ATA ACC CGG AGG GGC CCT GAT GGG GAG CCC CAG CCT GGG CTG      6122
Gln Ser Ile Thr Arg Arg Gly Pro Asp Gly Glu Pro Gln Pro Gly Leu
        1980            1985                1990

GAG AGC CAG GGT CGA GCG GCC TCC ATG CCC CGC CTT GCG GCC GAG ACT      6170
Glu Ser Gln Gly Arg Ala Ala Ser Met Pro Arg Leu Ala Ala Glu Thr
    1995                2000                2005

CAG CCC GTC ACA GAT GCC AGC CCC ATG AAG CGC TCC ATC TCC ACG CTG      6218
Gln Pro Val Thr Asp Ala Ser Pro Met Lys Arg Ser Ile Ser Thr Leu
2010                2015                2020                2025

GCC CAG CGG CCC CGT GGG ACT CAT CTT TGC AGC ACC ACC CCG GAC CGC      6266
Ala Gln Arg Pro Arg Gly Thr His Leu Cys Ser Thr Thr Pro Asp Arg
            2030                2035                2040

CCA CCC CCT AGC CAG GCG TCG TCG CAC CAC CAC CAC CAC CGC TGC CAC      6314
Pro Pro Pro Ser Gln Ala Ser Ser His His His His His Arg Cys His
                2045                2050                2055

CGC CGC AGG GAC AGG AAG CAG AGG TCC CTG GAG AAG GGG CCC AGC CTG      6362
Arg Arg Arg Asp Arg Lys Gln Arg Ser Leu Glu Lys Gly Pro Ser Leu
        2060                2065                2070

TCT GCC GAT ATG GAT GGC GCA CCA AGC AGT GCT GTG GGG CCG GGG CTG      6410
Ser Ala Asp Met Asp Gly Ala Pro Ser Ser Ala Val Gly Pro Gly Leu
    2075                2080                2085

CCC CCG GGA GAG GGG CCT ACA GGC TGC CGG CGG GAA CGA GAG CGC CGG      6458
Pro Pro Gly Glu Gly Pro Thr Gly Cys Arg Arg Glu Arg Glu Arg Arg
2090                2095                2100                2105

CAG GAG CGG GGC CGG TCC CAG GAG CGG AGG CAG CCC TCA TCC TCC TCC      6506
Gln Glu Arg Gly Arg Ser Gln Glu Arg Arg Gln Pro Ser Ser Ser Ser
            2110                2115                2120

TCG GAG AAG CAG CGC TTC TAC TCC TGC GAC CGC TTT GGG GGC CGT GAG      6554
Ser Glu Lys Gln Arg Phe Tyr Ser Cys Asp Arg Phe Gly Gly Arg Glu
                2125                2130                2135

CCC CCG AAG CCC AAG CCC TCC CTC AGC AGC CAC CCA ACG TCG CCA ACA      6602
Pro Pro Lys Pro Lys Pro Ser Leu Ser Ser His Pro Thr Ser Pro Thr
        2140                2145                2150

GCT GGC CAG GAG CCG GGA CCC CAC CCA CAG GGC AGT GGT TCC GTG AAT      6650
Ala Gly Gln Glu Pro Gly Pro His Pro Gln Gly Ser Gly Ser Val Asn
    2155                2160                2165

GGG AGC CCC TTG CTG TCA ACA TCT GGT GCT AGC ACC CCC GGC CGC GGT      6698
Gly Ser Pro Leu Leu Ser Thr Ser Gly Ala Ser Thr Pro Gly Arg Gly
2170                2175                2180                2185

GGG CGG AGG CAG CTC CCC CAG ACG CCC CTG ACT CCC CGC CCC AGC ATC      6746
Gly Arg Arg Gln Leu Pro Gln Thr Pro Leu Thr Pro Arg Pro Ser Ile
            2190                2195                2200

ACC TAC AAG ACG GCC AAC TCC TCA CCC ATC CAC TTC GCC GGG GCT CAG      6794
Thr Tyr Lys Thr Ala Asn Ser Ser Pro Ile His Phe Ala Gly Ala Gln
                2205                2210                2215

ACC AGC CTC CCT GCC TTC TCC CCA GGC CGG CTC AGC CGT GGG CTT TCC      6842
Thr Ser Leu Pro Ala Phe Ser Pro Gly Arg Leu Ser Arg Gly Leu Ser
        2220                2225                2230

GAA CAC AAC GCC CTG CTG CAG AGA GAC CCC CTC AGC CAG CCC CTG GCC      6890
Glu His Asn Ala Leu Leu Gln Arg Asp Pro Leu Ser Gln Pro Leu Ala
    2235                2240                2245

CCT GGC TCT CGA ATT GGC TCT GAC CCT TAC CTG GGG CAG CGT CTG GAC      6938
Pro Gly Ser Arg Ile Gly Ser Asp Pro Tyr Leu Gly Gln Arg Leu Asp
2250                2255                2260                2265

AGT GAG GCC TCT GTC CAC GCC CTG CCT GAG GAC ACG CTC ACT TTC GAG      6986
Ser Glu Ala Ser Val His Ala Leu Pro Glu Asp Thr Leu Thr Phe Glu
            2270                2275                2280

GAG GCT GTG GCC ACC AAC TCG GGC CGC TCC TCC AGG ACT TCC TAC GTG      7034
Glu Ala Val Ala Thr Asn Ser Gly Arg Ser Ser Arg Thr Ser Tyr Val
                2285                2290                2295
```

-continued

```
TCC TCC CTG ACC TCC CAG TCT CAC CCT CTC CGC CGC GTG CCC AAC GGT      7082
Ser Ser Leu Thr Ser Gln Ser His Pro Leu Arg Arg Val Pro Asn Gly
        2300            2305            2310

TAC CAC TGC ACC CTG GGA CTC AGC TCG GGT GGC CGA GCA CGG CAC AGC      7130
Tyr His Cys Thr Leu Gly Leu Ser Ser Gly Gly Arg Ala Arg His Ser
        2315            2320            2325

TAC CAC CAC CCT GAC CAA GAC CAC TGG TGC TAGCTGCACC GTGACCGCTC        7180
Tyr His His Pro Asp Gln Asp His Trp Cys
2330            2335            234

AGACGCCTGC ATGCAGCAGG CGTGTGTTCC AGTGGATGAG TTTTATCATC CACACGGGGC    7240

AGTCGGCCCT CGGGGGAGGC CTTGCCCACC TTGGTGAGGC TCCTGTGGCC CCTCCCTCCC    7300

CCTCCTCCCC TCTTTTACTC TAGACGACGA ATAAAGCCCT GTTGCTTGAG TGTACGTACC    7360

GC                                                                   7362
```

(2) INFORMATION FOR SEQ ID NO:8:

(i) SEQUENCE CHARACTERISTICS:
        (A) LENGTH: 7175 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 144..6857

(ix) FEATURE:
        (A) NAME/KEY: 5'UTR
        (B) LOCATION: 1..143

(ix) FEATURE:
        (A) NAME/KEY: 3'UTR
        (B) LOCATION: 6855..7175

(xi) SEQUENCE DESCRIPTION: SEQ ID NO:8:

```
GCGGCGGCGG CTGCGGCGGT GGGGCCGGGC GAGGTCCGTG CGGTCCCGGC GGCTCCGTGG       60

CTGCTCCGCT CTGAGCGCCT GCGCGCCCCG CGCCCTCCCT GCCGGGGCCG CTGGGCCGGG      120

GATGCACGCG GGGCCCGGGA GCC ATG GTC CGC TTC GGG GAC GAG CTG GGC         170
                         Met Val Arg Phe Gly Asp Glu Leu Gly
                           1               5

GGC CGC TAT GGA GGC CCC GGC GGC GGA GAG CGG GCC CGG GGC GGC GGG       218
Gly Arg Tyr Gly Gly Pro Gly Gly Gly Glu Arg Ala Arg Gly Gly Gly
 10              15              20              25

GCC GGC GGG GCG GGG GGC CCG GGT CCC GGG GGG CTG CAG CCC GGC CAG       266
Ala Gly Gly Ala Gly Gly Pro Gly Pro Gly Gly Leu Gln Pro Gly Gln
             30              35              40

CGG GTC CTC TAC AAG CAA TCG ATC GCG CAG CGC GCG CGG ACC ATG GCG       314
Arg Val Leu Tyr Lys Gln Ser Ile Ala Gln Arg Ala Arg Thr Met Ala
         45              50              55

CTG TAC AAC CCC ATC CCG GTC AAG CAG AAC TGC TTC ACC GTC AAC CGC       362
Leu Tyr Asn Pro Ile Pro Val Lys Gln Asn Cys Phe Thr Val Asn Arg
     60              65              70

TCG CTC TTC GTC TTC AGC GAG GAC AAC GTC GTC CGC AAA TAC GCG AAG       410
Ser Leu Phe Val Phe Ser Glu Asp Asn Val Val Arg Lys Tyr Ala Lys
         75              80              85

CGC ATC ACC GAG TGG CCT CCA TTC GAG AAT ATG ATC CTG GCC ACC ATC       458
Arg Ile Thr Glu Trp Pro Pro Phe Glu Asn Met Ile Leu Ala Thr Ile
 90              95             100             105

ATC GCC AAC TGC ATC GTG CTG GCC CTG GAG CAG CAC CTC CCT GAT GGG       506
```

```
Ile Ala Asn Cys Ile Val Leu Ala Leu Glu Gln His Leu Pro Asp Gly
                110                 115                 120

GAC AAA ACG CCC ATG TCC GAG CGG CTG GAC GAC ACG GAG CCC TAT TTC      554
Asp Lys Thr Pro Met Ser Glu Arg Leu Asp Asp Thr Glu Pro Tyr Phe
            125                 130                 135

ATC GGG ATC TTT TGC TTC GAG GCA GGG ATC AAA ATC ATC GCT CTG GGC      602
Ile Gly Ile Phe Cys Phe Glu Ala Gly Ile Lys Ile Ile Ala Leu Gly
        140                 145                 150

TTT GTC TTC CAC AAG GGC TCT TAC CTG CGG AAC GGC TGG AAC GTC ATG      650
Phe Val Phe His Lys Gly Ser Tyr Leu Arg Asn Gly Trp Asn Val Met
    155                 160                 165

GAC TTC GTG GTC GTC CTC ACA GGG ATC CTT GCC ACG GCT GGA ACT GAC      698
Asp Phe Val Val Val Leu Thr Gly Ile Leu Ala Thr Ala Gly Thr Asp
170                 175                 180                 185

TTC GAC CTG CGA ACA CTG AGG GCT GTG CGT GTG CTG AGG CCC CTG AAG      746
Phe Asp Leu Arg Thr Leu Arg Ala Val Arg Val Leu Arg Pro Leu Lys
                190                 195                 200

CTG GTG TCT GGG ATT CCA AGT TTG CAG GTG GTG CTC AAG TCC ATC ATG      794
Leu Val Ser Gly Ile Pro Ser Leu Gln Val Val Leu Lys Ser Ile Met
            205                 210                 215

AAG GCC ATG GTT CCA CTC CTG CAG ATT GGG CTG CTT CTC TTC TTT GCC      842
Lys Ala Met Val Pro Leu Leu Gln Ile Gly Leu Leu Leu Phe Phe Ala
        220                 225                 230

ATC CTC ATG TTT GCC ATC ATT GGC CTG GAG TTC TAC ATG GGC AAG TTC      890
Ile Leu Met Phe Ala Ile Ile Gly Leu Glu Phe Tyr Met Gly Lys Phe
    235                 240                 245

CAC AAG GCC TGT TTC CCC AAC AGC ACA GAT GCG GAG CCC GTG GGT GAC      938
His Lys Ala Cys Phe Pro Asn Ser Thr Asp Ala Glu Pro Val Gly Asp
250                 255                 260                 265

TTC CCC TGT GGC AAG GAG GCC CCA GCC CGG CTG TGC GAG GGC GAC ACT      986
Phe Pro Cys Gly Lys Glu Ala Pro Ala Arg Leu Cys Glu Gly Asp Thr
                270                 275                 280

GAG TGC CGG GAG TAC TGG CCA GGA CCC AAC TTT GGC ATC ACC AAC TTT     1034
Glu Cys Arg Glu Tyr Trp Pro Gly Pro Asn Phe Gly Ile Thr Asn Phe
            285                 290                 295

GAC AAT ATC CTG TTT GCC ATC TTG ACG GTG TTC CAG TGC ATC ACC ATG     1082
Asp Asn Ile Leu Phe Ala Ile Leu Thr Val Phe Gln Cys Ile Thr Met
        300                 305                 310

GAG GGC TGG ACT GAC ATC CTC TAT AAT ACA AAC GAT GCG GCC GGC AAC     1130
Glu Gly Trp Thr Asp Ile Leu Tyr Asn Thr Asn Asp Ala Ala Gly Asn
    315                 320                 325

ACC TGG AAC TGG CTC TAC TTC ATC CCT CTC ATC ATC ATC GGC TCC TTC     1178
Thr Trp Asn Trp Leu Tyr Phe Ile Pro Leu Ile Ile Ile Gly Ser Phe
330                 335                 340                 345

TTC ATG CTC AAC CTG GTG CTG GGC GTG CTC TCG GGG GAG TTT GCC AAG     1226
Phe Met Leu Asn Leu Val Leu Gly Val Leu Ser Gly Glu Phe Ala Lys
                350                 355                 360

GAG CGA GAG AGG GTG GAG AAC CGC CGC GCC TTC CTG AAG CTG CGC CGG     1274
Glu Arg Glu Arg Val Glu Asn Arg Arg Ala Phe Leu Lys Leu Arg Arg
            365                 370                 375

CAG CAG CAG ATC GAG CGA GAG CTC AAC GGG TAC CTG GAG TGG ATC TTC     1322
Gln Gln Gln Ile Glu Arg Glu Leu Asn Gly Tyr Leu Glu Trp Ile Phe
        380                 385                 390

AAG GCG GAG GAA GTC ATG CTG GCC GAG GAG GAC AGG AAT GCA GAG GAG     1370
Lys Ala Glu Glu Val Met Leu Ala Glu Glu Asp Arg Asn Ala Glu Glu
    395                 400                 405

AAG TCC CCT TTG GAC GTG CTG AAG AGA GCG GCC ACC AAG AAG AGC AGA     1418
Lys Ser Pro Leu Asp Val Leu Lys Arg Ala Ala Thr Lys Lys Ser Arg
410                 415                 420                 425
```

-continued

| | |
|---|---|
| AAT GAC CTG ATC CAC GCA GAG GAG GGA GAG GAC CGG TTT GCA GAT CTC<br>Asn Asp Leu Ile His Ala Glu Glu Gly Glu Asp Arg Phe Ala Asp Leu<br>                                430                          435                          440 | 1466 |
| TGT GCT GTT GGA TCC CCC TTC GCC CGC GCC AGC CTC AAG AGC GGG AAG<br>Cys Ala Val Gly Ser Pro Phe Ala Arg Ala Ser Leu Lys Ser Gly Lys<br>                       445                       450                     455 | 1514 |
| ACA GAG AGC TCG TCA TAC TTC CGG AGG AAG GAG AAG ATG TTC CGG TTT<br>Thr Glu Ser Ser Ser Tyr Phe Arg Arg Lys Glu Lys Met Phe Arg Phe<br>          460                     465                     470 | 1562 |
| TTT ATC CGG CGC ATG GTG AAG GCT CAG AGC TTC TAC TGG GTG GTG CTG<br>Phe Ile Arg Arg Met Val Lys Ala Gln Ser Phe Tyr Trp Val Val Leu<br>     475                     480                     485 | 1610 |
| TGC GTG GTG GCC CTG AAC ACA CTG TGT GTG GCC ATG GTG CAT TAC AAC<br>Cys Val Val Ala Leu Asn Thr Leu Cys Val Ala Met Val His Tyr Asn<br>490                     495                     500                     505 | 1658 |
| CAG CCG CGG CGG CTT ACC ACG ACC CTG TAT TTT GCA GAG TTT GTT TTC<br>Gln Pro Arg Arg Leu Thr Thr Thr Leu Tyr Phe Ala Glu Phe Val Phe<br>                510                     515                     520 | 1706 |
| CTG GGT CTC TTC CTC ACA GAG ATG TCC CTG AAG ATG TAT GGC CTG GGG<br>Leu Gly Leu Phe Leu Thr Glu Met Ser Leu Lys Met Tyr Gly Leu Gly<br>              525                     530                     535 | 1754 |
| CCC AGA AGC TAC TTC CGG TCC TCC TTC AAC TGC TTC GAC TTT GGG GTC<br>Pro Arg Ser Tyr Phe Arg Ser Ser Phe Asn Cys Phe Asp Phe Gly Val<br>         540                     545                     550 | 1802 |
| ATC GTG GGG AGC GTC TTT GAA GTG GTC TGG GCG GCC ATC AAG CCG GGA<br>Ile Val Gly Ser Val Phe Glu Val Val Trp Ala Ala Ile Lys Pro Gly<br>    555                     560                     565 | 1850 |
| AGC TCC TTT GGG ATC AGT GTG CTG CGG GCC CTC CGC CTG CTG AGG ATC<br>Ser Ser Phe Gly Ile Ser Val Leu Arg Ala Leu Arg Leu Leu Arg Ile<br>570                     575                     580                     585 | 1898 |
| TTC AAA GTC ACG AAG TAC TGG AGC TCC CTG CGG AAC CTG GTG GTG TCC<br>Phe Lys Val Thr Lys Tyr Trp Ser Ser Leu Arg Asn Leu Val Val Ser<br>              590                     595                     600 | 1946 |
| CTG CTG AAC TCC ATG AAG TCC ATC ATC AGC CTG CTC TTC TTG CTC TTC<br>Leu Leu Asn Ser Met Lys Ser Ile Ile Ser Leu Leu Phe Leu Leu Phe<br>         605                     610                     615 | 1994 |
| CTG TTC ATT GTG GTC TTC GCC CTG CTG GGG ATG CAG CTG TTT GGG GGA<br>Leu Phe Ile Val Val Phe Ala Leu Leu Gly Met Gln Leu Phe Gly Gly<br>             620                     625                     630 | 2042 |
| CAG TTC AAC TTC CAG GAT GAG ACT CCC ACA ACC AAC TTC GAC ACC TTC<br>Gln Phe Asn Phe Gln Asp Glu Thr Pro Thr Thr Asn Phe Asp Thr Phe<br>        635                     640                     645 | 2090 |
| CCT GCC GCC ATC CTC ACT GTC TTC CAG ATC CTG ACG GGA GAG GAC TGG<br>Pro Ala Ala Ile Leu Thr Val Phe Gln Ile Leu Thr Gly Glu Asp Trp<br>650                     655                     660                     665 | 2138 |
| AAT GCA GTG ATG TAT CAC GGG ATC GAA TCG CAA GGC GGC GTC AGC AAA<br>Asn Ala Val Met Tyr His Gly Ile Glu Ser Gln Gly Gly Val Ser Lys<br>                 670                     675                     680 | 2186 |
| GGC ATG TTC TCG TCC TTT TAC TTC ATT GTC CTG ACA CTG TTC GGA AAC<br>Gly Met Phe Ser Ser Phe Tyr Phe Ile Val Leu Thr Leu Phe Gly Asn<br>            685                     690                     695 | 2234 |
| TAC ACT CTG CTG AAT GTC TTT CTG GCC ATC GCT GTG GAC AAC CTG GCC<br>Tyr Thr Leu Leu Asn Val Phe Leu Ala Ile Ala Val Asp Asn Leu Ala<br>          700                     705                     710 | 2282 |
| AAC GCC CAA GAG CTG ACC AAG GAT GAA GAG GAG ATG GAA GAA GCA GCC<br>Asn Ala Gln Glu Leu Thr Lys Asp Glu Glu Glu Met Glu Glu Ala Ala<br>       715                     720                     725 | 2330 |
| AAT CAG AAG CTT GCT CTG CAA AAG GCC AAA GAA GTG GCT GAA GTC AGC<br>Asn Gln Lys Leu Ala Leu Gln Lys Ala Lys Glu Val Ala Glu Val Ser<br>730                     735                     740                     745 | 2378 |

-continued

| | | |
|---|---|---|
| CCC ATG TCT GCC GCG AAC ATC TCC ATC GCC GCC AGG CAG CAG AAC TCG<br>Pro Met Ser Ala Ala Asn Ile Ser Ile Ala Ala Arg Gln Gln Asn Ser<br>              750                  755                  760 | 2426 | |
| GCC AAG GCG CGC TCG GTG TGG GAG CAG CGG GCC AGC CAG CTA CGG CTG<br>Ala Lys Ala Arg Ser Val Trp Glu Gln Arg Ala Ser Gln Leu Arg Leu<br>              765                  770                  775 | 2474 | |
| CAG AAC CTG CGG GCC AGC TGC GAG GCG CTG TAC AGC GAG ATG GAC CCC<br>Gln Asn Leu Arg Ala Ser Cys Glu Ala Leu Tyr Ser Glu Met Asp Pro<br>              780                  785                  790 | 2522 | |
| GAG GAG CGG CTG CGC TTC GCC ACT ACG CGC CAC CTG CGG CCC GAC ATG<br>Glu Glu Arg Leu Arg Phe Ala Thr Thr Arg His Leu Arg Pro Asp Met<br>795                  800                  805 | 2570 | |
| AAG ACG CAC CTG GAC CGG CCG CTG GTG GTG GAG CTG GGC CGC GAC GGC<br>Lys Thr His Leu Asp Arg Pro Leu Val Val Glu Leu Gly Arg Asp Gly<br>810                  815                  820                  825 | 2618 | |
| GCG CGG GGG CCC GTG GGA GGC AAA GCC CGA CCT GAG GCT GCG GAG GCC<br>Ala Arg Gly Pro Val Gly Gly Lys Ala Arg Pro Glu Ala Ala Glu Ala<br>              830                  835                  840 | 2666 | |
| CCC GAG GGC GTC GAC CCT CCG CGC AGG CAC CAC CGG CAC CGC GAC AAG<br>Pro Glu Gly Val Asp Pro Pro Arg Arg His His Arg His Arg Asp Lys<br>              845                  850                  855 | 2714 | |
| GAC AAG ACC CCC GCG GCG GGG GAC CAG GAC CGA GCA GAG GCC CCG AAG<br>Asp Lys Thr Pro Ala Ala Gly Asp Gln Asp Arg Ala Glu Ala Pro Lys<br>              860                  865                  870 | 2762 | |
| GCG GAG AGC GGG GAG CCC GGT GCC CGG GAG GAG CGG CCG CGG CCG CAC<br>Ala Glu Ser Gly Glu Pro Gly Ala Arg Glu Glu Arg Pro Arg Pro His<br>875                  880                  885 | 2810 | |
| CGC AGC CAC AGC AAG GAG GCC GCG GGG CCC CCG GAG GCG CGG AGC GAG<br>Arg Ser His Ser Lys Glu Ala Ala Gly Pro Pro Glu Ala Arg Ser Glu<br>890                  895                  900                  905 | 2858 | |
| CGC GGC CGA GGC CCA GGC CCC GAG GGC GGC CGG CGG CAC CAC CGG CGC<br>Arg Gly Arg Gly Pro Gly Pro Glu Gly Gly Arg Arg His His Arg Arg<br>              910                  915                  920 | 2906 | |
| GGC TCC CCG GAG GAG GCG GCC GAG CGG GAG CCC CGA CGC CAC CGC GCG<br>Gly Ser Pro Glu Glu Ala Ala Glu Arg Glu Pro Arg Arg His Arg Ala<br>              925                  930                  935 | 2954 | |
| CAC CGG CAC CAG GAT CCG AGC AAG GAG TGC GCC GGC GCC AAG GGC GAG<br>His Arg His Gln Asp Pro Ser Lys Glu Cys Ala Gly Ala Lys Gly Glu<br>              940                  945                  950 | 3002 | |
| CGG CGC GCG CGG CAC CGC GGC GGC CCC CGA GCG GGG CCC CGG GAG GCG<br>Arg Arg Ala Arg His Arg Gly Gly Pro Arg Ala Gly Pro Arg Glu Ala<br>955                  960                  965 | 3050 | |
| GAG AGC GGG GAG GAG CCG GCG CGG CGG CAC CGG GCC CGG CAC AAG GCG<br>Glu Ser Gly Glu Glu Pro Ala Arg Arg His Arg Ala Arg His Lys Ala<br>970                  975                  980                  985 | 3098 | |
| CAG CCT GCT CAC GAG GCT GTG GAG AAG GAG ACC ACG GAG AAG GAG GCC<br>Gln Pro Ala His Glu Ala Val Glu Lys Glu Thr Thr Glu Lys Glu Ala<br>              990                  995                1000 | 3146 | |
| ACG GAG AAG GAG GCT GAG ATA GTG GAA GCC GAC AAG GAA AAG GAG CTC<br>Thr Glu Lys Glu Ala Glu Ile Val Glu Ala Asp Lys Glu Lys Glu Leu<br>            1005                1010                1015 | 3194 | |
| CGG AAC CAC CAG CCC CGG GAG CCA CAC TGT GAC CTG GAG ACC AGT GGG<br>Arg Asn His Gln Pro Arg Glu Pro His Cys Asp Leu Glu Thr Ser Gly<br>            1020                1025                1030 | 3242 | |
| ACT GTG ACT GTG GGT CCC ATG CAC ACA CTG CCC AGC ACC TGT CTC CAG<br>Thr Val Thr Val Gly Pro Met His Thr Leu Pro Ser Thr Cys Leu Gln<br>            1035                1040                1045 | 3290 | |
| AAG GTG GAG GAA CAG CCA GAG GAT GCA GAC AAT CAG CGG AAC GTC ACT<br>Lys Val Glu Glu Gln Pro Glu Asp Ala Asp Asn Gln Arg Asn Val Thr | 3338 | |

-continued

| | |
|---|---|
| CGC ATG GGC AGT CAG CCC CCA GAC CCG AAC ACT ATT GTA CAT ATC CCA<br>Arg Met Gly Ser Gln Pro Pro Asp Pro Asn Thr Ile Val His Ile Pro<br>                   1070                      1075                  1080 | 3386 |
| GTG ATG CTG ACG GGC CCT CTT GGG GAA GCC ACG GTC GTT CCC AGT GGT<br>Val Met Leu Thr Gly Pro Leu Gly Glu Ala Thr Val Val Pro Ser Gly<br>                 1085                      1090                 1095 | 3434 |
| AAC GTG GAC CTG GAA AGC CAA GCA GAG GGG AAG AAG GAG GTG GAA GCG<br>Asn Val Asp Leu Glu Ser Gln Ala Glu Gly Lys Lys Glu Val Glu Ala<br>          1100                     1105                  1110 | 3482 |
| GAT GAC GTG ATG AGG AGC GGC CCC CGG CCT ATC GTC CCA TAC AGC TCC<br>Asp Asp Val Met Arg Ser Gly Pro Arg Pro Ile Val Pro Tyr Ser Ser<br>          1115                     1120                  1125 | 3530 |
| ATG TTC TGT TTA AGC CCC ACC AAC CTG CTC CGC CGC TTC TGC CAC TAC<br>Met Phe Cys Leu Ser Pro Thr Asn Leu Leu Arg Arg Phe Cys His Tyr<br>1130                  1135                  1140                  1145 | 3578 |
| ATC GTG ACC ATG AGG TAC TTC GAG GTG GTC ATT CTC GTG GTC ATC GCC<br>Ile Val Thr Met Arg Tyr Phe Glu Val Val Ile Leu Val Val Ile Ala<br>                 1150                     1155                 1160 | 3626 |
| TTG AGC AGC ATC GCC CTG GCT GCT GAG GAC CCA GTG CGC ACA GAC TCG<br>Leu Ser Ser Ile Ala Leu Ala Ala Glu Asp Pro Val Arg Thr Asp Ser<br>          1165                     1170                  1175 | 3674 |
| CCC AGG AAC AAC GCT CTG AAA TAC CTG GAT TAC ATT TTC ACT GGT GTC<br>Pro Arg Asn Asn Ala Leu Lys Tyr Leu Asp Tyr Ile Phe Thr Gly Val<br>                 1180                     1185                 1190 | 3722 |
| TTT ACC TTT GAG ATG GTG ATA AAG ATG ATC GAC TTG GGA CTG CTG CTT<br>Phe Thr Phe Glu Met Val Ile Lys Met Ile Asp Leu Gly Leu Leu Leu<br>          1195                     1200                  1205 | 3770 |
| CAC CCT GGA GCC TAT TTC CGG GAC TTG TGG AAC ATT CTG GAC TTC ATT<br>His Pro Gly Ala Tyr Phe Arg Asp Leu Trp Asn Ile Leu Asp Phe Ile<br>1210                  1215                  1220                  1225 | 3818 |
| GTG GTC AGT GGC GCC CTG GTG GCG TTT GCT TTC TCA GGA TCC AAA GGG<br>Val Val Ser Gly Ala Leu Val Ala Phe Ala Phe Ser Gly Ser Lys Gly<br>                 1230                     1235                 1240 | 3866 |
| AAA GAC ATC AAT ACC ATC AAG TCT CTG AGA GTC CTT CGT GTC CTG CGG<br>Lys Asp Ile Asn Thr Ile Lys Ser Leu Arg Val Leu Arg Val Leu Arg<br>          1245                     1250                  1255 | 3914 |
| CCC CTC AAG ACC ATC AAA CGG CTG CCC AAG CTC AAG GCT GTG TTT GAC<br>Pro Leu Lys Thr Ile Lys Arg Leu Pro Lys Leu Lys Ala Val Phe Asp<br>                 1260                     1265                 1270 | 3962 |
| TGT GTG GTG AAC TCC CTG AAG AAT GTC CTC AAC ATC TTG ATT GTC TAC<br>Cys Val Val Asn Ser Leu Lys Asn Val Leu Asn Ile Leu Ile Val Tyr<br>          1275                     1280                  1285 | 4010 |
| ATG CTC TTC ATG TTC ATA TTT GCC GTC ATT GCG GTG CAG CTC TTC AAA<br>Met Leu Phe Met Phe Ile Phe Ala Val Ile Ala Val Gln Leu Phe Lys<br>1290                  1295                  1300                  1305 | 4058 |
| GGG AAG TTT TTC TAC TGC ACA GAT GAA TCC AAG GAG CTG GAG AGG GAC<br>Gly Lys Phe Phe Tyr Cys Thr Asp Glu Ser Lys Glu Leu Glu Arg Asp<br>                 1310                     1315                 1320 | 4106 |
| TGC AGG GGT CAG TAT TTG GAT TAT GAG AAG GAG GAA GTG GAA GCT CAG<br>Cys Arg Gly Gln Tyr Leu Asp Tyr Glu Lys Glu Glu Val Glu Ala Gln<br>          1325                     1330                  1335 | 4154 |
| CCC AGG CAG TGG AAG AAA TAC GAC TTT CAC TAC GAC AAT GTG CTC TGG<br>Pro Arg Gln Trp Lys Lys Tyr Asp Phe His Tyr Asp Asn Val Leu Trp<br>                 1340                     1345                 1350 | 4202 |
| GCT CTG CTG ACG CTG TTC ACA GTG TCC ACG GGA GAA GGC TGG CCC ATG<br>Ala Leu Leu Thr Leu Phe Thr Val Ser Thr Gly Glu Gly Trp Pro Met<br>          1355                     1360                  1365 | 4250 |
| GTG CTG AAA CAC TCC GTG GAT GCC ACC TAT GAG GAG CAG GGT CCA AGC | 4298 |

```
                                                        -continued

Val Leu Lys His Ser Val Asp Ala Thr Tyr Glu Glu Gln Gly Pro Ser
1370            1375                1380            1385

CCT GGG TAC CGC ATG GAG CTG TCC ATC TTC TAC GTG GTC TAC TTT GTG           4346
Pro Gly Tyr Arg Met Glu Leu Ser Ile Phe Tyr Val Val Tyr Phe Val
                1390                1395                1400

GTC TTT CCC TTC TTC TTC GTC AAC ATC TTT GTG GCT TTG ATC ATC ATC           4394
Val Phe Pro Phe Phe Phe Val Asn Ile Phe Val Ala Leu Ile Ile Ile
                1405                1410                1415

ACC TTC CAG GAG CAG GGG GAC AAG GTG ATG TCT GAA TGC AGC CTG GAG           4442
Thr Phe Gln Glu Gln Gly Asp Lys Val Met Ser Glu Cys Ser Leu Glu
                1420                1425                1430

AAG AAC GAG AGG GCT TGC ATT GAC TTC GCC ATC AGC GCC AAA CCC CTG           4490
Lys Asn Glu Arg Ala Cys Ile Asp Phe Ala Ile Ser Ala Lys Pro Leu
            1435                1440                1445

ACA CGG TAC ATG CCC CAA AAC CGG CAG TCG TTC CAG TAT AAG ACG TGG           4538
Thr Arg Tyr Met Pro Gln Asn Arg Gln Ser Phe Gln Tyr Lys Thr Trp
1450            1455                1460                1465

ACA TTT GTG GTC TCC CCG CCC TTT GAA TAC TTC ATC ATG GCC ATG ATA           4586
Thr Phe Val Val Ser Pro Pro Phe Glu Tyr Phe Ile Met Ala Met Ile
                1470                1475                1480

GCC CTC AAC ACT GTG GTG CTG ATG ATG AAG TTC TAT GAT GCA CCC TAT           4634
Ala Leu Asn Thr Val Val Leu Met Met Lys Phe Tyr Asp Ala Pro Tyr
            1485                1490                1495

GAG TAC GAG CTG ATG CTG AAA TGC CTG AAC ATC GTG TTC ACA TCC ATG           4682
Glu Tyr Glu Leu Met Leu Lys Cys Leu Asn Ile Val Phe Thr Ser Met
            1500                1505                1510

TTC TCC ATG GAA TGC GTG CTG AAG ATC ATC GCC TTT GGG GTG CTG AAC           4730
Phe Ser Met Glu Cys Val Leu Lys Ile Ile Ala Phe Gly Val Leu Asn
            1515                1520                1525

TAT TTC AGA GAT GCC TGG AAT GTC TTT GAC TTT GTC ACT GTG TTG GGA           4778
Tyr Phe Arg Asp Ala Trp Asn Val Phe Asp Phe Val Thr Val Leu Gly
1530            1535                1540                1545

AGT ATT ACT GAT ATT TTA GTA ACA GAG ATT GCG GAA ACG AAC AAT TTC           4826
Ser Ile Thr Asp Ile Leu Val Thr Glu Ile Ala Glu Thr Asn Asn Phe
                1550                1555                1560

ATC AAC CTC AGC TTC CTC CGC CTC TTT CGA GCT GCG CGG CTG ATC AAG           4874
Ile Asn Leu Ser Phe Leu Arg Leu Phe Arg Ala Ala Arg Leu Ile Lys
            1565                1570                1575

CTG CTC CGC CAG GGC TAC ACC ATC CGC ATC CTG CTG TGG ACC TTT GTC           4922
Leu Leu Arg Gln Gly Tyr Thr Ile Arg Ile Leu Leu Trp Thr Phe Val
            1580                1585                1590

CAG TCC TTC AAG GCC CTG CCC TAC GTG TGT CTG CTC ATT GCC ATG CTG           4970
Gln Ser Phe Lys Ala Leu Pro Tyr Val Cys Leu Leu Ile Ala Met Leu
            1595                1600                1605

TTC TTC ATC TAC GCC ATC ATC GGC ATG CAG GTG TTT GGG AAT ATT GCC           5018
Phe Phe Ile Tyr Ala Ile Ile Gly Met Gln Val Phe Gly Asn Ile Ala
1610            1615                1620                1625

CTG GAT GAT GAC ACC AGC ATC AAC CGC CAC AAC AAC TTC CGG ACG TTT           5066
Leu Asp Asp Asp Thr Ser Ile Asn Arg His Asn Asn Phe Arg Thr Phe
                1630                1635                1640

TTG CAA GCC CTG ATG CTG CTG TTC AGG AGC GCC ACG GGG GAG GCC TGG           5114
Leu Gln Ala Leu Met Leu Leu Phe Arg Ser Ala Thr Gly Glu Ala Trp
            1645                1650                1655

CAC GAG ATC ATG CTG TCC TGC CTG AGC AAC CAG GCC TGT GAT GAG CAG           5162
His Glu Ile Met Leu Ser Cys Leu Ser Asn Gln Ala Cys Asp Glu Gln
            1660                1665                1670

GCC AAT GCC ACC GAG TGT GGA AGT GAC TTT GCC TAC TTC TAC TTC GTC           5210
Ala Asn Ala Thr Glu Cys Gly Ser Asp Phe Ala Tyr Phe Tyr Phe Val
                1675                1680                1685
```

-continued

```
TCC TTC ATC TTC CTG TGC TCC TTT CTG ATG TTG AAC CTC TTT GTG GCT    5258
Ser Phe Ile Phe Leu Cys Ser Phe Leu Met Leu Asn Leu Phe Val Ala
1690                1695                1700                1705

GTG ATC ATG GAC AAT TTT GAG TAC CTC ACG CGG GAC TCT TCC ATC CTA    5306
Val Ile Met Asp Asn Phe Glu Tyr Leu Thr Arg Asp Ser Ser Ile Leu
        1710                1715                1720

GGT CCT CAC CAC TTG GAT GAG TTC ATC CGG GTC TGG GCT GAA TAC GAC    5354
Gly Pro His His Leu Asp Glu Phe Ile Arg Val Trp Ala Glu Tyr Asp
            1725                1730                1735

CCG GCT GCG TGT GGG CGC ATC AGT TAC AAT GAC ATG TTT GAG ATG CTG    5402
Pro Ala Ala Cys Gly Arg Ile Ser Tyr Asn Asp Met Phe Glu Met Leu
                1740                1745                1750

AAA CAC ATG TCC CCG CCT CTG GGG CTG GGG AAG AAA TGC CCT GCT CGA    5450
Lys His Met Ser Pro Pro Leu Gly Leu Gly Lys Lys Cys Pro Ala Arg
        1755                1760                1765

GTT GCT TAC AAG CGC CTG GTT CGC ATG AAC ATG CCC ATC TCC AAC GAG    5498
Val Ala Tyr Lys Arg Leu Val Arg Met Asn Met Pro Ile Ser Asn Glu
1770                1775                1780                1785

GAC ATG ACT GTT CAC TTC ACG TCC ACG CTG ATG GCC CTC ATC CGG ACG    5546
Asp Met Thr Val His Phe Thr Ser Thr Leu Met Ala Leu Ile Arg Thr
            1790                1795                1800

GCA CTG GAG ATC AAG CTG GCC CCA GCT GGG ACA AAG CAG CAT CAG TGT    5594
Ala Leu Glu Ile Lys Leu Ala Pro Ala Gly Thr Lys Gln His Gln Cys
                1805                1810                1815

GAC GCG GAG TTG AGG AAG GAG ATT TCC GTT GTG TGG GCC AAT CTG CCC    5642
Asp Ala Glu Leu Arg Lys Glu Ile Ser Val Val Trp Ala Asn Leu Pro
        1820                1825                1830

CAG AAG ACT TTG GAC TTG CTG GTA CCA CCC CAT AAG CCT GAT GAG ATG    5690
Gln Lys Thr Leu Asp Leu Leu Val Pro Pro His Lys Pro Asp Glu Met
1835                1840                1845

ACA GTG GGG AAG GTT TAT GCA GCT CTG ATG ATA TTT GAC TTC TAC AAG    5738
Thr Val Gly Lys Val Tyr Ala Ala Leu Met Ile Phe Asp Phe Tyr Lys
1850                1855                1860                1865

CAG AAC AAA ACC ACC AGA GAC CAG ATG CAG CAG GCT CCT GGA GGC CTC    5786
Gln Asn Lys Thr Thr Arg Asp Gln Met Gln Gln Ala Pro Gly Gly Leu
            1870                1875                1880

TCC CAG ATG GGT CCT GTG TCC CTG TTC CAC CCT CTG AAG GCC ACC CTG    5834
Ser Gln Met Gly Pro Val Ser Leu Phe His Pro Leu Lys Ala Thr Leu
                1885                1890                1895

GAG CAG ACA CAG CCG GCT GTG CTC CGA GGA GCC CGG GTT TTC CTT CGA    5882
Glu Gln Thr Gln Pro Ala Val Leu Arg Gly Ala Arg Val Phe Leu Arg
        1900                1905                1910

CAG AAG AGT TCC ACC TCC CTC AGC AAT GGC GGG GCC ATA CAA AAC CAA    5930
Gln Lys Ser Ser Thr Ser Leu Ser Asn Gly Gly Ala Ile Gln Asn Gln
1915                1920                1925

GAG AGT GGC ATC AAA GAG TCT GTC TCC TGG GGC ACT CAA AGG ACC CAG    5978
Glu Ser Gly Ile Lys Glu Ser Val Ser Trp Gly Thr Gln Arg Thr Gln
1930                1935                1940                1945

GAT GCA CCC CAT GAG GCC AGG CCA CCC CTG GAG CGT GGC CAC TCC ACA    6026
Asp Ala Pro His Glu Ala Arg Pro Pro Leu Glu Arg Gly His Ser Thr
            1950                1955                1960

GAG ATC CCT GTG GGG CGG TCA GGA GCA CTG GCT GTG GAC GTT CAG ATG    6074
Glu Ile Pro Val Gly Arg Ser Gly Ala Leu Ala Val Asp Val Gln Met
                1965                1970                1975

CAG AGC ATA ACC CGG AGG GGC CCT GAT GGG GAG CCC CAG CCT GGG CTG    6122
Gln Ser Ile Thr Arg Arg Gly Pro Asp Gly Glu Pro Gln Pro Gly Leu
        1980                1985                1990

GAG AGC CAG GGT CGA GCG GCC TCC ATG CCC CGC CTT GCG GCC GAG ACT    6170
Glu Ser Gln Gly Arg Ala Ala Ser Met Pro Arg Leu Ala Ala Glu Thr
1995                2000                2005
```

```
CAG CCC GTC ACA GAT GCC AGC CCC ATG AAG CGC TCC ATC TCC ACG CTG         6218
Gln Pro Val Thr Asp Ala Ser Pro Met Lys Arg Ser Ile Ser Thr Leu
2010                2015                2020                2025

GCC CAG CGG CCC CGT GGG ACT CAT CTT TGC AGC ACC ACC CCG GAC CGC         6266
Ala Gln Arg Pro Arg Gly Thr His Leu Cys Ser Thr Thr Pro Asp Arg
            2030                2035                2040

CCA CCC CCT AGC CAG GCG TCG TCG CAC CAC CAC CAC CAC CGC TGC CAC         6314
Pro Pro Pro Ser Gln Ala Ser Ser His His His His His Arg Cys His
                2045                2050                2055

CGC CGC AGG GAC AGG AAG CAG AGG TCC CTG GAG AAG GGG CCC AGC CTG         6362
Arg Arg Arg Asp Arg Lys Gln Arg Ser Leu Glu Lys Gly Pro Ser Leu
        2060                2065                2070

TCT GCC GAT ATG GAT GGC GCA CCA AGC AGT GCT GTG GGG CCG GGG CTG         6410
Ser Ala Asp Met Asp Gly Ala Pro Ser Ser Ala Val Gly Pro Gly Leu
    2075                2080                2085

CCC CCG GGA GAG GGG CCT ACA GGC TGC CGG CGG GAA CGA GAG CGC CGG         6458
Pro Pro Gly Glu Gly Pro Thr Gly Cys Arg Arg Glu Arg Glu Arg Arg
2090                2095                2100                2105

CAG GAG CGG GGC CGG TCC CAG GAG CGG AGG CAG CCC TCA TCC TCC TCC         6506
Gln Glu Arg Gly Arg Ser Gln Glu Arg Arg Gln Pro Ser Ser Ser Ser
            2110                2115                2120

TCG GAG AAG CAG CGC TTC TAC TCC TGC GAC CGC TTT GGG GGC CGT GAG         6554
Ser Glu Lys Gln Arg Phe Tyr Ser Cys Asp Arg Phe Gly Gly Arg Glu
                2125                2130                2135

CCC CCG AAG CCC AAG CCC TCC CTC AGC AGC CAC CCA ACG TCG CCA ACA         6602
Pro Pro Lys Pro Lys Pro Ser Leu Ser Ser His Pro Thr Ser Pro Thr
        2140                2145                2150

GCT GGC CAG GAG CCG GGA CCC CAC CCA CAG GCC GGC TCA GCC GTG GGC         6650
Ala Gly Gln Glu Pro Gly Pro His Pro Gln Ala Gly Ser Ala Val Gly
    2155                2160                2165

TTT CCG AAC ACA ACG CCC TGC TGC AGA GAG ACC CCC TCA GCC AGC CCC         6698
Phe Pro Asn Thr Thr Pro Cys Cys Arg Glu Thr Pro Ser Ala Ser Pro
2170                2175                2180                2185

TGG CCC CTG GCT CTC GAA TTG GCT CTG ACC CTT ACC TGG GGC AGC GTC         6746
Trp Pro Leu Ala Leu Glu Leu Ala Leu Thr Leu Thr Trp Gly Ser Val
            2190                2195                2200

TGG ACA GTG AGG CCT CTG TCC ACG CCC TGC CTG AGG ACA CGC TCA CTT         6794
Trp Thr Val Arg Pro Leu Ser Thr Pro Cys Leu Arg Thr Arg Ser Leu
                2205                2210                2215

TCG AGG AGG CTG TGG CCA CCA ACT CGG GCC GCT CCT CCA GGA CTT CCT         6842
Ser Arg Arg Leu Trp Pro Pro Thr Arg Ala Ala Pro Pro Gly Leu Pro
        2220                2225                2230

ACG TGT CCT CCC TGACCTCCCA GTCTCACCCT CTCCGCCGCG TGCCCAACGG             6894
Thr Cys Pro Pro
    2235

TTACCACTGC ACCCTGGGAC TCAGCTCGGG TGGCCGAGCA CGGCACAGCT ACCACCACCC       6954

TGACCAAGAC CACTGGTGCT AGCTGCACCG TGACCGCTCA GACGCCTGCA TGCAGCAGGC       7014

GTGTGTTCCA GTGGATGAGT TTTATCATCC ACACGGGGCA GTCGGCCCTC GGGGGAGGCC       7074

TTGCCCACCT TGGTGAGGCT CCTGTGGCCC CTCCCTCCCC CTCCTCCCCT CTTTTACTCT       7134

AGACGACGAA TAAAGCCCTG TTGCTTGAGT GTACGTACCG C                          7175
```

(2) INFORMATION FOR SEQ ID NO:9:

(i) SEQUENCE CHARACTERISTICS:
        (A) LENGTH: 1546 base pairs
        (B) TYPE: nucleic acid
        (C) STRANDEDNESS: double
        (D) TOPOLOGY: linear (ii) MOLECULE TYPE: DNA (genomic)

(ix) FEATURE:
          (A) NAME/KEY: CDS
          (B) LOCATION: 1..1437

(ix) FEATURE:
          (A) NAME/KEY: 3'UTR
          (B) LOCATION: 1435..1546

(xi) SEQUENCE DESCRIPTION: SEQ ID NO:9:

| | | | | | | | | | | | | | | | | |
|---|---|---|---|---|---|---|---|---|---|---|---|---|---|---|---|---|
| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |
| GAG | ATC | CCC | ATG | GAG | GTC | TTC | GAC | CCC | AGC | CCG | CAG | GGC | AAA | TAC | AGC | 96 |
| Glu | Ile | Pro | Met | Glu | Val | Phe | Asp | Pro | Ser | Pro | Gln | Gly | Lys | Tyr | Ser | |
| | | | 20 | | | | | 25 | | | | | 30 | | | |
| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp | |
| | | | | 35 | | | | | 40 | | | | | 45 | | |
| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |
| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | | 70 | | | | | 75 | | | | | 80 | |
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | | | 115 | | | | | 120 | | | | | 125 | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | | | 195 | | | | | 200 | | | | | 205 | | |
| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |
| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |
| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |

```
                    260                 265                 270
ATT TCC CTG GCT AAG CGC TCA GTT CTC AAC AAC CCC AGC AAA CAC ATC     864
Ile Ser Leu Ala Lys Arg Ser Val Leu Asn Asn Pro Ser Lys His Ile
        275                 280                 285

ATC ATT GAG CGC TCC AAC ACA CGC TCC AGC CTG GCT GAG GTG CAG AGT     912
Ile Ile Glu Arg Ser Asn Thr Arg Ser Ser Leu Ala Glu Val Gln Ser
290                 295                 300

GAA ATC GAG CGA ATC TTC GAG CTG GCC CGG ACC CTT CAG TTG GTC GCT     960
Glu Ile Glu Arg Ile Phe Glu Leu Ala Arg Thr Leu Gln Leu Val Ala
305                 310                 315                 320

CTG GAT GCT GAC ACC ATC AAT CAC CCA GCC CAG CTG TCC AAG ACC TCG    1008
Leu Asp Ala Asp Thr Ile Asn His Pro Ala Gln Leu Ser Lys Thr Ser
                325                 330                 335

CTG GCC CCC ATC ATT GTT TAC ATC AAG ATC ACC TCT CCC AAG GTA CTT    1056
Leu Ala Pro Ile Ile Val Tyr Ile Lys Ile Thr Ser Pro Lys Val Leu
                340                 345                 350

CAA AGG CTC ATC AAG TCC CGA GGA AAG TCT CAG TCC AAA CAC CTC AAT    1104
Gln Arg Leu Ile Lys Ser Arg Gly Lys Ser Gln Ser Lys His Leu Asn
                355                 360                 365

GTC CAA ATA GCG GCC TCG GAA AAG CTG GCA CAG TGC CCC CCT GAA ATG    1152
Val Gln Ile Ala Ala Ser Glu Lys Leu Ala Gln Cys Pro Pro Glu Met
    370                 375                 380

TTT GAC ATC ATC CTG GAT GAG AAC CAA TTG GAG GAT GCC TGC GAG CAT    1200
Phe Asp Ile Ile Leu Asp Glu Asn Gln Leu Glu Asp Ala Cys Glu His
385                 390                 395                 400

CTG GCG GAG TAC TTG GAA GCC TAT TGG AAG GCC ACA CAC CCG CCC AGC    1248
Leu Ala Glu Tyr Leu Glu Ala Tyr Trp Lys Ala Thr His Pro Pro Ser
                405                 410                 415

AGC ACG CCA CCC AAT CCG CTG CTG AAC CGC ACC ATG GCT ACC GCA GCC    1296
Ser Thr Pro Pro Asn Pro Leu Leu Asn Arg Thr Met Ala Thr Ala Ala
                420                 425                 430

CTG GCT GCC AGC CCT GCC CCT GTC TCC AAC CTC CAG GTA CAG GTG CTC    1344
Leu Ala Ala Ser Pro Ala Pro Val Ser Asn Leu Gln Val Gln Val Leu
                435                 440                 445

ACC TCG CTC AGG AGA AAC CTC GGC TTC TGG GGC GGG CTG GAG TCC TCA    1392
Thr Ser Leu Arg Arg Asn Leu Gly Phe Trp Gly Gly Leu Glu Ser Ser
450                 455                 460

CAG CGG GGC AGT GTG GTG CCC CAG GAG CAG GAA CAT GCC ATG TAGTGGGCGC 1444
Gln Arg Gly Ser Val Val Pro Gln Glu Gln Glu His Ala Met
465                 470                 475

CCTGCCCGTC TTCCCTCCTG CTCTGGGGTC GGAACTGGAG TGCAGGGAAC ATGGAGGAGG  1504

AAGGGAAGAG CTTTATTTTG TAAAAAAATA AGATGAGCGG CA                    1546

(2) INFORMATION FOR SEQ ID NO:10:

(i) SEQUENCE CHARACTERISTICS:
        (A) LENGTH: 1851 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1797
        (D) OTHER INFORMATION: /standard_name= "Beta1-3"

(ix) FEATURE:
        (A) NAME/KEY: 3'UTR
        (B) LOCATION: 1795..1851

(xi) SEQUENCE DESCRIPTION: SEQ ID NO:10:
```

-continued

```
ATG GTC CAG AAG ACC AGC ATG TCC CGG GGC CCT TAC CCA CCC TCC CAG        48
Met Val Gln Lys Thr Ser Met Ser Arg Gly Pro Tyr Pro Pro Ser Gln
 1               5                  10                  15

GAG ATC CCC ATG GGA GTC TTC GAC CCC AGC CCG CAG GGC AAA TAC AGC        96
Glu Ile Pro Met Gly Val Phe Asp Pro Ser Pro Gln Gly Lys Tyr Ser
                20                  25                  30

AAG AGG AAA GGG CGA TTC AAA CGG TCA GAT GGG AGC ACG TCC TCG GAT       144
Lys Arg Lys Gly Arg Phe Lys Arg Ser Asp Gly Ser Thr Ser Ser Asp
            35                  40                  45

ACC ACA TCC AAC AGC TTT GTC CGC CAG GGC TCA GCG GAG TCC TAC ACC       192
Thr Thr Ser Asn Ser Phe Val Arg Gln Gly Ser Ala Glu Ser Tyr Thr
 50                  55                  60

AGC CGT CCA TCA GAC TCT GAT GTA TCT CTG GAG GAG GAC CGG GAA GCC       240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC       288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT       336
Lys Thr Lys Pro Val Ala Phe Ala Val Arg Thr Asn Val Gly Tyr Asn
                100                 105                 110

CCG TCT CCA GGG GAT GAG GTG CCT GTG CAG GGA GTG GCC ATC ACC TTC       384
Pro Ser Pro Gly Asp Glu Val Pro Val Gln Gly Val Ala Ile Thr Phe
            115                 120                 125

GAG CCC AAA GAC TTC CTG CAC ATC AAG GAG AAA TAC AAT AAT GAC TGG       432
Glu Pro Lys Asp Phe Leu His Ile Lys Glu Lys Tyr Asn Asn Asp Trp
        130                 135                 140

TGG ATC GGG CGG CTG GTG AAG GAG GGC TGT GAG GTT GGC TTC ATT CCC       480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG       528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC       576
Arg Gln Asn Arg Leu Gly Ser Ser Lys Ser Gly Asp Asn Ser Ser Ser
                180                 185                 190

AGT CTG GGA GAT GTG GTG ACT GGC ACC CGC CGC CCC ACA CCC CCT GCC       624
Ser Leu Gly Asp Val Val Thr Gly Thr Arg Arg Pro Thr Pro Pro Ala
            195                 200                 205

AGT GCC AAA CAG AAG CAG AAG TCG ACA GAG CAT GTG CCC CCC TAT GAC       672
Ser Ala Lys Gln Lys Gln Lys Ser Thr Glu His Val Pro Pro Tyr Asp
        210                 215                 220

GTG GTG CCT TCC ATG AGG CCC ATC ATC CTG GTG GGA CCG TCG CTC AAG       720
Val Val Pro Ser Met Arg Pro Ile Ile Leu Val Gly Pro Ser Leu Lys
225                 230                 235                 240

GGC TAC GAG GTT ACA GAC ATG ATG CAG AAA GCT TTA TTT GAC TTC TTG       768
Gly Tyr Glu Val Thr Asp Met Met Gln Lys Ala Leu Phe Asp Phe Leu
                245                 250                 255

AAG CAT CGG TTT GAT GGC AGG ATC TCC ATC ACT CGT GTG ACG GCA GAT       816
Lys His Arg Phe Asp Gly Arg Ile Ser Ile Thr Arg Val Thr Ala Asp
                260                 265                 270

ATT TCC CTG GCT AAG CGC TCA GTT CTC AAC AAC CCC AGC AAA CAC ATC       864
Ile Ser Leu Ala Lys Arg Ser Val Leu Asn Asn Pro Ser Lys His Ile
            275                 280                 285

ATC ATT GAG CGC TCC AAC ACA CGC TCC AGC CTG GCT GAG GTG CAG AGT       912
Ile Ile Glu Arg Ser Asn Thr Arg Ser Ser Leu Ala Glu Val Gln Ser
        290                 295                 300

GAA ATC GAG CGA ATC TTC GAG CTG GCC CGG ACC CTT CAG TTG GTC GCT       960
Glu Ile Glu Arg Ile Phe Glu Leu Ala Arg Thr Leu Gln Leu Val Ala
```

```
                                              -continued
305                 310                 315                 320
CTG GAT GCT GAC ACC ATC AAT CAC CCA GCC CAG CTG TCC AAG ACC TCG    1008
Leu Asp Ala Asp Thr Ile Asn His Pro Ala Gln Leu Ser Lys Thr Ser
                325                 330                 335

CTG GCC CCC ATC ATT GTT TAC ATC AAG ATC ACC TCT CCC AAG GTA CTT    1056
Leu Ala Pro Ile Ile Val Tyr Ile Lys Ile Thr Ser Pro Lys Val Leu
                340                 345                 350

CAA AGG CTC ATC AAG TCC CGA GGA AAG TCT CAG TCC AAA CAC CTC AAT    1104
Gln Arg Leu Ile Lys Ser Arg Gly Lys Ser Gln Ser Lys His Leu Asn
                355                 360                 365

GTC CAA ATA GCG GCC TCG GAA AAG CTG GCA CAG TGC CCC CCT GAA ATG    1152
Val Gln Ile Ala Ala Ser Glu Lys Leu Ala Gln Cys Pro Pro Glu Met
        370                 375                 380

TTT GAC ATC ATC CTG GAT GAG AAC CAA TTG GAG GAT GCC TGC GAG CAT    1200
Phe Asp Ile Ile Leu Asp Glu Asn Gln Leu Glu Asp Ala Cys Glu His
385                 390                 395                 400

CTG GCG GAG TAC TTG GAA GCC TAT TGG AAG GCC ACA CAC CCG CCC AGC    1248
Leu Ala Glu Tyr Leu Glu Ala Tyr Trp Lys Ala Thr His Pro Pro Ser
                405                 410                 415

AGC ACG CCA CCC AAT CCG CTG CTG AAC CGC ACC ATG GCT ACC GCA GCC    1296
Ser Thr Pro Pro Asn Pro Leu Leu Asn Arg Thr Met Ala Thr Ala Ala
                420                 425                 430

CTG GCT GCC AGC CCT GCC CCT GTC TCC AAC CTC CAG GGA CCC TAC CTT    1344
Leu Ala Ala Ser Pro Ala Pro Val Ser Asn Leu Gln Gly Pro Tyr Leu
                435                 440                 445

GCT TCC GGG GAC CAG CCA CTG GAA CGG GCC ACC GGG GAG CAC GCC AGC    1392
Ala Ser Gly Asp Gln Pro Leu Glu Arg Ala Thr Gly Glu His Ala Ser
450                 455                 460

ATG CAC GAG TAC CCA GGG GAG CTG GGC CAG CCC CCA GGC CTT TAC CCC    1440
Met His Glu Tyr Pro Gly Glu Leu Gly Gln Pro Pro Gly Leu Tyr Pro
465                 470                 475                 480

AGC AGC CAC CCA CCA GGC CGG GCA GGC ACG CTA CGG GCA CTG TCC CGC    1488
Ser Ser His Pro Pro Gly Arg Ala Gly Thr Leu Arg Ala Leu Ser Arg
                485                 490                 495

CAA GAC ACT TTT GAT GCC GAC ACC CCC GGC AGC CGA AAC TCT GCC TAC    1536
Gln Asp Thr Phe Asp Ala Asp Thr Pro Gly Ser Arg Asn Ser Ala Tyr
                500                 505                 510

ACG GAG CTG GGA GAC TCA TGT GTG GAC ATG GAG ACT GAC CCC TCA GAG    1584
Thr Glu Leu Gly Asp Ser Cys Val Asp Met Glu Thr Asp Pro Ser Glu
                515                 520                 525

GGG CCA GGG CTT GGA GAC CCT GCA GGG GGC GGC ACG CCC CCA GCC CGA    1632
Gly Pro Gly Leu Gly Asp Pro Ala Gly Gly Thr Pro Pro Ala Arg
530                 535                 540

CAG GGA TCC TGG GAG GAC GAG GAA GAA GAC TAT GAG GAA GAG CTG ACC    1680
Gln Gly Ser Trp Glu Asp Glu Glu Glu Asp Tyr Glu Glu Glu Leu Thr
545                 550                 555                 560

GAC AAC CGG AAC CGG GGC CGG AAT AAG GCC CGC TAC TGC GCT GAG GGT    1728
Asp Asn Arg Asn Arg Gly Arg Asn Lys Ala Arg Tyr Cys Ala Glu Gly
                565                 570                 575

GGG GGT CCA GTT TTG GGG CGC AAC AAG AAT GAG CTG GAG GGC TGG GGA    1776
Gly Gly Pro Val Leu Gly Arg Asn Lys Asn Glu Leu Glu Gly Trp Gly
                580                 585                 590

CGA GGC GTC TAC ATT CGC TGAGAGGCAG GGGCCACACG GCGGGAGGAA           1824
Arg Gly Val Tyr Ile Arg
            595

GGGCTCTGAG CCCAGGGGAG GGGAGGG                                     1851

(2) INFORMATION FOR SEQ ID NO:11:
```

```
    (i) SEQUENCE CHARACTERISTICS:
        (A) LENGTH: 3600 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 35..3310
        (D) OTHER INFORMATION: /standard_name= "Alpha-2b"

(ix) FEATURE:
        (A) NAME/KEY: 5'UTR
        (B) LOCATION: 1..34

(ix) FEATURE:
        (A) NAME/KEY: 3'UTR
        (B) LOCATION: 3308..3600

(xi) SEQUENCE DESCRIPTION: SEQ ID NO:11:

GCGGGGAGG GGGCATTGAT CTTCGATCGC GAAG ATG GCT GCT GGC TGC CTG         52
                                    Met Ala Ala Gly Cys Leu
                                     1               5

CTG GCC TTG ACT CTG ACA CTT TTC CAA TCT TTG CTC ATC GGC CCC TCG     100
Leu Ala Leu Thr Leu Thr Leu Phe Gln Ser Leu Leu Ile Gly Pro Ser
             10                  15                  20

TCG GAG GAG CCG TTC CCT TCG GCC GTC ACT ATC AAA TCA TGG GTG GAT     148
Ser Glu Glu Pro Phe Pro Ser Ala Val Thr Ile Lys Ser Trp Val Asp
         25                  30                  35

AAG ATG CAA GAA GAC CTT GTC ACA CTG GCA AAA ACA GCA AGT GGA GTC     196
Lys Met Gln Glu Asp Leu Val Thr Leu Ala Lys Thr Ala Ser Gly Val
     40                  45                  50

AAT CAG CTT GTT GAT ATT TAT GAG AAA TAT CAA GAT TTG TAT ACT GTG     244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT     292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG     340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA     388
Glu Ala Glu Lys Val Gln Ala Ala His Gln Trp Arg Glu Asp Phe Ala
         105                 110                 115

AGC AAT GAA GTT GTC TAC TAC AAT GCA AAG GAT GAT CTC GAT CCT GAG     436
Ser Asn Glu Val Val Tyr Tyr Asn Ala Lys Asp Asp Leu Asp Pro Glu
120                 125                 130

AAA AAT GAC AGT GAG CCA GGC AGC CAG AGG ATA AAA CCT GTT TTC ATT     484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC     532
Glu Asp Ala Asn Phe Gly Arg Gln Ile Ser Tyr Gln His Ala Ala Val
                 155                 160                 165

CAT ATT CCT ACT GAC ATC TAT GAG GGC TCA ACA ATT GTG TTA AAT GAA     580
His Ile Pro Thr Asp Ile Tyr Glu Gly Ser Thr Ile Val Leu Asn Glu
             170                 175                 180

CTC AAC TGG ACA AGT GCC TTA GAT GAA GTT TTC AAA AAG AAT CGC GAG     628
Leu Asn Trp Thr Ser Ala Leu Asp Glu Val Phe Lys Lys Asn Arg Glu
         185                 190                 195

GAA GAC CCT TCA TTA TTG TGG CAG GTT TTT GGC AGT GCC ACT GGC CTA     676
Glu Asp Pro Ser Leu Leu Trp Gln Val Phe Gly Ser Ala Thr Gly Leu
     200                 205                 210
```

-continued

```
GCT CGA TAT TAT CCA GCT TCA CCA TGG GTT GAT AAT AGT AGA ACT CCA    724
Ala Arg Tyr Tyr Pro Ala Ser Pro Trp Val Asp Asn Ser Arg Thr Pro
215                 220                 225                 230

AAT AAG ATT GAC CTT TAT GAT GTA CGC AGA AGA CCA TGG TAC ATC CAA    772
Asn Lys Ile Asp Leu Tyr Asp Val Arg Arg Arg Pro Trp Tyr Ile Gln
                235                 240                 245

GGA GCT GCA TCT CCT AAA GAC ATG CTT ATT CTG GTG GAT GTG AGT GGA    820
Gly Ala Ala Ser Pro Lys Asp Met Leu Ile Leu Val Asp Val Ser Gly
            250                 255                 260

AGT GTT AGT GGA TTG ACA CTT AAA CTG ATC CGA ACA TCT GTC TCC GAA    868
Ser Val Ser Gly Leu Thr Leu Lys Leu Ile Arg Thr Ser Val Ser Glu
        265                 270                 275

ATG TTA GAA ACC CTC TCA GAT GAT GAT TTC GTG AAT GTA GCT TCA TTT    916
Met Leu Glu Thr Leu Ser Asp Asp Asp Phe Val Asn Val Ala Ser Phe
280                 285                 290

AAC AGC AAT GCT CAG GAT GTA AGC TGT TTT CAG CAC CTT GTC CAA GCA    964
Asn Ser Asn Ala Gln Asp Val Ser Cys Phe Gln His Leu Val Gln Ala
295                 300                 305                 310

AAT GTA AGA AAT AAA AAA GTG TTG AAA GAC GCG GTG AAT AAT ATC ACA    1012
Asn Val Arg Asn Lys Lys Val Leu Lys Asp Ala Val Asn Asn Ile Thr
                315                 320                 325

GCC AAA GGA ATT ACA GAT TAT AAG AAG GGC TTT AGT TTT GCT TTT GAA    1060
Ala Lys Gly Ile Thr Asp Tyr Lys Lys Gly Phe Ser Phe Ala Phe Glu
            330                 335                 340

CAG CTG CTT AAT TAT AAT GTT TCC AGA GCA AAC TGC AAT AAG ATT ATT    1108
Gln Leu Leu Asn Tyr Asn Val Ser Arg Ala Asn Cys Asn Lys Ile Ile
        345                 350                 355

ATG CTA TTC ACG GAT GGA GGA GAA GAG AGA GCC CAG GAG ATA TTT AAC    1156
Met Leu Phe Thr Asp Gly Gly Glu Glu Arg Ala Gln Glu Ile Phe Asn
360                 365                 370

AAA TAC AAT AAA GAT AAA AAA GTA CGT GTA TTC AGG TTT TCA GTT GGT    1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC    1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT    1300
Lys Gly Tyr Tyr Tyr Glu Ile Pro Ser Ile Gly Ala Ile Arg Ile Asn
            410                 415                 420

ACT CAG GAA TAT TTG GAT GTT TTG GGA AGA CCA ATG GTT TTA GCA GGA    1348
Thr Gln Glu Tyr Leu Asp Val Leu Gly Arg Pro Met Val Leu Ala Gly
        425                 430                 435

GAC AAA GCT AAG CAA GTC CAA TGG ACA AAT GTG TAC CTG GAT GCA TTG    1396
Asp Lys Ala Lys Gln Val Gln Trp Thr Asn Val Tyr Leu Asp Ala Leu
440                 445                 450

GAA CTG GGA CTT GTC ATT ACT GGA ACT CTT CCG GTC TTC AAC ATA ACC    1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT    1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA    1540
Val Met Gly Val Asp Val Ser Leu Glu Asp Ile Lys Arg Leu Thr Pro
            490                 495                 500

CGT TTT ACA CTG TGC CCC AAT GGG TAT TAC TTT GCA ATC GAT CCT AAT    1588
Arg Phe Thr Leu Cys Pro Asn Gly Tyr Tyr Phe Ala Ile Asp Pro Asn
        505                 510                 515

GGT TAT GTT TTA TTA CAT CCA AAT CTT CAG CCA AAG AAC CCC AAA TCT    1636
Gly Tyr Val Leu Leu His Pro Asn Leu Gln Pro Lys Asn Pro Lys Ser
```

```
              520                  525                 530
CAG GAG CCA GTA ACA TTG GAT TTC CTT GAT GCA GAG TTA GAG AAT GAT    1684
Gln Glu Pro Val Thr Leu Asp Phe Leu Asp Ala Glu Leu Glu Asn Asp
535                 540                 545                 550

ATT AAA GTG GAG ATT CGA AAT AAG ATG ATT GAT GGG GAA AGT GGA GAA    1732
Ile Lys Val Glu Ile Arg Asn Lys Met Ile Asp Gly Glu Ser Gly Glu
                555                 560                 565

AAA ACA TTC AGA ACT CTG GTT AAA TCT CAA GAT GAG AGA TAT ATT GAC    1780
Lys Thr Phe Arg Thr Leu Val Lys Ser Gln Asp Glu Arg Tyr Ile Asp
            570                 575                 580

AAA GGA AAC AGG ACA TAC ACA TGG ACA CCT GTC AAT GGC ACA GAT TAC    1828
Lys Gly Asn Arg Thr Tyr Thr Trp Thr Pro Val Asn Gly Thr Asp Tyr
        585                 590                 595

AGT TTG GCC TTG GTA TTA CCA ACC TAC AGT TTT TAC TAT ATA AAA GCC    1876
Ser Leu Ala Leu Val Leu Pro Thr Tyr Ser Phe Tyr Tyr Ile Lys Ala
    600                 605                 610

AAA CTA GAA GAG ACA ATA ACT CAG GCC AGA TCA AAA AAG GGC AAA ATG    1924
Lys Leu Glu Glu Thr Ile Thr Gln Ala Arg Ser Lys Lys Gly Lys Met
615                 620                 625                 630

AAG GAT TCG GAA ACC CTG AAG CCA GAT AAT TTT GAA GAA TCT GGC TAT    1972
Lys Asp Ser Glu Thr Leu Lys Pro Asp Asn Phe Glu Glu Ser Gly Tyr
                635                 640                 645

ACA TTC ATA GCA CCA AGA GAT TAC TGC AAT GAC CTG AAA ATA TCG GAT    2020
Thr Phe Ile Ala Pro Arg Asp Tyr Cys Asn Asp Leu Lys Ile Ser Asp
            650                 655                 660

AAT AAC ACT GAA TTT CTT TTA AAT TTC AAC GAG TTT ATT GAT AGA AAA    2068
Asn Asn Thr Glu Phe Leu Leu Asn Phe Asn Glu Phe Ile Asp Arg Lys
        665                 670                 675

ACT CCA AAC AAC CCA TCA TGT AAC GCG GAT TTG ATT AAT AGA GTC TTG    2116
Thr Pro Asn Asn Pro Ser Cys Asn Ala Asp Leu Ile Asn Arg Val Leu
    680                 685                 690

CTT GAT GCA GGC TTT ACA AAT GAA CTT GTC CAA AAT TAC TGG AGT AAG    2164
Leu Asp Ala Gly Phe Thr Asn Glu Leu Val Gln Asn Tyr Trp Ser Lys
695                 700                 705                 710

CAG AAA AAT ATC AAG GGA GTG AAA GCA CGA TTT GTT GTG ACT GAT GGT    2212
Gln Lys Asn Ile Lys Gly Val Lys Ala Arg Phe Val Val Thr Asp Gly
                715                 720                 725

GGG ATT ACC AGA GTT TAT CCC AAA GAG GCT GGA GAA AAT TGG CAA GAA    2260
Gly Ile Thr Arg Val Tyr Pro Lys Glu Ala Gly Glu Asn Trp Gln Glu
            730                 735                 740

AAC CCA GAG ACA TAT GAG GAC AGC TTC TAT AAA AGG AGC CTA GAT AAT    2308
Asn Pro Glu Thr Tyr Glu Asp Ser Phe Tyr Lys Arg Ser Leu Asp Asn
        745                 750                 755

GAT AAC TAT GTT TTC ACT GCT CCC TAC TTT AAC AAA AGT GGA CCT GGT    2356
Asp Asn Tyr Val Phe Thr Ala Pro Tyr Phe Asn Lys Ser Gly Pro Gly
    760                 765                 770

GCC TAT GAA TCG GGC ATT ATG GTA AGC AAA GCT GTA GAA ATA TAT ATT    2404
Ala Tyr Glu Ser Gly Ile Met Val Ser Lys Ala Val Glu Ile Tyr Ile
775                 780                 785                 790

CAA GGG AAA CTT CTT AAA CCT GCA GTT GTT GGA ATT AAA ATT GAT GTA    2452
Gln Gly Lys Leu Leu Lys Pro Ala Val Val Gly Ile Lys Ile Asp Val
                795                 800                 805

AAT TCC TGG ATA GAG AAT TTC ACC AAA ACC TCA ATC AGA GAT CCG TGT    2500
Asn Ser Trp Ile Glu Asn Phe Thr Lys Thr Ser Ile Arg Asp Pro Cys
            810                 815                 820

GCT GGT CCA GTT TGT GAC TGC AAA AGA AAC AGT GAC GTA ATG GAT TGT    2548
Ala Gly Pro Val Cys Asp Cys Lys Arg Asn Ser Asp Val Met Asp Cys
        825                 830                 835

GTG ATT CTG GAT GAT GGT GGG TTT CTT CTG ATG GCA AAT CAT GAT GAT    2596
```

```
         Val Ile Leu Asp Asp Gly Gly Phe Leu Leu Met Ala Asn His Asp Asp
             840             845                 850

TAT ACT AAT CAG ATT GGA AGA TTT TTT GGA GAG ATT GAT CCC AGC TTG          2644
Tyr Thr Asn Gln Ile Gly Arg Phe Phe Gly Glu Ile Asp Pro Ser Leu
855                 860                 865                 870

ATG AGA CAC CTG GTT AAT ATA TCA GTT TAT GCT TTT AAC AAA TCT TAT          2692
Met Arg His Leu Val Asn Ile Ser Val Tyr Ala Phe Asn Lys Ser Tyr
                    875                 880                 885

GAT TAT CAG TCA GTA TGT GAG CCC GGT GCT GCA CCA AAA CAA GGA GCA          2740
Asp Tyr Gln Ser Val Cys Glu Pro Gly Ala Ala Pro Lys Gln Gly Ala
                890                 895                 900

GGA CAT CGC TCA GCA TAT GTG CCA TCA GTA GCA GAC ATA TTA CAA ATT          2788
Gly His Arg Ser Ala Tyr Val Pro Ser Val Ala Asp Ile Leu Gln Ile
            905                 910                 915

GGC TGG TGG GCC ACT GCT GCT GCC TGG TCT ATT CTA CAG CAG TTT CTC          2836
Gly Trp Trp Ala Thr Ala Ala Ala Trp Ser Ile Leu Gln Gln Phe Leu
        920                 925                 930

TTG AGT TTG ACC TTT CCA CGA CTC CTT GAG GCA GTT GAG ATG GAG GAT          2884
Leu Ser Leu Thr Phe Pro Arg Leu Leu Glu Ala Val Glu Met Glu Asp
935                 940                 945                 950

GAT GAC TTC ACG GCC TCC CTG TCC AAG CAG AGC TGC ATT ACT GAA CAA          2932
Asp Asp Phe Thr Ala Ser Leu Ser Lys Gln Ser Cys Ile Thr Glu Gln
                955                 960                 965

ACC CAG TAT TTC TTC GAT AAC GAC AGT AAA TCA TTC AGT GGT GTA TTA          2980
Thr Gln Tyr Phe Phe Asp Asn Asp Ser Lys Ser Phe Ser Gly Val Leu
                    970                 975                 980

GAC TGT GGA AAC TGT TCC AGA ATC TTT CAT GGA GAA AAG CTT ATG AAC          3028
Asp Cys Gly Asn Cys Ser Arg Ile Phe His Gly Glu Lys Leu Met Asn
                985                 990                 995

ACC AAC TTA ATA TTC ATA ATG GTT GAG AGC AAA GGG ACA TGT CCA TGT          3076
Thr Asn Leu Ile Phe Ile Met Val Glu Ser Lys Gly Thr Cys Pro Cys
            1000                1005                1010

GAC ACA CGA CTG CTC ATA CAA GCG GAG CAG ACT TCT GAC GGT CCA AAT          3124
Asp Thr Arg Leu Leu Ile Gln Ala Glu Gln Thr Ser Asp Gly Pro Asn
1015                1020                1025                1030

CCT TGT GAC ATG GTT AAG CAA CCT AGA TAC CGA AAA GGG CCT GAT GTC          3172
Pro Cys Asp Met Val Lys Gln Pro Arg Tyr Arg Lys Gly Pro Asp Val
                1035                1040                1045

TGC TTT GAT AAC AAT GTC TTG GAG GAT TAT ACT GAC TGT GGT GGT GTT          3220
Cys Phe Asp Asn Asn Val Leu Glu Asp Tyr Thr Asp Cys Gly Gly Val
                    1050                1055                1060

TCT GGA TTA AAT CCC TCC CTG TGG TAT ATC ATT GGA ATC CAG TTT CTA          3268
Ser Gly Leu Asn Pro Ser Leu Trp Tyr Ile Ile Gly Ile Gln Phe Leu
                1065                1070                1075

CTA CTT TGG CTG GTA TCT GGC AGC ACA CAC CGG CTG TTA TGACCTTCTA          3317
Leu Leu Trp Leu Val Ser Gly Ser Thr His Arg Leu Leu
        1080                1085                1090

AAAACCAAAT CTGCATAGTT AAACTCCAGA CCCTGCCAAA ACATGAGCCC TGCCCTCAAT       3377

TACAGTAACG TAGGGTCAGC TATAAAATCA GACAAACATT AGCTGGGCCT GTTCCATGGC       3437

ATAACACTAA GGCGCAGACT CCTAAGGCAC CCACTGGCTG CATGTCAGGG TGTCAGATCC       3497

TTAAACGTGT GTGAATGCTG CATCATCTAT GTGTAACATC AAAGCAAAAT CCTATACGTG       3557

TCCTCTATTG GAAATTTGG GCGTTTGTTG TTGCATTGTT GGT                          3600

(2) INFORMATION FOR SEQ ID NO:12:

(i) SEQUENCE CHARACTERISTICS:
        (A) LENGTH: 323 base pairs
        (B) TYPE: nucleic acid
```

```
        (C) STRANDEDNESS: double
        (D) TOPOLOGY: linear (ii) MOLECULE TYPE: DNA (genomic)

(xi) SEQUENCE DESCRIPTION: SEQ ID NO:12:

CCCCCTGCCA GTGGCCAAAC AGAAGCAGAA GTCGGGTAAT GAAATGACTA ACTTAGCCTT       60

TGAACTAGAC CCCCTAGAGT TAGAGGAGGA AGAGGCTGAG CTTGGTGAGC AGAGTGGCTC      120

TGCCAAGACT AGTGTTAGCA GTGTCACCAC CCCGCCACCC CATGGCAAAC GCATCCCCTT      180

CTTTAAGAAG ACAGAGCATG TGCCCCCCTA TGACGTGGTG CCTTCCATGA GGCCCATCAT      240

CCTGGTGGGA CCGTCGCTCA AGGGCTACGA GGTTACAGAC ATGATGCAGA AAGCTTTATT      300

TGACTTCTTG AAGCATCGGT TTG                                             323

(2) INFORMATION FOR SEQ ID NO:13:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

CCTATTGGTG TAGGTATACC AACAATTAAT TTAAGAAAAA GGAGACCCAA TATCCAG          57

(2) INFORMATION FOR SEQ ID NO:14:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..132

(xi) SEQUENCE DESCRIPTION: SEQ ID NO:14:

TGG TCC TTT GCC TGC GCC TGT GCC GCC TTC ATC CTC CTC TTT CTC GGC        48
Trp Ser Phe Ala Cys Ala Cys Ala Ala Phe Ile Leu Leu Phe Leu Gly
 1               5                  10                  15

GGT CTC GCC CTC CTG CTG TTC TCC CTG CCT CGA ATG CCC CGG AAC CCA        96
Gly Leu Ala Leu Leu Leu Phe Ser Leu Pro Arg Met Pro Arg Asn Pro
             20                  25                  30

TGG GAG TCC TGC ATG GAT GCT GAG CCC GAG CAC TAACCCTCCT GCGGCCCTAG     149
Trp Glu Ser Cys Met Asp Ala Glu Pro Glu His
         35                  40

CGACCCTCAG GCTTCTTCCC AGGAAGCGGG G                                    180

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:15:
```

```
AATTCGGTAC GTACACTCGA GC                                                         22

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:16:

GCTCGAGTGT ACGTACCG                                                              18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:17:

CCATGGTACC TTCGTTGACG                                                            20

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:18:

AATTCGTCAA CGAAGGTACC ATGG                                                       24

(2) INFORMATION FOR SEQ ID NO:19:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:19:

CGGTACGTAC ACTCGAGCGA CTGTGTCATG ATGTTTATTA GTGATGACAG TGAGGTGAGG                 60

CAGGGGCTTG TGGAGCATGC TCTGTAGGTC ACACACTAGA GCCATAAGGC AAGAGTAGGC                120

GGGGAGACAG GTCCTCTGTG CCCTGTCTCT CCCCATCTAA CCCTAACCTA ACAAGCGGTA                180

GTTATGAGTC AGGGAACAAC GTCTGGAGCC CCGTCCTCCA AAGATGTTTG AGGGACAAGA                240

ACAGAAATG                                                                       249

(2) INFORMATION FOR SEQ ID NO:20:

(i) SEQUENCE CHARACTERISTICS:
        (A) LENGTH: 402 base pairs
        (B) TYPE: nucleic acid
```

```
            (C) STRANDEDNESS: double
            (D) TOPOLOGY: linear (ii) MOLECULE TYPE: cDNA (xi) SEQUENCE DESCRIPTION: SEQ ID NO:20:

CCACCTAGCA CGGGTTCGTT CCCCTCTCCC GGCCTGGCCC GGGCTCCCCG GTGGCCGCCG      60

CCCCCTCGCC GCCCATCTCT GGACTCAGAC GTCTCCCTGG AGGAGGACCG GGAGAGTGCC     120

CGGCGTGAAG TAGAGAGCCA GGCTCAGCAG CAGCTCGAAA GGGCCAAGCA CAAACCTGTG     180

GCATTTGCGG TGAGGACCAA TGTCAGCTAC TGTGGCGTAC TGGATGAGGA GTGCCCAGTC     240

CAGGGCTCTG GAGTCAACTT TGAGGCCAAA GATTTTCTGC ACATTAAAGA GAAGTACAGC     300

AATGACTGGT GGATCGGGCG GCTAGTGAAA GAGGGCGGGG ACATCGCCTT CATCCCCAGC     360

CCCCAGTGCC TGGTGAGCAT CCGCTCAAAC AGGAGCAGAA GG                       402

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO:21:

CTCAGTACCA TCTCTGATAC CAGCCCCA                                        28

(2) INFORMATION FOR SEQ ID NO:22:

(i) SEQUENCE CHARACTERISTICS:
        (A) LENGTH: 7808 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 240..7769
        (D) OTHER INFORMATION: /product= "Alpha1A-1 subunit of
            human calcium channel"

(xi) SEQUENCE DESCRIPTION: SEQ ID NO:22:

GATGTCCCGA GCTGCTATCC CCGGCTCGGC CCGGGCAGCC GCCTTCTGAG CCCCCGACCC      60

GAGGCGCCGA GCCGCCGCCG CCCGATGGGC TGGGCCGTGG AGCGTCTCCG CAGTCGTAGC     120

TCCAGCCGCC GCGCTCCCAG CCCCGGCAGC CTCAGCATCA GCGGCGGCGG CGGCGGCGGC     180

GGCGTCTTCC GCATCGTTCG CCGCAGCGTA ACCCGGAGCC CTTTGCTCTT TGCAGAATGG     240

CCCGCTTCGG AGACGAGATG CCGGCCCGCT ACGGGGAGG AGGCTCCGGG GCAGCCGCCG      300

GGGTGGTCGT GGGCAGCGGA GGCGGGCGAG GAGCCGGGGG CAGCCGGCAG GGCGGGCAGC     360

CCGGGGCGCA AAGGATGTAC AAGCAGTCAA TGGCGCAGAG AGCGCGGACC ATGGCACTCT     420

ACAACCCCAT CCCCGTCCGA CAGAACTGCC TCACGGTTAA CCGGTCTCTC TTCCTCTTCA     480

GCGAAGACAA CGTGGTGAGA AAATACGCCA AAAAGATCAC CGAATGGCCT CCCTTTGAAT     540

ATATGATTTT AGCCACCATC ATAGCGAATT GCATCGTCCT CGCACTGGAG CAGCATCTGC     600

CTGATGATGA CAAGACCCCG ATGTCTGAAC GGCTGGATGA CACAGAACCA TACTTCATTG     660

GAATTTTTTG TTTCGAGGCT GGAATTAAAA TCATTGCCCT TGGGTTTGCC TTCCACAAAG     720
```

```
GCTCCTACTT GAGGAATGGC TGGAATGTCA TGGACTTTGT GGTGGTGCTA ACGGGCATCT      780

TGGCGACAGT TGGGACGGAG TTTGACCTAC GGACGCTGAG GGCAGTTCGA GTGCTGCGGC      840

CGCTCAAGCT GGTGTCTGGA ATCCCAAGTT TACAAGTCGT CCTGAAGTCG ATCATGAAGG      900

CGATGATCCC TTTGCTGCAG ATCGGCCTCC TCCTATTTTT TGCAATCCTT ATTTTTGCAA      960

TCATAGGGTT AGAATTTTAT ATGGGAAAAT TTCATACCAC CTGCTTTGAA GAGGGGACAG     1020

ATGACATTCA GGGTGAGTCT CCGGCTCCAT GTGGGACAGA AGAGCCCGCC CGCACCTGCC     1080

CCAATGGGAC CAAATGTCAG CCCTACTGGG AAGGGCCCAA CAACGGGATC ACTCAGTTCG     1140

ACAACATCCT GTTTGCAGTG CTGACTGTTT TCCAGTGCAT AACCATGGAA GGGTGGACTG     1200

ATCTCCTCTA CAATAGCAAC GATGCCTCAG GGAACACTTG GAACTGGTTG TACTTCATCC     1260

CCCTCATCAT CATCGGCTCC TTTTTTATGC TGAACCTTGT GCTGGGTGTG CTGTCAGGGG     1320

AGTTTGCCAA AGAAAGGGAA CGGGTGGAGA ACCGGCGGGC TTTTCTGAAG CTGAGGCGGC     1380

AACAACAGAT TGAACGTGAG CTCAATGGGT ACATGGAATG GATCTCAACA GCAGAAGAGG     1440

TGATCCTCGC CGAGGATGAA ACTGCCGGGG AGCAGAGGCA TCCCTTTGAT GGAGCTCTGC     1500

GGAGAACCAC CATAAAGAAA AGCAAGACAG ATTTGCTCAA CCCCGAAGAG CTGAGGATC      1560

AGCTGGCTGA TATAGCCTCT GTGGGTTCTC CCTTCGCCCG AGCCAGCATT AAAAGTGCCA     1620

AGCTGGAGAA CTCGACCTTT TTTCACAAAA AGGAGAGGAG GATGCGTTTC TACATCCGCC     1680

GCATGGTCAA AACTCAGGCC TTCTACTGGA CTGTACTCAG TGTGGTAGCT CTCAACACGC     1740

TGTGTGTTGC TATTGTTCAC TACAACCAGC CCGAGTGGCT CTCCGACTTC CTTTACTATG     1800

CAGAATTCAT TTTCTTAGGA CTCTTTATGT CCGAAATGTT TATAAAAATG TACGGGCTTG     1860

GGACGCGGCC TTACTTCCAC TCTTCCTTCA ACTGCTTTGA CTGTGGGGTT ATCATTGGGA     1920

GCATCTTCGA GGTCATCTGG GCTGTCATAA AACCTGGCAC ATCCTTTGGA ATCAGCGTGT     1980

TACGAGCCCT CAGGTTATTG CGTATTTTCA AAGTCACAAA GTACTGGGCA TCTCTCAGAA     2040

ACCTGGTCGT CTCTCTCCTC AACTCCATGA AGTCCATCAT CAGCCTGTTG TTTCTCCTTT     2100

TCCTGTTCAT TGTCGTCTTC GCCCTTTTGG GAATGCAACT CTTCGGCGGC CAGTTTAATT     2160

TCGATGAAGG GACTCCTCCC ACCAACTTCG ATACTTTTCC AGCAGCAATA ATGACGGTGT     2220

TTCAGATCCT GACGGGCGAA GACTGGAACG AGGTCATGTA CGACGGGATC AAGTCTCAGG     2280

GGGGCGTGCA GGGCGGCATG GTGTTCTCCA TCTATTTCAT TGTACTGACG CTCTTTGGGA     2340

ACTACACCCT CCTGAATGTG TTCTTGGCCA TCGCTGTGGA CAATCTGGCC AACGCCCAGG     2400

AGCTCACCAA GGTGGAGGCG GACGAGCAAG AGGAAGAAGA AGCAGCGAAC CAGAAACTTG     2460

CCCTACAGAA AGCCAAGGAG GTGGCAGAAG TGAGTCCTCT GTCCGCGGCC AACATGTCTA     2520

TAGCTGTGAA AGAGCAACAG AAGAATCAAA AGCCAGCCAA GTCCGTGTGG GAGCAGCGGA     2580

CCAGTGAGAT GCGAAAGCAG AACTTGCTGG CCAGCCGGGA GGCCCTGTAT AACGAAATGG     2640

ACCCGGACGA GCGCTGGAAG GCTGCCTACA CGCGGCACCT GCGGCCAGAC ATGAAGACGC     2700

ACTTGGACCG GCCGCTGGTG GTGGACCCGC AGGAGAACCG CAACAACAAC ACCAACAAGA     2760

GCCGGGCGGC CGAGYCCACC GTGGACCAGA GCCTCGGCCA GCAGCGCGCC GAGGACTTCC     2820

TCAGGAAACA GGCCCGCTAC CACGATCGGG CCCGGKAMCC CAGCGGTTCG GCGGGCCTGG     2880

ACGCACGGAG GCCCTGGGCG GGAAGCCAGG AGGCCGAGCT TAGCCGGGAG GGACCYWWCG     2940

GCCGCGAGTC GGACCACCAC GCCCGGGAGG RCARCCTGGA GCAWCCCGGG TTCTGGGAGG     3000

GCGAKKCCGA GCGAGRCAAG TYCGGGGAMC CCCACCGGAG GCACGTTCAC CSGCAGGGGG     3060
```

-continued

```
GCAGCAGGGA GATCCTCAGC GGGTCTCCGC TCACGGGCGC GGACGGGGAC GATCGACGTC    3120
ATCGCGCGCA CCGCAGGCCC GGGGAGGAGG GTCCGGAGGA CAAGGCGGAG CGGAGGGCGC    3180
GGCACCGCGA GGGCAGCCGG CCGGCCCGGG GCGGCGAGGG CGAGGGCGAG GTCCCCGACG    3240
GGGGCGATCG CAGGAGAAGG CACCGGCATG GCGCTCCAGC CACGTACGAG GGGGACGCGC    3300
GGAGGGAGGA CAAGGAGCGG AGGCATCGGA GGAGGAAAGA GAACCAGGGC TCCGGGGTCC    3360
CTGTGTCGGG CCCCAACCTG TCAACCACCC GGCCAATCCA GCAGGACCTG GGCCGCCAAG    3420
ACCCACCCCT GGCAGAGGAT ATTGACAACA TGAAGAACAA CAAGCTGGCC ACCGCGGAGT    3480
CGGCCGCTCC CCACGGCAGC CTTGGCCACG CCGGCCTGCC CCAGAGCCCA GCCAAGATGG    3540
GAAACAGCAC CGACCCCGGC CCCATGCTGG CCATCCCTGC CATGGCCACC AACCCCCAGA    3600
ACGCCGCCAG CCGCCGGACG CCCAACAACC CGGGGAACCC ATCCAATCCC GGCCCCCCCA    3660
AGACCCCCGA GAATAGCCTT ATCGTCACCA ACCCCAGCGG CACCCAGACC AATTCAGCTA    3720
AGACTGCCAG GAAACCCGAC CACACCACAG TGGACATCCC CCCAGCCTGC CCACCCCCCC    3780
TCAACCACAC CGTCGTACAA GTGAACAAAA ACGCCAACCC AGACCCACTG CCAAAAAAAG    3840
AGGAAGAGAA GAAGGAGGAG GAGGAAGACG ACCGTGGGGA AGACGGCCCT AAGCCAATGC    3900
CTCCCTATAG CTCCATGTTC ATCCTGTCCA CGACCAACCC CCTTCGCCGC CTGTGCCATT    3960
ACATCCTGAA CCTGCGCTAC TTTGAGATGT GCATCCTCAT GGTCATTGCC ATGAGCAGCA    4020
TCGCCCTGGC CGCCGAGGAC CCTGTGCAGC CCAACGCACC TCGGAACAAC GTGCTGCGAT    4080
ACTTTGACTA CGTTTTTACA GGCGTCTTCA CCTTTGAGAT GGTGATCAAG ATGATTGACC    4140
TGGGGCTCGT CCTGCATCAG GGTGCCTACT TCCGTGACCT CTGGAATATT CTCGACTTCA    4200
TAGTGGTCAG TGGGGCCCTG GTAGCCTTTG CCTTCACTGG CAATAGCAAA GGAAAAGACA    4260
TCAACACGAT TAAATCCCTC CGAGTCCTCC GGGTGCTACG ACCTCTTAAA ACCATCAAGC    4320
GGCTGCCAAA GCTCAAGGCT GTGTTTGACT GTGTGGTGAA CTCACTTAAA AACGTCTTCA    4380
ACATCCTCAT CGTCTACATG CTATTCATGT TCATCTTCGC CGTGGTGGCT GTGCAGCTCT    4440
TCAAGGGGAA ATTCTTCCAC TGCACTGACG AGTCCAAAGA GTTTGAGAAA GATTGTCGAG    4500
GCAAATACCT CCTCTACGAG AAGAATGAGG TGAAGGCGCG AGACCGGGAG TGGAAGAAGT    4560
ATGAATTCCA TTACGACAAT GTGCTGTGGG CTCTGCTGAC CCTCTTCACC GTGTCCACGG    4620
GAGAAGGCTG GCCACAGGTC CTCAAGCATT CGGTGGACGC CACCTTTGAG AACCAGGGCC    4680
CCAGCCCCGG GTACCGCATG GAGATGTCCA TTTTCTACGT CGTCTACTTT GTGGTGTTCC    4740
CCTTCTTCTT TGTCAATATC TTTGTGGCCT TGATCATCAT CACCTTCCAG GAGCAAGGGG    4800
ACAAGATGAT GGAGGAATAC AGCCTGGAGA AAAATGAGAG GGCCTGCATT GATTTCGCCA    4860
TCAGCGCCAA GCCGCTGACC CGACACATGC CGCAGAACAA GCAGAGCTTC CAGTACCGCA    4920
TGTGGCAGTT CGTGGTGTCT CCGCCTTTCG AGTACACGAT CATGGCCATG ATCGCCCTCA    4980
ACACCATCGT GCTTATGATG AAGTTCTATG GGGCTTCTGT TGCTTATGAA AATGCCCTGC    5040
GGGTGTTCAA CATCGTCTTC ACCTCCCTCT TCTCTCTGGA ATGTGTGCTG AAAGTCATGG    5100
CTTTGGGGAT TCTGAATTAT TTCCGCGATG CCTGGAACAT CTTCGACTTT GTGACTGTTC    5160
TGGGCAGCAT CACCGATATC CTCGTGACTG AGTTTGGGAA TCCGAATAAC TTCATCAACC    5220
TGAGCTTTCT CCGCCTCTTC CGAGCTGCCC GGCTCATCAA ACTTCTCCGT CAGGGTTACA    5280
CCATCCGCAT TCTTCTCTGG ACCTTTGTGC AGTCCTTCAA GGCCCTGCCT TATGTCTGTC    5340
TGCTGATCGC CATGCTCTTC TTCATCTATG CCATCATTGG GATGCAGGTG TTTGGTAACA    5400
TTGGCATCGA CGTGGAGGAC GAGGACAGTG ATGAAGATGA GTTCCAAATC ACTGAGCACA    5460
```

```
ATAACTTCCG GACCTTCTTC CAGGCCCTCA TGCTTCTCTT CCGGAGTGCC ACCGGGGAAG    5520

CTTGGCACAA CATCATGCTT TCCTGCCTCA GCGGGAAACC GTGTGATAAG AACTCTGGCA    5580

TCCTGACTCG AGAGTGTGGC AATGAATTTG CTTATTTTTA CTTTGTTTCC TTCATCTTCC    5640

TCTGCTCGTT TCTGATGCTG AATCTCTTTG TCGCCGTCAT CATGGACAAC TTTGAGTACC    5700

TCACCCGAGA CTCCTCCATC CTGGGCCCCC ACCACCTGGA TGAGTACGTG CGTGTCTGGG    5760

CCGAGTATGA CCCCGCAGCT TGGGGCCGCA TGCCTTACCT GGACATGTAT CAGATGCTGA    5820

GACACATGTC TCCGCCCCTG GGTCTGGGGA AGAAGTGTCC GGCCAGAGTG GCTTACAAGC    5880

GGCTTCTGCG GATGGACCTG CCCGTCGCAG ATGACAACAC CGTCCACTTC AATTCCACCC    5940

TCATGGCTCT GATCCGCACA GCCCTGGACA TCAAGATTGC CAAGGGAGGA GCCGACAAAC    6000

AGCAGATGGA CGCTGAGCTG CGGAAGGAGA TGATGGCGAT TTGGCCCAAT CTGTCCCAGA    6060

AGACGCTAGA CCTGCTGGTC ACACCTCACA AGTCCACGGA CCTCACCGTG GGAAGATCT    6120

ACGCAGCCAT GATGATCATG GAGTACTACC GGCAGAGCAA GGCCAAGAAG CTGCAGGCCA    6180

TGCGCGAGGA GCAGGACCGG ACACCCCTCA TGTTCCAGCG CATGGAGCCC CCGTCCCCAA    6240

CGCAGGAAGG GGGACCTGGC CAGAACGCCC TCCCCTCCAC CCAGCTGGAC CCAGGAGGAG    6300

CCCTGATGGC TCACGAAAGC GGCCTCAAGG AGAGCCCGTC CTGGGTGACC CAGCGTGCCC    6360

AGGAGATGTT CCAGAAGACG GGCACATGGA GTCCGGAACA AGGCCCCCCT ACCGACATGC    6420

CCAACAGCCA GCCTAACTCT CAGTCCGTGG AGATGCGAGA GATGGGCAGA GATGGCTACT    6480

CCGACAGCGA GCACTACCTC CCCATGGAAG CCAGGGCCG GGCTGCCTCC ATGCCCCGCC    6540

TCCCTGCAGA GAACCAGAGG AGAAGGGGCC GGCCACGTGG GAATAACCTC AGTACCATCT    6600

CAGACACCAG CCCCATGAAG CGTTCAGCCT CCGTGCTGGG CCCCAAGGCC CGACGCCTGG    6660

ACGATTACTC GCTGGAGCGG GTCCCGCCCC AGGAGAACCA GCGGCACCAC CAGCGGCGCC    6720

GCGACCGCAG CCACCGCGCC TCTGAGCGCT CCCTGGGCCG CTACACCGAT GTGGACACAG    6780

GCTTGGGGAC AGACCTGAGC ATGACCACCC AATCCGGGGA CCTGCCGTCG AAGGAGCGGG    6840

ACCAGGAGCG GGGCCGGCCC AAGGATCGGA AGCATCGACA GCACCACCAC CACCACCACC    6900

ACCACCACCA TCCCCCGCCC CCGACAAGG ACCGCTATGC CCAGGAACGG CCGGACCACG    6960

GCCGGGCACG GGCTCGGGAC CAGCGCTGGT CCCGCTCGCC CAGCGAGGGC CGAGAGCACA    7020

TGGCGCACCG GCAGGGCAGT AGTTCCGTAA GTGGAAGCCC AGCCCCCTCA ACATCTGGTA    7080

CCAGCACTCC GCKGCGGGGC CGCCGCCAGC TCCCCCAGAC CCCCTCCACC CCCCGGCCAC    7140

ACGTGTCCTA TTCCCCTGTG ATCCGTAAGG CCGGCGGCTC GGGGCCCCCG CAGCAGCAGC    7200

AGCAGCAGCA GCAGCAGCAG CAGGCGGTGG CCAGGCCGGG CCGGGCGGCC ACCAGCGGCC    7260

CTCGGAGGTA CCCAGGCCCC ACGGCCGAGC TCTGGCCGG AGATCGGCCG CCCACGGGGG    7320

GCCACAGCAG CGGCCGCTCG CCCAGGATGG AGAGGCGGGT CCCAGGCCCG CCCGGAGCG    7380

AGTCCCCCAG GGCCTGTCGA CACGGCGGGG CCCGGTGGCC GGCATCTGGC CGCACGTGT    7440

CCGAGGGGCC CCCGGGTCCC CGGCACCATG GCTACTACCG GGCTCCGAC TACGACGAGG    7500

CCGATGGCCC GGGCAGCGGG GGCGGCGAGG AGGCCATGGC CGGGGCCTAC GACGCGCCAC    7560

CCCCCGTACG ACACGCGTCC TCGGGCGCCA CCGGGCGCTC GCCCAGGACT CCCCGGGCCT    7620

CGGGCCCGGC CTGCGCCTCG CCTTCTCGGC ACGGCCGGCG ACTCCCCAAC GGCTACTACC    7680

CGGCGCACGG ACTGGCCAGG CCCCGCGGGC CGGGCTCCAG GAAGGGCCTG CACGAACCCT    7740

ACAGCGAGAG TGACGATGAT TGGTGCTAAG CCCGGGCGAG GTGGCGCCCG CCCGGCCCCC    7800
```

| | |
|---|---:|
| CACGCACC | 7808 |

(2) INFORMATION FOR SEQ ID NO:23:

(i) SEQUENCE CHARACTERISTICS:
        (A) LENGTH: 7791 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 240..7037
        (D) OTHER INFORMATION: /product= "Alpha1A-2 subunit of
           human calcium channel"

(xi) SEQUENCE DESCRIPTION: SEQ ID NO:23:

| | |
|---|---:|
| GATGTCCCGA GCTGCTATCC CCGGCTCGGC CCGGGCAGCC GCCTTCTGAG CCCCCGACCC | 60 |
| GAGGCGCCGA GCCGCCGCCG CCCGATGGGC TGGGCCGTGG AGCGTCTCCG CAGTCGTAGC | 120 |
| TCCAGCCGCC GCGCTCCCAG CCCCGGCAGC CTCAGCATCA GCGGCGGCGG CGGCGGCGGC | 180 |
| GGCGTCTTCC GCATCGTTCG CCGCAGCGTA ACCCGGAGCC CTTTGCTCTT TGCAGAATGG | 240 |
| CCCGCTTCGG AGACGAGATG CCGGCCCGCT ACGGGGAGG AGGCTCCGGG GCAGCCGCCG | 300 |
| GGGTGGTCGT GGGCAGCGGA GGCGGGCGAG GAGCCGGGGG CAGCCGGCAG GGCGGGCAGC | 360 |
| CCGGGGCGCA AGGATGTAC AAGCAGTCAA TGGCGCAGAG AGCGCGGACC ATGGCACTCT | 420 |
| ACAACCCCAT CCCCGTCCGA CAGAACTGCC TCACGGTTAA CCGGTCTCTC TTCCTCTTCA | 480 |
| GCGAAGACAA CGTGGTGAGA AAATACGCCA AAAAGATCAC CGAATGGCCT CCCTTTGAAT | 540 |
| ATATGATTTT AGCCACCATC ATAGCGAATT GCATCGTCCT CGCACTGGAG CAGCATCTGC | 600 |
| CTGATGATGA CAAGACCCCG ATGTCTGAAC GGCTGGATGA CACAGAACCA TACTTCATTG | 660 |
| GAATTTTTTG TTTCGAGGCT GGAATTAAAA TCATTGCCCT TGGGTTTGCC TTCCACAAAG | 720 |
| GCTCCTACTT GAGGAATGGC TGGAATGTCA TGGACTTTGT GGTGGTGCTA ACGGGCATCT | 780 |
| TGGCGACAGT TGGGACGGAG TTTGACCTAC GGACGCTGAG GGCAGTTCGA GTGCTGCGGC | 840 |
| CGCTCAAGCT GGTGTCTGGA ATCCCAAGTT TACAAGTCGT CCTGAAGTCG ATCATGAAGG | 900 |
| CGATGATCCC TTTGCTGCAG ATCGGCCTCC TCCTATTTTT TGCAATCCTT ATTTTTGCAA | 960 |
| TCATAGGGTT AGAATTTTAT ATGGGAAAAT TCATACCAC CTGCTTTGAA GAGGGGACAG | 1020 |
| ATGACATTCA GGGTGAGTCT CCGGCTCCAT GTGGGACAGA AGAGCCCGCC CGCACCTGCC | 1080 |
| CCAATGGGAC CAAATGTCAG CCCTACTGGG AAGGGCCCAA CAACGGGATC ACTCAGTTCG | 1140 |
| ACAACATCCT GTTTGCAGTG CTGACTGTTT TCCAGTGCAT AACCATGGAA GGGTGGACTG | 1200 |
| ATCTCCTCTA CAATAGCAAC GATGCCTCAG GAACACTTG AACTGGTTG TACTTCATCC | 1260 |
| CCCTCATCAT CATCGGCTCC TTTTTTATGC TGAACCTTGT GCTGGGTGTG CTGTCAGGGG | 1320 |
| AGTTTGCCAA AGAAAGGGAA CGGGTGGAGA ACCGGCGGGC TTTTCTGAAG CTGAGGCGGC | 1380 |
| AACAACAGAT TGAACGTGAG CTCAATGGGT ACATGGAATG GATCTCAACA GCAGAAGAGG | 1440 |
| TGATCCTCGC CGAGGATGAA ACTGCCGGGG AGCAGAGGCA TCCCTTTGAT GGAGCTCTGC | 1500 |
| GGAGAACCAC CATAAAGAAA AGCAAGACAG ATTTGCTCAA CCCCGAAGAG CTGAGGATC | 1560 |
| AGCTGGCTGA TATAGCCTCT GTGGGTTCTC CCTTCGCCCG AGCCAGCATT AAAAGTGCCA | 1620 |
| AGCTGGAGAA CTCGACCTTT TTTCACAAAA AGGAGAGGAG GATGCGTTTC TACATCCGCC | 1680 |
| GCATGGTCAA AACTCAGGCC TTCTACTGGA CTGTACTCAG TGTGGTAGCT CTCAACACGC | 1740 |

-continued

```
TGTGTGTTGC TATTGTTCAC TACAACCAGC CCGAGTGGCT CTCCGACTTC CTTTACTATG   1800

CAGAATTCAT TTTCTTAGGA CTCTTTATGT CCGAAATGTT TATAAAAATG TACGGGCTTG   1860

GGACGCGGCC TTACTTCCAC TCTTCCTTCA ACTGCTTTGA CTGTGGGGTT ATCATTGGGA   1920

GCATCTTCGA GGTCATCTGG GCTGTCATAA AACCTGGCAC ATCCTTTGGA ATCAGCGTGT   1980

TACGAGCCCT CAGGTTATTG CGTATTTTCA AAGTCACAAA GTACTGGGCA TCTCTCAGAA   2040

ACCTGGTCGT CTCTCTCCTC AACTCCATGA AGTCCATCAT CAGCCTGTTG TTTCTCCTTT   2100

TCCTGTTCAT TGTCGTCTTC GCCCTTTTGG GAATGCAACT CTTCGGCGGC CAGTTTAATT   2160

TCGATGAAGG GACTCCTCCC ACCAACTTCG ATACTTTTCC AGCAGCAATA ATGACGGTGT   2220

TTCAGATCCT GACGGGCGAA GACTGGAACG AGGTCATGTA CGACGGGATC AAGTCTCAGG   2280

GGGGCGTGCA GGGCGGCATG GTGTTCTCCA TCTATTTCAT TGTACTGACG CTCTTTGGGA   2340

ACTACACCCT CCTGAATGTG TTCTTGGCCA TCGCTGTGGA CAATCTGGCC AACGCCCAGG   2400

AGCTCACCAA GGTGGAGGCG GACGAGCAAG AGGAAGAAGA AGCAGCGAAC CAGAAACTTG   2460

CCCTACAGAA AGCCAAGGAG GTGGCAGAAG TGAGTCCTCT GTCCGCGGCC AACATGTCTA   2520

TAGCTGTGAA AGAGCAACAG AAGAATCAAA AGCCAGCCAA GTCCGTGTGG GAGCAGCGGA   2580

CCAGTGAGAT GCGAAAGCAG AACTTGCTGG CCAGCCGGGA GGCCCTGTAT AACGAAATGG   2640

ACCCGGACGA GCGCTGGAAG GCTGCCTACA CGCGGCACCT GCGGCCAGAC ATGAAGACGC   2700

ACTTGGACCG GCCGCTGGTG GTGGACCCGC AGGAGAACCG CAACAACAAC ACCAACAAGA   2760

GCCGGGCGGC CGAGYCCACC GTGGACCAGA GCCTCGGCCA GCAGCGCGCC GAGGACTTCC   2820

TCAGGAAACA GGCCCGCTAC CACGATCGGG CCCGGKAMCC CAGCGGTTCG GCGGGCCTGG   2880

ACGCACGGAG GCCCTGGGCG GGAAGCCAGG AGGCCGAGCT TAGCCGGGAG GGACCYWWCG   2940

GCCGCGAGTC GGACCACCAC GCCCGGGAGG RCARCCTGGA GCAWCCCGGG TTCTGGGAGG   3000

GCGAKKCCGA GCGAGRCAAG TYCGGGGAMC CCCACCGGAG GCACGTTCAC CSGCAGGGGG   3060

GCAGCAGGGA GATCCTCAGC GGGTCTCCGC TCACGGGCGC GGACGGGGAC GATCGACGTC   3120

ATCGCGCGCA CCGCAGGCCC GGGGAGGAGG GTCGGAGGA CAAGGCGGAG CGGAGGGCGC   3180

GGCACCGCGA GGGCAGCCGG CCGGCCCGGG GCGGCGAGGG CGAGGGCGAG GTCCCCGACG   3240

GGGGCGATCG CAGGAGAAGG CACCGGCATG GCGCTCCAGC CACGTACGAG GGGGACGCGC   3300

GGAGGGAGGA CAAGGAGCGG AGGCATCGGA GGAGGAAAGA GAACCAGGGC TCCGGGGTCC   3360

CTGTGTCGGG CCCCAACCTG TCAACCACCC GGCCAATCCA GCAGGACCTG GCCGCCAAG   3420

ACCCACCCCT GGCAGAGGAT ATTGACAACA TGAAGAACAA CAAGCTGGCC ACCGCGGAGT   3480

CGGCCGCTCC CCACGGCAGC CTTGGCCACG CCGGCCTGCC CCAGAGCCCA GCCAAGATGG   3540

GAAACAGCAC CGACCCCGGC CCCATGCTGG CCATCCCTGC CATGGCCACC AACCCCCAGA   3600

ACGCCGCCAG CCGCCGGACG CCCAACAACC CGGGGAACCC ATCCAATCCC GGCCCCCCCA   3660

AGACCCCCGA GAATAGCCTT ATCGTCACCA ACCCCAGCGG CACCCAGACC AATTCAGCTA   3720

AGACTGCCAG GAAACCCGAC CACACCACAG TGGACATCCC CCAGCCTGC CCACCCCCCC   3780

TCAACCACAC CGTCGTACAA GTGAACAAAA ACGCCAACCC AGACCACTG CCAAAAAAAG   3840

AGGAAGAGAA GAAGGAGGAG GAGGAAGACG ACCGTGGGGA AGACGGCCCT AAGCCAATGC   3900

CTCCCTATAG CTCCATGTTC ATCCTGTCCA CGACCAACCC CCTTCGCCGC CTGTGCCATT   3960

ACATCCTGAA CCTGCGCTAC TTTGAGATGT GCATCCTCAT GGTCATTGCC ATGAGCAGCA   4020

TCGCCCTGGC CGCCGAGGAC CCTGTGCAGC CCAACGCACC TCGGAACAAC GTGCTGCGAT   4080

ACTTTGACTA CGTTTTTACA GGCGTCTTCA CCTTTGAGAT GGTGATCAAG ATGATTGACC   4140
```

```
TGGGGCTCGT CCTGCATCAG GGTGCCTACT TCCGTGACCT CTGGAATATT CTCGACTTCA    4200

TAGTGGTCAG TGGGGCCCTG GTAGCCTTTG CCTTCACTGG CAATAGCAAA GGAAAAGACA    4260

TCAACACGAT TAAATCCCTC CGAGTCCTCC GGGTGCTACG ACCTCTTAAA ACCATCAAGC    4320

GGCTGCCAAA GCTCAAGGCT GTGTTTGACT GTGTGGTGAA CTCACTTAAA AACGTCTTCA    4380

ACATCCTCAT CGTCTACATG CTATTCATGT TCATCTTCGC CGTGGTGGCT GTGCAGCTCT    4440

TCAAGGGGAA ATTCTTCCAC TGCACTGACG AGTCCAAAGA GTTTGAGAAA GATTGTCGAG    4500

GCAAATACCT CCTCTACGAG AAGAATGAGG TGAAGGCGCG AGACCGGGAG TGGAAGAAGT    4560

ATGAATTCCA TTACGACAAT GTGCTGTGGG CTCTGCTGAC CCTCTTCACC GTGTCCACGG    4620

GAGAAGGCTG GCCACAGGTC CTCAAGCATT CGGTGGACGC CACCTTTGAG AACCAGGGCC    4680

CCAGCCCCGG GTACCGCATG GAGATGTCCA TTTTCTACGT CGTCTACTTT GTGGTGTTCC    4740

CCTTCTTCTT TGTCAATATC TTTGTGGCCT TGATCATCAT CACCTTCCAG GAGCAAGGGG    4800

ACAAGATGAT GGAGGAATAC AGCCTGGAGA AAAATGAGAG GGCCTGCATT GATTTCGCCA    4860

TCAGCGCCAA GCCGCTGACC CGACACATGC CGCAGAACAA GCAGAGCTTC CAGTACCGCA    4920

TGTGGCAGTT CGTGGTGTCT CCGCCTTTCG AGTACACGAT CATGGCCATG ATCGCCCTCA    4980

ACACCATCGT GCTTATGATG AAGTTCTATG GGCTTCTGT TGCTTATGAA AATGCCCTGC    5040

GGGTGTTCAA CATCGTCTTC ACCTCCCTCT TCTCTCTGGA ATGTGTGCTG AAAGTCATGG    5100

CTTTGGGGAT TCTGAATTAT TTCCGCGATG CCTGGAACAT CTTCGACTTT GTGACTGTTC    5160

TGGGCAGCAT CACCGATATC CTCGTGACTG AGTTTGGGAA TCCGAATAAC TTCATCAACC    5220

TGAGCTTTCT CCGCCTCTTC CGAGCTGCCC GGCTCATCAA ACTTCTCCGT CAGGGTTACA    5280

CCATCCGCAT TCTTCTCTGG ACCTTTGTGC AGTCCTTCAA GGCCCTGCCT TATGTCTGTC    5340

TGCTGATCGC CATGCTCTTC TTCATCTATG CCATCATTGG GATGCAGGTG TTTGGTAACA    5400

TTGGCATCGA CGTGGAGGAC GAGGACAGTG ATGAAGATGA GTTCCAAATC ACTGAGCACA    5460

ATAACTTCCG GACCTTCTTC CAGGCCCTCA TGCTTCTCTT CCGGAGTGCC ACCGGGGAAG    5520

CTTGGCACAA CATCATGCTT TCCTGCCTCA GCGGGAAACC GTGTGATAAG AACTCTGGCA    5580

TCCTGACTCG AGAGTGTGGC AATGAATTTG CTTATTTTTA CTTTGTTTCC TTCATCTTCC    5640

TCTGCTCGTT TCTGATGCTG AATCTCTTTG TCGCCGTCAT CATGGACAAC TTTGAGTACC    5700

TCACCCGAGA CTCCTCCATC CTGGGCCCCC ACCACCTGGA TGAGTACGTG CGTGTCTGGG    5760

CCGAGTATGA CCCCGCAGCT TGGGGCCGCA TGCCTTACCT GGACATGTAT CAGATGCTGA    5820

GACACATGTC TCCGCCCCTG GGTCTGGGGA AGAAGTGTCC GGCCAGAGTG GCTTACAAGC    5880

GGCTTCTGCG GATGGACCTG CCCGTCGCAG ATGACAACAC CGTCCACTTC AATTCCACCC    5940

TCATGGCTCT GATCCGCACA GCCCTGGACA TCAAGATTGC CAAGGGAGGA GCCGACAAAC    6000

AGCAGATGGA CGCTGAGCTG CGGAAGGAGA TGATGGCGAT TTGGCCCAAT CTGTCCCAGA    6060

AGACGCTAGA CCTGCTGGTC ACACCTCACA AGTCCACGGA CCTCACCGTG GGAAGATCT    6120

ACGCAGCCAT GATGATCATG GAGTACTACC GGCAGAGCAA GGCCAAGAAG CTGCAGGCCA    6180

TGCGCGAGGA GCAGGACCGG ACACCCCTCA TGTTCCAGCG CATGGAGCCC CCGTCCCCAA    6240

CGCAGGAAGG GGGACCTGGC CAGAACGCCC TCCCCTCCAC CCAGCTGGAC CCAGGAGGAG    6300

CCCTGATGGC TCACGAAAGC GGCCTCAAGG AGAGCCCGTC CTGGGTGACC CAGCGTGCCC    6360

AGGAGATGTT CCAGAAGACG GGCACATGGA GTCGGAACA AGGCCCCCCT ACCGACATGC    6420

CCAACAGCCA GCCTAACTCT CAGTCCGTGG AGATGCGAGA GATGGGCAGA GATGGCTACT    6480
```

```
CCGACAGCGA GCACTACCTC CCCATGGAAG GCCAGGGCCG GGCTGCCTCC ATGCCCCGCC    6540

TCCCTGCAGA GAACCAGAGG AGAAGGGGCC GGCCACGTGG GAATAACCTC AGTACCATCT    6600

CAGACACCAG CCCCATGAAG CGTTCAGCCT CCGTGCTGGG CCCCAAGGCC CGACGCCTGG    6660

ACGATTACTC GCTGGAGCGG GTCCCGCCCG AGGAGAACCA GCGGCACCAC CAGCGGCGCC    6720

GCGACCGCAG CCACCGCGCC TCTGAGCGCT CCCTGGGCCG CTACACCGAT GTGGACACAG    6780

GCTTGGGGAC AGACCTGAGC ATGACCACCC AATCCGGGGA CCTGCCGTCG AAGGAGCGGG    6840

ACCAGGAGCG GGGCCGGCCC AAGGATCGGA AGCATCGACA GCACCACCAC CACCACCACC    6900

ACCACCACCA TCCCCCGCCC CCCGACAAGG ACCGCTATGC CCAGGAACGG CCGGACCACG    6960

GCCGGGCACG GGCTCGGGAC CAGCGCTGGT CCCGCTCGCC CAGCGAGGGC CGAGAGCACA    7020

TGGCGCACCG GCAGTAGTTC CGTAAGTGGA AGCCCAGCCC CCTCAACATC TGGTACCAGC    7080

ACTCCGCKGC GGGGCCGCCG CCAGCTCCCC CAGACCCCCT CCACCCCCG GCCACACGTG     7140

TCCTATTCCC CTGTGATCCG TAAGGCCGGC GGCTCGGGGC CCCCGCAGCA GCAGCAGCAG    7200

CAGCAGGCGG TGGCCAGGCC GGGCCGGGCG GCCACCAGCG GCCCTCGGAG GTACCCAGGC    7260

CCCACGGCCG AGCCTCTGGC CGGAGATCGG CCGCCCACGG GGGGCCACAG CAGCGGCCGC    7320

TCGCCCAGGA TGGAGAGGCG GGTCCCAGGC CCGGCCCGGA GCGAGTCCCC CAGGGCCTGT    7380

CGACACGGCG GGGCCCGGTG GCCGGCATCT GGCCCGCACG TGTCCGAGGG GCCCCCGGGT    7440

CCCCGGCACC ATGGCTACTA CCGGGGCTCC GACTACGACG AGGCCGATGG CCCGGGCAGC    7500

GGGGGCGGCG AGGAGGCCAT GGCCGGGGCC TACGACGCGC CACCCCCGGT ACGACACGCG    7560

TCCTCGGGCG CCACCGGGCG CTCGCCCAGG ACTCCCCGGG CCTCGGGCCC GGCCTGCGCC    7620

TCGCCTTCTC GGCACGGCCG GCGACTCCCC AACGGCTACT ACCCGGCGCA CGGACTGGCC    7680

AGGCCCCGCG GGCCGGGCTC CAGGAAGGGC CTGCACGAAC CCTACAGCGA GAGTGACGAT    7740

GATTGGTGCT AAGCCCGGGC GAGGTGGCGC CCGCCCGGCC CCCCACGCAC C             7791

(2) INFORMATION FOR SEQ ID NO:24:

(i) SEQUENCE CHARACTERISTICS:
        (A) LENGTH: 7032 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 169..6921
        (D) OTHER INFORMATION: /product= "Alpha1E-1 subunit of
            human calcium channel"

(xi) SEQUENCE DESCRIPTION: SEQ ID NO:24:

GCTGCTGCTG CCTCTCCGAA GAGCTCGCGG AGCTCCCCAG AGGCGGTGGT CCCCGTGCTT      60

GTCTGGATGC GGCTCTGAGT CTCCGTGTGT CTTTCTGCTT GTTGCTGTGT GCGGGTGTTC     120

GGCCGCGATC ACCTTTGTGT GTCTTCTGTC TGTTTAAACC TCAGGATGGC TCGCTTCGGG     180

GAGGCGGTGG TCGCCAGGCC AGGGTCCGGC GATGGAGACT CGGACCAGAG CAGGAACCGG     240

CAAGGAACCC CCGTGCCGGC CTCGGGGCAG GCGGCCGCCT ACAAGCAGAC GAAAGCACAG     300

AGGGCGCGGA CTATGGCTTT GTACAACCCC ATTCCCGTCC GGCAGAACTG TTTCACCGTC     360

AACAGATCCC TGTTCATCTT CGGAGAAGAT AACATTGTCA GGAAATATGC CAAGAAGCTC     420

ATCGATTGGC CGCCATTTGA GTACATGATC CTGGCCACCA TCATTGCCAA CTGCATCGTC     480
```

| | |
|---|---|
| CTGGCCCTGG AGCAGCATCT TCCTGAGGAT GACAAGACCC CCATGTCCCG AAGACTGGAG | 540 |
| AAGACAGAAC CTTATTTCAT TGGGATCTTT TGCTTTGAAG CTGGGATCAA AATTGTGGCC | 600 |
| CTGGGGTTCA TCTTCCATAA GGGCTCTTAC CTCCGCAATG GCTGGAATGT CATGGACTTC | 660 |
| ATCGTGGTCC TCAGTGGCAT CCTGGCCACT GCAGGAACCC ACTTCAATAC TCACGTGGAC | 720 |
| CTGAGGACCC TCCGGGCTGT GCGTGTCCTG CGGCCTTTGA AGCTCGTGTC AGGGATACCT | 780 |
| AGCCTGCAGA TTGTGTTGAA GTCCATCATG AAGGCCATGG TACCTCTTCT GCAGATTGGC | 840 |
| CTTCTGCTCT TCTTTGCCAT CCTGATGTTT GCTATCATTG GTTTGGAGTT CTACAGTGGC | 900 |
| AAGTTACATC GAGCRTGCTT CATGAACAAT TCAGGTATTC TAGAAGGATT TGACCCCCCT | 960 |
| CACCCATGTG GTGTGCAGGG CTGCCCAGCT GGTTATGAAT GCAAGGACTG GATCGGCCCC | 1020 |
| AATGATGGGA TCACCCAGTT TGATAACATC CTTTTTGCTG TGCTGACTGT CTTCCAGTGC | 1080 |
| ATCACCATGG AAGGGTGGAC CACTGTGCTG TACAATACCA ATGATGCCTT AGGAGCCACC | 1140 |
| TGGAATTGGC TGTACTTCAT CCCCCTCATC ATCATTGGAT CCTTCTTTGT TCTCAACCTA | 1200 |
| GTCCTGGGAG TGCTTTCCGG GGAATTTGCC AAAGAGAGAG AGAGTGGA GAACCGAAGG | 1260 |
| GCTTTCATGA AGCTGCGGCG CCAGCAGCAG ATTGAGCGTG AGCTGAATGG CTACCGTGCC | 1320 |
| TGGATAGACA AAGCAGAGGA AGTCATGCTC GCTGAAGAAA ATAAAAATGC TGGAACATCC | 1380 |
| GCCTTAGAAG TGCTTCGAAG GGCAACCATC AAGAGGAGCC GGACAGAGGC CATGACTCGA | 1440 |
| GACTCCAGTG ATGAGCACTG TGTTGATATC TCCTCTGTGG GCACACCTCT GGCCCGAGCC | 1500 |
| AGTATCAAAA GTGCAAAGGT AGACGGGGTC TCTTATTTCC GGCACAAGGA AAGGCTTCTG | 1560 |
| CGCATCTCCA TTCGCCACAT GGTTAAATCC CAGGTGTTTT ACTGGATTGT GCTGAGCCTT | 1620 |
| GTGGCACTCA ACACTGCCTG TGTGGCCATT GTCCATCACA ACCAGCCCCA GTGGCTCACC | 1680 |
| CACCTCCTCT ACTATGCAGA ATTTCTGTTT CTGGGACTCT TCCTCTTGGA GATGTCCCTG | 1740 |
| AAGATGTATG GCATGGGGCC TCGCCTTTAT TTTCACTCTT CATTCAACTG CTTTGATTTT | 1800 |
| GGGGTCACAG TGGGCAGTAT CTTTGAAGTG GTCTGGGCAA TCTTCAGACC TGGTACGTCT | 1860 |
| TTTGGAATCA GTGTCTTGCG AGCCCTCCGG CTTCTAAGAA TATTTAAAAT AACCAAGTAT | 1920 |
| TGGGCTTCCC TACGGAATTT GGTGGTCTCC TTGATGAGCT CAATGAAGTC TATCATCAGT | 1980 |
| TTGCTTTTCC TCCTCTTCCT CTTCATCGTT GTCTTTGCTC TCCTAGGAAT GCAGTTATTT | 2040 |
| GGAGGCAGGT TTAACTTTAA TGATGGGACT CCTTCGGCAA ATTTTGATAC CTTCCCTGCA | 2100 |
| GCCATCATGA CTGTGTTCCA GATCCTGACG GGTGAGGACT GGAATGAGGT GATGTACAAT | 2160 |
| GGGATCCGCT CCCAGGGTGG GGTCAGCTCA GGCATGTGGT CTGCCATCTA CTTCATTGTG | 2220 |
| CTCACCTTGT TTGGCAACTA CACGCTACTG AATGTGTTCT TGGCTATCGC TGTGGATAAT | 2280 |
| CTCGCCAACG CCCAGGAACT GACCAAGGAT GAACAGGAGG AAGAAGAGGC CTTCAACCAG | 2340 |
| AAACATGCAC TGCAGAAGGC CAAGGAGGTC AGCCCGATGT CTGCACCCAA CATGCCTTCG | 2400 |
| ATCGAGAGGG AGCGGAGGCG CCGGCACCAC ATGTCCGTGT GGGAGCAGCG TACCAGCCAG | 2460 |
| CTGAGGAAGC ACATGCAGAT GTCCAGCCAG GAGGCCCTCA ACAGAGAGGA GGCGCCGACC | 2520 |
| ATGAACCCGC TCAACCCCCT CAACCCGCTC AGCTCCCTCA ACCCGCTCAA TGCCCACCCC | 2580 |
| AGCCTTTATC GGCGACCCAG GGCCATTGAG GGCCTGGCCC TGGGCCTGGC CCTGGAGAAG | 2640 |
| TTCGAGGAGG AGCGCATCAG CCGTGGGGGG TCCCTCAAGG GGATGGAGG GACCGATCC | 2700 |
| AGTGCCCTGG ACAACCAGAG GACCCCTTTG TCCCTGGGCC AGCGGGAGCC ACCATGGCTG | 2760 |
| GCCAGGCCCT GTCATGGAAA CTGTGACCCG ACTCAGCAGG AGGCAGGGG AGGAGAGGCT | 2820 |
| GTGGTGACCT TGAGGACCG GGCCAGGCAC AGGCAGAGCC AACGCGCAG CCGGCATCGC | 2880 |

```
CGCGTCAGGA CAGAAGGCAA GGAGTCCTCT TCAGCCTCCC GGAGCAGGTC TGCCAGCCAG    2940

GAACGCAGTC TGGATGAAGC CATGCCCACT GAAGGGGAGA AGGACCATGA GCTCAGGGGC    3000

AACCATGGTG CCAAGGAGCC AACGATCCAA GAAGAGAGAG CCCAGGATTT AAGGAGGACC    3060

AACAGTCTGA TGGTGTCCAG AGGCTCCGGG CTGGCAGGAG GCCTTGATGA GGCTGACACC    3120

CCCCTAGTCC TGCCCCATCC TGAGCTGGAA GTGGGGAAGC ACGTGGTGCT GACGGAGCAG    3180

GAGCCAGAAG GCAGCAGTGA GCAGGCCCTG CTGGGGAATG TGCAGCTAGA CATGGGCCGG    3240

GTCATCAGCC AGAGCGAGCC TGACCTCTCC TGCATCACGG CCAACACGGA CAAGGCCACC    3300

ACCGAGAGCA CCAGCGTCAC CGTCGCCATC CCCGACGTGG ACCCCTTGGT GGACTCAACC    3360

GTGGTGCACA TTAGCAACAA GACGGATGGG GAAGCCAGTC CCTTGAAGGA GGCAGAGATC    3420

AGAGAGGATG AGGAGGAGGT GGAGAAGAAG AAGCAGAAGA AGGAGAAGCG TGAGACAGGC    3480

AAAGCCATGG TGCCCCACAG CTCAATGTTC ATCTTCAGCA CCACCAACCC GATCCGGAGG    3540

GCCTGCCACT ACATCGTGAA CCTGCGCTAC TTTGAGATGT GCATCCTCCT GGTGATTGCA    3600

GCCAGCAGCA TCGCCCTGGC GGCAGAGGAC CCCGTCCTGA CCAACTCGGA GCGCAACAAA    3660

GTCCTGAGGT ATTTTGACTA TGTGTTCACG GGCGTGTTCA CCTTTGAGAT GGTTATAAAG    3720

ATGATAGACC AAGGCTTGAT CCTGCAGGAT GGGTCCTACT TCCGAGACTT GTGGAACATC    3780

CTGGACTTTG TGGTGGTCGT TGGCGCATTG GTGGCCTTTG CTCTGGCGAA CGCTTTGGGA    3840

ACCAACAAAG GACGGGACAT CAAGACCATC AAGTCTCTGC GGGTGCTCCG AGTTCTAAGG    3900

CCACTGAAAA CCATCAAGCG CTTGCCCAAG CTCAAGGCCG TCTTCGACTG CGTAGTGACC    3960

TCCTTGAAGA ATGTCTTCAA CATACTCATT GTGTACAAGC TCTTCATGTT CATCTTTGCT    4020

GTCATCGCAG TTCAGCTCTT CAAGGGAAAG TTCTTTTATT GCACGGACAG TTCCAAGGAC    4080

ACAGAGAAGG AGTGCATAGG CAACTATGTA GATCACGAGA AAAACAAGAT GGAGGTGAAG    4140

GGCCGGGAAT GGAAGCGCCA TGAATTCCAC TACGACAACA TTATCTGGGC CCTGCTGACC    4200

CTCTTCACCG TCTCCACAGG GGAAGGATGG CCTCAAGTTC TGCAGCACTC TGTAGATGTG    4260

ACAGAGGAAG ACCGAGGCCC AAGCCGCAGC AACCGCATGG AGATGTCTAT CTTTTATGTA    4320

GTCTACTTTG TGGTCTTCCC CTTCTTCTTT GTCAATATCT TTGTGGCTCT CATCATCATC    4380

ACCTTCCAGG AGCAAGGGGA TAAGATGATG GAGGAGTGCA GCCTGGAGAA GAATGAGAGG    4440

GCGTGCATCG ACTTCGCCAT CAGCGCCAAA CCTCTCACCC GCTACATGCC GCAGAACAGA    4500

CACACCTTCC AGTACCGCGT GTGGCACTTT GTGGTGTCTC CGTCCTTTGA GTACACCATT    4560

ATGGCCATGA TCGCCTTGAA TACTGTTGTG CTGATGATGA AGTATTATTC TGCTCCCTGT    4620

ACCTATGAGC TGGCCCTGAA GTACCTGAAT ATCGCCTTCA CCATGGTGTT TTCCCTGGAA    4680

TGTGTCCTGA AGGTCATCGC TTTTGGCTTT TTGAACTATT TCCGAGACAC CTGGAATATC    4740

TTTGACTTCA TCACCGTGAT TGGCAGTATC ACAGAAATTA TCCTGACAGA CAGCAAGCTG    4800

GTGAACACCA GTGGCTTCAA TATGAGCTTT CTGAAGCTCT TCCGAGCTGC CCGCCTCATA    4860

AAGCTCCTGC GTCAGGGCTA TACCATACGC ATTTTGCTGT GGACCTTTGT GCAGTCCTTT    4920

AAGGCCCTCC CTTATGTCTG CCTTTTAATT GCCATGCTTT TCTTCATTTA TGCCATCATT    4980

GGGATGCAGG TATTTGGAAA CATAAAAATTA GACGAGGAGA GTCACATCAA CCGGCACAAC    5040

AACTTCCGGA GTTTCTTTGG GTCCCTAATG CTACTCTTCA GGAGTGCCAC AGGTGAGGCC    5100

TGGCAGGAGA TTATGCTGTC ATGCCTTGGG GAGAAGGGCT GTGAGCCTGA CACCACCGCA    5160

CCATCAGGGC AGAACGAGAA TGAACGCTGC GGCACCGATC TGGCCTACGT GTACTTTGTC    5220
```

-continued

```
TCCTTCATCT TCTTCTGCTC CTTCTTGATG CTCAACCTGT TTGTGGCCGT CATCATGGAC      5280

AACTTTGAGT ACCTGACTCG GGACTCCTCC ATCCTGGGGC CTCACCACTT GGACGAGTTT      5340

GTCCGCGTCT GGGCAGAATA TGACCGAGCA GCATGTGGCC GCATCCATTA CACTGAGATG      5400

TATGAAATGC TGACTCTCAT GTCACCTCCG CTAGGCCTCG GCAAGAGATG TCCCTCCAAA      5460

GTGGCATATA AGAGGTTGGT CCTGATGAAC ATGCCAGTAG CTGAGGACAT GACGGTCCAC      5520

TTCACCTCCA CACTTATGGC TCTGATCCGG ACAGCTCTGG ACATTAAAAT TGCCAAAGGT      5580

GGTGCAGACA GGCAGCAGCT AGACTCAGAG CTACAAAAGG AGACCCTAGC CATCTGGCCT      5640

CACCTATCCC AGAAGATGCT GGATCTGCTT GTGCCCATGC CCAAAGCCTC TGACCTGACT      5700

GTGGGCAAAA TCTATGCAGC AATGATGATC ATGGACTACT ATAAGCAGAG TAAGGTGAAG      5760

AAGCAGAGGC AGCAGCTGGA GGAACAGAAA AATGCCCCCA TGTTCCAGCG CATGGAGCCT      5820

TCATCTCTGC CTCAGGAGAT CATTGCTAAT GCCAAAGCCC TGCCTTACCT CCAGCAGGAC      5880

CCCGTTTCAG GCCTGAGTGG CCGGAGTGGA TACCCTTCGA TGAGTCCACT CTCTCCCCAG      5940

GATATATTCC AGTTGGCTTG TATGGACCCC GCCGATGACG GACAGTTCCA AGAACGGCAG      6000

TCTCTGGTGG TGACAGACCC TAGCTCCATG AGACGTTCAT TTTCCACTAT TCGGGATAAG      6060

CGTTCAAATT CCTCGTGGTT GGAGGAATTC TCCATGGAGC GAAGCAGTGA AAATACCTAC      6120

AAGTCCCGTC GCCGGAGTTA CCACTCCTCC TTGCGGCTGT CAGCCCACCG CCTGAACTCT      6180

GATTCAGGCC ACAAGTCTGA CACTCACCCC TCAGGGGCA GGGAGCGGCG ACGATCAAAA      6240

GAGCGAAAGC ATCTTCTCTC TCCTGATGTC TCCCGCTGCA ATTCAGAAGA GCGAGGGACC      6300

CAGGCTGACT GGGAGTCCCC AGAGCGCCGT CAATCCAGGT CACCCAGTGA GGGCAGGTCA      6360

CAGACGCCCA ACAGACAGGG CACAGGTTCC CTAAGTGAGA GCTCCATCCC CTCTGTCTCT      6420

GACACCAGCA CCCCAAGAAG AAGTCGTCGG CAGCTCCCAC CCGTCCCGCC AAAGCCCCGG      6480

CCCCTCCTTT CCTACAGCTC CCTGATTCGA CACGCGGGCA GCATCTCTCC ACCTGCTGAT      6540

GGAAGCGAGG AGGGCTCCCC GCTGACCTCC CAAGCTCTGG AGAGCAACAA TGCTTGGCTG      6600

ACCGAGTCTT CCAACTCTCC GCACCCCCAG CAGAGGCAAC ATGCCTCCCC ACAGCGCTAC      6660

ATCTCCGAGC CCTACTTGGC CCTGCACGAA GACTCCCACG CCTCAGACTG TGTTGAGGAG      6720

GAGACGCTCA CTTTCGAAGC AGCCGTGGCT ACTAGCCTGG GCCGTTCCAA CACCATCGGC      6780

TCAGCCCCAC CCCTGCGGCA TAGCTGGCAG ATGCCCAACG GCACTATCG GCGGCGGAGG      6840

CGCGGGGGGC CTGGGCCAGG CATGATGTGT GGGGCTGTCA ACAACCTGCT AAGTGACACG      6900

GAAGAAGATG ACAAATGCTA GAGGCTGCTC CCCCCTCCGA TGCATGCTCT TCTCTCACAT      6960

GGAGAAAACC AAGACAGAAT TGGGAAGCCA GTGCGGCCCC GCGGGGAGGA AGAGGGAAAA      7020

GGAAGATGGA AG                                                          7032
```

(2) INFORMATION FOR SEQ ID NO:25:

(i) SEQUENCE CHARACTERISTICS:
        (A) LENGTH: 57 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: misc_feature
        (B) LOCATION: 1..57
        (D) OTHER INFORMATION: /product= "AlphaE-3 subunit of human
            calcium channel is made upon insertion of this
            sequence into alphaE-1 between nucleotides 2405 and 2406"

(xi) SEQUENCE DESCRIPTION: SEQ ID NO:25:

```
AAGAGACAGA AGGAGAAGAC ACCACATGTC GATGTGGGAG CCACGCAGCA GCCACCT         57
```

(2) INFORMATION FOR SEQ ID NO:26:

(i) SEQUENCE CHARACTERISTICS:
        (A) LENGTH: 2264 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 2..1951
        (D) OTHER INFORMATION: /product= "Beta2D subunit of human
            calcium channel"

(xi) SEQUENCE DESCRIPTION: SEQ ID NO:26:

```
AATTCCGGCG GCGGCGGTGG CGCAGGAGAT CCAGATGGAA CTGCTAGAGA ACGTGGCTCC         60

CGCGGGGGCG CTCGGAGCCG CCGCACAGTC ATATGGAAAA GGAGCCAGAA GGAAAAACAG        120

ATTTAAAGGA TCTGATGGAA GCACGTCATC TGATACTACC TCAAATAGTT TTGTTCGCCA        180

GGGTTCGGCA GACTCCTACA CTAGCCGTCC ATCCGATTCC GATGTATCTC TGGAGGAGGA        240

CCGGGAGGCA GTGCGCAGAG AAGCGGAGCG GCAGGCCCAG GCACAGTTGG AAAAAGCAAA        300

GACAAAGCCC GTTGCATTTG CGGTTCGGAC AAATGTCAGC TACAGTGCGG CCCATGAAGA        360

TGATGTTCCA GTGCCTGGCA TGGCCATCTC ATTCGAAGCA AAAGATTTTC TGCATGTTAA        420

GGAAAAATTT AACAATGACT GGTGGATAGG GCGATTGGTA AAAGAAGGCT GTGAAATCGG        480

ATTCATTCCA AGCCCAGTCA AACTAGAAAA CATGAGGCTG CAGCATGAAC AGAGAGCCAA        540

GCAAGGGAAA TTCTACTCCA GTAAATCAGG AGGAAATTCA TCATCCAGTT TGGGTGACAT        600

AGTACCTAGT TCCAGAAAAT CAACACCTCC ATCATCTGCT ATAGACATAG ATGCTACTGG        660

CTTAGATGCA GAAGAAAATG ATATTCCAGC AAACCACCGC TCCCCTAAAC CCAGTGCAAA        720

CAGTGTAACG TCACCCCACT CCAAAGAGAA AAGAATGCCC TTCTTTAAGA AGACAGAGCA        780

CACTCCTCCG TATGATGTGG TACCTTCCAT GCGACCAGTG GTCCTAGTGG GCCCTTCTCT        840

GAAGGGCTAC GAGGTCACAG ATATGATGCA AAAGCGCTG TTTGATTTTT TAAAACACAG        900

ATTTGAAGGG CGGATATCCA TCACAAGGGT CACCGCTGAC ATCTCGCTTG CCAAACGCTC        960

GGTATTAAAC AATCCCAGTA AGCACGCAAT AATAGAAAGA TCCAACACAA GGTCAAGCTT       1020

AGCGGAAGTT CAGAGTGAAA TCGAAAGGAT TTTTGAACTT GCAAGAACAT TGCAGTTGGT       1080

GGTCCTTGAC GCGGATACAA TTAATCATCC AGCTCAACTC AGTAAAACCT CCTTGGCCCC       1140

TATTATAGTA TATGTAAAGA TTTCTTCTCC TAAGGTTTTA CAAAGGTTAA TAAAATCTCG       1200

AGGGAAATCT CAAGCTAAAC ACCTCAACGT CCAGATGGTA GCAGCTGATA AACTGGCTCA       1260

GTGTCCTCCA GAGCTGTTCG ATGTGATCTT GGATGAGAAC CAGCTTGAGG ATGCCTGTGA       1320

GCACCTTGCC GACTATCTGG AGGCCTACTG GAAGGCCACC CATCCTCCCA GCAGTAGCCT       1380

CCCCAACCCT CTCCTTAGCC GTACATTAGC CACTTCAAGT CTGCCTCTTA GCCCCACCCT       1440

AGCCTCTAAT TCACAGGGTT CTCAAGGTGA TCAGAGGACT GATCGCTCCG CTCCTATCCG       1500

TTCTGCTTCC CAAGCTGAAG AAGAACCTAG TGTGGAACCA GTCAAGAAAT CCCAGCACCG       1560

CTCTTCCTCC TCAGCCCCAC ACCACAACCA TCGCAGTGGG ACAAGTCGCG GCCTCTCCAG       1620

GCAAGAGACA TTTGACTCGG AAACCCAGGA GAGTCGAGAC TCTGCCTACG TAGAGCCAAA       1680
```

-continued

```
GGAAGATTAT TCCCATGACC ACGTGGACCA CTATGCCTCA CACCGTGACC ACAACCACAG    1740

AGACGAGACC CACGGGAGCA GTGACCACAG ACACAGGGAG TCCCGGCACC GTTCCCGGGA    1800

CGTGGATCGA GAGCAGGACC ACAACGAGTG CAACAAGCAG CGCAGCCGTC ATAAATCCAA    1860

GGATGGCTAC TGTGAAAAGG ATGGAGAAGT GATATCAAAA AAACGGAATG AGGCTGGGGA    1920

GTGGCACAGG GATGTTCACA TCCCCCAATG AGTGGCGCCC TCGCGTGTTT TTTNTTTTTT    1980

TGGGGGGGNG TCTTGTTTAT CTAACAGCAC CCCCAAAAAA AAATGTCTGG GGGGTCTACA    2040

CTACACACAT TTGTGCTCTC TCTTGTAATA TTGGGTATTA TTGCTGGCGC TCGTATAGCA    2100

ATAGCATGGA TAGAGTATTG AGATACTTCC TCTGGGCAA GTGCTACATA AATTGCCCTG     2160

GTATGGCTAC AGCCCTCCGG GTGCATACTG CTCTCTACAA AAACTGGGGG GGGTCGCTCC    2220

CACTAGAACA ACTTCTTGCC CCCACCCAGG GCGAATGTTA AGTG                     2264
```

(2) INFORMATION FOR SEQ ID NO:27:

(i) SEQUENCE CHARACTERISTICS:
        (A) LENGTH: 7089 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 166..6978
        (D) OTHER INFORMATION: /standard_name= "Alpha-1E-3"

(xi) SEQUENCE DESCRIPTION: SEQ ID NO:27:

```
GCTGCTGCTG CCTCTCCGAA GAGCTCGCGG AGCTCCCCAG AGGCGGTGGT CCCCGTGCTT     60

GTCTGGATGC GGCTCTGAGT CTCCGTGTGT CTTTCTGCTT GTTGCTGTGT GCGGGTGTTC    120

GGCCGCGATC ACCTTTGTGT GTCTTCTGTC TGTTTAAACC TCAGG ATG GCT CGC        174
                                                  Met Ala Arg
                                                    1

TTC GGG GAG GCG GTG GTC GCC AGG CCA GGG TCC GGC GAT GGA GAC TCG      222
Phe Gly Glu Ala Val Val Ala Arg Pro Gly Ser Gly Asp Gly Asp Ser
      5                  10                 15

GAC CAG AGC AGG AAC CGG CAA GGA ACC CCC GTG CCG GCC TCG GGG CAG      270
Asp Gln Ser Arg Asn Arg Gln Gly Thr Pro Val Pro Ala Ser Gly Gln
 20                  25                  30                  35

GCG GCC GCC TAC AAG CAG ACG AAA GCA CAG AGG GCG CGG ACT ATG GCT      318
Ala Ala Ala Tyr Lys Gln Thr Lys Ala Gln Arg Ala Arg Thr Met Ala
             40                  45                  50

TTG TAC AAC CCC ATT CCC GTC CGG CAG AAC TGT TTC ACC GTC AAC AGA      366
Leu Tyr Asn Pro Ile Pro Val Arg Gln Asn Cys Phe Thr Val Asn Arg
                 55                  60                  65

TCC CTG TTC ATC TTC GGA GAA GAT AAC ATT GTC AGG AAA TAT GCC AAG      414
Ser Leu Phe Ile Phe Gly Glu Asp Asn Ile Val Arg Lys Tyr Ala Lys
         70                  75                  80

AAG CTC ATC GAT TGG CCG CCA TTT GAG TAC ATG ATC CTG GCC ACC ATC      462
Lys Leu Ile Asp Trp Pro Pro Phe Glu Tyr Met Ile Leu Ala Thr Ile
     85                  90                  95

ATT GCC AAC TGC ATC GTC CTG GCC CTG GAG CAG CAT CTT CCT GAG GAT      510
Ile Ala Asn Cys Ile Val Leu Ala Leu Glu Gln His Leu Pro Glu Asp
100                 105                 110                 115

GAC AAG ACC CCC ATG TCC CGA AGA CTG GAG AAG ACA GAA CCT TAT TTC      558
Asp Lys Thr Pro Met Ser Arg Arg Leu Glu Lys Thr Glu Pro Tyr Phe
                120                 125                 130
```

```
ATT GGG ATC TTT TGC TTT GAA GCT GGG ATC AAA ATT GTG GCC CTG GGG    606
Ile Gly Ile Phe Cys Phe Glu Ala Gly Ile Lys Ile Val Ala Leu Gly
            135                 140                 145

TTC ATC TTC CAT AAG GGC TCT TAC CTC CGC AAT GGC TGG AAT GTC ATG    654
Phe Ile Phe His Lys Gly Ser Tyr Leu Arg Asn Gly Trp Asn Val Met
        150                 155                 160

GAC TTC ATC GTG GTC CTC AGT GGC ATC CTG GCC ACT GCA GGA ACC CAC    702
Asp Phe Ile Val Val Leu Ser Gly Ile Leu Ala Thr Ala Gly Thr His
    165                 170                 175

TTC AAT ACT CAC GTG GAC CTG AGG ACC CTC CGG GCT GTG CGT GTC CTG    750
Phe Asn Thr His Val Asp Leu Arg Thr Leu Arg Ala Val Arg Val Leu
180                 185                 190                 195

CGG CCT TTG AAG CTC GTG TCA GGG ATA CCT AGC CTG CAG ATT GTG TTG    798
Arg Pro Leu Lys Leu Val Ser Gly Ile Pro Ser Leu Gln Ile Val Leu
                200                 205                 210

AAG TCC ATC ATG AAG GCC ATG GTA CCT CTT CTG CAG ATT GGC CTT CTG    846
Lys Ser Ile Met Lys Ala Met Val Pro Leu Leu Gln Ile Gly Leu Leu
            215                 220                 225

CTC TTC TTT GCC ATC CTG ATG TTT GCT ATC ATT GGT TTG GAG TTC TAC    894
Leu Phe Phe Ala Ile Leu Met Phe Ala Ile Ile Gly Leu Glu Phe Tyr
        230                 235                 240

AGT GGC AAG TTA CAT CGA GCG TGC TTC ATG AAC AAT TCA GGT ATT CTA    942
Ser Gly Lys Leu His Arg Ala Cys Phe Met Asn Asn Ser Gly Ile Leu
    245                 250                 255

GAA GGA TTT GAC CCC CCT CAC CCA TGT GGT GTG CAG GGC TGC CCA GCT    990
Glu Gly Phe Asp Pro Pro His Pro Cys Gly Val Gln Gly Cys Pro Ala
260                 265                 270                 275

GGT TAT GAA TGC AAG GAC TGG ATC GGC CCC AAT GAT GGG ATC ACC CAG   1038
Gly Tyr Glu Cys Lys Asp Trp Ile Gly Pro Asn Asp Gly Ile Thr Gln
                280                 285                 290

TTT GAT AAC ATC CTT TTT GCT GTG CTG ACT GTC TTC CAG TGC ATC ACC   1086
Phe Asp Asn Ile Leu Phe Ala Val Leu Thr Val Phe Gln Cys Ile Thr
            295                 300                 305

ATG GAA GGG TGG ACC ACT GTG CTG TAC AAT ACC AAT GAT GCC TTA GGA   1134
Met Glu Gly Trp Thr Thr Val Leu Tyr Asn Thr Asn Asp Ala Leu Gly
        310                 315                 320

GCC ACC TGG AAT TGG CTG TAC TTC ATC CCC CTC ATC ATC ATT GGA TCC   1182
Ala Thr Trp Asn Trp Leu Tyr Phe Ile Pro Leu Ile Ile Ile Gly Ser
    325                 330                 335

TTC TTT GTT CTC AAC CTA GTC CTG GGA GTG CTT TCC GGG GAA TTT GCC   1230
Phe Phe Val Leu Asn Leu Val Leu Gly Val Leu Ser Gly Glu Phe Ala
340                 345                 350                 355

AAA GAG AGA GAG AGA GTG GAG AAC CGA AGG GCT TTC ATG AAG CTG CGG   1278
Lys Glu Arg Glu Arg Val Glu Asn Arg Arg Ala Phe Met Lys Leu Arg
                360                 365                 370

CGC CAG CAG CAG ATT GAG CGT GAG CTG AAT GGC TAC CGT GCC TGG ATA   1326
Arg Gln Gln Gln Ile Glu Arg Glu Leu Asn Gly Tyr Arg Ala Trp Ile
            375                 380                 385

GAC AAA GCA GAG GAA GTC ATG CTC GCT GAA GAA AAT AAA AAT GCT GGA   1374
Asp Lys Ala Glu Glu Val Met Leu Ala Glu Glu Asn Lys Asn Ala Gly
        390                 395                 400

ACA TCC GCC TTA GAA GTG CTT CGA AGG GCA ACC ATC AAG AGG AGC CGG   1422
Thr Ser Ala Leu Glu Val Leu Arg Arg Ala Thr Ile Lys Arg Ser Arg
    405                 410                 415

ACA GAG GCC ATG ACT CGA GAC TCC AGT GAT GAG CAC TGT GTT GAT ATC   1470
Thr Glu Ala Met Thr Arg Asp Ser Ser Asp Glu His Cys Val Asp Ile
420                 425                 430                 435

TCC TCT GTG GGC ACA CCT CTG GCC CGA GCC AGT ATC AAA AGT GCA AAG   1518
Ser Ser Val Gly Thr Pro Leu Ala Arg Ala Ser Ile Lys Ser Ala Lys
                440                 445                 450
```

-continued

```
GTA GAC GGG GTC TCT TAT TTC CGG CAC AAG GAA AGG CTT CTG CGC ATC    1566
Val Asp Gly Val Ser Tyr Phe Arg His Lys Glu Arg Leu Leu Arg Ile
            455                 460                 465

TCC ATT CGC CAC ATG GTT AAA TCC CAG GTG TTT TAC TGG ATT GTG CTG    1614
Ser Ile Arg His Met Val Lys Ser Gln Val Phe Tyr Trp Ile Val Leu
            470                 475                 480

AGC CTT GTG GCA CTC AAC ACT GCC TGT GTG GCC ATT GTC CAT CAC AAC    1662
Ser Leu Val Ala Leu Asn Thr Ala Cys Val Ala Ile Val His His Asn
            485                 490                 495

CAG CCC CAG TGG CTC ACC CAC CTC CTC TAC TAT GCA GAA TTT CTG TTT    1710
Gln Pro Gln Trp Leu Thr His Leu Leu Tyr Tyr Ala Glu Phe Leu Phe
500                 505                 510                 515

CTG GGA CTC TTC CTC TTG GAG ATG TCC CTG AAG ATG TAT GGC ATG GGG    1758
Leu Gly Leu Phe Leu Leu Glu Met Ser Leu Lys Met Tyr Gly Met Gly
                520                 525                 530

CCT CGC CTT TAT TTT CAC TCT TCA TTC AAC TGC TTT GAT TTT GGG GTC    1806
Pro Arg Leu Tyr Phe His Ser Ser Phe Asn Cys Phe Asp Phe Gly Val
                535                 540                 545

ACA GTG GGC AGT ATC TTT GAA GTG GTC TGG GCA ATC TTC AGA CCT GGT    1854
Thr Val Gly Ser Ile Phe Glu Val Val Trp Ala Ile Phe Arg Pro Gly
                550                 555                 560

ACG TCT TTT GGA ATC AGT GTC TTG CGA GCC CTC CGG CTT CTA AGA ATA    1902
Thr Ser Phe Gly Ile Ser Val Leu Arg Ala Leu Arg Leu Leu Arg Ile
            565                 570                 575

TTT AAA ATA ACC AAG TAT TGG GCT TCC CTA CGG AAT TTG GTG GTC TCC    1950
Phe Lys Ile Thr Lys Tyr Trp Ala Ser Leu Arg Asn Leu Val Val Ser
580                 585                 590                 595

TTG ATG AGC TCA ATG AAG TCT ATC ATC AGT TTG CTT TTC CTC CTC TTC    1998
Leu Met Ser Ser Met Lys Ser Ile Ile Ser Leu Leu Phe Leu Leu Phe
                600                 605                 610

CTC TTC ATC GTT GTC TTT GCT CTC CTA GGA ATG CAG TTA TTT GGA GGC    2046
Leu Phe Ile Val Val Phe Ala Leu Leu Gly Met Gln Leu Phe Gly Gly
                615                 620                 625

AGG TTT AAC TTT AAT GAT GGG ACT CCT TCG GCA AAT TTT GAT ACC TTC    2094
Arg Phe Asn Phe Asn Asp Gly Thr Pro Ser Ala Asn Phe Asp Thr Phe
            630                 635                 640

CCT GCA GCC ATC ATG ACT GTG TTC CAG ATC CTG ACG GGT GAG GAC TGG    2142
Pro Ala Ala Ile Met Thr Val Phe Gln Ile Leu Thr Gly Glu Asp Trp
645                 650                 655

AAT GAG GTG ATG TAC AAT GGG ATC CGC TCC CAG GGT GGG GTC AGC TCA    2190
Asn Glu Val Met Tyr Asn Gly Ile Arg Ser Gln Gly Gly Val Ser Ser
660                 665                 670                 675

GGC ATG TGG TCT GCC ATC TAC TTC ATT GTG CTC ACC TTG TTT GGC AAC    2238
Gly Met Trp Ser Ala Ile Tyr Phe Ile Val Leu Thr Leu Phe Gly Asn
                680                 685                 690

TAC ACG CTA CTG AAT GTG TTC TTG GCT ATC GCT GTG GAT AAT CTC GCC    2286
Tyr Thr Leu Leu Asn Val Phe Leu Ala Ile Ala Val Asp Asn Leu Ala
            695                 700                 705

AAC GCC CAG GAA CTG ACC AAG GAT GAA CAG GAG GAA GAG GCC TTC        2334
Asn Ala Gln Glu Leu Thr Lys Asp Glu Gln Glu Glu Glu Ala Phe
            710                 715                 720

AAC CAG AAA CAT GCA CTG CAG AAG GCC AAG GAG GTC AGC CCG ATG TCT    2382
Asn Gln Lys His Ala Leu Gln Lys Ala Lys Glu Val Ser Pro Met Ser
            725                 730                 735

GCA CCC AAC ATG CCT TCG ATC GAA AGA GAC AGA AGG AGA AGA CAC CAC    2430
Ala Pro Asn Met Pro Ser Ile Glu Arg Asp Arg Arg Arg Arg His His
740                 745                 750                 755

ATG TCG ATG TGG GAG CCA CGC AGC AGC CAC CTG AGG GAG CGG AGG CGC    2478
Met Ser Met Trp Glu Pro Arg Ser Ser His Leu Arg Glu Arg Arg Arg
```

-continued

|   |   |
|---|---|
| 760 765 770 | |
| CGG CAC CAC ATG TCC GTG TGG GAG CAG CGT ACC AGC CAG CTG AGG AAG<br>Arg His His Met Ser Val Trp Glu Gln Arg Thr Ser Gln Leu Arg Lys<br>775 780 785 | 2526 |
| CAC ATG CAG ATG TCC AGC CAG GAG GCC CTC AAC AGA GAG GAG GCG CCG<br>His Met Gln Met Ser Ser Gln Glu Ala Leu Asn Arg Glu Glu Ala Pro<br>790 795 800 | 2574 |
| ACC ATG AAC CCG CTC AAC CCC CTC AAC CCG CTC AGC TCC CTC AAC CCG<br>Thr Met Asn Pro Leu Asn Pro Leu Asn Pro Leu Ser Ser Leu Asn Pro<br>805 810 815 | 2622 |
| CTC AAT GCC CAC CCC AGC CTT TAT CGG CGA CCC AGG GCC ATT GAG GGC<br>Leu Asn Ala His Pro Ser Leu Tyr Arg Arg Pro Arg Ala Ile Glu Gly<br>820 825 830 835 | 2670 |
| CTG GCC CTG GGC CTG GCC CTG GAG AAG TTC GAG GAG GAG CGC ATC AGC<br>Leu Ala Leu Gly Leu Ala Leu Glu Lys Phe Glu Glu Glu Arg Ile Ser<br>840 845 850 | 2718 |
| CGT GGG GGG TCC CTC AAG GGG GAT GGA GGG GAC CGA TCC AGT GCC CTG<br>Arg Gly Gly Ser Leu Lys Gly Asp Gly Gly Asp Arg Ser Ser Ala Leu<br>855 860 865 | 2766 |
| GAC AAC CAG AGG ACC CCT TTG TCC CTG GGC CAG CGG GAG CCA CCA TGG<br>Asp Asn Gln Arg Thr Pro Leu Ser Leu Gly Gln Arg Glu Pro Pro Trp<br>870 875 880 | 2814 |
| CTG GCC AGG CCC TGT CAT GGA AAC TGT GAC CCG ACT CAG CAG GAG GCA<br>Leu Ala Arg Pro Cys His Gly Asn Cys Asp Pro Thr Gln Gln Glu Ala<br>885 890 895 | 2862 |
| GGG GGA GGA GAG GCT GTG GTG ACC TTT GAG GAC CGG GCC AGG CAC AGG<br>Gly Gly Gly Glu Ala Val Val Thr Phe Glu Asp Arg Ala Arg His Arg<br>900 905 910 915 | 2910 |
| CAG AGC CAA CGG CGC AGC CGG CAT CGC CGC GTC AGG ACA GAA GGC AAG<br>Gln Ser Gln Arg Arg Ser Arg His Arg Arg Val Arg Thr Glu Gly Lys<br>920 925 930 | 2958 |
| GAG TCC TCT TCA GCC TCC CGG AGC AGG TCT GCC AGC CAG GAA CGC AGT<br>Glu Ser Ser Ser Ala Ser Arg Ser Arg Ser Ala Ser Gln Glu Arg Ser<br>935 940 945 | 3006 |
| CTG GAT GAA GCC ATG CCC ACT GAA GGG GAG AAG GAC CAT GAG CTC AGG<br>Leu Asp Glu Ala Met Pro Thr Glu Gly Glu Lys Asp His Glu Leu Arg<br>950 955 960 | 3054 |
| GGC AAC CAT GGT GCC AAG GAG CCA ACG ATC CAA GAA GAG AGA GCC CAG<br>Gly Asn His Gly Ala Lys Glu Pro Thr Ile Gln Glu Glu Arg Ala Gln<br>965 970 975 | 3102 |
| GAT TTA AGG AGG ACC AAC AGT CTG ATG GTG TCC AGA GGC TCC GGG CTG<br>Asp Leu Arg Arg Thr Asn Ser Leu Met Val Ser Arg Gly Ser Gly Leu<br>980 985 990 995 | 3150 |
| GCA GGA GGC CTT GAT GAG GCT GAC ACC CCC TTA GTC CTG CCC CAT CCT<br>Ala Gly Gly Leu Asp Glu Ala Asp Thr Pro Leu Val Leu Pro His Pro<br>1000 1005 1010 | 3198 |
| GAG CTG GAA GTG GGG AAG CAC GTG GTG CTG ACG GAG CAG GAG CCA GAA<br>Glu Leu Glu Val Gly Lys His Val Val Leu Thr Glu Gln Glu Pro Glu<br>1015 1020 1025 | 3246 |
| GGC AGT AGT GAG CAG GCC CTG CTG GGG AAT GTG CAG CTA GAC ATG GGC<br>Gly Ser Ser Glu Gln Ala Leu Leu Gly Asn Val Gln Leu Asp Met Gly<br>1030 1035 1040 | 3294 |
| CGG GTC ATC AGC CAG AGC GAG CCT GAC CTC TCC TGC ATC ACG GCC AAC<br>Arg Val Ile Ser Gln Ser Glu Pro Asp Leu Ser Cys Ile Thr Ala Asn<br>1045 1050 1055 | 3342 |
| ACG GAC AAG GCC ACC ACC GAG AGC ACC AGC GTC ACC GTC GCC ATC CCC<br>Thr Asp Lys Ala Thr Thr Glu Ser Thr Ser Val Thr Val Ala Ile Pro<br>1060 1065 1070 1075 | 3390 |
| GAC GTG GAC CCC TTG GTG GAC TCA ACC GTG GTG CAC ATT AGC AAC AAG | 3438 |

-continued

```
Asp Val Asp Pro Leu Val Asp Ser Thr Val Val His Ile Ser Asn Lys
            1080                1085                1090

ACG GAT GGG GAA GCC AGT CCC TTG AAG GAG GCA GAG ATC AGA GAG GAT     3486
Thr Asp Gly Glu Ala Ser Pro Leu Lys Glu Ala Glu Ile Arg Glu Asp
            1095                1100                1105

GAG GAG GAG GTG GAG AAG AAG AAG CAG AAG AAG GAG AAG CGT GAG ACA     3534
Glu Glu Glu Val Glu Lys Lys Lys Gln Lys Lys Glu Lys Arg Glu Thr
            1110                1115                1120

GGC AAA GCC ATG GTG CCC CAC AGC TCA ATG TTC ATC TTC AGC ACC ACC     3582
Gly Lys Ala Met Val Pro His Ser Ser Met Phe Ile Phe Ser Thr Thr
        1125                1130                1135

AAC CCG ATC CGG AGG GCC TGC CAC TAC ATC GTG AAC CTG CGC TAC TTT     3630
Asn Pro Ile Arg Arg Ala Cys His Tyr Ile Val Asn Leu Arg Tyr Phe
1140                1145                1150                1155

GAG ATG TGC ATC CTC CTG GTG ATT GCA GCC AGC AGC ATC GCC CTG GCG     3678
Glu Met Cys Ile Leu Leu Val Ile Ala Ala Ser Ser Ile Ala Leu Ala
            1160                1165                1170

GCA GAG GAC CCC GTC CTG ACC AAC TCG GAG CGC AAC AAA GTC CTG AGG     3726
Ala Glu Asp Pro Val Leu Thr Asn Ser Glu Arg Asn Lys Val Leu Arg
            1175                1180                1185

TAT TTT GAC TAT GTG TTC ACG GGC GTG TTC ACC TTT GAG ATG GTT ATA     3774
Tyr Phe Asp Tyr Val Phe Thr Gly Val Phe Thr Phe Glu Met Val Ile
            1190                1195                1200

AAG ATG ATA GAC CAA GGC TTG ATC CTG CAG GAT GGG TCC TAC TTC CGA     3822
Lys Met Ile Asp Gln Gly Leu Ile Leu Gln Asp Gly Ser Tyr Phe Arg
        1205                1210                1215

GAC TTG TGG AAC ATC CTG GAC TTT GTG GTG GTC GTT GGC GCA TTG GTG     3870
Asp Leu Trp Asn Ile Leu Asp Phe Val Val Val Val Gly Ala Leu Val
1220                1225                1230                1235

GCC TTT GCT CTG GCG AAC GCT TTG GGA ACC AAC AAA GGA CGG GAC ATC     3918
Ala Phe Ala Leu Ala Asn Ala Leu Gly Thr Asn Lys Gly Arg Asp Ile
            1240                1245                1250

AAG ACC ATC AAG TCT CTG CGG GTG CTC CGA GTT CTA AGG CCA CTG AAA     3966
Lys Thr Ile Lys Ser Leu Arg Val Leu Arg Val Leu Arg Pro Leu Lys
        1255                1260                1265

ACC ATC AAG CGC TTG CCC AAG CTC AAG GCC GTC TTC GAC TGC GTA GTG     4014
Thr Ile Lys Arg Leu Pro Lys Leu Lys Ala Val Phe Asp Cys Val Val
            1270                1275                1280

ACC TCC TTG AAG AAT GTC TTC AAC ATA CTC ATT GTG TAC AAG CTC TTC     4062
Thr Ser Leu Lys Asn Val Phe Asn Ile Leu Ile Val Tyr Lys Leu Phe
        1285                1290                1295

ATG TTC ATC TTT GCT GTC ATC GCA GTT CAG CTC TTC AAG GGA AAG TTC     4110
Met Phe Ile Phe Ala Val Ile Ala Val Gln Leu Phe Lys Gly Lys Phe
1300                1305                1310                1315

TTT TAT TGC ACG GAC AGT TCC AAG GAC ACA GAG AAG GAG TGC ATA GGC     4158
Phe Tyr Cys Thr Asp Ser Ser Lys Asp Thr Glu Lys Glu Cys Ile Gly
            1320                1325                1330

AAC TAT GTA GAT CAC GAG AAA AAC AAG ATG GAG GTG AAG GGC CGG GAA     4206
Asn Tyr Val Asp His Glu Lys Asn Lys Met Glu Val Lys Gly Arg Glu
            1335                1340                1345

TGG AAG CGC CAT GAA TTC CAC TAC GAC AAC ATT ATC TGG GCC CTG CTG     4254
Trp Lys Arg His Glu Phe His Tyr Asp Asn Ile Ile Trp Ala Leu Leu
            1350                1355                1360

ACC CTC TTC ACC GTC TCC ACA GGG GAA GGA TGG CCT CAA GTT CTG CAG     4302
Thr Leu Phe Thr Val Ser Thr Gly Glu Gly Trp Pro Gln Val Leu Gln
        1365                1370                1375

CAC TCT GTA GAT GTG ACA GAG GAA GAC CGA GGC CCA AGC CGC AGC AAC     4350
His Ser Val Asp Val Thr Glu Glu Asp Arg Gly Pro Ser Arg Ser Asn
1380                1385                1390                1395
```

-continued

| | |
|---|---|
| CGC ATG GAG ATG TCT ATC TTT TAT GTA GTC TAC TTT GTG GTC TTC CCC<br>Arg Met Glu Met Ser Ile Phe Tyr Val Val Tyr Phe Val Val Phe Pro<br>             1400                  1405               1410 | 4398 |
| TTC TTC TTT GTC AAT ATC TTT GTG GCT CTC ATC ATC ATC ACC TTC CAG<br>Phe Phe Phe Val Asn Ile Phe Val Ala Leu Ile Ile Ile Thr Phe Gln<br>             1415                  1420               1425 | 4446 |
| GAG CAA GGG GAT AAG ATG ATG GAG GAG TGC AGC CTG GAG AAG AAT GAG<br>Glu Gln Gly Asp Lys Met Met Glu Glu Cys Ser Leu Glu Lys Asn Glu<br>             1430                  1435               1440 | 4494 |
| AGG GCG TGC ATC GAC TTC GCC ATC AGC GCC AAA CCT CTC ACC CGC TAC<br>Arg Ala Cys Ile Asp Phe Ala Ile Ser Ala Lys Pro Leu Thr Arg Tyr<br>             1445                  1450               1455 | 4542 |
| ATG CCG CAG AAC AGA CAC ACC TTC CAG TAC CGC GTG TGG CAC TTT GTG<br>Met Pro Gln Asn Arg His Thr Phe Gln Tyr Arg Val Trp His Phe Val<br>1460                  1465                  1470               1475 | 4590 |
| GTG TCT CCG TCC TTT GAG TAC ACC ATT ATG GCC ATG ATC GCC TTG AAT<br>Val Ser Pro Ser Phe Glu Tyr Thr Ile Met Ala Met Ile Ala Leu Asn<br>             1480                  1485               1490 | 4638 |
| ACT GTT GTG CTG ATG ATG AAG TAT TAT TCT GCT CCC TGT ACC TAT GAG<br>Thr Val Val Leu Met Met Lys Tyr Tyr Ser Ala Pro Cys Thr Tyr Glu<br>             1495                  1500               1505 | 4686 |
| CTG GCC CTG AAG TAC CTG AAT ATC GCC TTC ACC ATG GTG TTT TCC CTG<br>Leu Ala Leu Lys Tyr Leu Asn Ile Ala Phe Thr Met Val Phe Ser Leu<br>             1510                  1515               1520 | 4734 |
| GAA TGT GTC CTG AAG GTC ATC GCT TTT GGC TTT TTG AAC TAT TTC CGA<br>Glu Cys Val Leu Lys Val Ile Ala Phe Gly Phe Leu Asn Tyr Phe Arg<br>             1525                  1530               1535 | 4782 |
| GAC ACC TGG AAT ATC TTT GAC TTC ATC ACC GTG ATT GGC AGT ATC ACA<br>Asp Thr Trp Asn Ile Phe Asp Phe Ile Thr Val Ile Gly Ser Ile Thr<br>1540                  1545                  1550               1555 | 4830 |
| GAA ATT ATC CTG ACA GAC AGC AAG CTG GTG AAC ACC AGT GGC TTC AAT<br>Glu Ile Ile Leu Thr Asp Ser Lys Leu Val Asn Thr Ser Gly Phe Asn<br>             1560                  1565               1570 | 4878 |
| ATG AGC TTT CTG AAG CTC TTC CGA GCT GCC CGC CTC ATA AAG CTC CTG<br>Met Ser Phe Leu Lys Leu Phe Arg Ala Ala Arg Leu Ile Lys Leu Leu<br>             1575                  1580               1585 | 4926 |
| CGT CAG GGC TAT ACC ATA CGC ATT TTG CTG TGG ACC TTT GTG CAG TCC<br>Arg Gln Gly Tyr Thr Ile Arg Ile Leu Leu Trp Thr Phe Val Gln Ser<br>             1590                  1595               1600 | 4974 |
| TTT AAG GCC CTC CCT TAT GTC TGC CTT TTA ATT GCC ATG CTT TTC TTC<br>Phe Lys Ala Leu Pro Tyr Val Cys Leu Leu Ile Ala Met Leu Phe Phe<br>             1605                  1610               1615 | 5022 |
| ATT TAT GCC ATC ATT GGG ATG CAG GTA TTT GGA AAC ATA AAA TTA GAC<br>Ile Tyr Ala Ile Ile Gly Met Gln Val Phe Gly Asn Ile Lys Leu Asp<br>1620                  1625                  1630               1635 | 5070 |
| GAG GAG AGT CAC ATC AAC CGG CAC AAC AAC TTC CGG AGT TTC TTT GGG<br>Glu Glu Ser His Ile Asn Arg His Asn Asn Phe Arg Ser Phe Phe Gly<br>             1640                  1645               1650 | 5118 |
| TCC CTA ATG CTA CTC TTC AGG AGT GCC ACA GGT GAG GCC TGG CAG GAG<br>Ser Leu Met Leu Leu Phe Arg Ser Ala Thr Gly Glu Ala Trp Gln Glu<br>             1655                  1660               1665 | 5166 |
| ATT ATG CTG TCA TGC CTT GGG GAG AAG GGC TGT GAG CCT GAC ACC ACC<br>Ile Met Leu Ser Cys Leu Gly Glu Lys Gly Cys Glu Pro Asp Thr Thr<br>             1670                  1675               1680 | 5214 |
| GCA CCA TCA GGG CAG AAC GAG AAT GAA CGC TGC GGC ACC GAT CTG GCC<br>Ala Pro Ser Gly Gln Asn Glu Asn Glu Arg Cys Gly Thr Asp Leu Ala<br>             1685                  1690               1695 | 5262 |
| TAC GTG TAC TTT GTC TCC TTC ATC TTC TTC TGC TCC TTC TTG ATG CTC<br>Tyr Val Tyr Phe Val Ser Phe Ile Phe Phe Cys Ser Phe Leu Met Leu<br>1700                  1705                  1710               1715 | 5310 |

```
                                            -continued

AAC CTG TTT GTG GCC GTC ATC ATG GAC AAC TTT GAG TAC CTG ACT CGG       5358
Asn Leu Phe Val Ala Val Ile Met Asp Asn Phe Glu Tyr Leu Thr Arg
            1720                1725                1730

GAC TCC TCC ATC CTG GGG CCT CAC CAC TTG GAC GAG TTT GTC CGC GTC       5406
Asp Ser Ser Ile Leu Gly Pro His His Leu Asp Glu Phe Val Arg Val
            1735                1740                1745

TGG GCA GAA TAT GAC CGA GCA GCA TGT GGC CGC ATC CAT TAC ACT GAG       5454
Trp Ala Glu Tyr Asp Arg Ala Ala Cys Gly Arg Ile His Tyr Thr Glu
            1750                1755                1760

ATG TAT GAA ATG CTG ACT CTC ATG TCA CCT CCG CTA GGC CTC GGC AAG       5502
Met Tyr Glu Met Leu Thr Leu Met Ser Pro Pro Leu Gly Leu Gly Lys
            1765                1770                1775

AGA TGT CCC TCC AAA GTG GCA TAT AAG AGG TTG GTC CTG ATG AAC ATG       5550
Arg Cys Pro Ser Lys Val Ala Tyr Lys Arg Leu Val Leu Met Asn Met
1780                1785                1790                1795

CCA GTA GCT GAG GAC ATG ACG GTC CAC TTC ACC TCC ACA CTT ATG GCT       5598
Pro Val Ala Glu Asp Met Thr Val His Phe Thr Ser Thr Leu Met Ala
            1800                1805                1810

CTG ATC CGG ACA GCT CTG GAC ATT AAA ATT GCC AAA GGT GGT GCA GAC       5646
Leu Ile Arg Thr Ala Leu Asp Ile Lys Ile Ala Lys Gly Gly Ala Asp
            1815                1820                1825

AGG CAG CAG CTA GAC TCA GAG CTA CAA AAG GAG ACC CTA GCC ATC TGG       5694
Arg Gln Gln Leu Asp Ser Glu Leu Gln Lys Glu Thr Leu Ala Ile Trp
            1830                1835                1840

CCT CAC CTA TCC CAG AAG ATG CTG GAT CTG CTT GTG CCC ATG CCC AAA       5742
Pro His Leu Ser Gln Lys Met Leu Asp Leu Leu Val Pro Met Pro Lys
            1845                1850                1855

GCC TCT GAC CTG ACT GTG GGC AAA ATC TAT GCA GCA ATG ATG ATC ATG       5790
Ala Ser Asp Leu Thr Val Gly Lys Ile Tyr Ala Ala Met Met Ile Met
1860                1865                1870                1875

GAC TAC TAT AAG CAG AGT AAG GTG AAG AAG CAG AGG CAG CAG CTG GAG       5838
Asp Tyr Tyr Lys Gln Ser Lys Val Lys Lys Gln Arg Gln Gln Leu Glu
            1880                1885                1890

GAA CAG AAA AAT GCC CCC ATG TTC CAG CGC ATG GAG CCT TCA TCT CTG       5886
Glu Gln Lys Asn Ala Pro Met Phe Gln Arg Met Glu Pro Ser Ser Leu
            1895                1900                1905

CCT CAG GAG ATC ATT GCT AAT GCC AAA GCC CTG CCT TAC CTC CAG CAG       5934
Pro Gln Glu Ile Ile Ala Asn Ala Lys Ala Leu Pro Tyr Leu Gln Gln
            1910                1915                1920

GAC CCC GTT TCA GGC CTG AGT GGC CGG AGT GGA TAC CCT TCG ATG AGT       5982
Asp Pro Val Ser Gly Leu Ser Gly Arg Ser Gly Tyr Pro Ser Met Ser
            1925                1930                1935

CCA CTC TCT CCC CAG GAT ATA TTC CAG TTG GCT TGT ATG GAC CCC GCC       6030
Pro Leu Ser Pro Gln Asp Ile Phe Gln Leu Ala Cys Met Asp Pro Ala
1940                1945                1950                1955

GAT GAC GGA CAG TTC CAA GAA CGG CAG TCT CTG GTG GTG ACA GAC CCT       6078
Asp Asp Gly Gln Phe Gln Glu Arg Gln Ser Leu Val Val Thr Asp Pro
            1960                1965                1970

AGC TCC ATG AGA CGT TCA TTT TCC ACT ATT CGG GAT AAG CGT TCA AAT       6126
Ser Ser Met Arg Arg Ser Phe Ser Thr Ile Arg Asp Lys Arg Ser Asn
            1975                1980                1985

TCC TCG TGG TTG GAG GAA TTC TCC ATG GAG CGA AGC AGT GAA AAT ACC       6174
Ser Ser Trp Leu Glu Glu Phe Ser Met Glu Arg Ser Ser Glu Asn Thr
            1990                1995                2000

TAC AAG TCC CGT CGC CGG AGT TAC CAC TCC TCC TTG CGG CTG TCA GCC       6222
Tyr Lys Ser Arg Arg Arg Ser Tyr His Ser Ser Leu Arg Leu Ser Ala
            2005                2010                2015

CAC CGC CTG AAC TCT GAT TCA GGC CAC AAG TCT GAC ACT CAC CCC TCA       6270
His Arg Leu Asn Ser Asp Ser Gly His Lys Ser Asp Thr His Pro Ser
```

```
                      2020                2025                2030                2035

GGG GGC AGG GAG CGG CGA CGA TCA AAA GAG CGA AAG CAT CTT CTC TCT         6318
Gly Gly Arg Glu Arg Arg Arg Ser Lys Glu Arg Lys His Leu Leu Ser
             2040                2045                2050

CCT GAT GTC TCC CGC TGC AAT TCA GAA GAG CGA GGG ACC CAG GCT GAC         6366
Pro Asp Val Ser Arg Cys Asn Ser Glu Glu Arg Gly Thr Gln Ala Asp
             2055                2060                2065

TGG GAG TCC CCA GAG CGC CGT CAA TCC AGG TCA CCC AGT GAG GGC AGG         6414
Trp Glu Ser Pro Glu Arg Arg Gln Ser Arg Ser Pro Ser Glu Gly Arg
             2070                2075                2080

TCA CAG ACG CCC AAC AGA CAG GGC ACA GGT TCC CTA AGT GAG AGC TCC         6462
Ser Gln Thr Pro Asn Arg Gln Gly Thr Gly Ser Leu Ser Glu Ser Ser
         2085                2090                2095

ATC CCC TCT GTC TCT GAC ACC AGC ACC CCA AGA AGA AGT CGT CGG CAG         6510
Ile Pro Ser Val Ser Asp Thr Ser Thr Pro Arg Arg Ser Arg Arg Gln
2100                2105                2110                2115

CTC CCA CCC GTC CCG CCA AAG CCC CGG CCC CTC CTT TCC TAC AGC TCC         6558
Leu Pro Pro Val Pro Pro Lys Pro Arg Pro Leu Leu Ser Tyr Ser Ser
             2120                2125                2130

CTG ATT CGA CAC GCG GGC AGC ATC TCT CCA CCT GCT GAT GGA AGC GAG         6606
Leu Ile Arg His Ala Gly Ser Ile Ser Pro Pro Ala Asp Gly Ser Glu
             2135                2140                2145

GAG GGC TCC CCG CTG ACC TCC CAA GCT CTG GAG AGC AAC AAT GCT TGG         6654
Glu Gly Ser Pro Leu Thr Ser Gln Ala Leu Glu Ser Asn Asn Ala Trp
             2150                2155                2160

CTG ACC GAG TCT TCC AAC TCT CCG CAC CCC CAG CAG AGG CAA CAT GCC         6702
Leu Thr Glu Ser Ser Asn Ser Pro His Pro Gln Gln Arg Gln His Ala
         2165                2170                2175

TCC CCA CAG CGC TAC ATC TCC GAG CCC TAC TTG GCC CTG CAC GAA GAC         6750
Ser Pro Gln Arg Tyr Ile Ser Glu Pro Tyr Leu Ala Leu His Glu Asp
2180                2185                2190                2195

TCC CAC GCC TCA GAC TGT GTT GAG GAG GAG ACG CTC ACT TTC GAA GCA         6798
Ser His Ala Ser Asp Cys Val Glu Glu Glu Thr Leu Thr Phe Glu Ala
             2200                2205                2210

GCC GTG GCT ACT AGC CTG GGC CGT TCC AAC ACC ATC GGC TCA GCC CCA         6846
Ala Val Ala Thr Ser Leu Gly Arg Ser Asn Thr Ile Gly Ser Ala Pro
             2215                2220                2225

CCC CTG CGG CAT AGC TGG CAG ATG CCC AAC GGG CAC TAT CGG CGG CGG         6894
Pro Leu Arg His Ser Trp Gln Met Pro Asn Gly His Tyr Arg Arg Arg
             2230                2235                2240

AGG CGC GGG GGG CCT GGG CCA GGC ATG ATG TGT GGG GCT GTC AAC AAC         6942
Arg Arg Gly Gly Pro Gly Pro Gly Met Met Cys Gly Ala Val Asn Asn
             2245                2250                2255

CTG CTA AGT GAC ACG GAA GAA GAT GAC AAA TGC TAGAGGCTGC TCCCCCCTCC       6995
Leu Leu Ser Asp Thr Glu Glu Asp Asp Lys Cys
2260                2265                2270

GATGCATGCT CTTCTCTCAC ATGGAGAAAA CCAAGACAGA ATTGGAAGC CAGTGCGGCC        7055

CCGCGGGGAG GAAGAGGGAA AAGGAAGATG GAAG                                   7089

(2) INFORMATION FOR SEQ ID NO:28:

(i) SEQUENCE CHARACTERISTICS:
        (A) LENGTH: 3636 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
```

-continued

```
        (B) LOCATION: 35..3346
        (D) OTHER INFORMATION: /standard_name= "Alpha-2a"

(ix) FEATURE:
        (A) NAME/KEY: 5'UTR
        (B) LOCATION: 1..34

(ix) FEATURE:
        (A) NAME/KEY: 3'UTR
        (B) LOCATION: 3347..3636

(xi) SEQUENCE DESCRIPTION: SEQ ID NO:28:
```

| | |
|---|---:|
| GCGGGGGAGG GGGCATTGAT CTTCGATCGC GAAG ATG GCT GCT GGC TGC CTG<br>                        Met Ala Ala Gly Cys Leu<br>                         1        5 | 52 |
| CTG GCC TTG ACT CTG ACA CTT TTC CAA TCT TTG CTC ATC GGC CCC TCG<br>Leu Ala Leu Thr Leu Thr Leu Phe Gln Ser Leu Leu Ile Gly Pro Ser<br>        10           15         20 | 100 |
| TCG GAG GAG CCG TTC CCT TCG GCC GTC ACT ATC AAA TCA TGG GTG GAT<br>Ser Glu Glu Pro Phe Pro Ser Ala Val Thr Ile Lys Ser Trp Val Asp<br>    25          30           35 | 148 |
| AAG ATG CAA GAA GAC CTT GTC ACA CTG GCA AAA ACA GCA AGT GGA GTC<br>Lys Met Gln Glu Asp Leu Val Thr Leu Ala Lys Thr Ala Ser Gly Val<br>40          45           50 | 196 |
| AAT CAG CTT GTT GAT ATT TAT GAG AAA TAT CAA GAT TTG TAT ACT GTG<br>Asn Gln Leu Val Asp Ile Tyr Glu Lys Tyr Gln Asp Leu Tyr Thr Val<br>55          60           65         70 | 244 |
| GAA CCA AAT AAT GCA CGC CAG CTG GTA GAA ATT GCA GCC AGG GAT ATT<br>Glu Pro Asn Asn Ala Arg Gln Leu Val Glu Ile Ala Ala Arg Asp Ile<br>        75         80         85 | 292 |
| GAG AAA CTT CTG AGC AAC AGA TCT AAA GCC CTG GTG AGC CTG GCA TTG<br>Glu Lys Leu Leu Ser Asn Arg Ser Lys Ala Leu Val Ser Leu Ala Leu<br>    90          95         100 | 340 |
| GAA GCG GAG AAA GTT CAA GCA GCT CAC CAG TGG AGA GAA GAT TTT GCA<br>Glu Ala Glu Lys Val Gln Ala Ala His Gln Trp Arg Glu Asp Phe Ala<br>        105         110         115 | 388 |
| AGC AAT GAA GTT GTC TAC TAC AAT GCA AAG GAT GAT CTC GAT CCT GAG<br>Ser Asn Glu Val Val Tyr Tyr Asn Ala Lys Asp Asp Leu Asp Pro Glu<br>120          125           130 | 436 |
| AAA AAT GAC AGT GAG CCA GGC AGC CAG AGG ATA AAA CCT GTT TTC ATT<br>Lys Asn Asp Ser Glu Pro Gly Ser Gln Arg Ile Lys Pro Val Phe Ile<br>135          140          145         150 | 484 |
| GAA GAT GCT AAT TTT GGA CGA CAA ATA TCT TAT CAG CAC GCA GCA GTC<br>Glu Asp Ala Asn Phe Gly Arg Gln Ile Ser Tyr Gln His Ala Ala Val<br>          155          160         165 | 532 |
| CAT ATT CCT ACT GAC ATC TAT GAG GGC TCA ACA ATT GTG TTA AAT GAA<br>His Ile Pro Thr Asp Ile Tyr Glu Gly Ser Thr Ile Val Leu Asn Glu<br>        170         175         180 | 580 |
| CTC AAC TGG ACA AGT GCC TTA GAT GAA GTT TTC AAA AAG AAT CGC GAG<br>Leu Asn Trp Thr Ser Ala Leu Asp Glu Val Phe Lys Lys Asn Arg Glu<br>    185          190         195 | 628 |
| GAA GAC CCT TCA TTA TTG TGG CAG GTT TTT GGC AGT GCC ACT GGC CTA<br>Glu Asp Pro Ser Leu Leu Trp Gln Val Phe Gly Ser Ala Thr Gly Leu<br>200          205          210 | 676 |
| GCT CGA TAT TAT CCA GCT TCA CCA TGG GTT GAT AAT AGT AGA ACT CCA<br>Ala Arg Tyr Tyr Pro Ala Ser Pro Trp Val Asp Asn Ser Arg Thr Pro<br>215          220          225         230 | 724 |
| AAT AAG ATT GAC CTT TAT GAT GTA CGC AGA AGA CCA TGG TAC ATC CAA<br>Asn Lys Ile Asp Leu Tyr Asp Val Arg Arg Arg Pro Trp Tyr Ile Gln<br>          235          240         245 | 772 |
| GGA GCT GCA TCT CCT AAA GAC ATG CTT ATT CTG GTG GAT GTG AGT GGA<br>Gly Ala Ala Ser Pro Lys Asp Met Leu Ile Leu Val Asp Val Ser Gly | 820 |

-continued

```
          250               255               260
AGT GTT AGT GGA TTG ACA CTT AAA CTG ATC CGA ACA TCT GTC TCC GAA          868
Ser Val Ser Gly Leu Thr Leu Lys Leu Ile Arg Thr Ser Val Ser Glu
        265               270               275

ATG TTA GAA ACC CTC TCA GAT GAT GAT TTC GTG AAT GTA GCT TCA TTT          916
Met Leu Glu Thr Leu Ser Asp Asp Asp Phe Val Asn Val Ala Ser Phe
        280               285               290

AAC AGC AAT GCT CAG GAT GTA AGC TGT TTT CAG CAC CTT GTC CAA GCA          964
Asn Ser Asn Ala Gln Asp Val Ser Cys Phe Gln His Leu Val Gln Ala
295               300               305               310

AAT GTA AGA AAT AAA AAA GTG TTG AAA GAC GCG GTG AAT AAT ATC ACA         1012
Asn Val Arg Asn Lys Lys Val Leu Lys Asp Ala Val Asn Asn Ile Thr
                315               320               325

GCC AAA GGA ATT ACA GAT TAT AAG AAG GGC TTT AGT TTT GCT TTT GAA         1060
Ala Lys Gly Ile Thr Asp Tyr Lys Lys Gly Phe Ser Phe Ala Phe Glu
        330               335               340

CAG CTG CTT AAT TAT AAT GTT TCC AGA GCA AAC TGC AAT AAG ATT ATT         1108
Gln Leu Leu Asn Tyr Asn Val Ser Arg Ala Asn Cys Asn Lys Ile Ile
        345               350               355

ATG CTA TTC ACG GAT GGA GGA GAA GAG AGA GCC CAG GAG ATA TTT AAC         1156
Met Leu Phe Thr Asp Gly Gly Glu Glu Arg Ala Gln Glu Ile Phe Asn
        360               365               370

AAA TAC AAT AAA GAT AAA AAA GTA CGT GTA TTC AGG TTT TCA GTT GGT         1204
Lys Tyr Asn Lys Asp Lys Lys Val Arg Val Phe Arg Phe Ser Val Gly
375               380               385               390

CAA CAC AAT TAT GAG AGA GGA CCT ATT CAG TGG ATG GCC TGT GAA AAC         1252
Gln His Asn Tyr Glu Arg Gly Pro Ile Gln Trp Met Ala Cys Glu Asn
                395               400               405

AAA GGT TAT TAT TAT GAA ATT CCT TCC ATT GGT GCA ATA AGA ATC AAT         1300
Lys Gly Tyr Tyr Tyr Glu Ile Pro Ser Ile Gly Ala Ile Arg Ile Asn
        410               415               420

ACT CAG GAA TAT TTG GAT GTT TTG GGA AGA CCA ATG GTT TTA GCA GGA         1348
Thr Gln Glu Tyr Leu Asp Val Leu Gly Arg Pro Met Val Leu Ala Gly
        425               430               435

GAC AAA GCT AAG CAA GTC CAA TGG ACA AAT GTG TAC CTG GAT GCA TTG         1396
Asp Lys Ala Lys Gln Val Gln Trp Thr Asn Val Tyr Leu Asp Ala Leu
        440               445               450

GAA CTG GGA CTT GTC ATT ACT GGA ACT CTT CCG GTC TTC AAC ATA ACC         1444
Glu Leu Gly Leu Val Ile Thr Gly Thr Leu Pro Val Phe Asn Ile Thr
455               460               465               470

GGC CAA TTT GAA AAT AAG ACA AAC TTA AAG AAC CAG CTG ATT CTT GGT         1492
Gly Gln Phe Glu Asn Lys Thr Asn Leu Lys Asn Gln Leu Ile Leu Gly
                475               480               485

GTG ATG GGA GTA GAT GTG TCT TTG GAA GAT ATT AAA AGA CTG ACA CCA         1540
Val Met Gly Val Asp Val Ser Leu Glu Asp Ile Lys Arg Leu Thr Pro
        490               495               500

CGT TTT ACA CTG TGC CCC AAT GGG TAT TAC TTT GCA ATC GAT CCT AAT         1588
Arg Phe Thr Leu Cys Pro Asn Gly Tyr Tyr Phe Ala Ile Asp Pro Asn
        505               510               515

GGT TAT GTT TTA TTA CAT CCA AAT CTT CAG CCA AAG CCT ATT GGT GTA         1636
Gly Tyr Val Leu Leu His Pro Asn Leu Gln Pro Lys Pro Ile Gly Val
        520               525               530

GGT ATA CCA ACA ATT AAT TTA AGA AAA AGG AGA CCC AAT ATC CAG AAC         1684
Gly Ile Pro Thr Ile Asn Leu Arg Lys Arg Arg Pro Asn Ile Gln Asn
535               540               545               550

CCC AAA TCT CAG GAG CCA GTA ACA TTG GAT TTC CTT GAT GCA GAG TTA         1732
Pro Lys Ser Gln Glu Pro Val Thr Leu Asp Phe Leu Asp Ala Glu Leu
                555               560               565

GAG AAT GAT ATT AAA GTG GAG ATT CGA AAT AAG ATG ATT GAT GGG GAA         1780
```

```
Glu Asn Asp Ile Lys Val Glu Ile Arg Asn Lys Met Ile Asp Gly Glu
            570                 575                 580

AGT GGA GAA AAA ACA TTC AGA ACT CTG GTT AAA TCT CAA GAT GAG AGA      1828
Ser Gly Glu Lys Thr Phe Arg Thr Leu Val Lys Ser Gln Asp Glu Arg
            585                 590                 595

TAT ATT GAC AAA GGA AAC AGG ACA TAC ACA TGG ACA CCT GTC AAT GGC      1876
Tyr Ile Asp Lys Gly Asn Arg Thr Tyr Thr Trp Thr Pro Val Asn Gly
            600                 605                 610

ACA GAT TAC AGT TTG GCC TTG GTA TTA CCA ACC TAC AGT TTT TAC TAT      1924
Thr Asp Tyr Ser Leu Ala Leu Val Leu Pro Thr Tyr Ser Phe Tyr Tyr
615                 620                 625                 630

ATA AAA GCC AAA CTA GAA GAG ACA ATA ACT CAG GCC AGA TAT TCG GAA      1972
Ile Lys Ala Lys Leu Glu Glu Thr Ile Thr Gln Ala Arg Tyr Ser Glu
            635                 640                 645

ACC CTG AAG CCA GAT AAT TTT GAA GAA TCT GGC TAT ACA TTC ATA GCA      2020
Thr Leu Lys Pro Asp Asn Phe Glu Glu Ser Gly Tyr Thr Phe Ile Ala
            650                 655                 660

CCA AGA GAT TAC TGC AAT GAC CTG AAA ATA TCG GAT AAT AAC ACT GAA      2068
Pro Arg Asp Tyr Cys Asn Asp Leu Lys Ile Ser Asp Asn Asn Thr Glu
            665                 670                 675

TTT CTT TTA AAT TTC AAC GAG TTT ATT GAT AGA AAA ACT CCA AAC AAC      2116
Phe Leu Leu Asn Phe Asn Glu Phe Ile Asp Arg Lys Thr Pro Asn Asn
            680                 685                 690

CCA TCA TGT AAC GCG GAT TTG ATT AAT AGA GTC TTG CTT GAT GCA GGC      2164
Pro Ser Cys Asn Ala Asp Leu Ile Asn Arg Val Leu Leu Asp Ala Gly
695                 700                 705                 710

TTT ACA AAT GAA CTT GTC CAA AAT TAC TGG AGT AAG CAG AAA AAT ATC      2212
Phe Thr Asn Glu Leu Val Gln Asn Tyr Trp Ser Lys Gln Lys Asn Ile
            715                 720                 725

AAG GGA GTG AAA GCA CGA TTT GTT GTG ACT GAT GGT GGG ATT ACC AGA      2260
Lys Gly Val Lys Ala Arg Phe Val Val Thr Asp Gly Gly Ile Thr Arg
            730                 735                 740

GTT TAT CCC AAA GAG GCT GGA GAA AAT TGG CAA GAA AAC CCA GAG ACA      2308
Val Tyr Pro Lys Glu Ala Gly Glu Asn Trp Gln Glu Asn Pro Glu Thr
            745                 750                 755

TAT GAG GAC AGC TTC TAT AAA AGG AGC CTA GAT AAT GAT AAC TAT GTT      2356
Tyr Glu Asp Ser Phe Tyr Lys Arg Ser Leu Asp Asn Asp Asn Tyr Val
            760                 765                 770

TTC ACT GCT CCC TAC TTT AAC AAA AGT GGA CCT GGT GCC TAT GAA TCG      2404
Phe Thr Ala Pro Tyr Phe Asn Lys Ser Gly Pro Gly Ala Tyr Glu Ser
775                 780                 785                 790

GGC ATT ATG GTA AGC AAA GCT GTA GAA ATA TAT ATT CAA GGG AAA CTT      2452
Gly Ile Met Val Ser Lys Ala Val Glu Ile Tyr Ile Gln Gly Lys Leu
            795                 800                 805

CTT AAA CCT GCA GTT GTT GGA ATT AAA ATT GAT GTA AAT TCC TGG ATA      2500
Leu Lys Pro Ala Val Val Gly Ile Lys Ile Asp Val Asn Ser Trp Ile
            810                 815                 820

GAG AAT TTC ACC AAA ACC TCA ATC AGA GAT CCG TGT GCT GGT CCA GTT      2548
Glu Asn Phe Thr Lys Thr Ser Ile Arg Asp Pro Cys Ala Gly Pro Val
            825                 830                 835

TGT GAC TGC AAA AGA AAC AGT GAC GTA ATG GAT TGT GTG ATT CTG GAT      2596
Cys Asp Cys Lys Arg Asn Ser Asp Val Met Asp Cys Val Ile Leu Asp
840                 845                 850

GAT GGT GGG TTT CTT CTG ATG GCA AAT CAT GAT GAT TAT ACT AAT CAG      2644
Asp Gly Gly Phe Leu Leu Met Ala Asn His Asp Asp Tyr Thr Asn Gln
855                 860                 865                 870

ATT GGA AGA TTT TTT GGA GAG ATT GAT CCC AGC TTG ATG AGA CAC CTG      2692
Ile Gly Arg Phe Phe Gly Glu Ile Asp Pro Ser Leu Met Arg His Leu
            875                 880                 885
```

```
GTT AAT ATA TCA GTT TAT GCT TTT AAC AAA TCT TAT GAT TAT CAG TCA    2740
Val Asn Ile Ser Val Tyr Ala Phe Asn Lys Ser Tyr Asp Tyr Gln Ser
            890                 895                 900

GTA TGT GAG CCC GGT GCT GCA CCA AAA CAA GGA GCA GGA CAT CGC TCA    2788
Val Cys Glu Pro Gly Ala Ala Pro Lys Gln Gly Ala Gly His Arg Ser
        905                 910                 915

GCA TAT GTG CCA TCA GTA GCA GAC ATA TTA CAA ATT GGC TGG TGG GCC    2836
Ala Tyr Val Pro Ser Val Ala Asp Ile Leu Gln Ile Gly Trp Trp Ala
    920                 925                 930

ACT GCT GCT GCC TGG TCT ATT CTA CAG CAG TTT CTC TTG AGT TTG ACC    2884
Thr Ala Ala Ala Trp Ser Ile Leu Gln Gln Phe Leu Leu Ser Leu Thr
935                 940                 945                 950

TTT CCA CGA CTC CTT GAG GCA GTT GAG ATG GAG GAT GAT GAC TTC ACG    2932
Phe Pro Arg Leu Leu Glu Ala Val Glu Met Glu Asp Asp Asp Phe Thr
                955                 960                 965

GCC TCC CTG TCC AAG CAG AGC TGC ATT ACT GAA CAA ACC CAG TAT TTC    2980
Ala Ser Leu Ser Lys Gln Ser Cys Ile Thr Glu Gln Thr Gln Tyr Phe
            970                 975                 980

TTC GAT AAC GAC AGT AAA TCA TTC AGT GGT GTA TTA GAC TGT GGA AAC    3028
Phe Asp Asn Asp Ser Lys Ser Phe Ser Gly Val Leu Asp Cys Gly Asn
        985                 990                 995

TGT TCC AGA ATC TTT CAT GGA GAA AAG CTT ATG AAC ACC AAC TTA ATA    3076
Cys Ser Arg Ile Phe His Gly Glu Lys Leu Met Asn Thr Asn Leu Ile
    1000                1005                1010

TTC ATA ATG GTT GAG AGC AAA GGG ACA TGT CCA TGT GAC ACA CGA CTG    3124
Phe Ile Met Val Glu Ser Lys Gly Thr Cys Pro Cys Asp Thr Arg Leu
1015                1020                1025                1030

CTC ATA CAA GCG GAG CAG ACT TCT GAC GGT CCA AAT CCT TGT GAC ATG    3172
Leu Ile Gln Ala Glu Gln Thr Ser Asp Gly Pro Asn Pro Cys Asp Met
                1035                1040                1045

GTT AAG CAA CCT AGA TAC CGA AAA GGG CCT GAT GTC TGC TTT GAT AAC    3220
Val Lys Gln Pro Arg Tyr Arg Lys Gly Pro Asp Val Cys Phe Asp Asn
            1050                1055                1060

AAT GTC TTG GAG GAT TAT ACT GAC TGT GGT GGT GTT TCT GGA TTA AAT    3268
Asn Val Leu Glu Asp Tyr Thr Asp Cys Gly Gly Val Ser Gly Leu Asn
        1065                1070                1075

CCC TCC CTG TGG TAT ATC ATT GGA ATC CAG TTT CTA CTA CTT TGG CTG    3316
Pro Ser Leu Trp Tyr Ile Ile Gly Ile Gln Phe Leu Leu Leu Trp Leu
    1080                1085                1090

GTA TCT GGC AGC ACA CAC CGG CTG TTA TGACCTTCTA AAAACCAAAT          3363
Val Ser Gly Ser Thr His Arg Leu Leu
1095                1100

CTGCATAGTT AAACTCCAGA CCCTGCCAAA ACATGAGCCC TGCCCTCAAT TACAGTAACG    3423

TAGGGTCAGC TATAAAATCA GACAAACATT AGCTGGGCCT GTTCCATGGC ATAACACTAA    3483

GGCGCAGACT CCTAAGGCAC CCACTGGCTG CATGTCAGGG TGTCAGATCC TTAAACGTGT    3543

GTGAATGCTG CATCATCTAT GTGTAACATC AAAGCAAAAT CCTATACGTG TCCTCTATTG    3603

GAAAATTTGG GCGTTTGTTG TTGCATTGTT GGT                                  3636

(2) INFORMATION FOR SEQ ID NO:29:

(i) SEQUENCE CHARACTERISTICS:
        (A) LENGTH: 3585 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
```

(B) LOCATION: 35..3295
(D) OTHER INFORMATION: /standard_name= "Alpha-2c"

(ix) FEATURE:
(A) NAME/KEY: 5'UTR
(B) LOCATION: 1..34

(ix) FEATURE:
(A) NAME/KEY: 3'UTR
(B) LOCATION: 3296..3585

(xi) SEQUENCE DESCRIPTION: SEQ ID NO:29:

| | | |
|---|---|---|
| GCGGGGGAGG GGGCATTGAT CTTCGATCGC GAAG ATG GCT GCT GGC TGC CTG<br>Met Ala Ala Gly Cys Leu<br>1                 5 | | 52 |
| CTG GCC TTG ACT CTG ACA CTT TTC CAA TCT TTG CTC ATC GGC CCC TCG<br>Leu Ala Leu Thr Leu Thr Leu Phe Gln Ser Leu Leu Ile Gly Pro Ser<br>10                 15                 20 | | 100 |
| TCG GAG GAG CCG TTC CCT TCG GCC GTC ACT ATC AAA TCA TGG GTG GAT<br>Ser Glu Glu Pro Phe Pro Ser Ala Val Thr Ile Lys Ser Trp Val Asp<br>25                 30                 35 | | 148 |
| AAG ATG CAA GAA GAC CTT GTC ACA CTG GCA AAA ACA GCA AGT GGA GTC<br>Lys Met Gln Glu Asp Leu Val Thr Leu Ala Lys Thr Ala Ser Gly Val<br>40                 45                 50 | | 196 |
| AAT CAG CTT GTT GAT ATT TAT GAG AAA TAT CAA GAT TTG TAT ACT GTG<br>Asn Gln Leu Val Asp Ile Tyr Glu Lys Tyr Gln Asp Leu Tyr Thr Val<br>55                 60                 65                 70 | | 244 |
| GAA CCA AAT AAT GCA CGC CAG CTG GTA GAA ATT GCA GCC AGG GAT ATT<br>Glu Pro Asn Asn Ala Arg Gln Leu Val Glu Ile Ala Ala Arg Asp Ile<br>75                 80                 85 | | 292 |
| GAG AAA CTT CTG AGC AAC AGA TCT AAA GCC CTG GTG AGC CTG GCA TTG<br>Glu Lys Leu Leu Ser Asn Arg Ser Lys Ala Leu Val Ser Leu Ala Leu<br>90                 95                 100 | | 340 |
| GAA GCG GAG AAA GTT CAA GCA GCT CAC CAG TGG AGA GAA GAT TTT GCA<br>Glu Ala Glu Lys Val Gln Ala Ala His Gln Trp Arg Glu Asp Phe Ala<br>105                110               115 | | 388 |
| AGC AAT GAA GTT GTC TAC TAC AAT GCA AAG GAT GAT CTC GAT CCT GAG<br>Ser Asn Glu Val Val Tyr Tyr Asn Ala Lys Asp Asp Leu Asp Pro Glu<br>120                125               130 | | 436 |
| AAA AAT GAC AGT GAG CCA GGC AGC CAG AGG ATA AAA CCT GTT TTC ATT<br>Lys Asn Asp Ser Glu Pro Gly Ser Gln Arg Ile Lys Pro Val Phe Ile<br>135                140               145               150 | | 484 |
| GAA GAT GCT AAT TTT GGA CGA CAA ATA TCT TAT CAG CAC GCA GCA GTC<br>Glu Asp Ala Asn Phe Gly Arg Gln Ile Ser Tyr Gln His Ala Ala Val<br>155                160               165 | | 532 |
| CAT ATT CCT ACT GAC ATC TAT GAG GGC TCA ACA ATT GTG TTA AAT GAA<br>His Ile Pro Thr Asp Ile Tyr Glu Gly Ser Thr Ile Val Leu Asn Glu<br>170                175               180 | | 580 |
| CTC AAC TGG ACA AGT GCC TTA GAT GAA GTT TTC AAA AAG AAT CGC GAG<br>Leu Asn Trp Thr Ser Ala Leu Asp Glu Val Phe Lys Lys Asn Arg Glu<br>185                190               195 | | 628 |
| GAA GAC CCT TCA TTA TTG TGG CAG GTT TTT GGC AGT GCC ACT GGC CTA<br>Glu Asp Pro Ser Leu Leu Trp Gln Val Phe Gly Ser Ala Thr Gly Leu<br>200                205               210 | | 676 |
| GCT CGA TAT TAT CCA GCT TCA CCA TGG GTT GAT AAT AGT AGA ACT CCA<br>Ala Arg Tyr Tyr Pro Ala Ser Pro Trp Val Asp Asn Ser Arg Thr Pro<br>215                220               225               230 | | 724 |
| AAT AAG ATT GAC CTT TAT GAT GTA CGC AGA AGA CCA TGG TAC ATC CAA<br>Asn Lys Ile Asp Leu Tyr Asp Val Arg Arg Arg Pro Trp Tyr Ile Gln<br>235                240               245 | | 772 |
| GGA GCT GCA TCT CCT AAA GAC ATG CTT ATT CTG GTG GAT GTG AGT GGA<br>Gly Ala Ala Ser Pro Lys Asp Met Leu Ile Leu Val Asp Val Ser Gly | | 820 |

```
                250                 255                 260
AGT GTT AGT GGA TTG ACA CTT AAA CTG ATC CGA ACA TCT GTC TCC GAA      868
Ser Val Ser Gly Leu Thr Leu Lys Leu Ile Arg Thr Ser Val Ser Glu
        265                 270                 275

ATG TTA GAA ACC CTC TCA GAT GAT GAT TTC GTG AAT GTA GCT TCA TTT      916
Met Leu Glu Thr Leu Ser Asp Asp Asp Phe Val Asn Val Ala Ser Phe
        280                 285                 290

AAC AGC AAT GCT CAG GAT GTA AGC TGT TTT CAG CAC CTT GTC CAA GCA      964
Asn Ser Asn Ala Gln Asp Val Ser Cys Phe Gln His Leu Val Gln Ala
295                 300                 305                 310

AAT GTA AGA AAT AAA AAA GTG TTG AAA GAC GCG GTG AAT AAT ATC ACA     1012
Asn Val Arg Asn Lys Lys Val Leu Lys Asp Ala Val Asn Asn Ile Thr
                315                 320                 325

GCC AAA GGA ATT ACA GAT TAT AAG AAG GGC TTT AGT TTT GCT TTT GAA     1060
Ala Lys Gly Ile Thr Asp Tyr Lys Lys Gly Phe Ser Phe Ala Phe Glu
        330                 335                 340

CAG CTG CTT AAT TAT AAT GTT TCC AGA GCA AAC TGC AAT AAG ATT ATT     1108
Gln Leu Leu Asn Tyr Asn Val Ser Arg Ala Asn Cys Asn Lys Ile Ile
        345                 350                 355

ATG CTA TTC ACG GAT GGA GGA GAA GAG AGA GCC CAG GAG ATA TTT AAC     1156
Met Leu Phe Thr Asp Gly Gly Glu Glu Arg Ala Gln Glu Ile Phe Asn
        360                 365                 370

AAA TAC AAT AAA GAT AAA AAA GTA CGT GTA TTC AGG TTT TCA GTT GGT     1204
Lys Tyr Asn Lys Asp Lys Lys Val Arg Val Phe Arg Phe Ser Val Gly
375                 380                 385                 390

CAA CAC AAT TAT GAG AGA GGA CCT ATT CAG TGG ATG GCC TGT GAA AAC     1252
Gln His Asn Tyr Glu Arg Gly Pro Ile Gln Trp Met Ala Cys Glu Asn
                395                 400                 405

AAA GGT TAT TAT TAT GAA ATT CCT TCC ATT GGT GCA ATA AGA ATC AAT     1300
Lys Gly Tyr Tyr Tyr Glu Ile Pro Ser Ile Gly Ala Ile Arg Ile Asn
        410                 415                 420

ACT CAG GAA TAT TTG GAT GTT TTG GGA AGA CCA ATG GTT TTA GCA GGA     1348
Thr Gln Glu Tyr Leu Asp Val Leu Gly Arg Pro Met Val Leu Ala Gly
        425                 430                 435

GAC AAA GCT AAG CAA GTC CAA TGG ACA AAT GTG TAC CTG GAT GCA TTG     1396
Asp Lys Ala Lys Gln Val Gln Trp Thr Asn Val Tyr Leu Asp Ala Leu
        440                 445                 450

GAA CTG GGA CTT GTC ATT ACT GGA ACT CTT CCG GTC TTC AAC ATA ACC     1444
Glu Leu Gly Leu Val Ile Thr Gly Thr Leu Pro Val Phe Asn Ile Thr
455                 460                 465                 470

GGC CAA TTT GAA AAT AAG ACA AAC TTA AAG AAC CAG CTG ATT CTT GGT     1492
Gly Gln Phe Glu Asn Lys Thr Asn Leu Lys Asn Gln Leu Ile Leu Gly
                475                 480                 485

GTG ATG GGA GTA GAT GTG TCT TTG GAA GAT ATT AAA AGA CTG ACA CCA     1540
Val Met Gly Val Asp Val Ser Leu Glu Asp Ile Lys Arg Leu Thr Pro
        490                 495                 500

CGT TTT ACA CTG TGC CCC AAT GGG TAT TAC TTT GCA ATC GAT CCT AAT     1588
Arg Phe Thr Leu Cys Pro Asn Gly Tyr Tyr Phe Ala Ile Asp Pro Asn
        505                 510                 515

GGT TAT GTT TTA TTA CAT CCA AAT CTT CAG CCA AAG GAG CCA GTA ACA     1636
Gly Tyr Val Leu Leu His Pro Asn Leu Gln Pro Lys Glu Pro Val Thr
520                 525                 530

TTG GAT TTC CTT GAT GCA GAG TTA GAG AAT GAT ATT AAA GTG GAG ATT     1684
Leu Asp Phe Leu Asp Ala Glu Leu Glu Asn Asp Ile Lys Val Glu Ile
535                 540                 545                 550

CGA AAT AAG ATG ATT GAT GGG GAA AGT GGA GAA AAA ACA TTC AGA ACT     1732
Arg Asn Lys Met Ile Asp Gly Glu Ser Gly Glu Lys Thr Phe Arg Thr
                555                 560                 565

CTG GTT AAA TCT CAA GAT GAG AGA TAT ATT GAC AAA GGA AAC AGG ACA     1780
```

```
                                                      -continued

Leu Val Lys Ser Gln Asp Glu Arg Tyr Ile Asp Lys Gly Asn Arg Thr
            570                 575                 580

TAC ACA TGG ACA CCT GTC AAT GGC ACA GAT TAC AGT TTG GCC TTG GTA        1828
Tyr Thr Trp Thr Pro Val Asn Gly Thr Asp Tyr Ser Leu Ala Leu Val
        585                 590                 595

TTA CCA ACC TAC AGT TTT TAC TAT ATA AAA GCC AAA CTA GAA GAG ACA        1876
Leu Pro Thr Tyr Ser Phe Tyr Tyr Ile Lys Ala Lys Leu Glu Glu Thr
    600                 605                 610

ATA ACT CAG GCC AGA TCA AAA AAG GGC AAA ATG AAG GAT TCG GAA ACC        1924
Ile Thr Gln Ala Arg Ser Lys Lys Gly Lys Met Lys Asp Ser Glu Thr
615                 620                 625                 630

CTG AAG CCA GAT AAT TTT GAA GAA TCT GGC TAT ACA TTC ATA GCA CCA        1972
Leu Lys Pro Asp Asn Phe Glu Glu Ser Gly Tyr Thr Phe Ile Ala Pro
                635                 640                 645

AGA GAT TAC TGC AAT GAC CTG AAA ATA TCG GAT AAT AAC ACT GAA TTT        2020
Arg Asp Tyr Cys Asn Asp Leu Lys Ile Ser Asp Asn Asn Thr Glu Phe
            650                 655                 660

CTT TTA AAT TTC AAC GAG TTT ATT GAT AGA AAA ACT CCA AAC AAC CCA        2068
Leu Leu Asn Phe Asn Glu Phe Ile Asp Arg Lys Thr Pro Asn Asn Pro
        665                 670                 675

TCA TGT AAC GCG GAT TTG ATT AAT AGA GTC TTG CTT GAT GCA GGC TTT        2116
Ser Cys Asn Ala Asp Leu Ile Asn Arg Val Leu Leu Asp Ala Gly Phe
    680                 685                 690

ACA AAT GAA CTT GTC CAA AAT TAC TGG AGT AAG CAG AAA AAT ATC AAG        2164
Thr Asn Glu Leu Val Gln Asn Tyr Trp Ser Lys Gln Lys Asn Ile Lys
695                 700                 705                 710

GGA GTG AAA GCA CGA TTT GTT GTG ACT GAT GGT GGG ATT ACC AGA GTT        2212
Gly Val Lys Ala Arg Phe Val Val Thr Asp Gly Gly Ile Thr Arg Val
                715                 720                 725

TAT CCC AAA GAG GCT GGA GAA AAT TGG CAA GAA AAC CCA GAG ACA TAT        2260
Tyr Pro Lys Glu Ala Gly Glu Asn Trp Gln Glu Asn Pro Glu Thr Tyr
                730                 735                 740

GAG GAC AGC TTC TAT AAA AGG AGC CTA GAT AAT GAT AAC TAT GTT TTC        2308
Glu Asp Ser Phe Tyr Lys Arg Ser Leu Asp Asn Asp Asn Tyr Val Phe
            745                 750                 755

ACT GCT CCC TAC TTT AAC AAA AGT GGA CCT GGT GCC TAT GAA TCG GGC        2356
Thr Ala Pro Tyr Phe Asn Lys Ser Gly Pro Gly Ala Tyr Glu Ser Gly
        760                 765                 770

ATT ATG GTA AGC AAA GCT GTA GAA ATA TAT ATT CAA GGG AAA CTT CTT        2404
Ile Met Val Ser Lys Ala Val Glu Ile Tyr Ile Gln Gly Lys Leu Leu
    775                 780                 785                 790

AAA CCT GCA GTT GTT GGA ATT AAA ATT GAT GTA AAT TCC TGG ATA GAG        2452
Lys Pro Ala Val Val Gly Ile Lys Ile Asp Val Asn Ser Trp Ile Glu
                795                 800                 805

AAT TTC ACC AAA ACC TCA ATC AGA GAT CCG TGT GCT GGT CCA GTT TGT        2500
Asn Phe Thr Lys Thr Ser Ile Arg Asp Pro Cys Ala Gly Pro Val Cys
            810                 815                 820

GAC TGC AAA AGA AAC AGT GAC GTA ATG GAT TGT GTG ATT CTG GAT GAT        2548
Asp Cys Lys Arg Asn Ser Asp Val Met Asp Cys Val Ile Leu Asp Asp
        825                 830                 835

GGT GGG TTT CTT CTG ATG GCA AAT CAT GAT GAT TAT ACT AAT CAG ATT        2596
Gly Gly Phe Leu Leu Met Ala Asn His Asp Asp Tyr Thr Asn Gln Ile
    840                 845                 850

GGA AGA TTT TTT GGA GAG ATT GAT CCC AGC TTG ATG AGA CAC CTG GTT        2644
Gly Arg Phe Phe Gly Glu Ile Asp Pro Ser Leu Met Arg His Leu Val
855                 860                 865                 870

AAT ATA TCA GTT TAT GCT TTT AAC AAA TCT TAT GAT TAT CAG TCA GTA        2692
Asn Ile Ser Val Tyr Ala Phe Asn Lys Ser Tyr Asp Tyr Gln Ser Val
                875                 880                 885
```

```
TGT GAG CCC GGT GCT GCA CCA AAA CAA GGA GCA GGA CAT CGC TCA GCA    2740
Cys Glu Pro Gly Ala Ala Pro Lys Gln Gly Ala Gly His Arg Ser Ala
            890                 895                 900

TAT GTG CCA TCA GTA GCA GAC ATA TTA CAA ATT GGC TGG TGG GCC ACT    2788
Tyr Val Pro Ser Val Ala Asp Ile Leu Gln Ile Gly Trp Trp Ala Thr
            905                 910                 915

GCT GCT GCC TGG TCT ATT CTA CAG CAG TTT CTC TTG AGT TTG ACC TTT    2836
Ala Ala Ala Trp Ser Ile Leu Gln Gln Phe Leu Leu Ser Leu Thr Phe
            920                 925                 930

CCA CGA CTC CTT GAG GCA GTT GAG ATG GAG GAT GAT GAC TTC ACG GCC    2884
Pro Arg Leu Leu Glu Ala Val Glu Met Glu Asp Asp Asp Phe Thr Ala
935                 940                 945                 950

TCC CTG TCC AAG CAG AGC TGC ATT ACT GAA CAA ACC CAG TAT TTC TTC    2932
Ser Leu Ser Lys Gln Ser Cys Ile Thr Glu Gln Thr Gln Tyr Phe Phe
            955                 960                 965

GAT AAC GAC AGT AAA TCA TTC AGT GGT GTA TTA GAC TGT GGA AAC TGT    2980
Asp Asn Asp Ser Lys Ser Phe Ser Gly Val Leu Asp Cys Gly Asn Cys
            970                 975                 980

TCC AGA ATC TTT CAT GGA GAA AAG CTT ATG AAC ACC AAC TTA ATA TTC    3028
Ser Arg Ile Phe His Gly Glu Lys Leu Met Asn Thr Asn Leu Ile Phe
            985                 990                 995

ATA ATG GTT GAG AGC AAA GGG ACA TGT CCA TGT GAC ACA CGA CTG CTC    3076
Ile Met Val Glu Ser Lys Gly Thr Cys Pro Cys Asp Thr Arg Leu Leu
1000                1005                1010

ATA CAA GCG GAG CAG ACT TCT GAC GGT CCA AAT CCT TGT GAC ATG GTT    3124
Ile Gln Ala Glu Gln Thr Ser Asp Gly Pro Asn Pro Cys Asp Met Val
1015                1020                1025                1030

AAG CAA CCT AGA TAC CGA AAA GGG CCT GAT GTC TGC TTT GAT AAC AAT    3172
Lys Gln Pro Arg Tyr Arg Lys Gly Pro Asp Val Cys Phe Asp Asn Asn
            1035                1040                1045

GTC TTG GAG GAT TAT ACT GAC TGT GGT GGT GTT TCT GGA TTA AAT CCC    3220
Val Leu Glu Asp Tyr Thr Asp Cys Gly Gly Val Ser Gly Leu Asn Pro
            1050                1055                1060

TCC CTG TGG TAT ATC ATT GGA ATC CAG TTT CTA CTA CTT TGG CTG GTA    3268
Ser Leu Trp Tyr Ile Ile Gly Ile Gln Phe Leu Leu Leu Trp Leu Val
            1065                1070                1075

TCT GGC AGC ACA CAC CGG CTG TTA TGACCTTCTA AAAACCAAAT CTGCATAGTT    3322
Ser Gly Ser Thr His Arg Leu Leu
            1080            1085

AAACTCCAGA CCCTGCCAAA ACATGAGCCC TGCCCTCAAT TACAGTAACG TAGGGTCAGC    3382

TATAAAATCA GACAAACATT AGCTGGGCCT GTTCCATGGC ATAACACTAA GGCGCAGACT    3442

CCTAAGGCAC CCACTGGCTG CATGTCAGGG TGTCAGATCC TTAAACGTGT GTGAATGCTG    3502

CATCATCTAT GTGTAACATC AAAGCAAAAT CCTATACGTG TCCTCTATTG GAAAATTTGG    3562

GCGTTTGTTG TTGCATTGTT GGT                                          3585

(2) INFORMATION FOR SEQ ID NO:30:

(i) SEQUENCE CHARACTERISTICS:
        (A) LENGTH: 3564 base pairs
        (B) TYPE: nucleic acid
        (C) STRANDEDNESS: double
        (D) TOPOLOGY: linear (ii) MOLECULE TYPE: DNA (genomic)

(ix) FEATURE:
         (A) NAME/KEY: CDS
         (B) LOCATION: 35..3374 ([0081]1625 to 1639 & [0081]1908 to 1928)
         (D) OTHER INFORMATION: /standard_name= "Alpha-2d"

(ix) FEATURE:
```

(A) NAME/KEY: 5'UTR
(B) LOCATION: 1..34

(ix) FEATURE:
(A) NAME/KEY: 3'UTR
(B) LOCATION: 3375..3565

(xi) SEQUENCE DESCRIPTION: SEQ ID NO:30:

```
GCGGGGGAGG GGGCATTGAT CTTCGATCGC GAAG ATG GCT GCT GGC TGC CTG            52
                                     Met Ala Ala Gly Cys Leu
                                      1               5

CTG GCC TTG ACT CTG ACA CTT TTC CAA TCT TTG CTC ATC GGC CCC TCG          100
Leu Ala Leu Thr Leu Thr Leu Phe Gln Ser Leu Leu Ile Gly Pro Ser
             10                  15                  20

TCG GAG GAG CCG TTC CCT TCG GCC GTC ACT ATC AAA TCA TGG GTG GAT          148
Ser Glu Glu Pro Phe Pro Ser Ala Val Thr Ile Lys Ser Trp Val Asp
         25                  30                  35

AAG ATG CAA GAA GAC CTT GTC ACA CTG GCA AAA ACA GCA AGT GGA GTC          196
Lys Met Gln Glu Asp Leu Val Thr Leu Ala Lys Thr Ala Ser Gly Val
     40                  45                  50

AAT CAG CTT GTT GAT ATT TAT GAG AAA TAT CAA GAT TTG TAT ACT GTG          244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT          292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG          340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA          388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG          436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT          484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC          532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA          580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG          628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC TA           676
Glu Asp Pro Ser Leu Leu Trp Gln Val Phe Gly Ser Ala Thr Gly Leu
    200                 205                 210

GCT CGA TAT TAT CCA GCT TCA CCA TGG GTT GAT AAT AGT AGA ACT CCA          724
Ala Arg Tyr Tyr Pro Ala Ser Pro Trp Val Asp Asn Ser Arg Thr Pro
215                 220                 225                 230

AAT AAG ATT GAC CTT TAT GAT GTA CGC AGA AGA CCA TGG TAC ATC CAA          772
Asn Lys Ile Asp Leu Tyr Asp Val Arg Arg Arg Pro Trp Tyr Ile Gln
                235                 240                 245

GGA GCT GCA TCT CCT AAA GAC ATG CTT ATT CTG GTG GAT GTG AGT GGA          820
Gly Ala Ala Ser Pro Lys Asp Met Leu Ile Leu Val Asp Val Ser Gly
            250                 255                 260

AGT GTT AGT GGA TTG ACA CTT AAA CTG ATC CGA ACA TCT GTC TCC GAA          868
Ser Val Ser Gly Leu Thr Leu Lys Leu Ile Arg Thr Ser Val Ser Glu
```

|  |  |
|---|---|
| ATG TTA GAA ACC CTC TCA GAT GAT GAT TTC GTG AAT GTA GCT TCA TTT<br>Met Leu Glu Thr Leu Ser Asp Asp Asp Phe Val Asn Val Ala Ser Phe<br>    280                        285                      290 | 916 |
| AAC AGC AAT GCT CAG GAT GTA AGC TGT TTT CAG CAC CTT GTC CAA GCA<br>Asn Ser Asn Ala Gln Asp Val Ser Cys Phe Gln His Leu Val Gln Ala<br>295                        300                    305                  310 | 964 |
| AAT GTA AGA AAT AAA AAA GTG TTG AAA GAC GCG GTG AAT AAT ATC ACA<br>Asn Val Arg Asn Lys Lys Val Leu Lys Asp Ala Val Asn Asn Ile Thr<br>                          315                    320                  325 | 1012 |
| GCC AAA GGA ATT ACA GAT TAT AAG AAG GGC TTT AGT TTT GCT TTT GAA<br>Ala Lys Gly Ile Thr Asp Tyr Lys Lys Gly Phe Ser Phe Ala Phe Glu<br>            330                    335                    340 | 1060 |
| CAG CTG CTT AAT TAT AAT GTT TCC AGA GCA AAC TGC AAT AAG ATT ATT<br>Gln Leu Leu Asn Tyr Asn Val Ser Arg Ala Asn Cys Asn Lys Ile Ile<br>                345                    350                    355 | 1108 |
| ATG CTA TTC ACG GAT GGA GGA GAA GAG AGA GCC CAG GAG ATA TTT AAC<br>Met Leu Phe Thr Asp Gly Gly Glu Glu Arg Ala Gln Glu Ile Phe Asn<br>360                        365                    370 | 1156 |
| AAA TAC AAT AAA GAT AAA AAA GTA CGT GTA TTC AGG TTT TCA GTT GGT<br>Lys Tyr Asn Lys Asp Lys Lys Val Arg Val Phe Arg Phe Ser Val Gly<br>375                        380                    385                  390 | 1204 |
| CAA CAC AAT TAT GAG AGA GGA CCT ATT CAG TGG ATG GCC TGT GAA AAC<br>Gln His Asn Tyr Glu Arg Gly Pro Ile Gln Trp Met Ala Cys Glu Asn<br>                395                    400                    405 | 1252 |
| AAA GGT TAT TAT TAT GAA ATT CCT TCC ATT GGT GCA ATA AGA ATC AAT<br>Lys Gly Tyr Tyr Tyr Glu Ile Pro Ser Ile Gly Ala Ile Arg Ile Asn<br>            410                    415                    420 | 1300 |
| ACT CAG GAA TAT TTG GAT GTT TTG GGA AGA CCA ATG GTT TTA GCA GGA<br>Thr Gln Glu Tyr Leu Asp Val Leu Gly Arg Pro Met Val Leu Ala Gly<br>                425                    430                    435 | 1348 |
| GAC AAA GCT AAG CAA GTC CAA TGG ACA AAT GTG TAC CTG GAT GCA TTG<br>Asp Lys Ala Lys Gln Val Gln Trp Thr Asn Val Tyr Leu Asp Ala Leu<br>            440                    445                    450 | 1396 |
| GAA CTG GGA CTT GTC ATT ACT GGA ACT CTT CCG GTC TTC AAC ATA ACC<br>Glu Leu Gly Leu Val Ile Thr Gly Thr Leu Pro Val Phe Asn Ile Thr<br>455                        460                    465                  470 | 1444 |
| GGC CAA TTT GAA AAT AAG ACA AAC TTA AAG AAC CAG CTG ATT CTT GGT<br>Gly Gln Phe Glu Asn Lys Thr Asn Leu Lys Asn Gln Leu Ile Leu Gly<br>                475                    480                    485 | 1492 |
| GTG ATG GGA GTA GAT GTG TCT TTG GAA GAT ATT AAA AGA CTG ACA CCA<br>Val Met Gly Val Asp Val Ser Leu Glu Asp Ile Lys Arg Leu Thr Pro<br>            490                    495                    500 | 1540 |
| CGT TTT ACA CTG TGC CCC AAT GGG TAT TAC TTT GCA ATC GAT CCT AAT<br>Arg Phe Thr Leu Cys Pro Asn Gly Tyr Tyr Phe Ala Ile Asp Pro Asn<br>                505                    510                    515 | 1588 |
| GGT TAT GTT TTA TTA CAT CCA AAT CTT CAG CCA AAG GAG CCA GTA ACA<br>Gly Tyr Val Leu Leu His Pro Asn Leu Gln Pro Lys Glu Pro Val Thr<br>520                        525                    530 | 1636 |
| TTG GAT TTC CTT GAT GCA GAG TTA GAG AAT GAT ATT AAA GTG GAG ATT<br>Leu Asp Phe Leu Asp Ala Glu Leu Glu Asn Asp Ile Lys Val Glu Ile<br>535                        540                    545                  550 | 1684 |
| CGA AAT AAG ATG ATT GAT GGG GAA AGT GGA GAA AAA ACA TTC AGA ACT<br>Arg Asn Lys Met Ile Asp Gly Glu Ser Gly Glu Lys Thr Phe Arg Thr<br>                555                    560                    565 | 1732 |
| CTG GTT AAA TCT CAA GAT GAG AGA TAT ATT GAC AAA GGA AAC AGG ACA<br>Leu Val Lys Ser Gln Asp Glu Arg Tyr Ile Asp Lys Gly Asn Arg Thr<br>            570                    575                    580 | 1780 |
| TAC ACA TGG ACA CCT GTC AAT GGC ACA GAT TAC AGT TTG GCC TTG GTA<br>Tyr Thr Trp Thr Pro Val Asn Gly Thr Asp Tyr Ser Leu Ala Leu Val | 1828 |

-continued

```
Tyr Thr Trp Thr Pro Val Asn Gly Thr Asp Tyr Ser Leu Ala Leu Val
        585             590             595

TTA CCA ACC TAC AGT TTT TAC TAT ATA AAA GCC AAA CTA GAA GAG ACA    1876
Leu Pro Thr Tyr Ser Phe Tyr Tyr Ile Lys Ala Lys Leu Glu Glu Thr
600             605             610

ATA ACT CAG GCC AGA TAT TCG GAA ACC CTG AAG CCA GAT AAT TTT GAA    1924
Ile Thr Gln Ala Arg Tyr Ser Glu Thr Leu Lys Pro Asp Asn Phe Glu
615             620             625             630

GAA TCT GGC TAT ACA TTC ATA GCA CCA AGA GAT TAC TGC AAT GAC CTG    1972
Glu Ser Gly Tyr Thr Phe Ile Ala Pro Arg Asp Tyr Cys Asn Asp Leu
            635             640             645

AAA ATA TCG GAT AAT AAC ACT GAA TTT CTT TTA AAT TTC AAC GAG TTT    2020
Lys Ile Ser Asp Asn Asn Thr Glu Phe Leu Leu Asn Phe Asn Glu Phe
650             655             660

ATT GAT AGA AAA ACT CCA AAC AAC CCA TCA TGT AAC GCG GAT TTG ATT    2068
Ile Asp Arg Lys Thr Pro Asn Asn Pro Ser Cys Asn Ala Asp Leu Ile
            665             670             675

AAT AGA GTC TTG CTT GAT GCA GGC TTT ACA AAT GAA CTT GTC CAA AAT    2116
Asn Arg Val Leu Leu Asp Ala Gly Phe Thr Asn Glu Leu Val Gln Asn
            680             685             690

TAC TGG AGT AAG CAG AAA AAT ATC AAG GGA GTG AAA GCA CGA TTT GTT    2164
Tyr Trp Ser Lys Gln Lys Asn Ile Lys Gly Val Lys Ala Arg Phe Val
695             700             705             710

GTG ACT GAT GGT GGG ATT ACC AGA GTT TAT CCC AAA GAG GCT GGA GAA    2212
Val Thr Asp Gly Gly Ile Thr Arg Val Tyr Pro Lys Glu Ala Gly Glu
                715             720             725

AAT TGG CAA GAA AAC CCA GAG ACA TAT GAG GAC AGC TTC TAT AAA AGG    2260
Asn Trp Gln Glu Asn Pro Glu Thr Tyr Glu Asp Ser Phe Tyr Lys Arg
            730             735             740

AGC CTA GAT AAT GAT AAC TAT GTT TTC ACT GCT CCC TAC TTT AAC AAA    2308
Ser Leu Asp Asn Asp Asn Tyr Val Phe Thr Ala Pro Tyr Phe Asn Lys
            745             750             755

AGT GGA CCT GGT GCC TAT GAA TCG GGC ATT ATG GTA AGC AAA GCT GTA    2356
Ser Gly Pro Gly Ala Tyr Glu Ser Gly Ile Met Val Ser Lys Ala Val
            760             765             770

GAA ATA TAT ATT CAA GGG AAA CTT CTT AAA CCT GCA GTT GTT GGA ATT    2404
Glu Ile Tyr Ile Gln Gly Lys Leu Leu Lys Pro Ala Val Val Gly Ile
775             780             785             790

AAA ATT GAT GTA AAT TCC TGG ATA GAG AAT TTC ACC AAA ACC TCA ATC    2452
Lys Ile Asp Val Asn Ser Trp Ile Glu Asn Phe Thr Lys Thr Ser Ile
                795             800             805

AGA GAT CCG TGT GCT GGT CCA GTT TGT GAC TGC AAA AGA AAC AGT GAC    2500
Arg Asp Pro Cys Ala Gly Pro Val Cys Asp Cys Lys Arg Asn Ser Asp
            810             815             820

GTA ATG GAT TGT GTG ATT CTG GAT GAT GGT GGG TTT CTT CTG ATG GCA    2548
Val Met Asp Cys Val Ile Leu Asp Asp Gly Gly Phe Leu Leu Met Ala
            825             830             835

AAT CAT GAT GAT TAT ACT AAT CAG ATT GGA AGA TTT TTT GGA GAG ATT    2596
Asn His Asp Asp Tyr Thr Asn Gln Ile Gly Arg Phe Phe Gly Glu Ile
            840             845             850

GAT CCC AGC TTG ATG AGA CAC CTG GTT AAT ATA TCA GTT TAT GCT TTT    2644
Asp Pro Ser Leu Met Arg His Leu Val Asn Ile Ser Val Tyr Ala Phe
855             860             865             870

AAC AAA TCT TAT GAT TAT CAG TCA GTA TGT GAG CCC GGT GCT GCA CCA    2692
Asn Lys Ser Tyr Asp Tyr Gln Ser Val Cys Glu Pro Gly Ala Ala Pro
            875             880             885

AAA CAA GGA GCA GGA CAT CGC TCA GCA TAT GTG CCA TCA GTA GCA GAC    2740
Lys Gln Gly Ala Gly His Arg Ser Ala Tyr Val Pro Ser Val Ala Asp
            890             895             900
```

```
ATA TTA CAA ATT GGC TGG TGG GCC ACT GCT GCT GCC TGG TCT ATT CTA    2788
Ile Leu Gln Ile Gly Trp Trp Ala Thr Ala Ala Ala Trp Ser Ile Leu
        905                 910                 915

CAG CAG TTT CTC TTG AGT TTG ACC TTT CCA CGA CTC CTT GAG GCA GTT    2836
Gln Gln Phe Leu Leu Ser Leu Thr Phe Pro Arg Leu Leu Glu Ala Val
    920                 925                 930

GAG ATG GAG GAT GAT GAC TTC ACG GCC TCC CTG TCC AAG CAG AGC TGC    2884
Glu Met Glu Asp Asp Asp Phe Thr Ala Ser Leu Ser Lys Gln Ser Cys
935                 940                 945                 950

ATT ACT GAA CAA ACC CAG TAT TTC TTC GAT AAC GAC AGT AAA TCA TTC    2932
Ile Thr Glu Gln Thr Gln Tyr Phe Phe Asp Asn Asp Ser Lys Ser Phe
                955                 960                 965

AGT GGT GTA TTA GAC TGT GGA AAC TGT TCC AGA ATC TTT CAT GGA GAA    2980
Ser Gly Val Leu Asp Cys Gly Asn Cys Ser Arg Ile Phe His Gly Glu
            970                 975                 980

AAG CTT ATG AAC ACC AAC TTA ATA TTC ATA ATG GTT GAG AGC AAA GGG    3028
Lys Leu Met Asn Thr Asn Leu Ile Phe Ile Met Val Glu Ser Lys Gly
        985                 990                 995

ACA TGT CCA TGT GAC ACA CGA CTG CTC ATA CAA GCG GAG CAG ACT TCT    3076
Thr Cys Pro Cys Asp Thr Arg Leu Leu Ile Gln Ala Glu Gln Thr Ser
    1000                1005                1010

GAC GGT CCA AAT CCT TGT GAC ATG GTT AAG CAA CCT AGA TAC CGA AAA    3124
Asp Gly Pro Asn Pro Cys Asp Met Val Lys Gln Pro Arg Tyr Arg Lys
1015                1020                1025                1030

GGG CCT GAT GTC TGC TTT GAT AAC AAT GTC TTG GAG GAT TAT ACT GAC    3172
Gly Pro Asp Val Cys Phe Asp Asn Asn Val Leu Glu Asp Tyr Thr Asp
                1035                1040                1045

TGT GGT GGT GTT TCT GGA TTA AAT CCC TCC CTG TGG TAT ATC ATT GGA    3220
Cys Gly Gly Val Ser Gly Leu Asn Pro Ser Leu Trp Tyr Ile Ile Gly
            1050                1055                1060

ATC CAG TTT CTA CTA CTT TGG CTG GTA TCT GGC AGC ACA CAC CGG CTG    3268
Ile Gln Phe Leu Leu Leu Trp Leu Val Ser Gly Ser Thr His Arg Leu
        1065                1070                1075

TTA TGACCTTCTA AAAACCAAAT CTGCATAGTT AAACTCCAGA CCCTGCCAAA         3321
Leu

ACATGAGCCC TGCCCTCAAT TACAGTAACG TAGGGTCAGC TATAAAATCA GACAAACATT  3381

AGCTGGGCCT GTTCCATGGC ATAACACTAA GGCGCAGACT CCTAAGGCAC CCACTGGCTG  3441

CATGTCAGGG TGTCAGATCC TTAAACGTGT GTGAATGCTG CATCATCTAT GTGTAACATC  3501

AAAGCAAAAT CCTATACGTG TCCTCTATTG GAAAATTTGG GCGTTTGTTG TTGCATTGTT  3561

GGT                                                                3564
```

(2) INFORMATION FOR SEQ ID NO:31:

(i) SEQUENCE CHARACTERISTICS:
        (A) LENGTH: 3579 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 35..3289
        (D) OTHER INFORMATION: /standard_name= "Alpha-2e"

(ix) FEATURE:
        (A) NAME/KEY: 5'UTR
        (B) LOCATION: 1..34

(ix) FEATURE:
        (A) NAME/KEY: 3'UTR (B) LOCATION: 3289..3579

(xi) SEQUENCE DESCRIPTION: SEQ ID NO:31:

```
GCGGGGGAGG GGGCATTGAT CTTCGATCGC GAAG ATG GCT GCT GGC TGC CTG        52
                                     Met Ala Ala Gly Cys Leu
                                       1               5

CTG GCC TTG ACT CTG ACA CTT TTC CAA TCT TTG CTC ATC GGC CCC TCG      100
Leu Ala Leu Thr Leu Thr Leu Phe Gln Ser Leu Leu Ile Gly Pro Ser
            10                  15                  20

TCG GAG GAG CCG TTC CCT TCG GCC GTC ACT ATC AAA TCA TGG GTG GAT      148
Ser Glu Glu Pro Phe Pro Ser Ala Val Thr Ile Lys Ser Trp Val Asp
        25                  30                  35

AAG ATG CAA GAA GAC CTT GTC ACA CTG GCA AAA ACA GCA AGT GGA GTC      196
Lys Met Gln Glu Asp Leu Val Thr Leu Ala Lys Thr Ala Ser Gly Val
 40                  45                  50

AAT CAG CTT GTT GAT ATT TAT GAG AAA TAT CAA GAT TTG TAT ACT GTG      244
Asn Gln Leu Val Asp Ile Tyr Glu Lys Tyr Gln Asp Leu Tyr Thr Val
 55                  60                  65                  70

GAA CCA AAT AAT GCA CGC CAG CTG GTA GAA ATT GCA GCC AGG GAT ATT      292
Glu Pro Asn Asn Ala Arg Gln Leu Val Glu Ile Ala Ala Arg Asp Ile
                 75                  80                  85

GAG AAA CTT CTG AGC AAC AGA TCT AAA GCC CTG GTG AGC CTG GCA TTG      340
Glu Lys Leu Leu Ser Asn Arg Ser Lys Ala Leu Val Ser Leu Ala Leu
             90                  95                 100

GAA GCG GAG AAA GTT CAA GCA GCT CAC CAG TGG AGA GAA GAT TTT GCA      388
Glu Ala Glu Lys Val Gln Ala Ala His Gln Trp Arg Glu Asp Phe Ala
        105                 110                 115

AGC AAT GAA GTT GTC TAC TAC AAT GCA AAG GAT GAT CTC GAT CCT GAG      436
Ser Asn Glu Val Val Tyr Tyr Asn Ala Lys Asp Asp Leu Asp Pro Glu
    120                 125                 130

AAA AAT GAC AGT GAG CCA GGC AGC CAG AGG ATA AAA CCT GTT TTC ATT      484
Lys Asn Asp Ser Glu Pro Gly Ser Gln Arg Ile Lys Pro Val Phe Ile
135                 140                 145                 150

GAA GAT GCT AAT TTT GGA CGA CAA ATA TCT TAT CAG CAC GCA GCA GTC      532
Glu Asp Ala Asn Phe Gly Arg Gln Ile Ser Tyr Gln His Ala Ala Val
                155                 160                 165

CAT ATT CCT ACT GAC ATC TAT GAG GGC TCA ACA ATT GTG TTA AAT GAA      580
His Ile Pro Thr Asp Ile Tyr Glu Gly Ser Thr Ile Val Leu Asn Glu
            170                 175                 180

CTC AAC TGG ACA AGT GCC TTA GAT GAA GTT TTC AAA AAG AAT CGC GAG      628
Leu Asn Trp Thr Ser Ala Leu Asp Glu Val Phe Lys Lys Asn Arg Glu
        185                 190                 195

GAA GAC CCT TCA TTA TTG TGG CAG GTT TTT GGC AGT GCC ACT GGC CTA      676
Glu Asp Pro Ser Leu Leu Trp Gln Val Phe Gly Ser Ala Thr Gly Leu
    200                 205                 210

GCT CGA TAT TAT CCA GCT TCA CCA TGG GTT GAT AAT AGT AGA ACT CCA      724
Ala Arg Tyr Tyr Pro Ala Ser Pro Trp Val Asp Asn Ser Arg Thr Pro
215                 220                 225                 230

AAT AAG ATT GAC CTT TAT GAT GTA CGC AGA AGA CCA TGG TAC ATC CAA      772
Asn Lys Ile Asp Leu Tyr Asp Val Arg Arg Arg Pro Trp Tyr Ile Gln
                235                 240                 245

GGA GCT GCA TCT CCT AAA GAC ATG CTT ATT CTG GTG GAT GTG AGT GGA      820
Gly Ala Ala Ser Pro Lys Asp Met Leu Ile Leu Val Asp Val Ser Gly
            250                 255                 260

AGT GTT AGT GGA TTG ACA CTT AAA CTG ATC CGA ACA TCT GTC TCC GAA      868
Ser Val Ser Gly Leu Thr Leu Lys Leu Ile Arg Thr Ser Val Ser Glu
        265                 270                 275

ATG TTA GAA ACC CTC TCA GAT GAT GAT TTC GTG AAT GTA GCT TCA TTT      916
Met Leu Glu Thr Leu Ser Asp Asp Asp Phe Val Asn Val Ala Ser Phe
    280                 285                 290
```

| | | | | | | | | | | | | | | | | |
|---|---|---|---|---|---|---|---|---|---|---|---|---|---|---|---|---|
| AAC | AGC | AAT | GCT | CAG | GAT | GTA | AGC | TGT | TTT | CAG | CAC | CTT | GTC | CAA | GCA | 964 |
| Asn | Ser | Asn | Ala | Gln | Asp | Val | Ser | Cys | Phe | Gln | His | Leu | Val | Gln | Ala | |
| 295 | | | | 300 | | | | | 305 | | | | | 310 | | |
| AAT | GTA | AGA | AAT | AAA | AAA | GTG | TTG | AAA | GAC | GCG | GTG | AAT | AAT | ATC | ACA | 1012 |
| Asn | Val | Arg | Asn | Lys | Lys | Val | Leu | Lys | Asp | Ala | Val | Asn | Asn | Ile | Thr | |
| | | | | 315 | | | | | 320 | | | | | 325 | | |
| GCC | AAA | GGA | ATT | ACA | GAT | TAT | AAG | AAG | GGC | TTT | AGT | TTT | GCT | TTT | GAA | 1060 |
| Ala | Lys | Gly | Ile | Thr | Asp | Tyr | Lys | Lys | Gly | Phe | Ser | Phe | Ala | Phe | Glu | |
| | | | | 330 | | | | | 335 | | | | | 340 | | |
| CAG | CTG | CTT | AAT | TAT | AAT | GTT | TCC | AGA | GCA | AAC | TGC | AAT | AAG | ATT | ATT | 1108 |
| Gln | Leu | Leu | Asn | Tyr | Asn | Val | Ser | Arg | Ala | Asn | Cys | Asn | Lys | Ile | Ile | |
| | | | | 345 | | | | | 350 | | | | | 355 | | |
| ATG | CTA | TTC | ACG | GAT | GGA | GGA | GAA | GAG | AGA | GCC | CAG | GAG | ATA | TTT | AAC | 1156 |
| Met | Leu | Phe | Thr | Asp | Gly | Gly | Glu | Glu | Arg | Ala | Gln | Glu | Ile | Phe | Asn | |
| | | | | 360 | | | | | 365 | | | | | 370 | | |
| AAA | TAC | AAT | AAA | GAT | AAA | AAA | GTA | CGT | GTA | TTC | AGG | TTT | TCA | GTT | GGT | 1204 |
| Lys | Tyr | Asn | Lys | Asp | Lys | Lys | Val | Arg | Val | Phe | Arg | Phe | Ser | Val | Gly | |
| 375 | | | | 380 | | | | | 385 | | | | | | 390 | |
| CAA | CAC | AAT | TAT | GAG | AGA | GGA | CCT | ATT | CAG | TGG | ATG | GCC | TGT | GAA | AAC | 1252 |
| Gln | His | Asn | Tyr | Glu | Arg | Gly | Pro | Ile | Gln | Trp | Met | Ala | Cys | Glu | Asn | |
| | | | | 395 | | | | | 400 | | | | | 405 | | |
| AAA | GGT | TAT | TAT | TAT | GAA | ATT | CCT | TCC | ATT | GGT | GCA | ATA | AGA | ATC | AAT | 1300 |
| Lys | Gly | Tyr | Tyr | Tyr | Glu | Ile | Pro | Ser | Ile | Gly | Ala | Ile | Arg | Ile | Asn | |
| | | | | 410 | | | | | 415 | | | | | 420 | | |
| ACT | CAG | GAA | TAT | TTG | GAT | GTT | TTG | GGA | AGA | CCA | ATG | GTT | TTA | GCA | GGA | 1348 |
| Thr | Gln | Glu | Tyr | Leu | Asp | Val | Leu | Gly | Arg | Pro | Met | Val | Leu | Ala | Gly | |
| | | | | 425 | | | | | 430 | | | | | 435 | | |
| GAC | AAA | GCT | AAG | CAA | GTC | CAA | TGG | ACA | AAT | GTG | TAC | CTG | GAT | GCA | TTG | 1396 |
| Asp | Lys | Ala | Lys | Gln | Val | Gln | Trp | Thr | Asn | Val | Tyr | Leu | Asp | Ala | Leu | |
| | | | | 440 | | | | | 445 | | | | | 450 | | |
| GAA | CTG | GGA | CTT | GTC | ATT | ACT | GGA | ACT | CTT | CCG | GTC | TTC | AAC | ATA | ACC | 1444 |
| Glu | Leu | Gly | Leu | Val | Ile | Thr | Gly | Thr | Leu | Pro | Val | Phe | Asn | Ile | Thr | |
| 455 | | | | 460 | | | | | 465 | | | | | | 470 | |
| GGC | CAA | TTT | GAA | AAT | AAG | ACA | AAC | TTA | AAG | AAC | CAG | CTG | ATT | CTT | GGT | 1492 |
| Gly | Gln | Phe | Glu | Asn | Lys | Thr | Asn | Leu | Lys | Asn | Gln | Leu | Ile | Leu | Gly | |
| | | | | 475 | | | | | 480 | | | | | 485 | | |
| GTG | ATG | GGA | GTA | GAT | GTG | TCT | TTG | GAA | GAT | ATT | AAA | AGA | CTG | ACA | CCA | 1540 |
| Val | Met | Gly | Val | Asp | Val | Ser | Leu | Glu | Asp | Ile | Lys | Arg | Leu | Thr | Pro | |
| | | | | 490 | | | | | 495 | | | | | 500 | | |
| CGT | TTT | ACA | CTG | TGC | CCC | AAT | GGG | TAT | TAC | TTT | GCA | ATC | GAT | CCT | AAT | 1588 |
| Arg | Phe | Thr | Leu | Cys | Pro | Asn | Gly | Tyr | Tyr | Phe | Ala | Ile | Asp | Pro | Asn | |
| | | | | 505 | | | | | 510 | | | | | 515 | | |
| GGT | TAT | GTT | TTA | TTA | CAT | CCA | AAT | CTT | CAG | CCA | AAG | AAC | CCC | AAA | TCT | 1636 |
| Gly | Tyr | Val | Leu | Leu | His | Pro | Asn | Leu | Gln | Pro | Lys | Asn | Pro | Lys | Ser | |
| | | | | 520 | | | | | 525 | | | | | 530 | | |
| CAG | GAG | CCA | GTA | ACA | TTG | GAT | TTC | CTT | GAT | GCA | GAG | TTA | GAG | AAT | GAT | 1684 |
| Gln | Glu | Pro | Val | Thr | Leu | Asp | Phe | Leu | Asp | Ala | Glu | Leu | Glu | Asn | Asp | |
| 535 | | | | 540 | | | | | 545 | | | | | 550 | | |
| ATT | AAA | GTG | GAG | ATT | CGA | AAT | AAG | ATG | ATT | GAT | GGG | GAA | AGT | GGA | GAA | 1732 |
| Ile | Lys | Val | Glu | Ile | Arg | Asn | Lys | Met | Ile | Asp | Gly | Glu | Ser | Gly | Glu | |
| | | | | 555 | | | | | 560 | | | | | 565 | | |
| AAA | ACA | TTC | AGA | ACT | CTG | GTT | AAA | TCT | CAA | GAT | GAG | AGA | TAT | ATT | GAC | 1780 |
| Lys | Thr | Phe | Arg | Thr | Leu | Val | Lys | Ser | Gln | Asp | Glu | Arg | Tyr | Ile | Asp | |
| | | | | 570 | | | | | 575 | | | | | 580 | | |
| AAA | GGA | AAC | AGG | ACA | TAC | ACA | TGG | ACA | CCT | GTC | AAT | GGC | ACA | GAT | TAC | 1828 |
| Lys | Gly | Asn | Arg | Thr | Tyr | Thr | Trp | Thr | Pro | Val | Asn | Gly | Thr | Asp | Tyr | |
| | | | | 585 | | | | | 590 | | | | | 595 | | |
| AGT | TTG | GCC | TTG | GTA | TTA | CCA | ACC | TAC | AGT | TTT | TAC | TAT | ATA | AAA | GCC | 1876 |
| Ser | Leu | Ala | Leu | Val | Leu | Pro | Thr | Tyr | Ser | Phe | Tyr | Tyr | Ile | Lys | Ala | |

-continued

|  |  |
|---|---|
| AAA CTA GAA GAG ACA ATA ACT CAG GCC AGA TAT TCG GAA ACC CTG AAG<br>Lys Leu Glu Glu Thr Ile Thr Gln Ala Arg Tyr Ser Glu Thr Leu Lys<br>615                     620                   625                   630 | 1924 |
| CCA GAT AAT TTT GAA GAA TCT GGC TAT ACA TTC ATA GCA CCA AGA GAT<br>Pro Asp Asn Phe Glu Glu Ser Gly Tyr Thr Phe Ile Ala Pro Arg Asp<br>                635                   640                   645 | 1972 |
| TAC TGC AAT GAC CTG AAA ATA TCG GAT AAT AAC ACT GAA TTT CTT TTA<br>Tyr Cys Asn Asp Leu Lys Ile Ser Asp Asn Asn Thr Glu Phe Leu Leu<br>           650                   655                   660 | 2020 |
| AAT TTC AAC GAG TTT ATT GAT AGA AAA ACT CCA AAC AAC CCA TCA TGT<br>Asn Phe Asn Glu Phe Ile Asp Arg Lys Thr Pro Asn Asn Pro Ser Cys<br>           665                   670                   675 | 2068 |
| AAC GCG GAT TTG ATT AAT AGA GTC TTG CTT GAT GCA GGC TTT ACA AAT<br>Asn Ala Asp Leu Ile Asn Arg Val Leu Leu Asp Ala Gly Phe Thr Asn<br>           680                   685                   690 | 2116 |
| GAA CTT GTC CAA AAT TAC TGG AGT AAG CAG AAA AAT ATC AAG GGA GTG<br>Glu Leu Val Gln Asn Tyr Trp Ser Lys Gln Lys Asn Ile Lys Gly Val<br>695                     700                   705                   710 | 2164 |
| AAA GCA CGA TTT GTT GTG ACT GAT GGT GGG ATT ACC AGA GTT TAT CCC<br>Lys Ala Arg Phe Val Val Thr Asp Gly Gly Ile Thr Arg Val Tyr Pro<br>           715                   720                   725 | 2212 |
| AAA GAG GCT GGA GAA AAT TGG CAA GAA AAC CCA GAG ACA TAT GAG GAC<br>Lys Glu Ala Gly Glu Asn Trp Gln Glu Asn Pro Glu Thr Tyr Glu Asp<br>           730                   735                   740 | 2260 |
| AGC TTC TAT AAA AGG AGC CTA GAT AAT GAT AAC TAT GTT TTC ACT GCT<br>Ser Phe Tyr Lys Arg Ser Leu Asp Asn Asp Asn Tyr Val Phe Thr Ala<br>           745                   750                   755 | 2308 |
| CCC TAC TTT AAC AAA AGT GGA CCT GGT GCC TAT GAA TCG GGC ATT ATG<br>Pro Tyr Phe Asn Lys Ser Gly Pro Gly Ala Tyr Glu Ser Gly Ile Met<br>760                     765                   770 | 2356 |
| GTA AGC AAA GCT GTA GAA ATA TAT ATT CAA GGG AAA CTT CTT AAA CCT<br>Val Ser Lys Ala Val Glu Ile Tyr Ile Gln Gly Lys Leu Leu Lys Pro<br>775                     780                   785                   790 | 2404 |
| GCA GTT GTT GGA ATT AAA ATT GAT GTA AAT TCC TGG ATA GAG AAT TTC<br>Ala Val Val Gly Ile Lys Ile Asp Val Asn Ser Trp Ile Glu Asn Phe<br>           795                   800                   805 | 2452 |
| ACC AAA ACC TCA ATC AGA GAT CCG TGT GCT GGT CCA GTT TGT GAC TGC<br>Thr Lys Thr Ser Ile Arg Asp Pro Cys Ala Gly Pro Val Cys Asp Cys<br>           810                   815                   820 | 2500 |
| AAA AGA AAC AGT GAC GTA ATG GAT TGT GTG ATT CTG GAT GAT GGT GGG<br>Lys Arg Asn Ser Asp Val Met Asp Cys Val Ile Leu Asp Asp Gly Gly<br>           825                   830                   835 | 2548 |
| TTT CTT CTG ATG GCA AAT CAT GAT GAT TAT ACT AAT CAG ATT GGA AGA<br>Phe Leu Leu Met Ala Asn His Asp Asp Tyr Thr Asn Gln Ile Gly Arg<br>840                     845                   850 | 2596 |
| TTT TTT GGA GAG ATT GAT CCC AGC TTG ATG AGA CAC CTG GTT AAT ATA<br>Phe Phe Gly Glu Ile Asp Pro Ser Leu Met Arg His Leu Val Asn Ile<br>855                     860                   865                   870 | 2644 |
| TCA GTT TAT GCT TTT AAC AAA TCT TAT GAT TAT CAG TCA GTA TGT GAG<br>Ser Val Tyr Ala Phe Asn Lys Ser Tyr Asp Tyr Gln Ser Val Cys Glu<br>           875                   880                   885 | 2692 |
| CCC GGT GCT GCA CCA AAA CAA GGA GCA GGA CAT CGC TCA GCA TAT GTG<br>Pro Gly Ala Ala Pro Lys Gln Gly Ala Gly His Arg Ser Ala Tyr Val<br>           890                   895                   900 | 2740 |
| CCA TCA GTA GCA GAC ATA TTA CAA ATT GGC TGG TGG GCC ACT GCT GCT<br>Pro Ser Val Ala Asp Ile Leu Gln Ile Gly Trp Trp Ala Thr Ala Ala<br>           905                   910                   915 | 2788 |
| GCC TGG TCT ATT CTA CAG CAG TTT CTC TTG AGT TTG ACC TTT CCA CGA | 2836 |

```
Ala Trp Ser Ile Leu Gln Gln Phe Leu Leu Ser Leu Thr Phe Pro Arg
    920                 925                 930

CTC CTT GAG GCA GTT GAG ATG GAG GAT GAT GAC TTC ACG GCC TCC CTG        2884
Leu Leu Glu Ala Val Glu Met Glu Asp Asp Asp Phe Thr Ala Ser Leu
935                 940                 945                 950

TCC AAG CAG AGC TGC ATT ACT GAA CAA ACC CAG TAT TTC TTC GAT AAC        2932
Ser Lys Gln Ser Cys Ile Thr Glu Gln Thr Gln Tyr Phe Phe Asp Asn
                955                 960                 965

GAC AGT AAA TCA TTC AGT GGT GTA TTA GAC TGT GGA AAC TGT TCC AGA        2980
Asp Ser Lys Ser Phe Ser Gly Val Leu Asp Cys Gly Asn Cys Ser Arg
                970                 975                 980

ATC TTT CAT GGA GAA AAG CTT ATG AAC ACC AAC TTA ATA TTC ATA ATG        3028
Ile Phe His Gly Glu Lys Leu Met Asn Thr Asn Leu Ile Phe Ile Met
            985                 990                 995

GTT GAG AGC AAA GGG ACA TGT CCA TGT GAC ACA CGA CTG CTC ATA CAA        3076
Val Glu Ser Lys Gly Thr Cys Pro Cys Asp Thr Arg Leu Leu Ile Gln
    1000                1005                1010

GCG GAG CAG ACT TCT GAC GGT CCA AAT CCT TGT GAC ATG GTT AAG CAA        3124
Ala Glu Gln Thr Ser Asp Gly Pro Asn Pro Cys Asp Met Val Lys Gln
1015                1020                1025                1030

CCT AGA TAC CGA AAA GGG CCT GAT GTC TGC TTT GAT AAC AAT GTC TTG        3172
Pro Arg Tyr Arg Lys Gly Pro Asp Val Cys Phe Asp Asn Asn Val Leu
                1035                1040                1045

GAG GAT TAT ACT GAC TGT GGT GGT GTT TCT GGA TTA AAT CCC TCC CTG        3220
Glu Asp Tyr Thr Asp Cys Gly Gly Val Ser Gly Leu Asn Pro Ser Leu
                1050                1055                1060

TGG TAT ATC ATT GGA ATC CAG TTT CTA CTA CTT TGG CTG GTA TCT GGC        3268
Trp Tyr Ile Ile Gly Ile Gln Phe Leu Leu Leu Trp Leu Val Ser Gly
            1065                1070                1075

AGC ACA CAC CGG CTG TTA TGACCTTCTA AAAACCAAAT CTGCATAGTT               3316
Ser Thr His Arg Leu Leu
    1080                108

AAACTCCAGA CCCTGCCAAA ACATGAGCCC TGCCCTCAAT TACAGTAACG TAGGGTCAGC     3376

TATAAAATCA GACAAACATT AGCTGGGCCT GTTCCATGGC ATAACACTAA GGCGCAGACT     3436

CCTAAGGCAC CCACTGGCTG CATGTCAGGG TGTCAGATCC TTAAACGTGT GTGAATGCTG     3496

CATCATCTAT GTGTAACATC AAAGCAAAAT CCTATACGTG TCCTCTATTG GAAAATTTGG     3556

GCGTTTGTTG TTGCATTGTT GGT                                              3579

(2) INFORMATION FOR SEQ ID NO:32:

(i) SEQUENCE CHARACTERISTICS:
        (A) LENGTH: 1681 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1437
        (D) OTHER INFORMATION: /standard_name= "Beta1-1"

(ix) FEATURE:
        (A) NAME/KEY: 3'UTR
        (B) LOCATION: 1435..1681

(xi) SEQUENCE DESCRIPTION: SEQ ID NO:32:

ATG GTC CAG AAG ACC AGC ATG TCC CGG GGC CCT TAC CCA CCC TCC CAG          48
Met Val Gln Lys Thr Ser Met Ser Arg Gly Pro Tyr Pro Pro Ser Gln
1               5                   10                  15
```

-continued

| | |
|---|---|
| GAG ATC CCC ATG GAG GTC TTC GAC CCC AGC CCG CAG GGC AAA TAC AGC<br>Glu Ile Pro Met Glu Val Phe Asp Pro Ser Pro Gln Gly Lys Tyr Ser<br>             20                   25                 30 | 96 |
| AAG AGG AAA GGG CGA TTC AAA CGG TCA GAT GGG AGC ACG TCC TCG GAT<br>Lys Arg Lys Gly Arg Phe Lys Arg Ser Asp Gly Ser Thr Ser Ser Asp<br>    35                       40                      45 | 144 |
| ACC ACA TCC AAC AGC TTT GTC CGC CAG GGC TCA GCG GAG TCC TAC ACC<br>Thr Thr Ser Asn Ser Phe Val Arg Gln Gly Ser Ala Glu Ser Tyr Thr<br>    50                       55                   60 | 192 |
| AGC CGT CCA TCA GAC TCT GAT GTA TCT CTG GAG GAG GAC CGG GAA GCC<br>Ser Arg Pro Ser Asp Ser Asp Val Ser Leu Glu Glu Asp Arg Glu Ala<br>65                   70                   75                 80 | 240 |
| TTA AGG AAG GAA GCA GAG CGC CAG GCA TTA GCG CAG CTC GAG AAG GCC<br>Leu Arg Lys Glu Ala Glu Arg Gln Ala Leu Ala Gln Leu Glu Lys Ala<br>             85                   90                 95 | 288 |
| AAG ACC AAG CCA GTG GCA TTT GCT GTG CGG ACA AAT GTT GGC TAC AAT<br>Lys Thr Lys Pro Val Ala Phe Ala Val Arg Thr Asn Val Gly Tyr Asn<br>             100                 105              110 | 336 |
| CCG TCT CCA GGG GAT GAG GTG CCT GTG CAG GGA GTG GCC ATC ACC TTC<br>Pro Ser Pro Gly Asp Glu Val Pro Val Gln Gly Val Ala Ile Thr Phe<br>             115                 120              125 | 384 |
| GAG CCC AAA GAC TTC CTG CAC ATC AAG GAG AAA TAC AAT AAT GAC TGG<br>Glu Pro Lys Asp Phe Leu His Ile Lys Glu Lys Tyr Asn Asn Asp Trp<br>130                 135                 140 | 432 |
| TGG ATC GGG CGG CTG GTG AAG GAG GGC TGT GAG GTT GGC TTC ATT CCC<br>Trp Ile Gly Arg Leu Val Lys Glu Gly Cys Glu Val Gly Phe Ile Pro<br>145                 150                155              160 | 480 |
| AGC CCC GTC AAA CTG GAC AGC CTT CGC CTG CTG CAG GAA CAG AAG CTG<br>Ser Pro Val Lys Leu Asp Ser Leu Arg Leu Leu Gln Glu Gln Lys Leu<br>             165                 170              175 | 528 |
| CGC CAG AAC CGC CTC GGC TCC AGC AAA TCA GGC GAT AAC TCC AGT TCC<br>Arg Gln Asn Arg Leu Gly Ser Ser Lys Ser Gly Asp Asn Ser Ser Ser<br>             180                 185              190 | 576 |
| AGT CTG GGA GAT GTG GTG ACT GGC ACC CGC CGC CCC ACA CCC CCT GCC<br>Ser Leu Gly Asp Val Val Thr Gly Thr Arg Arg Pro Thr Pro Pro Ala<br>             195                 200              205 | 624 |
| AGT GGT AAT GAA ATG ACT AAC TTA GCC TTT GAA CTA GAC CCC CTA GAG<br>Ser Gly Asn Glu Met Thr Asn Leu Ala Phe Glu Leu Asp Pro Leu Glu<br>    210                     215                 220 | 672 |
| TTA GAG GAG GAA GAG GCT GAG CTT GGT GAG CAG AGT GGC TCT GCC AAG<br>Leu Glu Glu Glu Glu Ala Glu Leu Gly Glu Gln Ser Gly Ser Ala Lys<br>225                 230                235              240 | 720 |
| ACT AGT GTT AGC AGT GTC ACC ACC CCG CCA CCC CAT GGC AAA CGC ATC<br>Thr Ser Val Ser Ser Val Thr Thr Pro Pro Pro His Gly Lys Arg Ile<br>             245                 250              255 | 768 |
| CCC TTC TTT AAG AAG ACA GAG CAT GTG CCC CCC TAT GAC GTG GTG CCT<br>Pro Phe Phe Lys Lys Thr Glu His Val Pro Pro Tyr Asp Val Val Pro<br>             260                 265              270 | 816 |
| TCC ATG AGG CCC ATC ATC CTG GTG GGA CCG TCG CTC AAG GGC TAC GAG<br>Ser Met Arg Pro Ile Ile Leu Val Gly Pro Ser Leu Lys Gly Tyr Glu<br>    275                     280                 285 | 864 |
| GTT ACA GAC ATG ATG CAG AAA GCT TTA TTT GAC TTC TTG AAG CAT CGG<br>Val Thr Asp Met Met Gln Lys Ala Leu Phe Asp Phe Leu Lys His Arg<br>    290                     295                 300 | 912 |
| TTT GAT GGC AGG ATC TCC ATC ACT CGT GTG ACG GCA GAT ATT TCC CTG<br>Phe Asp Gly Arg Ile Ser Ile Thr Arg Val Thr Ala Asp Ile Ser Leu<br>305                 310                315              320 | 960 |
| GCT AAG CGC TCA GTT CTC AAC AAC CCC AGC AAA CAC ATC ATC ATT GAG<br>Ala Lys Arg Ser Val Leu Asn Asn Pro Ser Lys His Ile Ile Ile Glu<br>             325                 330              335 | 1008 |

```
CGC TCC AAC ACA CGC TCC AGC CTG GCT GAG GTG CAG AGT GAA ATC GAG       1056
Arg Ser Asn Thr Arg Ser Ser Leu Ala Glu Val Gln Ser Glu Ile Glu
            340                 345                 350

CGA ATC TTC GAG CTG GCC CGG ACC CTT CAG TTG GTC GCT CTG GAT GCT       1104
Arg Ile Phe Glu Leu Ala Arg Thr Leu Gln Leu Val Ala Leu Asp Ala
        355                 360                 365

GAC ACC ATC AAT CAC CCA GCC CAG CTG TCC AAG ACC TCG CTG GCC CCC       1152
Asp Thr Ile Asn His Pro Ala Gln Leu Ser Lys Thr Ser Leu Ala Pro
    370                 375                 380

ATC ATT GTT TAC ATC AAG ATC ACC TCT CCC AAG GTA CTT CAA AGG CTC       1200
Ile Ile Val Tyr Ile Lys Ile Thr Ser Pro Lys Val Leu Gln Arg Leu
385                 390                 395                 400

ATC AAG TCC CGA GGA AAG TCT CAG TCC AAA CAC CTC AAT GTC CAA ATA       1248
Ile Lys Ser Arg Gly Lys Ser Gln Ser Lys His Leu Asn Val Gln Ile
            405                 410                 415

GCG GCC TCG GAA AAG CTG GCA CAG TGC CCC CCT GAA ATG TTT GAC ATC       1296
Ala Ala Ser Glu Lys Leu Ala Gln Cys Pro Pro Glu Met Phe Asp Ile
        420                 425                 430

ATC CTG GAT GAG AAC CAA TTG GAG GAT GCC TGC GAG CAT CTG GCG GAG       1344
Ile Leu Asp Glu Asn Gln Leu Glu Asp Ala Cys Glu His Leu Ala Glu
    435                 440                 445

TAC TTG GAA GCC TAT TGG AAG GCC ACA CAC CCG CCC AGC AGC ACG CCA       1392
Tyr Leu Glu Ala Tyr Trp Lys Ala Thr His Pro Pro Ser Ser Thr Pro
450                 455                 460

CCC AAT CCG CTG CTG AAC CGC ACC ATG GCT ACC GCA GCC CTG GCT           1437
Pro Asn Pro Leu Leu Asn Arg Thr Met Ala Thr Ala Ala Leu Ala
465                 470                 475

GCCAGCCCTG CCCCTGTCTC AACCTCCAG GTACAGGTGC TCACCTCGCT CAGGAGAAAC      1497

CTCGGCTTCT GGGGCGGGCT GGAGTCCTCA CAGCGGGGCA GTGTGGTGCC CCAGGAGCAG     1557

GAACATGCCA TGTAGTGGGC GCCCTGCCCG TCTTCCCTCC TGCTCTGGGG TCGGAACTGG     1617

AGTGCAGGGA ACATGGAGGA GGAAGGGAAG AGCTTTATTT TGTAAAAAAA TAAGATGAGC     1677

GGCA                                                                  1681

(2) INFORMATION FOR SEQ ID NO:33:

(i) SEQUENCE CHARACTERISTICS:
        (A) LENGTH: 1526 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..651
        (D) OTHER INFORMATION: /standard_name= "Beta1-4"

(xi) SEQUENCE DESCRIPTION: SEQ ID NO:33:

ATG GTC CAG AAG ACC AGC ATG TCC CGG GGC CCT TAC CCA CCC TCC CAG        48
Met Val Gln Lys Thr Ser Met Ser Arg Gly Pro Tyr Pro Pro Ser Gln
1               5                   10                  15

GAG ATC CCC ATG GAG GTC TTC GAC CCC AGC CCG CAG GGC AAA TAC AGC        96
Glu Ile Pro Met Glu Val Phe Asp Pro Ser Pro Gln Gly Lys Tyr Ser
            20                  25                  30

AAG AGG AAA GGG CGA TTC AAA CGG TCA GAT GGG AGC ACG TCC TCG GAT       144
Lys Arg Lys Gly Arg Phe Lys Arg Ser Asp Gly Ser Thr Ser Ser Asp
        35                  40                  45

ACC ACA TCC AAC AGC TTT GTC CGC CAG GGC TCA GCG GAG TCC TAC ACC       192
Thr Thr Ser Asn Ser Phe Val Arg Gln Gly Ser Ala Glu Ser Tyr Thr
```

```
            50                  55                  60
AGC CGT CCA TCA GAC TCT GAT GTA TCT CTG GAG GAG GAC CGG GAA GCC        240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC        288
Leu Arg Lys Glu Ala Glu Arg Gln Ala Leu Ala Gln Leu Glu Lys Ala
                 85                  90                  95

AAG ACC AAG CCA GTG GCA TTT GCT GTG CGG ACA AAT GTT GGC TAC AAT        336
Lys Thr Lys Pro Val Ala Phe Ala Val Arg Thr Asn Val Gly Tyr Asn
            100                 105                 110

CCG TCT CCA GGG GAT GAG GTG CCT GTG CAG GGA GTG GCC ATC ACC TTC        384
Pro Ser Pro Gly Asp Glu Val Pro Val Gln Gly Val Ala Ile Thr Phe
        115                 120                 125

GAG CCC AAA GAC TTC CTG CAC ATC AAG GAG AAA TAC AAT AAT GAC TGG        432
Glu Pro Lys Asp Phe Leu His Ile Lys Glu Lys Tyr Asn Asn Asp Trp
    130                 135                 140

TGG ATC GGG CGG CTG GTG AAG GAG GGC TGT GAG GTT GGC TTC ATT CCC        480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG        528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC        576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC        624
Ser Leu Gly Asp Val Val Thr Gly Thr Arg Arg Pro Thr Pro Pro Ala
        195                 200                 205

AGT GAC AGA GCA TGT GCC CCC CTA TGACGTGGTG CCTTCCATGA GGCCCATCAT      678
Ser Asp Arg Ala Cys Ala Pro Leu
    210                 215

CCTGGTGGGA CCGTCGCTCA AGGGCTACGA GGTTACAGAC ATGATGCAGA AAGCTTTATT      738

TGACTTCTTG AAGCATCGGT TGATGGCAG  GATCTCCATC ACTCGTGTGA CGGCAGATAT      798

TTCCCTGGCT AAGCGCTCAG TTCTCAACAA CCCCAGCAAA CACATCATCA TTGAGCGCTC      858

CAACACACGC TCCAGCCTGG CTGAGGTGCA GAGTGAAATC GAGCGAATCT TCGAGCTGGC      918

CCGGACCCTT CAGTTGGTCG CTCTGGATGC TGACACCATC AATCACCCAG CCCAGCTGTC      978

CAAGACCTCG CTGGCCCCCA TCATTGTTTA CATCAAGATC ACCTCTCCCA AGGTACTTCA     1038

AAGGCTCATC AAGTCCCGAG AAAGTCTCA  GTCCAAACAC CTCAATGTCC AAATAGCGGC     1098

CTCGGAAAAG CTGGCACAGT GCCCCCCTGA AATGTTTGAC ATCATCCTGG ATGAGAACCA     1158

ATTGGAGGAT GCCTGCGAGC ATCTGGCGGA GTACTTGGAA GCCTATTGGA AGGCCACACA     1218

CCCGCCCAGC AGCACGCCAC CCAATCCGCT GCTGAACCGC ACCATGGCTA CCGCAGCCCT     1278

GGCTGCCAGC CCTGCCCCTG TCTCCAACCT CCAGGTACAG GTGCTCACCT CGCTCAGGAG     1338

AAACCTCGGC TTCTGGGGCG GCTGGAGTC  CTCACAGCGG GGCAGTGTGG TGCCCCAGGA     1398

GCAGGAACAT GCCATGTAGT GGGCGCCCTG CCCGTCTTCC CTCCTGCTCT GGGGTCGGAA     1458

CTGGAGTGCA GGGAACATGG AGGAGGAAGG GAAGAGCTTT ATTTTGTAAA AAAATAAGAT     1518

GAGCGGCA                                                              1526

(2) INFORMATION FOR SEQ ID NO:34:

(i) SEQUENCE CHARACTERISTICS:
        (A) LENGTH: 1393 base pairs
        (B) TYPE: nucleic acid
        (C) STRANDEDNESS: double
```

-continued (D) TOPOLOGY: linear (ii) MOLECULE TYPE: DNA (genomic)

(ix) FEATURE:
    (A) NAME/KEY: CDS
    (B) LOCATION: 1..660
    (D) OTHER INFORMATION: /standard_name= "Beta1-5"

(xi) SEQUENCE DESCRIPTION: SEQ ID NO:34:

```
ATG GTC CAG AAG ACC AGC ATG TCC CGG GGC CCT TAC CCA CCC TCC CAG        48
Met Val Gln Lys Thr Ser Met Ser Arg Gly Pro Tyr Pro Pro Ser Gln
 1               5                  10                  15

GAG ATC CCC ATG GAG GTC TTC GAC CCC AGC CCG CAG GGC AAA TAC AGC        96
Glu Ile Pro Met Glu Val Phe Asp Pro Ser Pro Gln Gly Lys Tyr Ser
                20                  25                  30

AAG AGG AAA GGG CGA TTC AAA CGG TCA GAT GGG AGC ACG TCC TCG GAT       144
Lys Arg Lys Gly Arg Phe Lys Arg Ser Asp Gly Ser Thr Ser Ser Asp
            35                  40                  45

ACC ACA TCC AAC AGC TTT GTC CGC CAG GGC TCA GCG GAG TCC TAC ACC       192
Thr Thr Ser Asn Ser Phe Val Arg Gln Gly Ser Ala Glu Ser Tyr Thr
         50                  55                  60

AGC CGT CCA TCA GAC TCT GAT GTA TCT CTG GAG GAG GAC CGG GAA GCC       240
Ser Arg Pro Ser Asp Ser Asp Val Ser Leu Glu Glu Asp Arg Glu Ala
 65                  70                  75                  80

TTA AGG AAG GAA GCA GAG CGC CAG GCA TTA GCG CAG CTC GAG AAG GCC       288
Leu Arg Lys Glu Ala Glu Arg Gln Ala Leu Ala Gln Leu Glu Lys Ala
                85                  90                  95

AAG ACC AAG CCA GTG GCA TTT GCT GTG CGG ACA AAT GTT GGC TAC AAT       336
Lys Thr Lys Pro Val Ala Phe Ala Val Arg Thr Asn Val Gly Tyr Asn
               100                 105                 110

CCG TCT CCA GGG GAT GAG GTG CCT GTG CAG GGA GTG GCC ATC ACC TTC       384
Pro Ser Pro Gly Asp Glu Val Pro Val Gln Gly Val Ala Ile Thr Phe
            115                 120                 125

GAG CCC AAA GAC TTC CTG CAC ATC AAG GAG AAA TAC AAT AAT GAC TGG       432
Glu Pro Lys Asp Phe Leu His Ile Lys Glu Lys Tyr Asn Asn Asp Trp
        130                 135                 140

TGG ATC GGG CGG CTG GTG AAG GAG GGC TGT GAG GTT GGC TTC ATT CCC       480
Trp Ile Gly Arg Leu Val Lys Glu Gly Cys Glu Val Gly Phe Ile Pro
145                 150                 155                 160

AGC CCC GTC AAA CTG GAC AGC CTT CGC CTG CTG CAG GAA CAG AAG CTG       528
Ser Pro Val Lys Leu Asp Ser Leu Arg Leu Leu Gln Glu Gln Lys Leu
                165                 170                 175

CGC CAG AAC CGC CTC GGC TCC AGC AAA TCA GGC GAT AAC TCC AGT TCC       576
Arg Gln Asn Arg Leu Gly Ser Ser Lys Ser Gly Asp Asn Ser Ser Ser
            180                 185                 190

AGT CTG GGA GAT GTG GTG ACT GGC ACC CGC CGC CCC ACA CCC CCT GCC       624
Ser Leu Gly Asp Val Val Thr Gly Thr Arg Arg Pro Thr Pro Pro Ala
        195                 200                 205

AGT GGT TAC AGA CAT GAT GCA GAA AGC TTT ATT TGACTTCTTG AAGCATCGGT     677
Ser Gly Tyr Arg His Asp Ala Glu Ser Phe Ile
    210                 215                 220

TTGATGGCAG GATCTCCATC ACTCGTGTGA CGGCAGATAT TTCCCTGGCT AAGCGCTCAG     737

TTCTCAACAA CCCCAGCAAA CACATCATCA TTGAGCGCTC CAACACACGC TCCAGCCTGG     797

CTGAGGTGCA GAGTGAAATC GAGCGAATCT TCGAGCTGGC CCGGACCCTT CAGTTGGTCG     857

CTCTGGATGC TGACACCATC AATCACCCAG CCCAGCTGTC CAAGACCTCG CTGGCCCCCA     917

TCATTGTTTA CATCAAGATC ACCTCTCCCA AGGTACTTCA AAGGCTCATC AAGTCCCGAG     977

GAAAGTCTCA GTCCAAACAC CTCAATGTCC AAATAGCGGC CTCGGAAAAG CTGGCACAGT    1037
```

-continued

| | | | | | |
|---|---|---|---|---|---|
| GCCCCCCTGA | AATGTTTGAC | ATCATCCTGG | ATGAGAACCA | ATTGGAGGAT | GCCTGCGAGC | 1097 |
| ATCTGGCGGA | GTACTTGGAA | GCCTATTGGA | AGGCCACACA | CCCGCCCAGC | AGCACGCCAC | 1157 |
| CCAATCCGCT | GCTGAACCGC | ACCATGGCTA | CCGCAGCCCT | GGCTGCCAGC | CCTGCCCCTG | 1217 |
| TCTCCAACCT | CCAGGTACAG | GTGCTCACCT | CGCTCAGGAG | AAACCTCGGC | TTCTGGGGCG | 1277 |
| GGCTGGAGTC | CTCACAGCGG | GGCAGTGTGG | TGCCCCAGGA | GCAGGAACAT | GCCATGTAGT | 1337 |
| GGGCGCCCTG | CCCGTCTTCC | CTCCTGCTCT | GGGGTCGGAA | CTGGAGTGCA | GGGAAC | 1393 |